(12) United States Patent
Shelton, IV et al.

(10) Patent No.: US 12,167,849 B2
(45) Date of Patent: Dec. 17, 2024

(54) TECHNIQUES FOR ADAPTIVE CONTROL OF MOTOR VELOCITY OF A SURGICAL STAPLING AND CUTTING INSTRUMENT

(71) Applicant: Cilag GmbH International, Zug (CH)

(72) Inventors: Frederick E. Shelton, IV, Hillsboro, OH (US); David C. Yates, Morrow, OH (US); Jason L. Harris, Lebanon, OH (US); Brett E. Swensgard, West Chester, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 0 days.

(21) Appl. No.: 18/137,792

(22) Filed: Apr. 21, 2023

(65) Prior Publication Data
US 2023/0293170 A1    Sep. 21, 2023

Related U.S. Application Data

(63) Continuation of application No. 17/097,346, filed on Nov. 13, 2020, now Pat. No. 11,672,532, which is a
(Continued)

(51) Int. Cl.
*A61B 17/068*    (2006.01)
*A61B 17/072*    (2006.01)
(Continued)

(52) U.S. Cl.
CPC ........ *A61B 17/0686* (2013.01); *A61B 17/068* (2013.01); *A61B 17/07207* (2013.01);
(Continued)

(58) Field of Classification Search
CPC ............ A61B 17/0686; A61B 17/1114; A61B 17/07207; A61B 17/068; A61B 17/1626;
(Continued)

(56) References Cited

U.S. PATENT DOCUMENTS 3,899,829 A    8/1975    Storm
5,611,813 A    3/1997    Lichtman
(Continued)

FOREIGN PATENT DOCUMENTS

CN    104921730 B    9/2017
EP    2153793 A2    2/2010
(Continued)

*Primary Examiner* — Thomas M Wittenschlaeger
(74) *Attorney, Agent, or Firm* — TROUTMAN PEPPER HAMILTON SANDERS LLP

(57) ABSTRACT

A method of controlling motor velocity in a surgical instrument is disclosed. The surgical instrument includes a displacement member, a motor coupled to the displacement member, a control circuit coupled to the motor, a position sensor coupled to the control circuit, and a timer coupled to the control circuit. The method includes receiving a first position of a displacement member from a position sensor, starting a timer, advancing the displacement member to a second position by setting a motor velocity to a first velocity, receiving the second positon from the position sensor, stopping the timer when the displacement member reaches the second position, receiving elapsed time from the timer, wherein the elapsed time is the time taken by the displacement to move from the first position to the second positon, and controlling, by the control circuit, velocity of the motor based on the elapsed time.

20 Claims, 79 Drawing Sheets

Related U.S. Application Data continuation of application No. 15/628,175, filed on Jun. 20, 2017, now Pat. No. 10,881,399.

(51) Int. Cl.
| | |
|---|---|
| *A61B 17/11* | (2006.01) |
| *A61B 17/00* | (2006.01) |
| *A61B 17/16* | (2006.01) |
| *A61B 17/29* | (2006.01) |
| *A61B 90/00* | (2016.01) |

(52) U.S. Cl.
CPC .. *A61B 17/1114* (2013.01); *A61B 2017/00017* (2013.01); *A61B 2017/00115* (2013.01); *A61B 2017/00398* (2013.01); *A61B 2017/0046* (2013.01); *A61B 2017/00734* (2013.01); *A61B 2017/07257* (2013.01); *A61B 2017/07278* (2013.01); *A61B 2017/07285* (2013.01); *A61B 17/1626* (2013.01); *A61B 2017/2927* (2013.01); *A61B 2017/2933* (2013.01); *A61B 90/03* (2016.02); *A61B 2090/064* (2016.02); *A61B 2090/067* (2016.02)

(58) Field of Classification Search
CPC ........... A61B 2017/00398; A61B 2017/00734; A61B 2017/2927; A61B 2017/00017; A61B 2017/00115; A61B 2017/07278; A61B 2017/0046; A61B 2017/07285; A61B 2017/2933; A61B 2017/07257
See application file for complete search history.

(56) References Cited

U.S. PATENT DOCUMENTS

| | | | |
|---|---|---|---|
| 5,704,792 | A | 1/1998 | Sobhani |
| 5,746,770 | A | 5/1998 | Zeitels |
| 5,798,752 | A | 8/1998 | Buxton |
| 5,922,001 | A | 7/1999 | Yoon |
| 5,922,003 | A | 7/1999 | Anctil |
| 6,023,275 | A | 2/2000 | Horvitz |
| 6,454,656 | B2 | 9/2002 | Brissette |
| 7,075,412 | B1 | 7/2006 | Reynolds |
| D580,942 | S | 11/2008 | Oshiro |
| 7,823,076 | B2 | 10/2010 | Borovsky |
| 7,845,537 | B2 | 12/2010 | Shelton, IV |
| 7,877,869 | B2 | 2/2011 | Mehdizadeh |
| 7,952,464 | B2 | 5/2011 | Nikitin |
| 8,210,411 | B2 | 7/2012 | Yates |
| 8,409,234 | B2 | 4/2013 | Stahler |
| 8,840,004 | B2 | 9/2014 | Holsten |
| 9,072,535 | B2 | 7/2015 | Shelton, IV |
| 9,226,686 | B2 | 1/2016 | Blair |
| 9,283,334 | B2 | 3/2016 | Mantell |
| 9,651,032 | B2 | 5/2017 | Weaver |
| 9,700,381 | B2 | 7/2017 | Amat Girbau |
| 9,713,466 | B2 | 7/2017 | Kostrzewski |
| 9,801,679 | B2 | 10/2017 | Trees |
| 9,901,358 | B2 | 2/2018 | Faller |
| 10,041,822 | B2 | 8/2018 | Zemlok |
| 10,285,750 | B2 | 5/2019 | Coulson |
| 10,307,170 | B2 | 6/2019 | Parfett |
| 10,314,579 | B2 | 6/2019 | Chowaniec |
| 10,327,767 | B2 | 6/2019 | Shelton, IV |
| 10,368,864 | B2 | 8/2019 | Harris |
| 10,368,866 | B2 | 8/2019 | Wang |
| 10,390,841 | B2 | 8/2019 | Shelton, IV |
| 10,512,464 | B2 | 12/2019 | Park |
| 10,524,870 | B2 | 1/2020 | Saraliev |
| D879,808 | S | 3/2020 | Harris |
| D879,809 | S | 3/2020 | Harris |
| 10,617,438 | B2 | 4/2020 | O'Keefe |
| 10,624,633 | B2 | 4/2020 | Shelton, IV |
| 10,646,220 | B2 | 5/2020 | Shelton, IV |
| D890,784 | S | 7/2020 | Shelton, IV |
| 10,729,434 | B2 | 8/2020 | Harris |
| 10,729,435 | B2 | 8/2020 | Richard |
| 10,736,702 | B2 | 8/2020 | Harris |
| 10,737,398 | B2 | 8/2020 | Remirez |
| 10,779,820 | B2 | 9/2020 | Harris |
| 10,813,639 | B2 | 10/2020 | Shelton, IV |
| 10,959,726 | B2 | 3/2021 | Williams |
| 11,039,849 | B2 | 6/2021 | Bucciaglia |
| 11,166,773 | B2 | 11/2021 | Ragosta |
| 11,172,580 | B2 | 11/2021 | Gaertner |
| 11,197,672 | B2 | 12/2021 | Dunki-Jacobs |
| 11,311,295 | B2 | 4/2022 | Wingardner |
| 11,317,912 | B2 | 5/2022 | Jenkins |
| 11,317,978 | B2 | 5/2022 | Cameron |
| D966,512 | S | 10/2022 | Shelton, IV |
| D967,421 | S | 10/2022 | Shelton, IV |
| D971,232 | S | 11/2022 | Siebel |
| 11,484,309 | B2 | 11/2022 | Harris |
| 11,484,312 | B2 | 11/2022 | Shelton, IV |
| 2002/0054158 | A1 | 5/2002 | Asami |
| 2002/0082612 | A1 | 6/2002 | Moll |
| 2002/0087148 | A1 | 7/2002 | Brock |
| 2002/0111621 | A1 | 8/2002 | Wallace |
| 2003/0018323 | A1 | 1/2003 | Wallace |
| 2003/0135204 | A1 | 7/2003 | Lee |
| 2005/0044489 | A1 | 2/2005 | Yamagami |
| 2006/0020272 | A1 | 1/2006 | Gildenberg |
| 2007/0043338 | A1 | 2/2007 | Moll |
| 2007/0221701 | A1 | 9/2007 | Ortiz |
| 2008/0046000 | A1 | 2/2008 | Lee |
| 2008/0126984 | A1 | 5/2008 | Fleishman |
| 2008/0216704 | A1 | 9/2008 | Eisenbeis |
| 2008/0255421 | A1 | 10/2008 | Hegeman |
| 2008/0308607 | A1 | 12/2008 | Timm |
| 2009/0007014 | A1 | 1/2009 | Coomer |
| 2009/0120994 | A1 | 5/2009 | Murray |
| 2009/0138003 | A1 | 5/2009 | Deville |
| 2009/0143797 | A1 | 6/2009 | Smith |
| 2009/0204925 | A1 | 8/2009 | Bhat |
| 2009/0206143 | A1 | 8/2009 | Huitema |
| 2010/0002013 | A1 | 1/2010 | Kagaya |
| 2010/0036441 | A1 | 2/2010 | Procter |
| 2010/0125786 | A1 | 5/2010 | Ozawa |
| 2010/0168741 | A1 | 7/2010 | Sanai |
| 2010/0198159 | A1 | 8/2010 | Voss |
| 2010/0325568 | A1 | 12/2010 | Pedersen |
| 2011/0118754 | A1 | 5/2011 | Dachs |
| 2011/0139851 | A1 | 6/2011 | McCuen |
| 2011/0278035 | A1 | 11/2011 | Chen |
| 2012/0143175 | A1 | 6/2012 | Hermann |
| 2012/0203213 | A1 | 8/2012 | Kimball |
| 2013/0069088 | A1 | 3/2013 | Speck |
| 2013/0289565 | A1 | 10/2013 | Hassler, Jr. |
| 2014/0069240 | A1 | 3/2014 | Dauvin |
| 2014/0188101 | A1 | 7/2014 | Bales, Jr. |
| 2014/0263541 | A1 | 9/2014 | Leimbach |
| 2014/0263551 | A1 | 9/2014 | Hall |
| 2014/0263552 | A1 | 9/2014 | Hall |
| 2015/0034697 | A1 | 2/2015 | Mastri |
| 2015/0060516 | A1 | 3/2015 | Collings |
| 2015/0067582 | A1 | 3/2015 | Donnelly |
| 2015/0216605 | A1 | 8/2015 | Baldwin |
| 2015/0272575 | A1* | 10/2015 | Leimbach .............. A61B 90/96 227/175.3 |
| 2016/0118201 | A1 | 4/2016 | Nicholas |
| 2016/0132026 | A1 | 5/2016 | Wingardner |
| 2017/0020616 | A1 | 1/2017 | Vale |
| 2017/0086932 | A1 | 3/2017 | Auld |
| 2017/0168187 | A1 | 6/2017 | Calderoni |
| 2017/0252060 | A1 | 9/2017 | Ellingson |
| 2017/0303984 | A1 | 10/2017 | Malackowski |
| 2018/0250002 | A1 | 9/2018 | Eschbach |
| 2018/0280073 | A1 | 10/2018 | Sanai |
| 2018/0360443 | A1 | 12/2018 | Shelton, IV |
| 2018/0360445 | A1 | 12/2018 | Shelton, IV |
| 2018/0360446 | A1 | 12/2018 | Shelton, IV |
| 2018/0360449 | A1 | 12/2018 | Shelton, IV |
| 2018/0360454 | A1 | 12/2018 | Shelton, IV |

(56) References Cited

U.S. PATENT DOCUMENTS

| | | |
|---|---|---|
| 2018/0360456 A1 | 12/2018 | Shelton, IV |
| 2018/0360471 A1 | 12/2018 | Parfett |
| 2018/0360472 A1 | 12/2018 | Harris |
| 2018/0360473 A1 | 12/2018 | Shelton, IV |
| 2019/0000535 A1 | 1/2019 | Messerly |
| 2019/0017311 A1 | 1/2019 | McGettrick |
| 2019/0200986 A1 | 7/2019 | Shelton, IV |
| 2019/0200987 A1 | 7/2019 | Shelton, IV |
| 2019/0201079 A1 | 7/2019 | Shelton, IV |
| 2019/0388091 A1 | 12/2019 | Eschbach |
| 2020/0008827 A1 | 1/2020 | Dearden |
| 2020/0114505 A1 | 4/2020 | Kikuchi |
| 2020/0205810 A1 | 7/2020 | Posey |
| 2020/0345363 A1 | 11/2020 | Shelton, IV |
| 2020/0405304 A1 | 12/2020 | Mozdzierz |
| 2021/0128153 A1 | 5/2021 | Sgroi |
| 2021/0189234 A1 | 6/2021 | Kobayashi |
| 2022/0023325 A1 | 1/2022 | Espagnolle |
| 2022/0024093 A1 | 1/2022 | Kodaira |
| 2022/0054125 A1 | 2/2022 | Ji |
| 2022/0160358 A1 | 5/2022 | Wixey |
| 2022/0175370 A1 | 6/2022 | Shelton, IV |
| 2022/0175371 A1 | 6/2022 | Hess |
| 2022/0175372 A1 | 6/2022 | Shelton, IV |
| 2022/0175375 A1 | 6/2022 | Harris |
| 2022/0175378 A1 | 6/2022 | Leimbach |
| 2022/0175381 A1 | 6/2022 | Scheib |
| 2022/0183685 A1 | 6/2022 | Shelton, IV |
| 2022/0211367 A1 | 7/2022 | Schmid |
| 2022/0218332 A1 | 7/2022 | Shelton, IV |
| 2022/0218333 A1 | 7/2022 | Parihar |
| 2022/0218334 A1 | 7/2022 | Parihar |
| 2022/0218336 A1 | 7/2022 | Timm |
| 2022/0218337 A1 | 7/2022 | Timm |
| 2022/0218338 A1 | 7/2022 | Shelton, IV |
| 2022/0218340 A1 | 7/2022 | Harris |
| 2022/0218344 A1 | 7/2022 | Leimbach |
| 2022/0218345 A1 | 7/2022 | Shelton, IV |
| 2022/0218346 A1 | 7/2022 | Shelton, IV |
| 2022/0218347 A1 | 7/2022 | Shelton, IV |
| 2022/0218348 A1 | 7/2022 | Swensgard |
| 2022/0218349 A1 | 7/2022 | Shelton, IV |
| 2022/0218350 A1 | 7/2022 | Shelton, IV |
| 2022/0218351 A1 | 7/2022 | Shelton, IV |
| 2022/0218376 A1 | 7/2022 | Shelton, IV |
| 2022/0218378 A1 | 7/2022 | Shelton, IV |
| 2022/0218381 A1 | 7/2022 | Leimbach |
| 2022/0218382 A1 | 7/2022 | Leimbach |
| 2022/0225980 A1 | 7/2022 | Shelton, IV |
| 2022/0225981 A1 | 7/2022 | Shelton, IV |
| 2022/0225982 A1 | 7/2022 | Yates |
| 2022/0225986 A1 | 7/2022 | Shelton, IV |
| 2022/0225992 A1 | 7/2022 | Smith |
| 2022/0225993 A1 | 7/2022 | Huitema |
| 2022/0225994 A1 | 7/2022 | Setser |
| 2022/0226012 A1 | 7/2022 | Shelton, IV |
| 2022/0226013 A1 | 7/2022 | Hall |
| 2022/0233184 A1 | 7/2022 | Parihar |
| 2022/0233185 A1 | 7/2022 | Parihar |
| 2022/0233186 A1 | 7/2022 | Timm |
| 2022/0233187 A1 | 7/2022 | Timm |
| 2022/0233188 A1 | 7/2022 | Timm |
| 2022/0233194 A1 | 7/2022 | Baxter, III |
| 2022/0233195 A1 | 7/2022 | Shelton, IV |
| 2022/0240927 A1 | 8/2022 | Timm |
| 2022/0240928 A1 | 8/2022 | Timm |
| 2022/0240929 A1 | 8/2022 | Timm |
| 2022/0240930 A1 | 8/2022 | Yates |
| 2022/0240936 A1 | 8/2022 | Huitema |
| 2022/0249095 A1 | 8/2022 | Shelton, IV |
| 2022/0265272 A1 | 8/2022 | Li |
| 2022/0273291 A1 | 9/2022 | Shelton, IV |
| 2022/0273292 A1 | 9/2022 | Shelton, IV |
| 2022/0273293 A1 | 9/2022 | Shelton, IV |
| 2022/0273294 A1 | 9/2022 | Creamer |
| 2022/0273299 A1 | 9/2022 | Shelton, IV |
| 2022/0273300 A1 | 9/2022 | Shelton, IV |
| 2022/0273301 A1 | 9/2022 | Creamer |
| 2022/0273302 A1 | 9/2022 | Shelton, IV |
| 2022/0273303 A1 | 9/2022 | Creamer |
| 2022/0273304 A1 | 9/2022 | Shelton, IV |
| 2022/0273305 A1 | 9/2022 | Shelton, IV |
| 2022/0273306 A1 | 9/2022 | Shelton, IV |
| 2022/0273307 A1 | 9/2022 | Shelton, IV |
| 2022/0273308 A1 | 9/2022 | Shelton, IV |
| 2022/0278438 A1 | 9/2022 | Shelton, IV |
| 2022/0287711 A1 | 9/2022 | Ming |
| 2022/0304679 A1 | 9/2022 | Bakos |
| 2022/0304680 A1 | 9/2022 | Shelton, IV |
| 2022/0304681 A1 | 9/2022 | Shelton, IV |
| 2022/0304682 A1 | 9/2022 | Shelton, IV |
| 2022/0304683 A1 | 9/2022 | Shelton, IV |
| 2022/0304684 A1 | 9/2022 | Bakos |
| 2022/0304685 A1 | 9/2022 | Bakos |
| 2022/0304686 A1 | 9/2022 | Shelton, IV |
| 2022/0304687 A1 | 9/2022 | Shelton, IV |
| 2022/0304688 A1 | 9/2022 | Shelton, IV |
| 2022/0304689 A1 | 9/2022 | Shelton, IV |
| 2022/0304690 A1 | 9/2022 | Baxter, III |
| 2022/0304714 A1 | 9/2022 | Shelton, IV |
| 2022/0304715 A1 | 9/2022 | Shelton, IV |

FOREIGN PATENT DOCUMENTS

| | | |
|---|---|---|
| EP | 3505095 A1 | 7/2019 |
| EP | 3791810 A1 | 3/2021 |
| JP | H0489041 A | 3/1992 |
| WO | 2018011664 A1 | 1/2018 |

\* cited by examiner

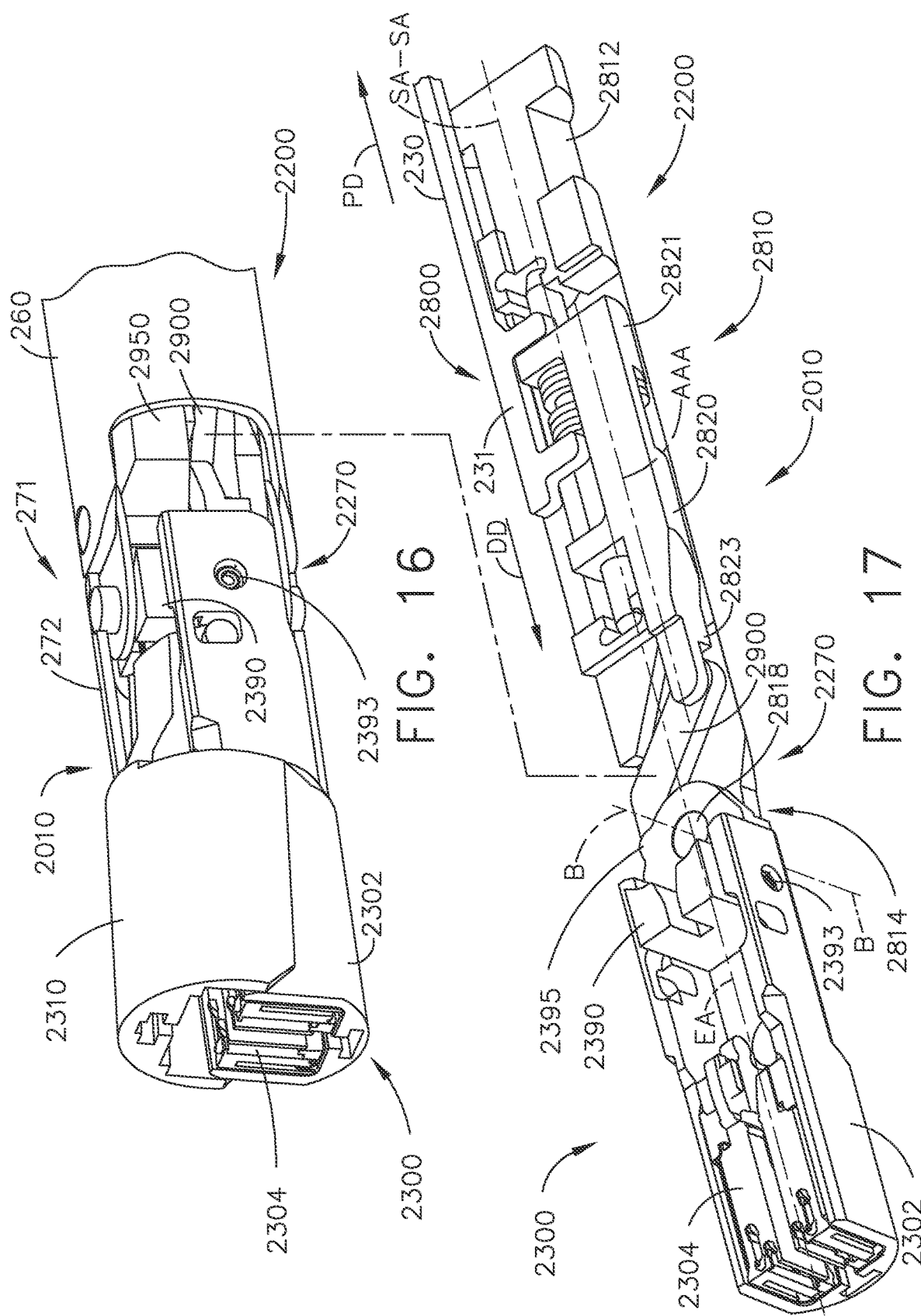

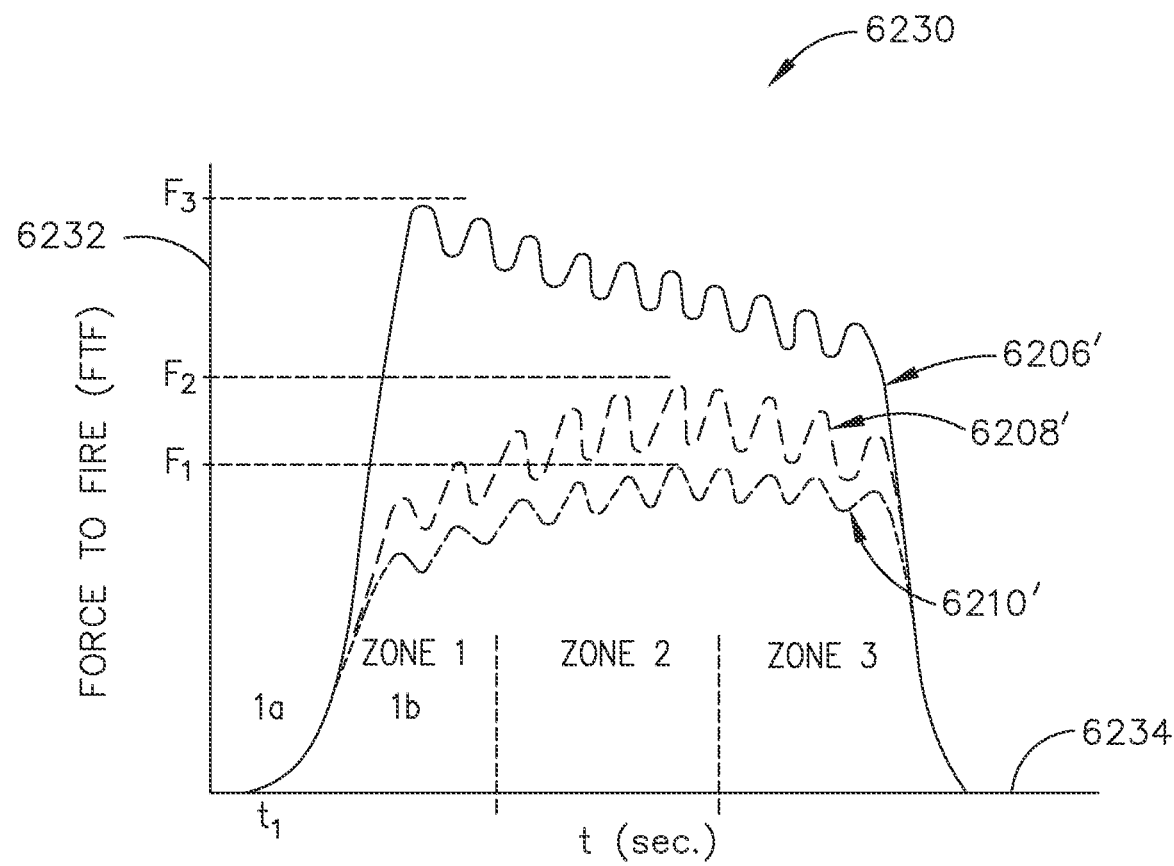
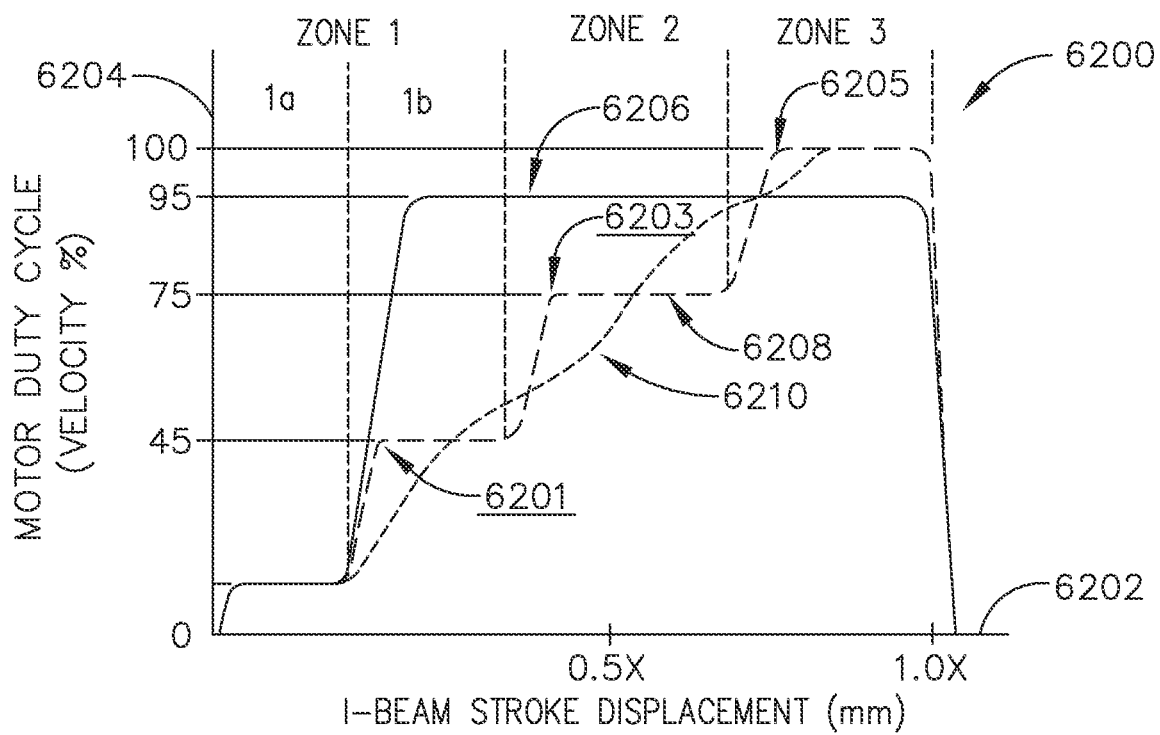
FIG. 62

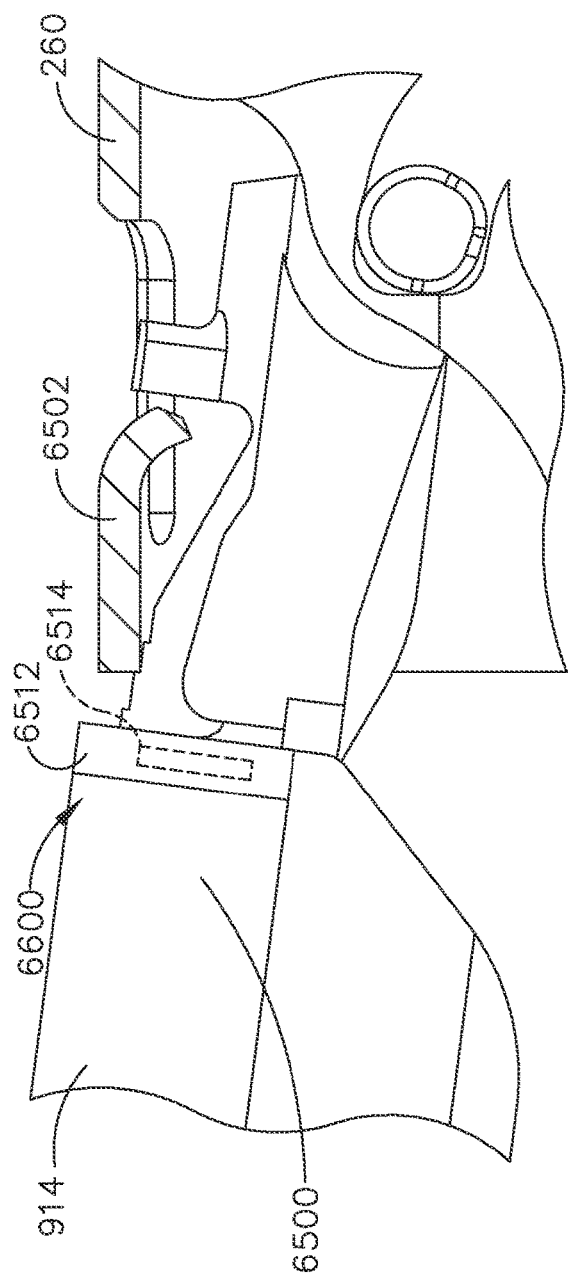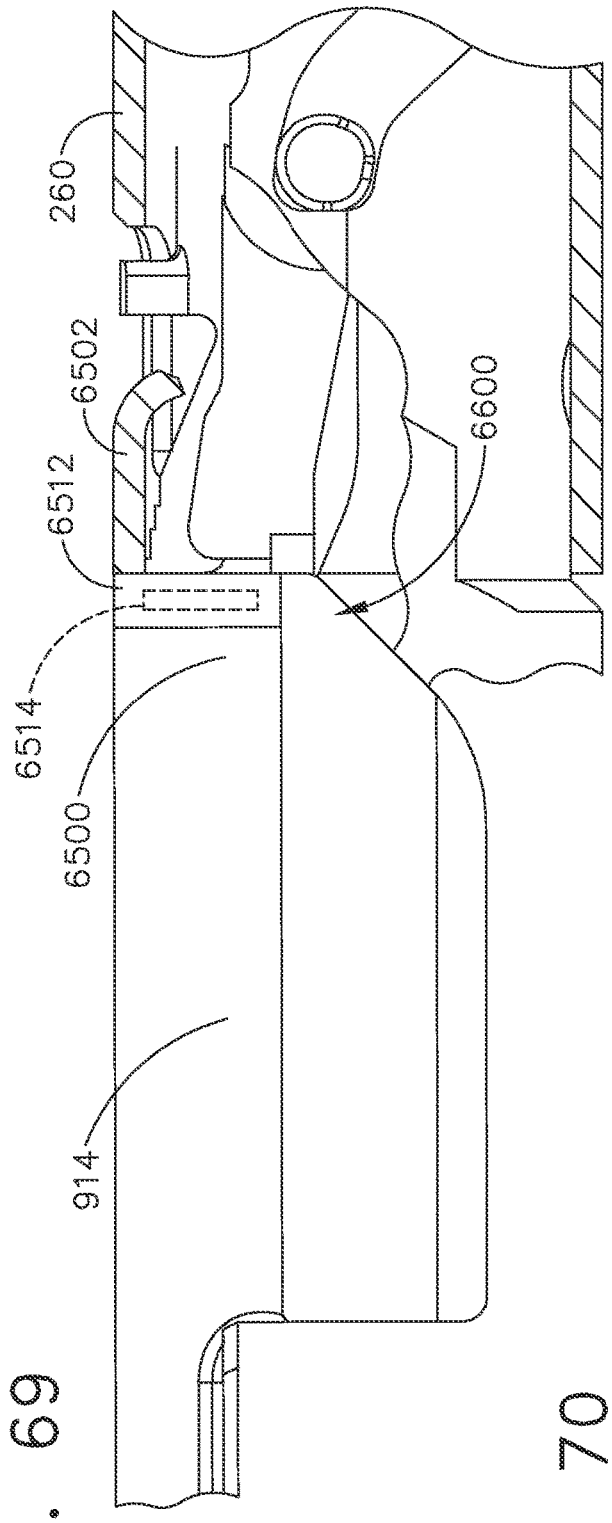

TECHNIQUES FOR ADAPTIVE CONTROL OF MOTOR VELOCITY OF A SURGICAL STAPLING AND CUTTING INSTRUMENT

CROSS-REFERENCE TO RELATED APPLICATIONS

The present application is a continuation application claiming priority under 35 U.S.C. § 120 to U.S. patent application Ser. No. 17/097,346, titled TECHNIQUES FOR ADAPTIVE CONTROL OF MOTOR VELOCITY OF A SURGICAL STAPLING AND CUTTING INSTRUMENT, filed Nov. 13, 2020, now U.S. Patent Application Publication No. 2021/0128146, which is a continuation application claiming priority under 35 U.S.C. § 120 to U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which issued on Jan. 5, 2021 as U.S. Pat. No. 10,881,399, the disclosures of each of which are herein incorporated by reference in their entireties.

TECHNICAL FIELD

The present disclosure relates to surgical instruments and, in various circumstances, to surgical stapling and cutting instruments and staple cartridges therefor that are designed to staple and cut tissue.

BACKGROUND

In a motorized surgical stapling and cutting instrument it may be useful to control the velocity of a cutting member or to control the articulation velocity of an end effector. Velocity of a displacement member may be determined by measuring elapsed time at predetermined position intervals of the displacement member or measuring the position of the displacement member at predetermined time intervals. The control may be open loop or closed loop. Such measurements may be useful to evaluate tissue conditions such as tissue thickness and adjust the velocity of the cutting member during a firing stroke to account for the tissue conditions. Tissue thickness may be determined by comparing expected velocity of the cutting member to the actual velocity of the cutting member. In some situations, it may be useful to articulate the end effector at a constant articulation velocity. In other situations, it may be useful to drive the end effector at a different articulation velocity than a default articulation velocity at one or more regions within a sweep range of the end effector.

In a motorized surgical stapling and cutting instrument it may be useful to adjust the velocity of a displacement member based on the actual velocity of the displacement member, which may vary from a set or command velocity due to external influences such as tissue type, tissue thickness, force exerted to fire the displacement member, or other external influences. Therefore, it would be desirable to control the firing speed of a displacement member in a surgical stapling and cutting instrument based on the time taken by the displacement member to move from a first location to a second location.

SUMMARY

A method of controlling motor velocity in a surgical instrument is provided. The surgical instrument comprises a displacement member configured to translate, a motor coupled to the displacement member to translate the displacement member, a control circuit coupled to the motor, a position sensor coupled to the control circuit, the position sensor configured to measure the position of the displacement member, a timer coupled to the control circuit, the timer configured to measure elapsed time, the method comprising: receiving, by a control circuit, a first position of a displacement member from a position sensor; starting, by the control circuit, a timer; advancing, by the control circuit, the displacement member to a second position by setting a motor velocity to a first velocity; receiving, by the control circuit, the second positon from the position sensor; stopping, by the control circuit, the timer when the displacement member reaches the second position; receiving, by the control circuit, elapsed time from the timer, wherein the elapsed time is the time taken by the displacement to move from the first position to the second positon; and controlling, by the control circuit, velocity of the motor based on the elapsed time.

FIGURES

The novel features of the aspects described herein are set forth with particularity in the appended claims. These aspects, however, both as to organization and methods of operation may be better understood by reference to the following description, taken in conjunction with the accompanying drawings.

FIG. 16 is a partial perspective view of a portion of an end effector of a surgical instrument showing an elongate shaft assembly in an unarticulated orientation with portions thereof omitted for clarity, according to one aspect of this disclosure.

FIG. 17 is another perspective view of the end effector of FIG. 16 showing the elongate shaft assembly an unarticulated orientation, according to one aspect of this disclosure.

FIG. 54 depicts a control algorithm for controlling an articulation velocity of an end effector utilizing variable voltage and no pulse width modulation.

FIG. 55 depicts a control algorithm for controlling an articulation velocity of an end effector utilizing constant voltage and pulse width modulation.

FIG. 56 depicts a control algorithm for controlling an articulation velocity of an end effector utilizing variable voltage and pulse width modulation.

FIG. 57 depicts a control algorithm for controlling an articulation velocity of an end effector utilizing constant voltage and no pulse width modulation.

FIG. 62 depicts two diagrams illustrating the force to fire (FTF) the surgical instrument of FIG. 1 as a function of time, and motor duty cycle (velocity %) of a motor driving the I-beam as a function of I-beam displacement (d) according to one aspect of this disclosure.

FIG. 69 is a sectional view of an anvil and closure tube sensor arrangement, wherein the anvil is in an open position according to one aspect of this disclosure.

FIG. 70 is a sectional view of an anvil and closure tube sensor arrangement, wherein the anvil is in a closed position according to one aspect of this disclosure.

DESCRIPTION

Figure 1:
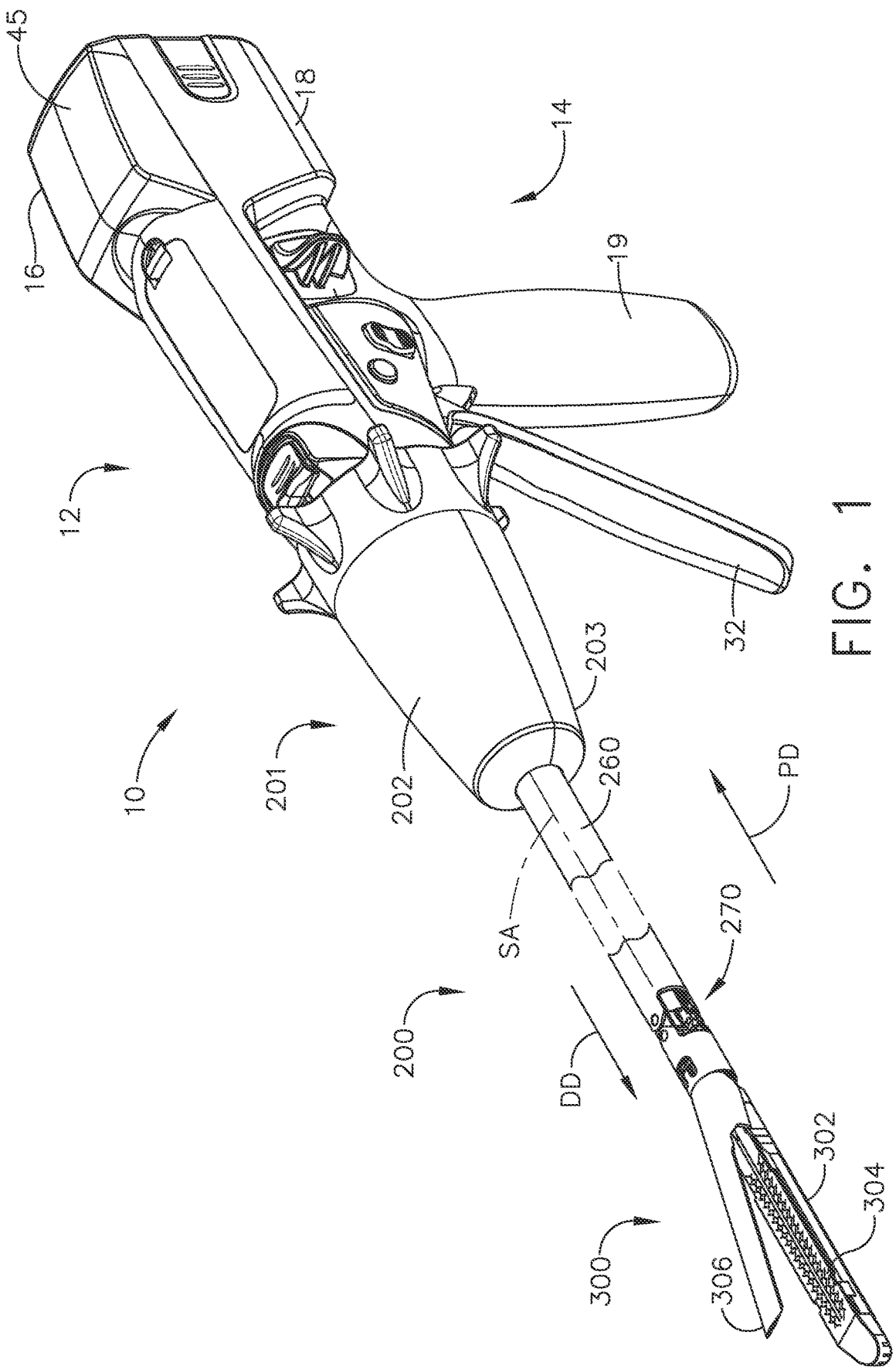
FIG. 1 is a perspective view of a surgical instrument that has an interchangeable shaft assembly operably coupled thereto according to one aspect of this disclosure.

Applicant of the present application owns the following patent applications filed on Jun. 20, 2017 and which are each herein incorporated by reference in their respective entireties:

U.S. patent application Ser. No. 15/627,998, titled CONTROL OF MOTOR VELOCITY OF A SURGICAL STAPLING AND CUTTING INSTRUMENT BASED ON ANGLE OF ARTICULATION, by inventors Frederick E. Shelton, IV et al., filed Jun. 20, 2017, now U.S. Pat. No. 10,390,841.

U.S. patent application Ser. No. 15/628,019, titled SURGICAL INSTRUMENT WITH VARIABLE DURATION TRIGGER ARRANGEMENT, by inventors Frederick E. Shelton, IV et al., filed Jun. 20, 2017, now U.S. Patent Application Publication No. 2018/0360443.

U.S. patent application Ser. No. 15/628,036, titled SYSTEMS AND METHODS FOR CONTROLLING DISPLACEMENT MEMBER MOTION OF A SURGICAL STAPLING AND CUTTING INSTRUMENT, by inventors Frederick E. Shelton, IV et al., filed Jun. 20, 2017, now U.S. Patent Application Publication No. 2018/0360445.

U.S. patent application Ser. No. 15/628,050, titled SYSTEMS AND METHODS FOR CONTROLLING MOTOR VELOCITY OF A SURGICAL STAPLING AND CUTTING INSTRUMENT ACCORDING TO ARTICULATION ANGLE OF END EFFECTOR, by inventors Frederick E. Shelton, IV et al., filed Jun. 20, 2017, now U.S. Patent Application Publication No. 2018/0360446.

U.S. patent application Ser. No. 15/628,075, titled SYSTEMS AND METHODS FOR CONTROLLING MOTOR VELOCITY OF A SURGICAL STAPLING AND CUTTING INSTRUMENT, by inventors Frederick E. Shelton, IV et al., filed Jun. 20, 2017, now U.S. Pat. No. 10,624,633.

U.S. patent application Ser. No. 15/628,154, titled SURGICAL INSTRUMENT HAVING CONTROLLABLE ARTICULATION VELOCITY, by inventors Frederick E. Shelton, IV et al., filed Jun. 20, 2017, now U.S. Patent Application Publication No. 2018/0360456.

U.S. patent application Ser. No. 15/628,158, titled SYSTEMS AND METHODS FOR CONTROLLING VELOCITY OF A DISPLACEMENT MEMBER OF A SURGICAL STAPLING AND CUTTING INSTRUMENT, by inventors Frederick E. Shelton, IV et al., filed Jun. 20, 2017, now U.S. Patent Application Publication No. 2018/0360449.

U.S. patent application Ser. No. 15/628,162, titled SYSTEMS AND METHODS FOR CONTROLLING DISPLACEMENT MEMBER VELOCITY FOR A SURGICAL INSTRUMENT, by inventors Frederick E. Shelton, IV et al., filed Jun. 20, 2017, now U.S. Pat. No. 10,646,220.

U.S. patent application Ser. No. 15/628,168, titled CONTROL OF MOTOR VELOCITY OF A SURGICAL STAPLING AND CUTTING INSTRUMENT BASED ON ANGLE OF ARTICULATION, by inventors Frederick E. Shelton, IV et al., filed Jun. 20, 2017, now U.S. Pat. No. 10,327,767.

U.S. patent application Ser. No. 15/628,045, titled TECHNIQUES FOR CLOSED LOOP CONTROL OF MOTOR VELOCITY OF A SURGICAL STAPLING AND CUTTING INSTRUMENT, by inventors Raymond E. Parfett et al., filed Jun. 20, 2017, now U.S. Pat. No. 10,307,170.

U.S. patent application Ser. No. 15/628,053, titled CLOSED LOOP FEEDBACK CONTROL OF MOTOR VELOCITY OF A SURGICAL STAPLING AND CUTTING INSTRUMENT BASED ON MAGNITUDE OF VELOCITY ERROR MEASUREMENTS, by inventors Raymond E. Parfett et al., filed Jun. 20, 2017, now U.S. Patent Application Publication No. 2018/0360471.

U.S. patent application Ser. No. 15/628,060, titled CLOSED LOOP FEEDBACK CONTROL OF MOTOR VELOCITY OF A SURGICAL STAPLING AND CUTTING INSTRUMENT BASED ON MEASURED TIME OVER A SPECIFIED DISPLACEMENT DISTANCE, by inventors Jason L. Harris et al., filed Jun. 20, 2017, now U.S. Patent Application Publication No. 2018/0360472.

U.S. patent application Ser. No. 15/628,067, titled CLOSED LOOP FEEDBACK CONTROL OF MOTOR VELOCITY OF A SURGICAL STAPLING AND CUTTING INSTRUMENT BASED ON MEASURED DISPLACEMENT DISTANCE TRAVELED OVER A SPECIFIED TIME INTERVAL, by inventors Frederick E. Shelton, IV et al., filed Jun. 20, 2017, now U.S. Patent Application Publication No. 2018/0360473.

U.S. patent application Ser. No. 15/628,072, titled CLOSED LOOP FEEDBACK CONTROL OF MOTOR VELOCITY OF A SURGICAL STAPLING AND CUTTING INSTRUMENT BASED ON MEASURED TIME OVER A SPECIFIED NUMBER OF SHAFT ROTATIONS, by inventors Frederick E. Shelton, IV et al., filed Jun. 20, 2017, now U.S. Patent Application Publication No. 2018/0360454.

U.S. patent application Ser. No. 15/628,029, titled SYSTEMS AND METHODS FOR CONTROLLING DISPLAYING MOTOR VELOCITY FOR A SURGICAL INSTRUMENT, by inventors Jason L. Harris et al., filed Jun. 20, 2017, now U.S. Pat. No. 10,368,864.

U.S. patent application Ser. No. 15/628,077, titled SYSTEMS AND METHODS FOR CONTROLLING MOTOR SPEED ACCORDING TO USER INPUT FOR A SURGICAL INSTRUMENT, by inventors Jason L. Harris et al., filed Jun. 20, 2017, now U.S. Pat. No. 10,779,820.

U.S. patent application Ser. No. 15/628,115, titled CLOSED LOOP FEEDBACK CONTROL OF MOTOR VELOCITY OF A SURGICAL STAPLING AND CUTTING INSTRUMENT BASED ON SYSTEM CONDITIONS, by inventors Frederick E. Shelton, I V et al., filed Jun. 20, 2017, now U.S. Pat. No. 10,813,639.

U.S. patent application Ser. No. 29/608,238, titled GRAPHICAL USER INTERFACE FOR A DISPLAY OR PORTION THEREOF, by inventors Jason L. Harris et al., filed Jun. 20, 2017, now U.S. Pat. No. D879,809.

U.S. patent application Ser. No. 29/608,231, titled GRAPHICAL USER INTERFACE FOR A DISPLAY OR PORTION THEREOF, by inventors Jason L. Harris et al., filed Jun. 20, 2017, now U.S. Pat. No. D879,808.

U.S. patent application Ser. No. 29/608,246, titled GRAPHICAL USER INTERFACE FOR A DISPLAY OR PORTION THEREOF, by inventors Frederick E. Shelton, I V et al., filed Jun. 20, 2017, now U.S. Pat. No. D890,784.

Certain aspects are shown and described to provide an understanding of the structure, function, manufacture, and use of the disclosed devices and methods. Features shown or described in one example may be combined with features of other examples and modifications and variations are within the scope of this disclosure.

The terms "proximal" and "distal" are relative to a clinician manipulating the handle of the surgical instrument where "proximal" refers to the portion closer to the clinician and "distal" refers to the portion located further from the clinician. For expediency, spatial terms "vertical," "horizontal," "up," and "down" used with respect to the drawings are not intended to be limiting and/or absolute, because surgical instruments can used in many orientations and positions.

Example devices and methods are provided for performing laparoscopic and minimally invasive surgical procedures. Such devices and methods, however, can be used in other surgical procedures and applications including open surgical procedures, for example. The surgical instruments can be inserted into a through a natural orifice or through an incision or puncture hole formed in tissue. The working portions or end effector portions of the instruments can be inserted directly into the body or through an access device that has a working channel through which the end effector and elongated shaft of the surgical instrument can be advanced.

FIGS. 1-4 depict a motor-driven surgical instrument 10 for cutting and fastening that may or may not be reused. In the illustrated examples, the surgical instrument 10 includes a housing 12 that comprises a handle assembly 14 that is configured to be grasped, manipulated, and actuated by the clinician. The housing 12 is configured for operable attachment to an interchangeable shaft assembly 200 that has an end effector 300 operably coupled thereto that is configured to perform one or more surgical tasks or procedures. In accordance with the present disclosure, various forms of interchangeable shaft assemblies may be effectively employed in connection with robotically controlled surgical systems. The term "housing" may encompass a housing or similar portion of a robotic system that houses or otherwise operably supports at least one drive system configured to generate and apply at least one control motion that could be used to actuate interchangeable shaft assemblies. The term "frame" may refer to a portion of a handheld surgical instrument. The term "frame" also may represent a portion of a robotically controlled surgical instrument and/or a portion of the robotic system that may be used to operably control a surgical instrument. Interchangeable shaft assemblies may be employed with various robotic systems, instruments, components, and methods disclosed in U.S. Pat. No. 9,072,535, entitled SURGICAL STAPLING INSTRUMENTS WITH ROTATABLE STAPLE DEPLOYMENT ARRANGEMENTS, which is herein incorporated by reference in its entirety.

FIG. 1 is a perspective view of a surgical instrument 10 that has an interchangeable shaft assembly 200 operably coupled thereto according to one aspect of this disclosure. The housing 12 includes an end effector 300 that comprises a surgical cutting and fastening device configured to operably support a surgical staple cartridge 304 therein. The housing 12 may be configured for use in connection with interchangeable shaft assemblies that include end effectors that are adapted to support different sizes and types of staple cartridges, have different shaft lengths, sizes, and types. The housing 12 may be employed with a variety of interchangeable shaft assemblies, including assemblies configured to apply other motions and forms of energy such as, radio frequency (RF) energy, ultrasonic energy, and/or motion to end effector arrangements adapted for use in connection with various surgical applications and procedures. The end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly.

The handle assembly 14 may comprise a pair of interconnectable handle housing segments 16, 18 interconnected by screws, snap features, adhesive, etc. The handle housing segments 16, 18 cooperate to form a pistol grip portion 19 that can be gripped and manipulated by the clinician. The handle assembly 14 operably supports a plurality of drive systems configured to generate and apply control motions to corresponding portions of the interchangeable shaft assembly that is operably attached thereto. A display may be provided below a cover 45.

Figure 2:
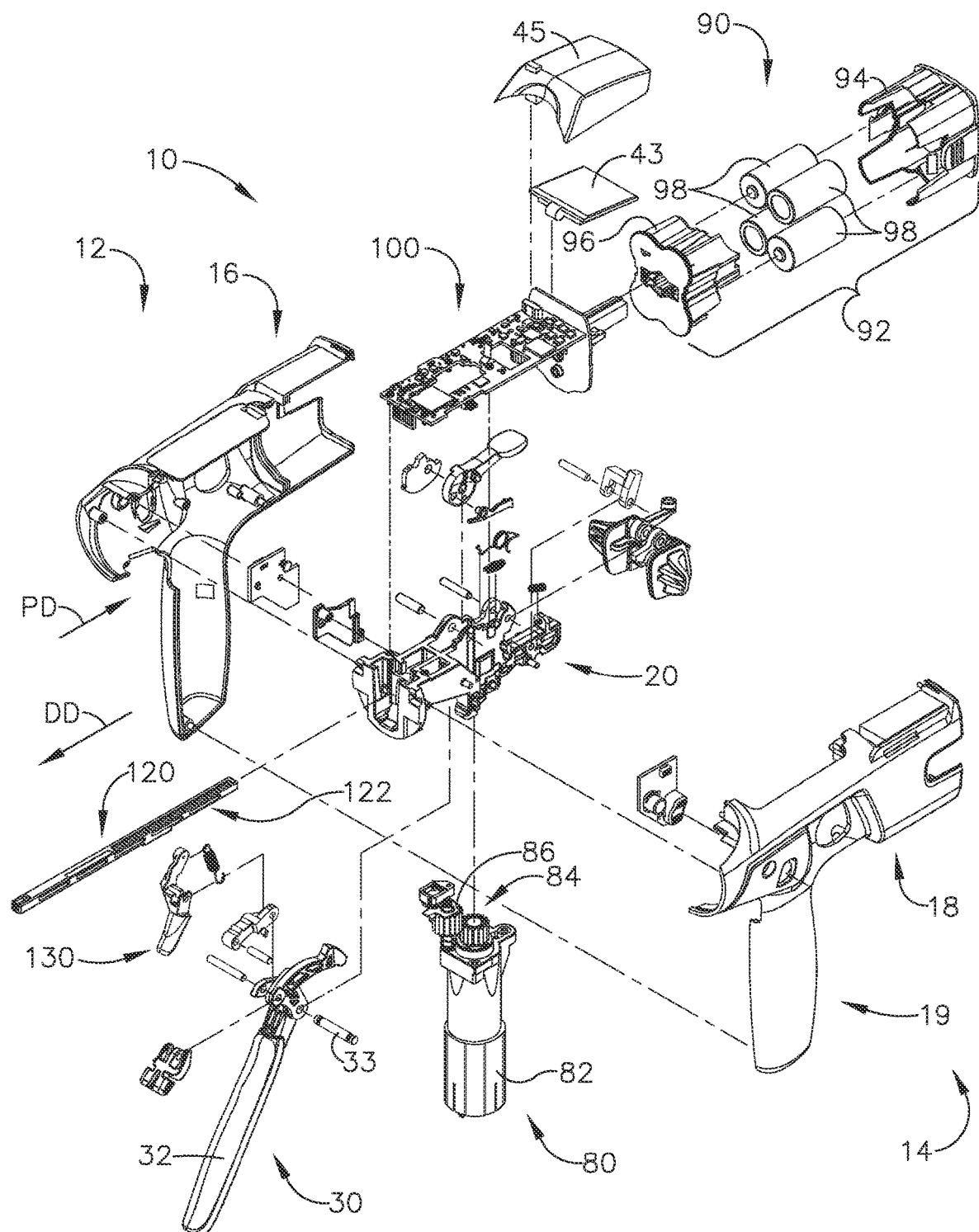
FIG. 2 is an exploded assembly view of a portion of the surgical instrument of FIG. 1 according to one aspect of this disclosure.

FIG. 2 is an exploded assembly view of a portion of the surgical instrument 10 of FIG. 1 according to one aspect of this disclosure. The handle assembly 14 may include a frame 20 that operably supports a plurality of drive systems. The frame 20 can operably support a "first" or closure drive system 30, which can apply closing and opening motions to the interchangeable shaft assembly 200. The closure drive system 30 may include an actuator such as a closure trigger 32 pivotally supported by the frame 20. The closure trigger 32 is pivotally coupled to the handle assembly 14 by a pivot pin 33 to enable the closure trigger 32 to be manipulated by a clinician. When the clinician grips the pistol grip portion 19 of the handle assembly 14, the closure trigger 32 can pivot from a starting or "unactuated" position to an "actuated" position and more particularly to a fully compressed or fully actuated position.

The handle assembly 14 and the frame 20 may operably support a firing drive system 80 configured to apply firing motions to corresponding portions of the interchangeable shaft assembly attached thereto. The firing drive system 80 may employ an electric motor 82 located in the pistol grip portion 19 of the handle assembly 14. The electric motor 82 may be a DC brushed motor having a maximum rotational speed of approximately 25,000 RPM, for example. In other arrangements, the motor may include a brushless motor, a cordless motor, a synchronous motor, a stepper motor, or any other suitable electric motor. The electric motor 82 may be powered by a power source 90 that may comprise a removable power pack 92. The removable power pack 92 may comprise a proximal housing portion 94 configured to attach to a distal housing portion 96. The proximal housing portion 94 and the distal housing portion 96 are configured to operably support a plurality of batteries 98 therein. Batteries 98 may each comprise, for example, a Lithium Ion (LI) or other suitable battery. The distal housing portion 96 is configured for removable operable attachment to a control circuit board 100, which is operably coupled to the electric motor 82. Several batteries 98 connected in series may power the surgical instrument 10. The power source 90 may be replaceable and/or rechargeable. A display 43, which is located below the cover 45, is electrically coupled to the control circuit board 100. The cover 45 may be removed to expose the display 43.

The electric motor 82 can include a rotatable shaft (not shown) that operably interfaces with a gear reducer assembly 84 mounted in meshing engagement with a with a set, or rack, of drive teeth 122 on a longitudinally movable drive member 120. The longitudinally movable drive member 120 has a rack of drive teeth 122 formed thereon for meshing engagement with a corresponding drive gear 86 of the gear reducer assembly 84.

In use, a voltage polarity provided by the power source 90 can operate the electric motor 82 in a clockwise direction wherein the voltage polarity applied to the electric motor by the battery can be reversed in order to operate the electric motor 82 in a counter-clockwise direction. When the electric motor 82 is rotated in one direction, the longitudinally movable drive member 120 will be axially driven in the distal direction "DD." When the electric motor 82 is driven in the opposite rotary direction, the longitudinally movable drive member 120 will be axially driven in a proximal direction "PD." The handle assembly 14 can include a switch that can be configured to reverse the polarity applied to the electric motor 82 by the power source 90. The handle assembly 14 may include a sensor configured to detect the position of the longitudinally movable drive member 120 and/or the direction in which the longitudinally movable drive member 120 is being moved.

Actuation of the electric motor 82 can be controlled by a firing trigger 130 that is pivotally supported on the handle assembly 14. The firing trigger 130 may be pivoted between an unactuated position and an actuated position.

Turning back to FIG. 1, the interchangeable shaft assembly 200 includes an end effector 300 comprising an elongated channel 302 configured to operably support a surgical staple cartridge 304 therein. The end effector 300 may include an anvil 306 that is pivotally supported relative to the elongated channel 302. The interchangeable shaft assembly 200 may include an articulation joint 270. Construction and operation of the end effector 300 and the articulation joint 270 are set forth in U.S. Patent Application Publication No. 2014/0263541, entitled ARTICULATABLE SURGICAL INSTRUMENT COMPRISING AN ARTICULATION LOCK, which is herein incorporated by reference in its entirety. The interchangeable shaft assembly 200 may include a proximal housing or nozzle 201 comprised of nozzle portions 202, 203. The interchangeable shaft assembly 200 may include a closure tube 260 extending along a shaft axis SA that can be utilized to close and/or open the anvil 306 of the end effector 300.

Turning back to FIG. 1, the closure tube 260 is translated distally (direction "DD") to close the anvil 306, for example, in response to the actuation of the closure trigger 32 in the manner described in the aforementioned reference U.S. Patent Application Publication No. 2014/0263541. The anvil 306 is opened by proximally translating the closure tube 260. In the anvil-open position, the closure tube 260 is moved to its proximal position.

Figure 3:
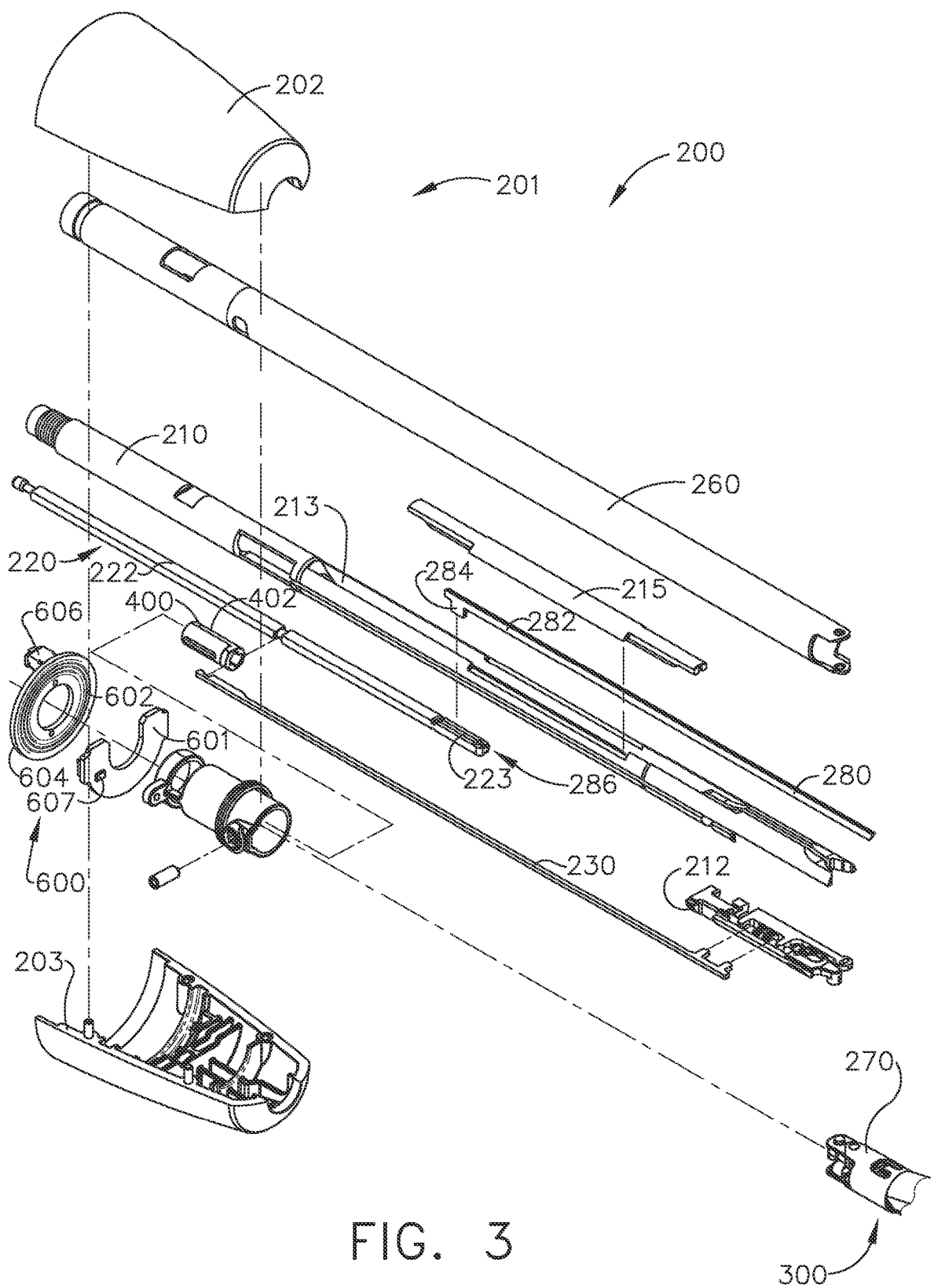
FIG. 3 is an exploded assembly view of portions of the interchangeable shaft assembly according to one aspect of this disclosure.

FIG. 3 is another exploded assembly view of portions of the interchangeable shaft assembly 200 according to one aspect of this disclosure. The interchangeable shaft assembly 200 may include a firing member 220 supported for axial travel within the spine 210. The firing member 220 includes an intermediate firing shaft 222 configured to attach to a distal cutting portion or knife bar 280. The firing member 220 may be referred to as a "second shaft" or a "second shaft assembly". The intermediate firing shaft 222 may include a longitudinal slot 223 in a distal end configured to receive a tab 284 on the proximal end 282 of the knife bar 280. The longitudinal slot 223 and the proximal end 282 may be configured to permit relative movement there between and can comprise a slip joint 286. The slip joint 286 can permit the intermediate firing shaft 222 of the firing member 220 to articulate the end effector 300 about the articulation joint 270 without moving, or at least substantially moving, the knife bar 280. Once the end effector 300 has been suitably oriented, the intermediate firing shaft 222 can be advanced distally until a proximal sidewall of the longitudinal slot 223 contacts the tab 284 to advance the knife bar 280 and fire the staple cartridge positioned within the channel 302. The spine 210 has an elongated opening or window 213 therein to facilitate assembly and insertion of the intermediate firing shaft 222 into the spine 210. Once the intermediate firing shaft 222 has been inserted therein, a top frame segment 215 may be engaged with the shaft frame 212 to enclose the intermediate firing shaft 222 and knife bar 280 therein. Operation of the firing member 220 may be found in U.S. Patent Application Publication No. 2014/0263541. A spine 210 can be configured to slidably support a firing member 220 and the closure tube 260 that extends around the spine 210. The spine 210 may slidably support an articulation driver 230.

The interchangeable shaft assembly 200 can include a clutch assembly 400 configured to selectively and releasably couple the articulation driver 230 to the firing member 220. The clutch assembly 400 includes a lock collar, or lock sleeve 402, positioned around the firing member 220 wherein the lock sleeve 402 can be rotated between an engaged position in which the lock sleeve 402 couples the articulation driver 230 to the firing member 220 and a disengaged position in which the articulation driver 230 is not operably coupled to the firing member 220. When the lock sleeve 402 is in the engaged position, distal movement of the firing member 220 can move the articulation driver 230 distally and, correspondingly, proximal movement of the firing member 220 can move the articulation driver 230 proximally. When the lock sleeve 402 is in the disengaged position, movement of the firing member 220 is not transmitted to the articulation driver 230 and, as a result, the firing member 220 can move independently of the articulation driver 230. The nozzle 201 may be employed to operably engage and disengage the articulation drive system with the firing drive system in the various manners described in U.S. Patent Application Publication No. 2014/0263541.

The interchangeable shaft assembly 200 can comprise a slip ring assembly 600 which can be configured to conduct electrical power to and/or from the end effector 300 and/or communicate signals to and/or from the end effector 300, for example. The slip ring assembly 600 can comprise a proximal connector flange 604 and a distal connector flange 601 positioned within a slot defined in the nozzle portions 202, 203. The proximal connector flange 604 can comprise a first face and the distal connector flange 601 can comprise a second face positioned adjacent to and movable relative to the first face. The distal connector flange 601 can rotate relative to the proximal connector flange 604 about the shaft axis SA-SA (FIG. 1). The proximal connector flange 604 can comprise a plurality of concentric, or at least substantially concentric, conductors 602 defined in the first face thereof. A connector 607 can be mounted on the proximal side of the distal connector flange 601 and may have a plurality of contacts wherein each contact corresponds to and is in electrical contact with one of the conductors 602. Such an arrangement permits relative rotation between the proximal connector flange 604 and the distal connector flange 601 while maintaining electrical contact there between. The proximal connector flange 604 can include an electrical connector 606 that can place the conductors 602 in signal communication with a shaft circuit board, for example. In at least one instance, a wiring harness comprising a plurality of conductors can extend between the electrical connector 606 and the shaft circuit board. The electrical connector 606 may extend proximally through a connector opening defined in the chassis mounting flange. U.S. Patent Application Publication No. 2014/0263551, entitled STAPLE CARTRIDGE TISSUE THICKNESS SENSOR SYSTEM, is incorporated herein by reference in its entirety. U.S. Patent Application Publication No. 2014/0263552, entitled STAPLE CARTRIDGE TISSUE THICKNESS SENSOR SYSTEM, is incorporated by reference in its entirety. Further details regarding slip ring assembly 600 may be found in U.S. Patent Application Publication No. 2014/0263541.

The interchangeable shaft assembly 200 can include a proximal portion fixably mounted to the handle assembly 14 and a distal portion that is rotatable about a longitudinal axis. The rotatable distal shaft portion can be rotated relative to the proximal portion about the slip ring assembly 600. The distal connector flange 601 of the slip ring assembly 600 can be positioned within the rotatable distal shaft portion.

Figure 4:
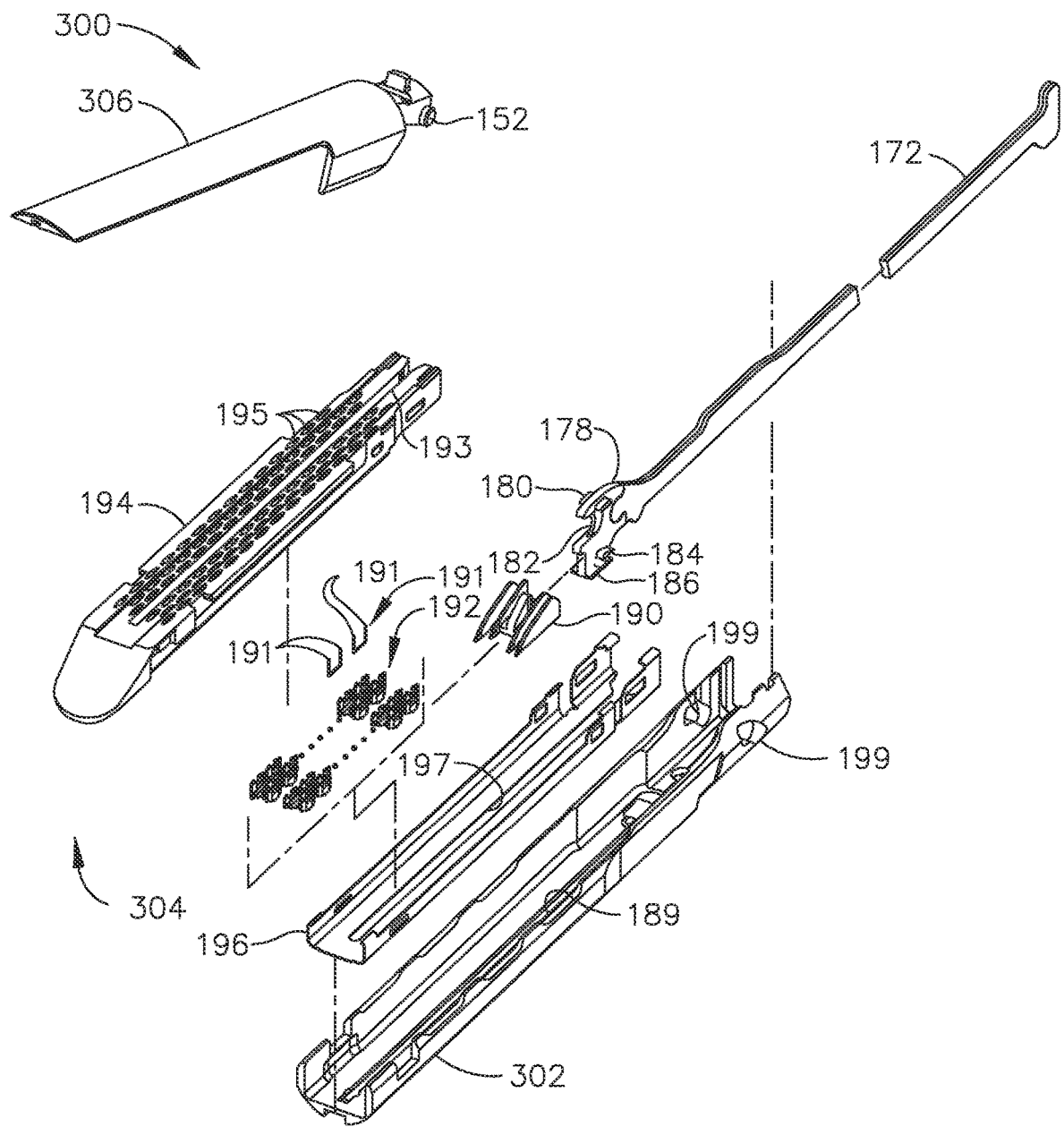
FIG. 4 is an exploded view of an end effector of the surgical instrument of FIG. 1 according to one aspect of this disclosure.

FIG. 4 is an exploded view of one aspect of an end effector 300 of the surgical instrument 10 of FIG. 1 according to one aspect of this disclosure. The end effector 300 may include the anvil 306 and the surgical staple cartridge 304. The anvil 306 may be coupled to an elongated channel 302. Apertures 199 can be defined in the elongated channel 302 to receive pins 152 extending from the anvil 306 to allow the anvil 306 to pivot from an open position to a closed position relative to the elongated channel 302 and surgical staple cartridge 304. A firing bar 172 is configured to longitudinally translate into the end effector 300. The firing bar 172 may be constructed from one solid section, or may include a laminate material comprising a stack of steel plates. The firing bar 172 comprises an I-beam 178 and a cutting edge 182 at a distal end thereof. A distally projecting end of the firing bar 172 can be attached to the I-beam 178 to assist in spacing the anvil 306 from a surgical staple cartridge 304 positioned in the elongated channel 302 when the anvil 306 is in a closed position. The I-beam 178 may include a sharpened cutting edge 182 to sever tissue as the I-beam 178 is advanced distally by the firing bar 172. In operation, the I-beam 178 may, or fire, the surgical staple cartridge 304. The surgical staple cartridge 304 can include a molded cartridge body 194 that holds a plurality of staples 191 resting upon staple drivers 192 within respective upwardly open staple cavities 195. A wedge sled 190 is driven distally by the I-beam 178, sliding upon a cartridge tray 196 of the surgical staple cartridge 304. The wedge sled 190 upwardly cams the staple drivers 192 to force out the staples 191 into deforming contact with the anvil 306 while the cutting edge 182 of the I-beam 178 severs clamped tissue.

The I-beam 178 can include upper pins 180 that engage the anvil 306 during firing. The I-beam 178 may include middle pins 184 and a bottom foot 186 to engage portions of the cartridge body 194, cartridge tray 196, and elongated channel 302. When a surgical staple cartridge 304 is positioned within the elongated channel 302, a slot 193 defined in the cartridge body 194 can be aligned with a longitudinal slot 197 defined in the cartridge tray 196 and a slot 189 defined in the elongated channel 302. In use, the I-beam 178 can slide through the aligned longitudinal slots 193, 197, and 189 wherein, as indicated in FIG. 4, the bottom foot 186 of the I-beam 178 can engage a groove running along the bottom surface of elongated channel 302 along the length of slot 189, the middle pins 184 can engage the top surfaces of cartridge tray 196 along the length of longitudinal slot 197, and the upper pins 180 can engage the anvil 306. The I-beam 178 can space, or limit the relative movement between, the anvil 306 and the surgical staple cartridge 304 as the firing bar 172 is advanced distally to fire the staples from the surgical staple cartridge 304 and/or incise the tissue captured between the anvil 306 and the surgical staple cartridge 304. The firing bar 172 and the I-beam 178 can be retracted proximally allowing the anvil 306 to be opened to release the two stapled and severed tissue portions.

Figure 5A:
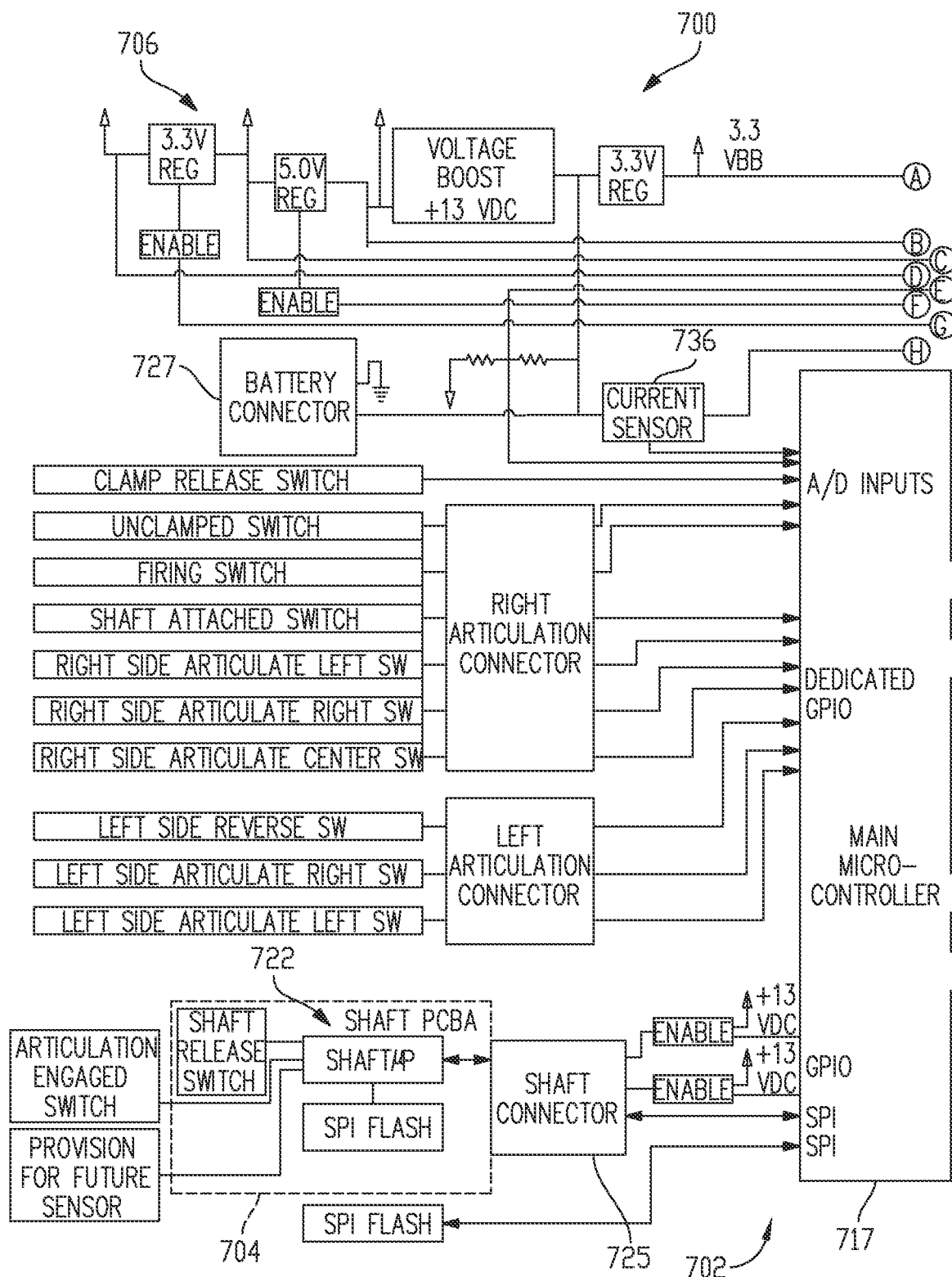
FIGS. 5A-5B is a block diagram of a control circuit of the surgical instrument of FIG. 1 spanning two drawing sheets according to one aspect of this disclosure.
Figure 5B:
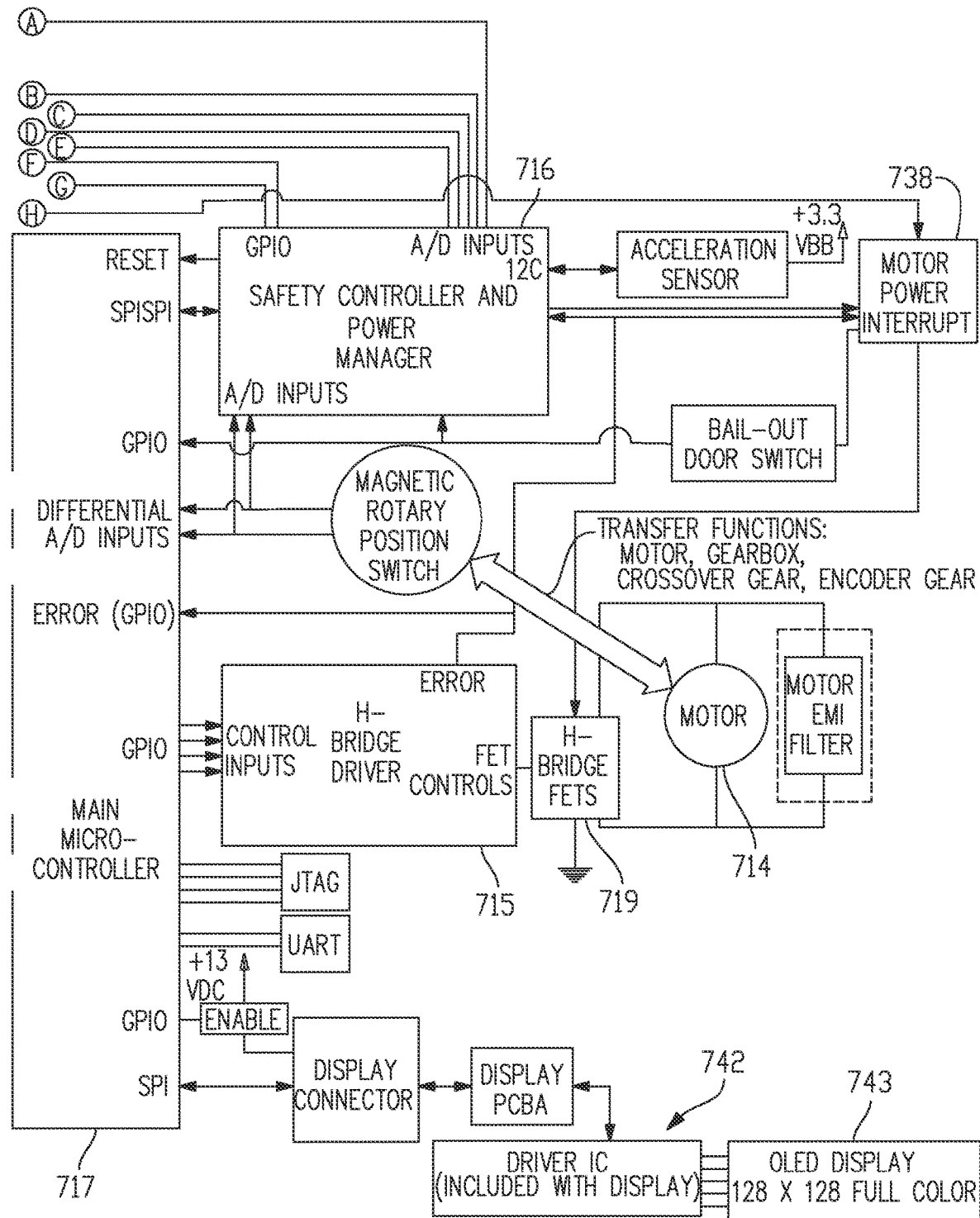

FIGS. 5A-5B is a block diagram of a control circuit 700 of the surgical instrument 10 of FIG. 1 spanning two drawing sheets according to one aspect of this disclosure. Referring primarily to FIGS. 5A-5B, a handle assembly 702 may include a motor 714 which can be controlled by a motor driver 715 and can be employed by the firing system of the surgical instrument 10. In various forms, the motor 714 may be a DC brushed driving motor having a maximum rotational speed of approximately 25,000 RPM. In other arrangements, the motor 714 may include a brushless motor, a cordless motor, a synchronous motor, a stepper motor, or any other suitable electric motor. The motor driver 715 may comprise an H-Bridge driver comprising field-effect transistors (FETs) 719, for example. The motor 714 can be powered by the power assembly 706 releasably mounted to the handle assembly 200 for supplying control power to the surgical instrument 10. The power assembly 706 may comprise a battery which may include a number of battery cells connected in series that can be used as the power source to power the surgical instrument 10. In certain circumstances, the battery cells of the power assembly 706 may be replaceable and/or rechargeable. In at least one example, the battery cells can be Lithium-Ion batteries which can be separably couplable to the power assembly 706.

The shaft assembly 704 may include a shaft assembly controller 722 which can communicate with a safety controller and power management controller 716 through an interface while the shaft assembly 704 and the power assembly 706 are coupled to the handle assembly 702. For example, the interface may comprise a first interface portion 725 which may include one or more electric connectors for coupling engagement with corresponding shaft assembly electric connectors and a second interface portion 727 which may include one or more electric connectors for coupling engagement with corresponding power assembly electric connectors to permit electrical communication between the shaft assembly controller 722 and the power management controller 716 while the shaft assembly 704 and the power assembly 706 are coupled to the handle assembly 702. One or more communication signals can be transmitted through the interface to communicate one or more of the power requirements of the attached interchangeable shaft assembly 704 to the power management controller 716. In response, the power management controller may modulate the power output of the battery of the power assembly 706, as described below in greater detail, in accordance with the power requirements of the attached shaft assembly 704. The connectors may comprise switches which can be activated after mechanical coupling engagement of the handle assembly 702 to the shaft assembly 704 and/or to the power assembly 706 to allow electrical communication between the shaft assembly controller 722 and the power management controller 716.

The interface can facilitate transmission of the one or more communication signals between the power management controller 716 and the shaft assembly controller 722 by routing such communication signals through a main controller 717 residing in the handle assembly 702, for example. In other circumstances, the interface can facilitate a direct line of communication between the power management controller 716 and the shaft assembly controller 722 through the handle assembly 702 while the shaft assembly 704 and the power assembly 706 are coupled to the handle assembly 702.

The main controller 717 may be any single core or multicore processor such as those known under the trade name ARM Cortex by Texas Instruments. In one aspect, the main controller 717 may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

The safety controller may be a safety controller platform comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The power assembly 706 may include a power management circuit which may comprise the power management controller 716, a power modulator 738, and a current sense circuit 736. The power management circuit can be configured to modulate power output of the battery based on the power requirements of the shaft assembly 704 while the shaft assembly 704 and the power assembly 706 are coupled to the handle assembly 702. The power management controller 716 can be programmed to control the power modulator 738 of the power output of the power assembly 706 and the current sense circuit 736 can be employed to monitor power output of the power assembly 706 to provide feedback to the power management controller 716 about the power output of the battery so that the power management controller 716 may adjust the power output of the power assembly 706 to maintain a desired output. The power management controller 716 and/or the shaft assembly controller 722 each may comprise one or more processors and/or memory units which may store a number of software modules.

The surgical instrument 10 (FIGS. 1-4) may comprise an output device 742 which may include devices for providing a sensory feedback to a user. Such devices may comprise, for example, visual feedback devices (e.g., an LCD display screen, LED indicators), audio feedback devices (e.g., a speaker, a buzzer) or tactile feedback devices (e.g., haptic actuators). In certain circumstances, the output device 742 may comprise a display 743 which may be included in the handle assembly 702. The shaft assembly controller 722 and/or the power management controller 716 can provide feedback to a user of the surgical instrument 10 through the output device 742. The interface can be configured to connect the shaft assembly controller 722 and/or the power management controller 716 to the output device 742. The output device 742 can instead be integrated with the power assembly 706. In such circumstances, communication between the output device 742 and the shaft assembly controller 722 may be accomplished through the interface while the shaft assembly 704 is coupled to the handle assembly 702.

The control circuit 700 comprises circuit segments configured to control operations of the powered surgical instrument 10. A safety controller segment (Segment 1) comprises a safety controller and the main controller 717 segment (Segment 2). The safety controller and/or the main controller 717 are configured to interact with one or more additional circuit segments such as an acceleration segment, a display segment, a shaft segment, an encoder segment, a motor segment, and a power segment. Each of the circuit segments may be coupled to the safety controller and/or the main controller 717. The main controller 717 is also coupled to a flash memory. The main controller 717 also comprises a serial communication interface. The main controller 717 comprises a plurality of inputs coupled to, for example, one or more circuit segments, a battery, and/or a plurality of switches. The segmented circuit may be implemented by any suitable circuit, such as, for example, a printed circuit board assembly (PCBA) within the powered surgical instrument 10. It should be understood that the term processor as used herein includes any microprocessor, processors, controller, controllers, or other basic computing device that incorporates the functions of a computer's central processing unit (CPU) on an integrated circuit or at most a few integrated circuits. The main controller 717 is a multipurpose, programmable device that accepts digital data as input, processes it according to instructions stored in its memory, and provides results as output. It is an example of sequential digital logic, as it has internal memory. The control circuit 700 can be configured to implement one or more of the processes described herein.

The acceleration segment (Segment 3) comprises an accelerometer. The accelerometer is configured to detect movement or acceleration of the powered surgical instrument 10. Input from the accelerometer may be used to transition to and from a sleep mode, identify an orientation of the powered surgical instrument, and/or identify when the surgical instrument has been dropped. In some examples, the acceleration segment is coupled to the safety controller and/or the main controller 717.

The display segment (Segment 4) comprises a display connector coupled to the main controller 717. The display connector couples the main controller 717 to a display through one or more integrated circuit drivers of the display. The integrated circuit drivers of the display may be integrated with the display and/or may be located separately from the display. The display may comprise any suitable display, such as, for example, an organic light-emitting diode (OLED) display, a liquid-crystal display (LCD), and/or any other suitable display. In some examples, the display segment is coupled to the safety controller.

The shaft segment (Segment 5) comprises controls for an interchangeable shaft assembly 200 (FIGS. 1 and 3) coupled to the surgical instrument 10 (FIGS. 1-4) and/or one or more controls for an end effector 300 coupled to the interchangeable shaft assembly 200. The shaft segment comprises a shaft connector configured to couple the main controller 717 to a shaft PCBA. The shaft PCBA comprises a low-power microcontroller with a ferroelectric random access memory (FRAM), an articulation switch, a shaft release Hall effect switch, and a shaft PCBA EEPROM. The shaft PCBA EEPROM comprises one or more parameters, routines, and/or programs specific to the interchangeable shaft assembly 200 and/or the shaft PCBA. The shaft PCBA may be coupled to the interchangeable shaft assembly 200 and/or integral with the surgical instrument 10. In some examples, the shaft segment comprises a second shaft EEPROM. The second shaft EEPROM comprises a plurality of algorithms, routines, parameters, and/or other data corresponding to one or more shaft assemblies 200 and/or end effectors 300 that may be interfaced with the powered surgical instrument 10.

The position encoder segment (Segment 6) comprises one or more magnetic angle rotary position encoders. The one or more magnetic angle rotary position encoders are configured to identify the rotational position of the motor 714, an interchangeable shaft assembly 200 (FIGS. 1 and 3), and/or an end effector 300 of the surgical instrument 10 (FIGS. 1-4). In some examples, the magnetic angle rotary position encoders may be coupled to the safety controller and/or the main controller 717.

The motor circuit segment (Segment 7) comprises a motor 714 configured to control movements of the powered surgical instrument 10 (FIGS. 1-4). The motor 714 is coupled to the main microcontroller processor 717 by an H-bridge driver comprising one or more H-bridge field-effect transistors (FETs) and a motor controller. The H-bridge driver is also coupled to the safety controller. A motor current sensor is coupled in series with the motor to measure the current draw of the motor. The motor current sensor is in signal communication with the main controller 717 and/or the safety controller. In some examples, the motor 714 is coupled to a motor electromagnetic interference (EMI) filter.

The motor controller controls a first motor flag and a second motor flag to indicate the status and position of the motor 714 to the main controller 717. The main controller 717 provides a pulse-width modulation (PWM) high signal, a PWM low signal, a direction signal, a synchronize signal, and a motor reset signal to the motor controller through a buffer. The power segment is configured to provide a segment voltage to each of the circuit segments.

The power segment (Segment 8) comprises a battery coupled to the safety controller, the main controller 717, and additional circuit segments. The battery is coupled to the segmented circuit by a battery connector and a current sensor. The current sensor is configured to measure the total current draw of the segmented circuit. In some examples, one or more voltage converters are configured to provide predetermined voltage values to one or more circuit segments. For example, in some examples, the segmented circuit may comprise 3.3V voltage converters and/or 5V voltage converters. A boost converter is configured to provide a boost voltage up to a predetermined amount, such as, for example, up to 13V. The boost converter is configured to provide additional voltage and/or current during power intensive operations and prevent brownout or low-power conditions.

A plurality of switches are coupled to the safety controller and/or the main controller 717. The switches may be configured to control operations of the surgical instrument 10 (FIGS. 1-4), of the segmented circuit, and/or indicate a status of the surgical instrument 10. A bail-out door switch and Hall effect switch for bailout are configured to indicate the status of a bail-out door. A plurality of articulation switches, such as, for example, a left side articulation left switch, a left side articulation right switch, a left side articulation center switch, a right side articulation left switch, a right side articulation right switch, and a right side articulation center switch are configured to control articulation of an interchangeable shaft assembly 200 (FIGS. 1 and 3) and/or the end effector 300 (FIGS. 1 and 4). A left side reverse switch and a right side reverse switch are coupled to the main controller 717. The left side switches comprising the left side articulation left switch, the left side articulation right switch, the left side articulation center switch, and the left side reverse switch are coupled to the main controller 717 by a left flex connector. The right side switches comprising the right side articulation left switch, the right side articulation right switch, the right side articulation center switch, and the right side reverse switch are coupled to the main controller 717 by a right flex connector. A firing switch, a clamp release switch, and a shaft engaged switch are coupled to the main controller 717.

Any suitable mechanical, electromechanical, or solid state switches may be employed to implement the plurality of switches, in any combination. For example, the switches may be limit switches operated by the motion of components associated with the surgical instrument 10 (FIGS. 1-4) or the presence of an object. Such switches may be employed to control various functions associated with the surgical instrument 10. A limit switch is an electromechanical device that consists of an actuator mechanically linked to a set of contacts. When an object comes into contact with the actuator, the device operates the contacts to make or break an electrical connection. Limit switches are used in a variety of applications and environments because of their ruggedness, ease of installation, and reliability of operation. They can determine the presence or absence, passing, positioning, and end of travel of an object. In other implementations, the switches may be solid state switches that operate under the influence of a magnetic field such as Hall-effect devices, magneto-resistive (MR) devices, giant magneto-resistive (GMR) devices, magnetometers, among others. In other implementations, the switches may be solid state switches that operate under the influence of light, such as optical sensors, infrared sensors, ultraviolet sensors, among others. Still, the switches may be solid state devices such as transistors (e.g., FET, Junction-FET, metal-oxide semiconductor-FET (MOSFET), bipolar, and the like). Other switches may include wireless switches, ultrasonic switches, accelerometers, inertial sensors, among others.

Figure 6:
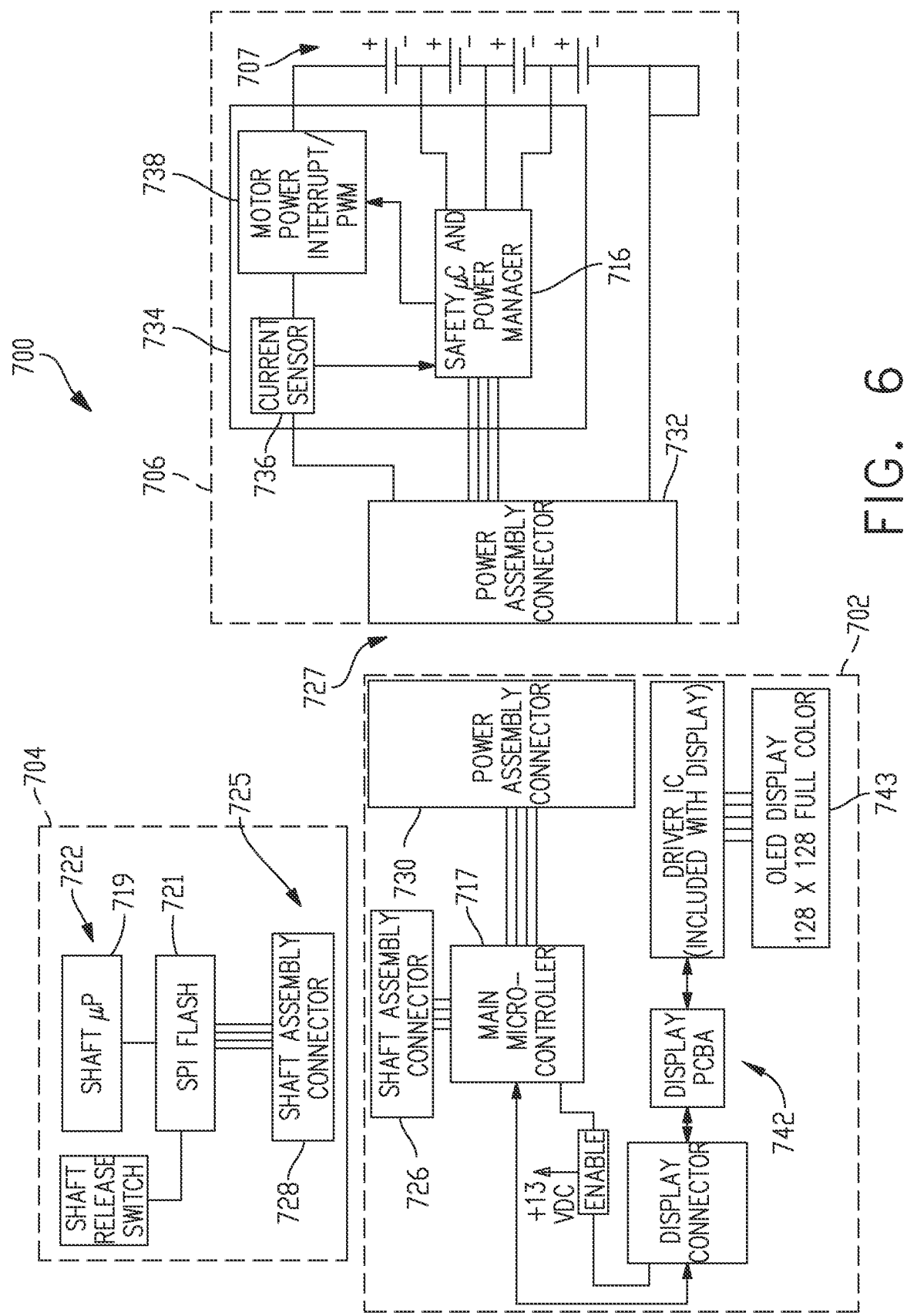
FIG. 6 is a block diagram of the control circuit of the surgical instrument of FIG. 1 illustrating interfaces between the handle assembly, the power assembly, and the handle assembly and the interchangeable shaft assembly according to one aspect of this disclosure.

FIG. 6 is another block diagram of the control circuit 700 of the surgical instrument of FIG. 1 illustrating interfaces between the handle assembly 702 and the power assembly 706 and between the handle assembly 702 and the interchangeable shaft assembly 704 according to one aspect of this disclosure. The handle assembly 702 may comprise a main controller 717, a shaft assembly connector 726 and a power assembly connector 730. The power assembly 706 may include a power assembly connector 732, a power management circuit 734 that may comprise the power management controller 716, a power modulator 738, and a current sense circuit 736. The shaft assembly connectors 730, 732 form an interface 727. The power management circuit 734 can be configured to modulate power output of the battery 707 based on the power requirements of the interchangeable shaft assembly 704 while the interchangeable shaft assembly 704 and the power assembly 706 are coupled to the handle assembly 702. The power management controller 716 can be programmed to control the power modulator 738 of the power output of the power assembly 706 and the current sense circuit 736 can be employed to monitor power output of the power assembly 706 to provide feedback to the power management controller 716 about the power output of the battery 707 so that the power management controller 716 may adjust the power output of the power assembly 706 to maintain a desired output. The shaft assembly 704 comprises a shaft processor 719 coupled to a non-volatile memory 721 and shaft assembly connector 728 to electrically couple the shaft assembly 704 to the handle assembly 702. The shaft assembly connectors 726, 728 form interface 725. The main controller 717, the shaft processor 719, and/or the power management controller 716 can be configured to implement one or more of the processes described herein.

The surgical instrument 10 (FIGS. 1-4) may comprise an output device 742 to a sensory feedback to a user. Such devices may comprise visual feedback devices (e.g., an LCD display screen, LED indicators), audio feedback devices (e.g., a speaker, a buzzer), or tactile feedback devices (e.g., haptic actuators). In certain circumstances, the output device 742 may comprise a display 743 that may be included in the handle assembly 702. The shaft assembly controller 722 and/or the power management controller 716 can provide feedback to a user of the surgical instrument 10 through the output device 742. The interface 727 can be configured to connect the shaft assembly controller 722 and/or the power management controller 716 to the output device 742. The output device 742 can be integrated with the power assembly 706. Communication between the output device 742 and the shaft assembly controller 722 may be accomplished through the interface 725 while the interchangeable shaft assembly 704 is coupled to the handle assembly 702. Having described a control circuit 700 (FIGS. 5A-5B and 6) for controlling the operation of the surgical instrument 10 (FIGS. 1-4), the disclosure now turns to various configurations of the surgical instrument 10 (FIGS. 1-4) and control circuit 700.

Figure 7:
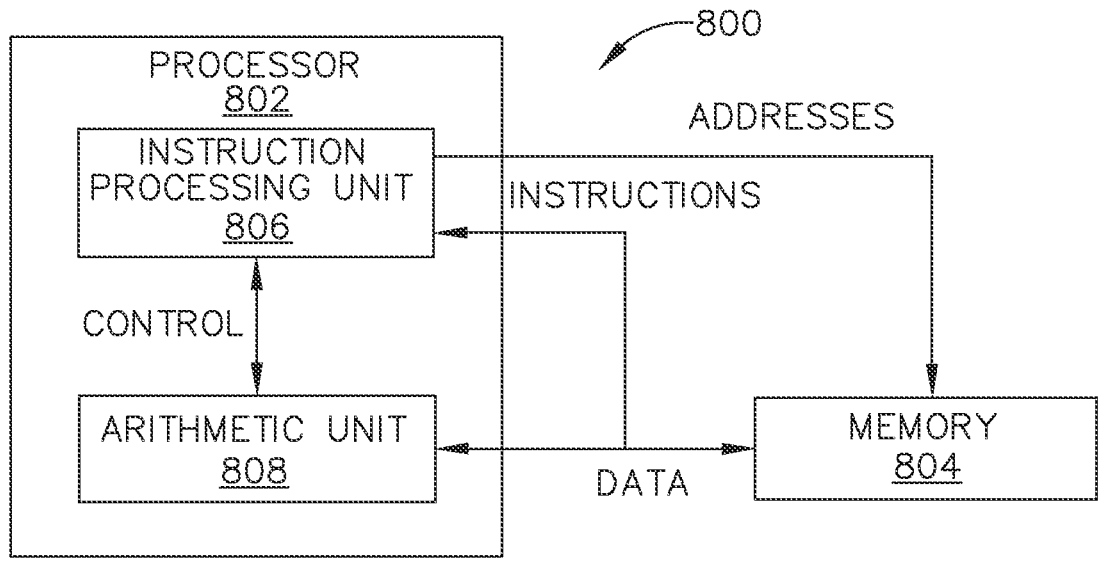
FIG. 7 illustrates a control circuit configured to control aspects of the surgical instrument of FIG. 1 according to one aspect of this disclosure.

FIG. 7 illustrates a control circuit 800 configured to control aspects of the surgical instrument 10 (FIGS. 1-4) according to one aspect of this disclosure. The control circuit 800 can be configured to implement various processes described herein. The control circuit 800 may comprise a controller comprising one or more processors 802 (e.g., microprocessor, microcontroller) coupled to at least one memory circuit 804. The memory circuit 804 stores machine executable instructions that when executed by the processor 802, cause the processor 802 to execute machine instructions to implement various processes described herein. The processor 802 may be any one of a number of single or multi-core processors known in the art. The memory circuit 804 may comprise volatile and non-volatile storage media. The processor 802 may include an instruction processing unit 806 and an arithmetic unit 808. The instruction processing unit may be configured to receive instructions from the memory circuit 804.

Figure 8:
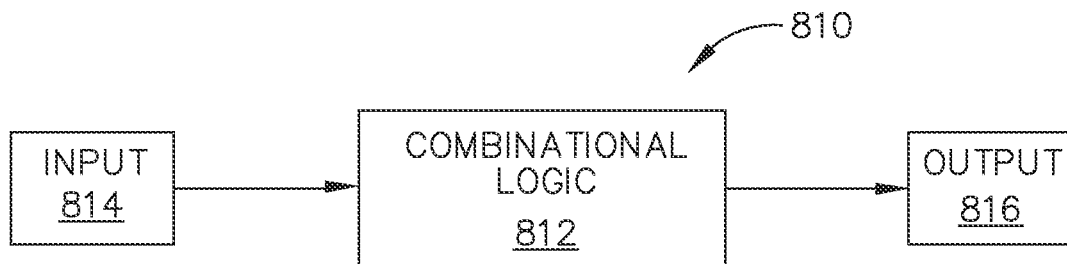
FIG. 8 illustrates a combinational logic circuit configured to control aspects of the surgical instrument of FIG. 1 according to one aspect of this disclosure.

FIG. 8 illustrates a combinational logic circuit 810 configured to control aspects of the surgical instrument 10 (FIGS. 1-4) according to one aspect of this disclosure. The combinational logic circuit 810 can be configured to implement various processes described herein. The circuit 810 may comprise a finite state machine comprising a combinational logic circuit 812 configured to receive data associated with the surgical instrument 10 at an input 814, process the data by the combinational logic 812, and provide an output 816.

Figure 9:
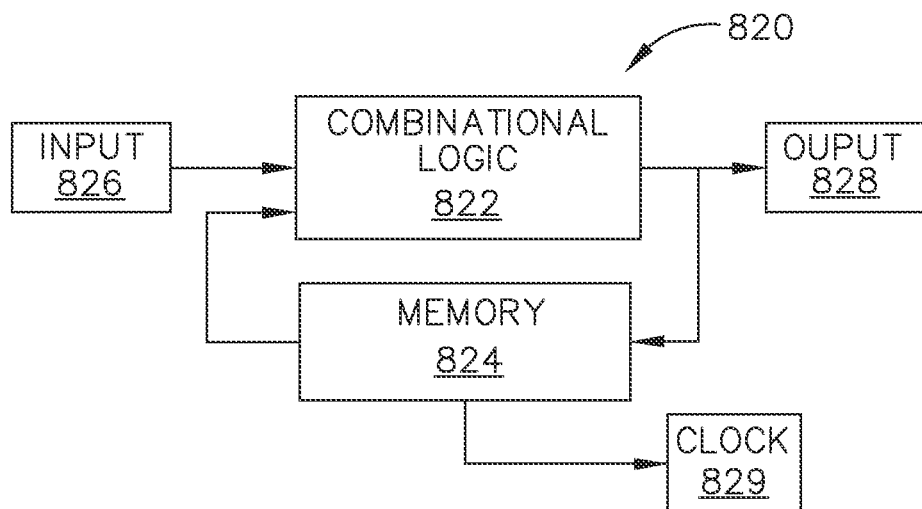
FIG. 9 illustrates a sequential logic circuit configured to control aspects of the surgical instrument of FIG. 1 according to one aspect of this disclosure.

FIG. 9 illustrates a sequential logic circuit 820 configured to control aspects of the surgical instrument 10 (FIGS. 1-4) according to one aspect of this disclosure. The sequential logic circuit 820 or the combinational logic circuit 822 can be configured to implement various processes described herein. The circuit 820 may comprise a finite state machine. The sequential logic circuit 820 may comprise a combinational logic circuit 822, at least one memory circuit 824, and a clock 829, for example. The at least one memory circuit 820 can store a current state of the finite state machine. In certain instances, the sequential logic circuit 820 may be synchronous or asynchronous. The combinational logic circuit 822 is configured to receive data associated with the surgical instrument 10 an input 826, process the data by the combinational logic circuit 822, and provide an output 828. In other aspects, the circuit may comprise a combination of the processor 802 and the finite state machine to implement various processes herein. In other aspects, the finite state machine may comprise a combination of the combinational logic circuit 810 and the sequential logic circuit 820.

Aspects may be implemented as an article of manufacture. The article of manufacture may include a computer readable storage medium arranged to store logic, instructions, and/or data for performing various operations of one or more aspects. For example, the article of manufacture may comprise a magnetic disk, optical disk, flash memory, or firmware containing computer program instructions suitable for execution by a general purpose processor or application specific processor.

Figure 10:
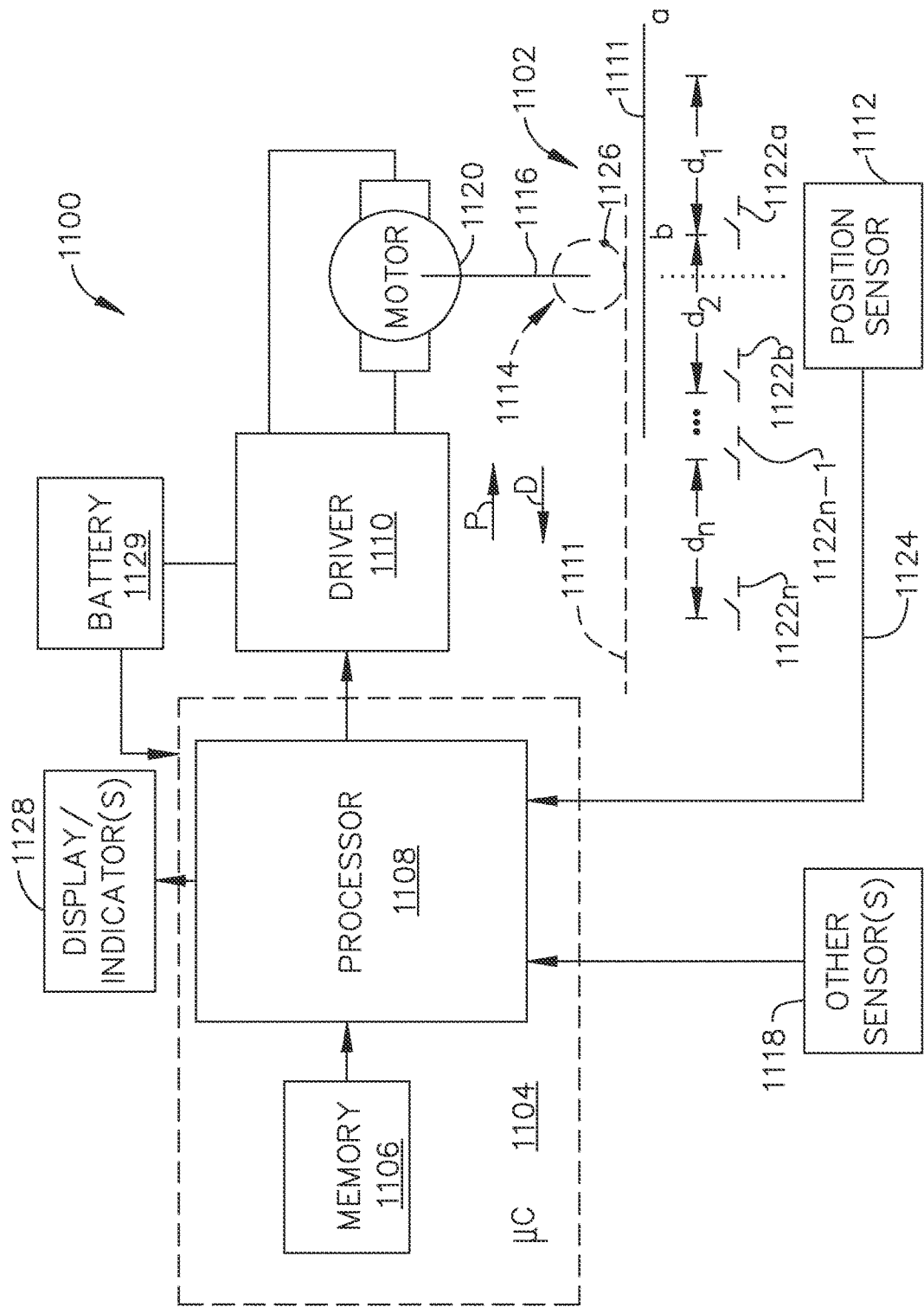
FIG. 10 is a diagram of an absolute positioning system of the surgical instrument of FIG. 1 where the absolute positioning system comprises a controlled motor drive circuit arrangement comprising a sensor arrangement according to one aspect of this disclosure.

FIG. 10 is a diagram of an absolute positioning system 1100 of the surgical instrument 10 (FIGS. 1-4) where the absolute positioning system 1100 comprises a controlled motor drive circuit arrangement comprising a sensor arrangement 1102 according to one aspect of this disclosure. The sensor arrangement 1102 for an absolute positioning system 1100 provides a unique position signal corresponding to the location of a displacement member 1111. Turning briefly to FIGS. 2-4, in one aspect the displacement member 1111 represents the longitudinally movable drive member 120 (FIG. 2) comprising a rack of drive teeth 122 for meshing engagement with a corresponding drive gear 86 of the gear reducer assembly 84. In other aspects, the displacement member 1111 represents the firing member 220 (FIG. 3), which could be adapted and configured to include a rack of drive teeth. In yet another aspect, the displacement member 1111 represents the firing bar 172 (FIG. 4) or the I-beam 178 (FIG. 4), each of which can be adapted and configured to include a rack of drive teeth. Accordingly, as used herein, the term displacement member is used generically to refer to any movable member of the surgical instrument 10 such as the drive member 120, the firing member 220, the firing bar 172, the I-beam 178, or any element that can be displaced. In one aspect, the longitudinally movable drive member 120 is coupled to the firing member 220, the firing bar 172, and the I-beam 178. Accordingly, the absolute positioning system 1100 can, in effect, track the linear displacement of the I-beam 178 by tracking the linear displacement of the longitudinally movable drive member 120. In various other aspects, the displacement member 1111 may be coupled to any sensor suitable for measuring linear displacement. Thus, the longitudinally movable drive member 120, the firing member 220, the firing bar 172, or the I-beam 178, or combinations, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable linearly arranged Hall effect sensors, an optical sensing system comprising a movable light source and a series of linearly arranged photo diodes or photo detectors, or an optical sensing system comprising a fixed light source and a series of movable linearly arranged photo diodes or photo detectors, or any combination thereof.

An electric motor 1120 can include a rotatable shaft 1116 that operably interfaces with a gear assembly 1114 that is mounted in meshing engagement with a set, or rack, of drive teeth on the displacement member 1111. A sensor element 1126 may be operably coupled to a gear assembly 1114 such that a single revolution of the sensor element 1126 corresponds to some linear longitudinal translation of the displacement member 1111. An arrangement of gearing and sensors 1118 can be connected to the linear actuator via a rack and pinion arrangement or a rotary actuator via a spur gear or other connection. A power source 1129 supplies power to the absolute positioning system 1100 and an output indicator 1128 may display the output of the absolute positioning system 1100. In FIG. 2, the displacement member 1111 represents the longitudinally movable drive member 120 comprising a rack of drive teeth 122 formed thereon for meshing engagement with a corresponding drive gear 86 of the gear reducer assembly 84. The displacement member 1111 represents the longitudinally movable firing member 220, firing bar 172, I-beam 178, or combinations thereof.

A single revolution of the sensor element 1126 associated with the position sensor 1112 is equivalent to a longitudinal linear displacement d1 of the of the displacement member 1111, where d1 is the longitudinal linear distance that the displacement member 1111 moves from point "a" to point "b" after a single revolution of the sensor element 1126 coupled to the displacement member 1111. The sensor arrangement 1102 may be connected via a gear reduction that results in the position sensor 1112 completing one or more revolutions for the full stroke of the displacement member 1111. The position sensor 1112 may complete multiple revolutions for the full stroke of the displacement member 1111.

A series of switches 1122a-1122n, where n is an integer greater than one, may be employed alone or in combination with gear reduction to provide a unique position signal for more than one revolution of the position sensor 1112. The state of the switches 1122a-1122n are fed back to a controller 1104 that applies logic to determine a unique position signal corresponding to the longitudinal linear displacement d1+d2+ . . . dn of the displacement member 1111. The output 1124 of the position sensor 1112 is provided to the controller 1104. The position sensor 1112 of the sensor arrangement 1102 may comprise a magnetic sensor, an analog rotary sensor like a potentiometer, an array of analog Hall-effect elements, which output a unique combination of position signals or values.

The absolute positioning system 1100 provides an absolute position of the displacement member 1111 upon power up of the instrument without retracting or advancing the displacement member 1111 to a reset (zero or home) position as may be required with conventional rotary encoders that merely count the number of steps forwards or backwards that the motor 1120 has taken to infer the position of a device actuator, drive bar, knife, and the like.

The controller 1104 may be programmed to perform various functions such as precise control over the speed and position of the knife and articulation systems. In one aspect, the controller 1104 includes a processor 1108 and a memory 1106. The electric motor 1120 may be a brushed DC motor with a gearbox and mechanical links to an articulation or knife system. In one aspect, a motor driver 1110 may be an A3941 available from Allegro Microsystems, Inc. Other motor drivers may be readily substituted for use in the absolute positioning system 1100. A more detailed description of the absolute positioning system 1100 is described in U.S. patent application Ser. No. 15/130,590, entitled SYSTEMS AND METHODS FOR CONTROLLING A SURGICAL STAPLING AND CUTTING INSTRUMENT, filed on Apr. 15, 2016, the entire disclosure of which is herein incorporated by reference.

The controller 1104 may be programmed to provide precise control over the speed and position of the displacement member 1111 and articulation systems. The controller 1104 may be configured to compute a response in the software of the controller 1104. The computed response is compared to a measured response of the actual system to obtain an "observed" response, which is used for actual feedback decisions. The observed response is a favorable, tuned, value that balances the smooth, continuous nature of the simulated response with the measured response, which can detect outside influences on the system.

The absolute positioning system 1100 may comprise and/or be programmed to implement a feedback controller, such as a PID, state feedback, and adaptive controller. A power source 1129 converts the signal from the feedback controller into a physical input to the system, in this case voltage. Other examples include pulse width modulation (PWM) of the voltage, current, and force. Other sensor(s) 1118 may be provided to measure physical parameters of the physical system in addition to position measured by the position sensor 1112. In a digital signal processing system, absolute positioning system 1100 is coupled to a digital data acquisition system where the output of the absolute positioning system 1100 will have finite resolution and sampling frequency. The absolute positioning system 1100 may comprise a compare and combine circuit to combine a computed response with a measured response using algorithms such as weighted average and theoretical control loop that drives the computed response towards the measured response. The computed response of the physical system takes into account properties like mass, inertial, viscous friction, inductance resistance, etc., to predict what the states and outputs of the physical system will be by knowing the input. The controller 1104 may be a control circuit 700 (FIGS. 5A-5B).

The motor driver 1110 may be an A3941 available from Allegro Microsystems, Inc. The A3941 driver 1110 is a full-bridge controller for use with external N-channel power metal oxide semiconductor field effect transistors (MOSFETs) specifically designed for inductive loads, such as brush DC motors. The driver 1110 comprises a unique charge pump regulator provides full (>10 V) gate drive for battery voltages down to 7 V and allows the A3941 to operate with a reduced gate drive, down to 5.5 V. A bootstrap capacitor may be employed to provide the above-battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the lowside FETs. The power FETs are protected from shoot-through by resistor adjustable dead time. Integrated diagnostics provide indication of undervoltage, overtemperature, and power bridge faults, and can be configured to protect the power MOSFETs under most short circuit conditions. Other motor drivers may be readily substituted for use in the absolute positioning system 1100.

Figure 11:
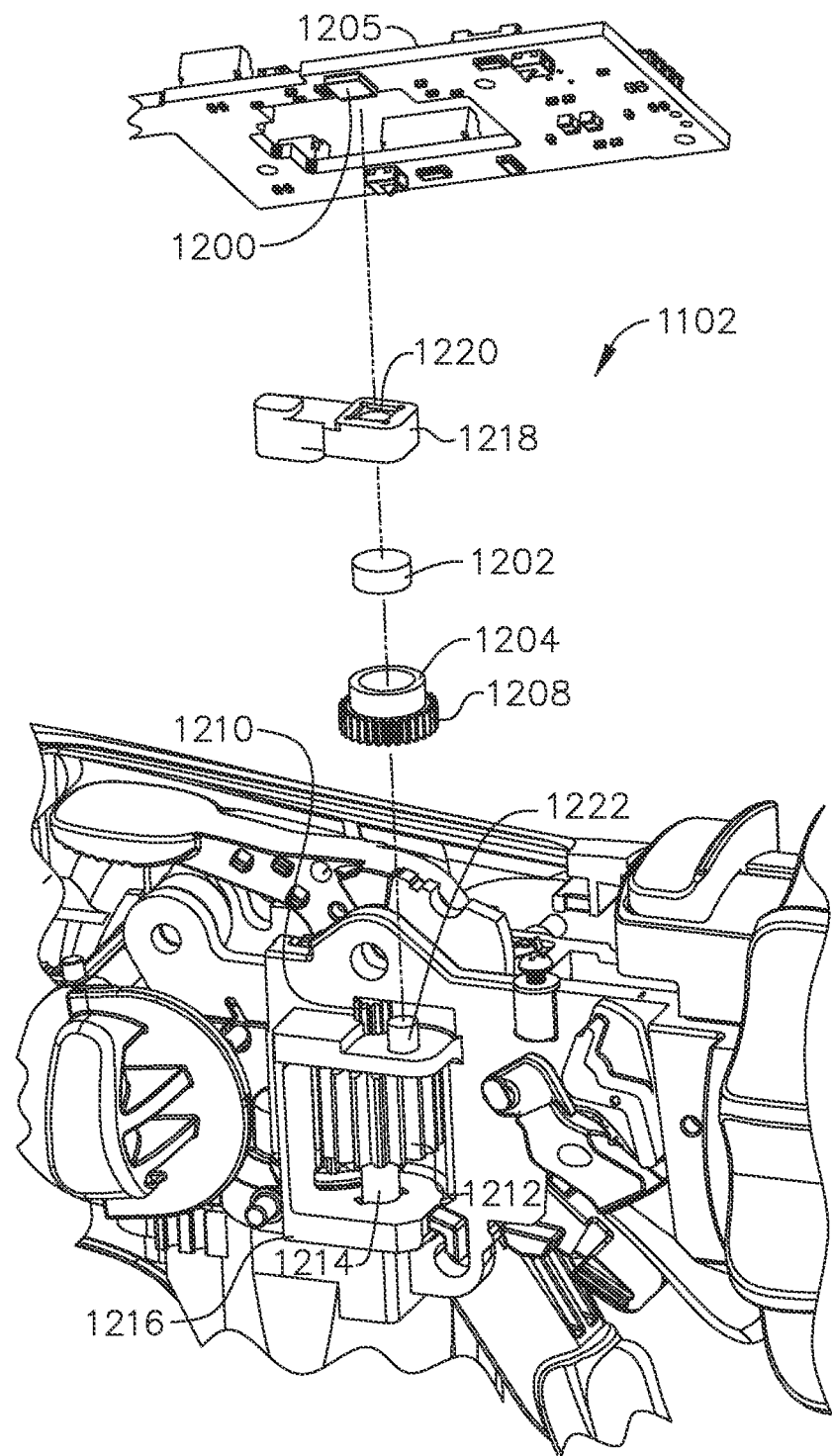
FIG. 11 is an exploded perspective view of the sensor arrangement for an absolute positioning system showing a control circuit board assembly and the relative alignment of the elements of the sensor arrangement according to one aspect of this disclosure.
Figure 12:
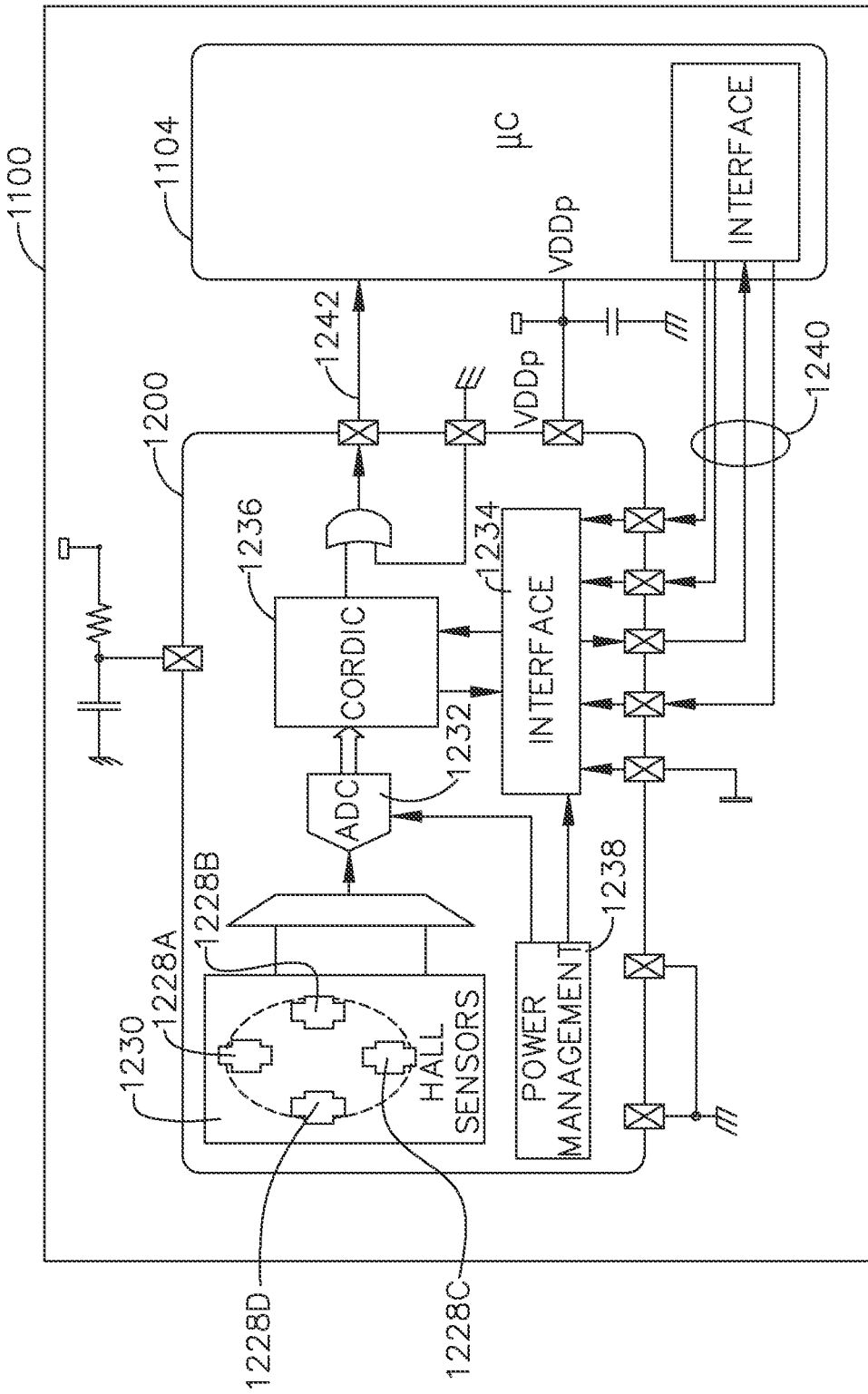
FIG. 12 is a diagram of a position sensor comprising a magnetic rotary absolute positioning system according to one aspect of this disclosure.

Having described a general architecture for implementing aspects of an absolute positioning system 1100 for a sensor arrangement 1102, the disclosure now turns to FIGS. 11 and 12 for a description of one aspect of a sensor arrangement 1102 for the absolute positioning system 1100. FIG. 11 is an exploded perspective view of the sensor arrangement 1102 for the absolute positioning system 1100 showing a circuit 1205 and the relative alignment of the elements of the sensor arrangement 1102, according to one aspect. The sensor arrangement 1102 for an absolute positioning system 1100 comprises a position sensor 1200, a magnet 1202 sensor element, a magnet holder 1204 that turns once every full stroke of the displacement member 1111, and a gear assembly 1206 to provide a gear reduction. With reference briefly to FIG. 2, the displacement member 1111 may represent the longitudinally movable drive member 120 comprising a rack of drive teeth 122 for meshing engagement with a corresponding drive gear 86 of the gear reducer assembly 84. Returning to FIG. 11, a structural element such as bracket 1216 is provided to support the gear assembly 1206, the magnet holder 1204, and the magnet 1202. The position sensor 1200 comprises magnetic sensing elements such as Hall elements and is placed in proximity to the magnet 1202. As the magnet 1202 rotates, the magnetic sensing elements of the position sensor 1200 determine the absolute angular position of the magnet 1202 over one revolution.

The sensor arrangement 1102 may comprises any number of magnetic sensing elements, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber optic, magnetooptic, and microelectromechanical systems-based magnetic sensors, among others.

A gear assembly comprises a first gear 1208 and a second gear 1210 in meshing engagement to provide a 3:1 gear ratio connection. A third gear 1212 rotates about a shaft 1214. The third gear 1212 is in meshing engagement with the displacement member 1111 (or 120 as shown in FIG. 2) and rotates in a first direction as the displacement member 1111 advances in a distal direction D and rotates in a second direction as the displacement member 1111 retracts in a proximal direction P. The second gear 1210 also rotates about the shaft 1214 and, therefore, rotation of the second gear 1210 about the shaft 1214 corresponds to the longitudinal translation of the displacement member 1111. Thus, one full stroke of the displacement member 1111 in either the distal or proximal directions D, P corresponds to three rotations of the second gear 1210 and a single rotation of the first gear 1208. Since the magnet holder 1204 is coupled to the first gear 1208, the magnet holder 1204 makes one full rotation with each full stroke of the displacement member 1111.

The position sensor 1200 is supported by a position sensor holder 1218 defining an aperture 1220 suitable to contain the position sensor 1200 in precise alignment with a magnet 1202 rotating below within the magnet holder 1204. The fixture is coupled to the bracket 1216 and to the circuit 1205 and remains stationary while the magnet 1202 rotates with the magnet holder 1204. A hub 1222 is provided to mate with the first gear 1208 and the magnet holder 1204. The second gear 1210 and third gear 1212 coupled to shaft 1214 also are shown.

Figure 15:
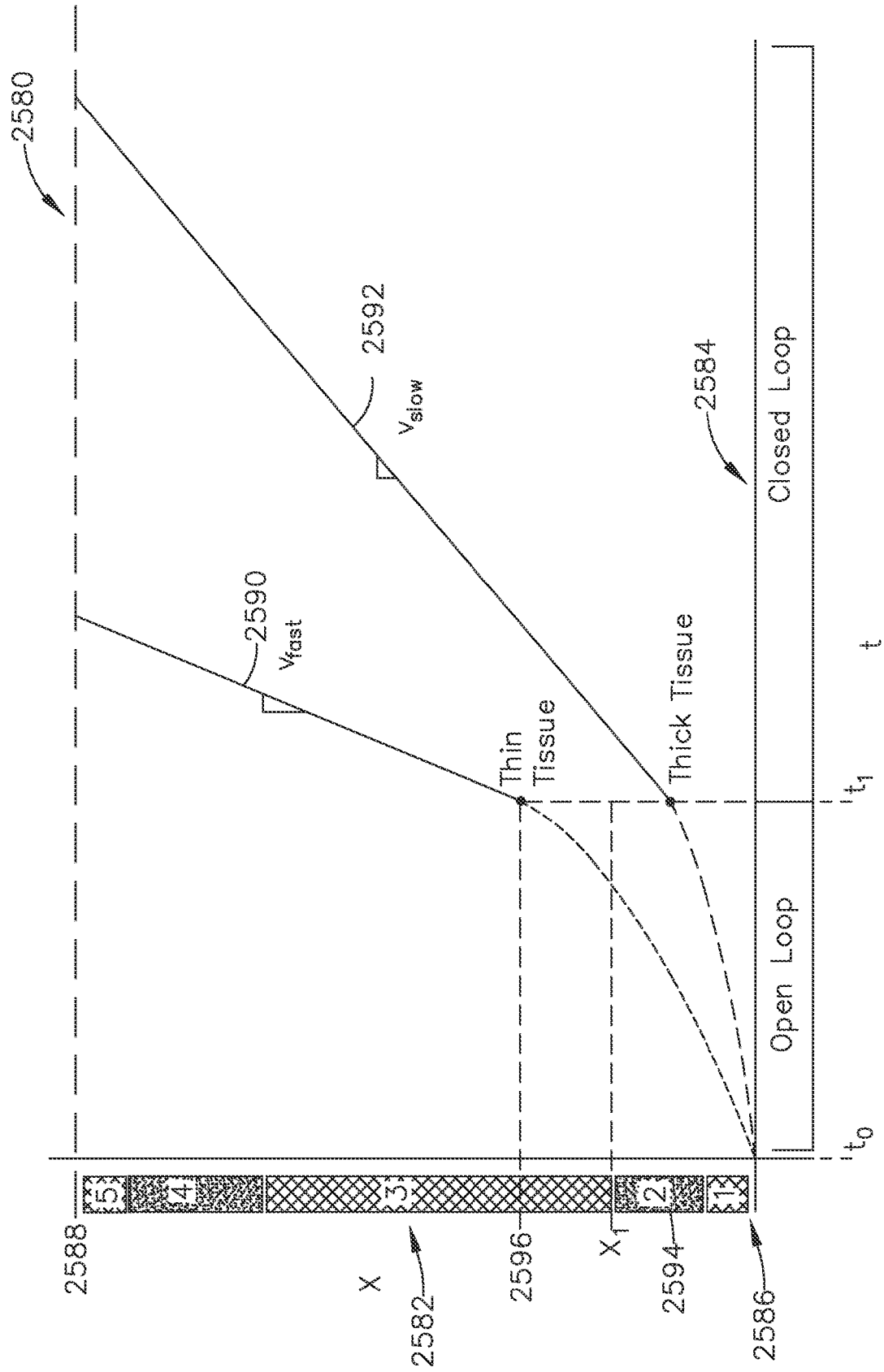
FIG. 15 illustrates a diagram plotting two example displacement member strokes executed according to one aspect of this disclosure.

FIG. 12 is a diagram of a position sensor 1200 for an absolute positioning system 1100 comprising a magnetic rotary absolute positioning system according to one aspect of this disclosure. The position sensor 1200 may be implemented as an AS5055EQFT single-chip magnetic rotary position sensor available from Austria Microsystems, AG. The position sensor 1200 is interfaced with the controller 1104 to provide an absolute positioning system 1100. The position sensor 1200 is a low-voltage and low-power component and includes four Hall-effect elements 1228A, 1228B, 1228C, 1228D in an area 1230 of the position sensor 1200 that is located above the magnet 1202 (FIGS. 15 and 16). A high-resolution ADC 1232 and a smart power management controller 1238 are also provided on the chip. A CORDIC processor 1236 (for Coordinate Rotation Digital Computer), also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface such as an SPI interface 1234 to the controller 1104. The position sensor 1200 provides 12 or 14 bits of resolution. The position sensor 1200 may be an AS5055 chip provided in a small QFN 16-pin 4×4×0.85 mm package.

The Hall-effect elements 1228A, 1228B, 1228C, 1228D are located directly above the rotating magnet 1202 (FIG. 11). The Hall-effect is a well-known effect and for expediency will not be described in detail herein, however, generally, the Hall-effect produces a voltage difference (the Hall voltage) across an electrical conductor transverse to an electric current in the conductor and a magnetic field perpendicular to the current. A Hall coefficient is defined as the ratio of the induced electric field to the product of the current density and the applied magnetic field. It is a characteristic of the material from which the conductor is made, since its value depends on the type, number, and properties of the charge carriers that constitute the current. In the AS5055 position sensor 1200, the Hall-effect elements 1228A, 1228B, 1228C, 1228D are capable producing a voltage signal that is indicative of the absolute position of the magnet 1202 in terms of the angle over a single revolution of the magnet 1202. This value of the angle, which is unique position signal, is calculated by the CORDIC processor 1236 is stored onboard the AS5055 position sensor 1200 in a register or memory. The value of the angle that is indicative of the position of the magnet 1202 over one revolution is provided to the controller 1104 in a variety of techniques, e.g., upon power up or upon request by the controller 1104.

The AS5055 position sensor 1200 requires only a few external components to operate when connected to the controller 1104. Six wires are needed for a simple application using a single power supply: two wires for power and four wires 1240 for the SPI interface 1234 with the controller 1104. A seventh connection can be added in order to send an interrupt to the controller 1104 to inform that a new valid angle can be read. Upon power-up, the AS5055 position sensor 1200 performs a full power-up sequence including one angle measurement. The completion of this cycle is indicated as an INT output 1242, and the angle value is stored in an internal register. Once this output is set, the AS5055 position sensor 1200 suspends to sleep mode. The controller 1104 can respond to the INT request at the INT output 1242 by reading the angle value from the AS5055 position sensor 1200 over the SPI interface 1234. Once the angle value is read by the controller 1104, the INT output 1242 is cleared again. Sending a "read angle" command by the SPI interface 1234 by the controller 1104 to the position sensor 1200 also automatically powers up the chip and starts another angle measurement. As soon as the controller 1104 has completed reading of the angle value, the INT output 1242 is cleared and a new result is stored in the angle register. The completion of the angle measurement is again indicated by setting the INT output 1242 and a corresponding flag in the status register.

Due to the measurement principle of the AS5055 position sensor 1200, only a single angle measurement is performed in very short time (~600 µs) after each power-up sequence. As soon as the measurement of one angle is completed, the AS5055 position sensor 1200 suspends to power-down state. An on-chip filtering of the angle value by digital averaging is not implemented, as this would require more than one angle measurement and, consequently, a longer power-up time that is not desired in low-power applications. The angle jitter can be reduced by averaging of several angle samples in the controller 1104. For example, an averaging of four samples reduces the jitter by 6 dB (50%).

Figure 13:
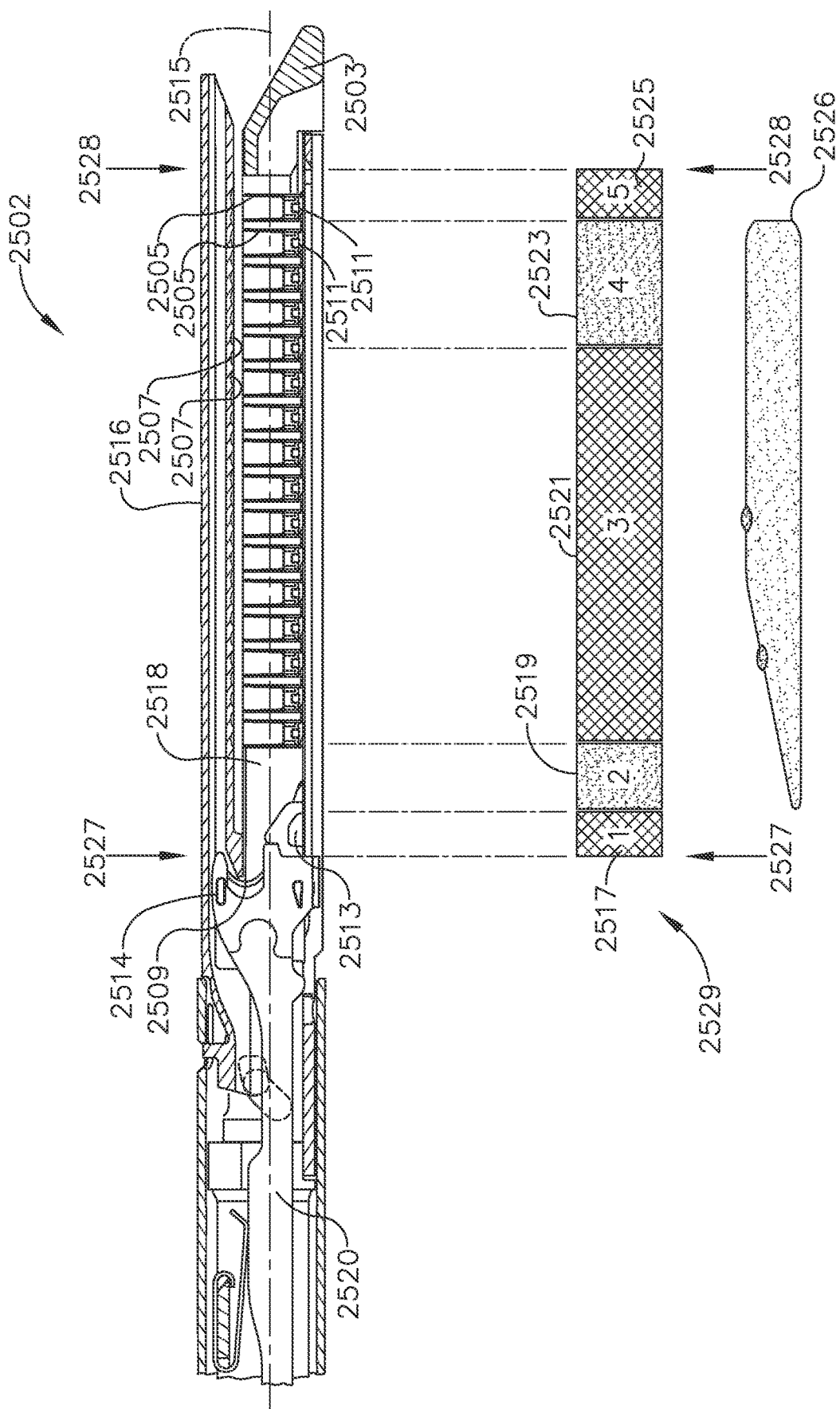
FIG. 13 is a section view of an end effector of the surgical instrument of FIG. 1 showing a firing member stroke relative to tissue grasped within the end effector according to one aspect of this disclosure.

FIG. 13 is a section view of an end effector 2502 of the surgical instrument 10 (FIGS. 1-4) showing an I-beam 2514 firing stroke relative to tissue 2526 grasped within the end effector 2502 according to one aspect of this disclosure. The end effector 2502 is configured to operate with the surgical instrument 10 shown in FIGS. 1-4. The end effector 2502 comprises an anvil 2516 and an elongated channel 2503 with a staple cartridge 2518 positioned in the elongated channel 2503. A firing bar 2520 is translatable distally and proximally along a longitudinal axis 2515 of the end effector 2502. When the end effector 2502 is not articulated, the end effector 2502 is in line with the shaft of the instrument. An I-beam 2514 comprising a cutting edge 2509 is illustrated at a distal portion of the firing bar 2520. A wedge sled 2513 is positioned in the staple cartridge 2518. As the I-beam 2514 translates distally, the cutting edge 2509 contacts and may cut tissue 2526 positioned between the anvil 2516 and the staple cartridge 2518. Also, the I-beam 2514 contacts the wedge sled 2513 and pushes it distally, causing the wedge sled 2513 to contact staple drivers 2511. The staple drivers 2511 may be driven up into staples 2505, causing the staples 2505 to advance through tissue and into pockets 2507 defined in the anvil 2516, which shape the staples 2505.

An example I-beam 2514 firing stroke is illustrated by a chart 2529 aligned with the end effector 2502. Example tissue 2526 is also shown aligned with the end effector 2502. The firing member stroke may comprise a stroke begin position 2527 and a stroke end position 2528. During an I-beam 2514 firing stroke, the I-beam 2514 may be advanced distally from the stroke begin position 2527 to the stroke end position 2528. The I-beam 2514 is shown at one example location of a stroke begin position 2527. The I-beam 2514 firing member stroke chart 2529 illustrates five firing member stroke regions 2517, 2519, 2521, 2523, 2525. In a first firing stroke region 2517, the I-beam 2514 may begin to advance distally. In the first firing stroke region 2517, the I-beam 2514 may contact the wedge sled 2513 and begin to move it distally. While in the first region, however, the cutting edge 2509 may not contact tissue and the wedge sled 2513 may not contact a staple driver 2511. After static friction is overcome, the force to drive the I-beam 2514 in the first region 2517 may be substantially constant.

Figure 18:
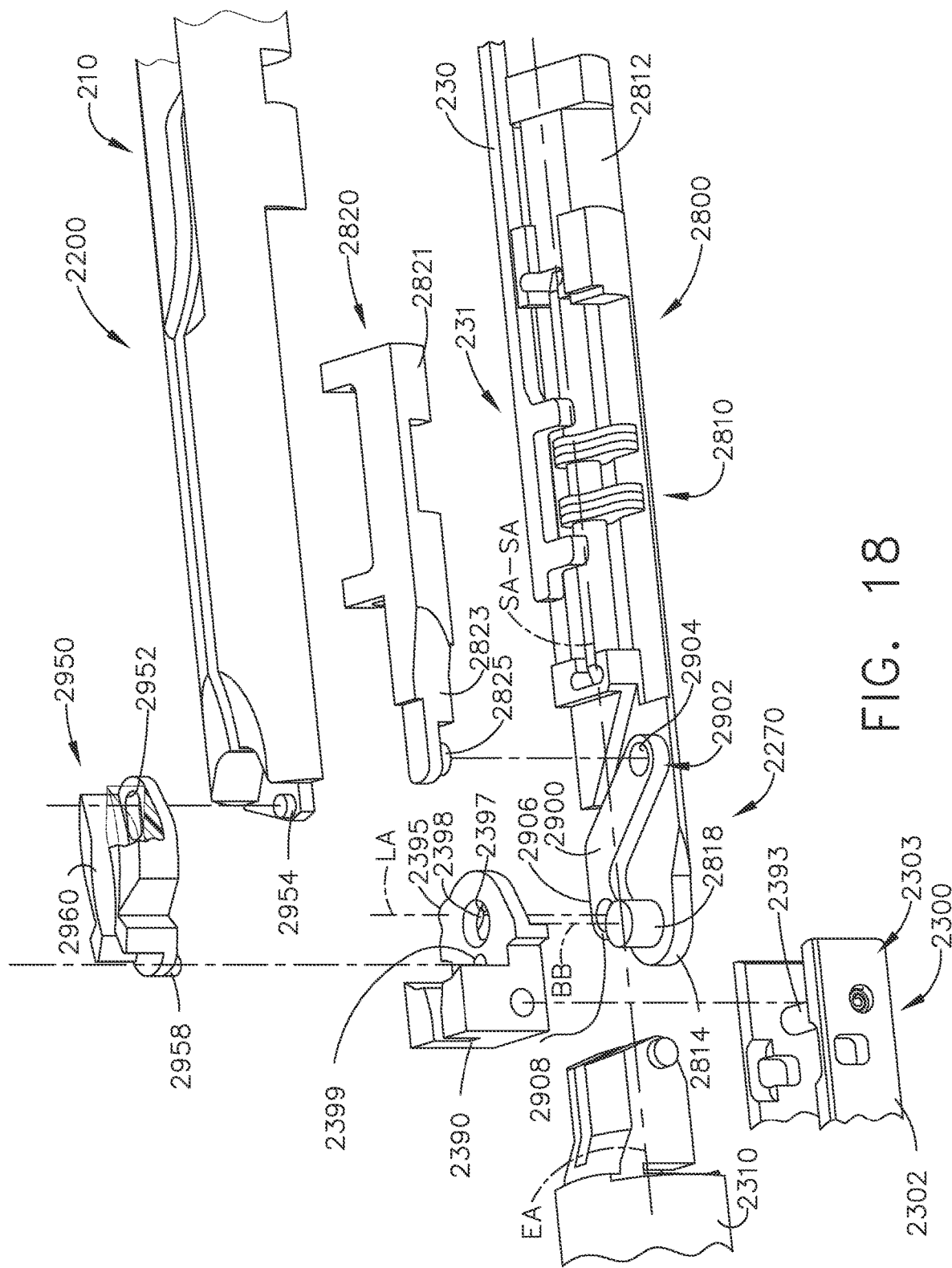
FIG. 18 is an exploded assembly perspective view of the end effector of FIG. 16 showing the elongate shaft assembly aspect, according to one aspect of this disclosure.

In the second firing member stroke region 2519, the cutting edge 2509 may begin to contact and cut tissue 2526. Also, the wedge sled 2513 may begin to contact staple drivers 2511 to drive staples 2505. Force to drive the I-beam 2514 may begin to ramp up. As shown, tissue encountered initially may be compressed and/or thinner because of the way that the anvil 2516 pivots relative to the staple cartridge 2518. In the third firing member stroke region 2521, the cutting edge 2509 may continuously contact and cut tissue 2526 and the wedge sled 2513 may repeatedly contact staple drivers 2511. Force to drive the I-beam 2514 may plateau in the third region 2521. By the fourth firing stroke region 2523, force to drive the I-beam 2514 may begin to decline. For example, tissue in the portion of the end effector 2502 corresponding to the fourth firing region 2523 may be less compressed than tissue closer to the pivot point of the anvil 2516, requiring less force to cut. Also, the cutting edge 2509 and wedge sled 2513 may reach the end of the tissue 2526 while in the fourth region 2523. When the I-beam 2514 reaches the fifth region 2525, the tissue 2526 may be completely severed. The wedge sled 2513 may contact one or more staple drivers 2511 at or near the end of the tissue. Force to advance the I-beam 2514 through the fifth region 2525 may be reduced and, in some examples, may be similar to the force to drive the I-beam 2514 in the first region 2517. At the conclusion of the firing member stroke, the I-beam 2514 may reach the stroke end position 2528. The positioning of firing member stroke regions 2517, 2519, 2521, 2523, 2525 in FIG. 18 is just one example. In some examples, different regions may begin at different positions along the end effector longitudinal axis 2515, for example, based on the positioning of tissue between the anvil 2516 and the staple cartridge 2518.

As discussed above and with reference now to FIGS. 10-13, the electric motor 1122 positioned within the handle assembly of the surgical instrument 10 (FIGS. 1-4) can be utilized to advance and/or retract the firing system of the shaft assembly, including the I-beam 2514, relative to the end effector 2502 of the shaft assembly in order to staple and/or incise tissue captured within the end effector 2502. The I-beam 2514 may be advanced or retracted at a desired speed, or within a range of desired speeds. The controller 1104 may be configured to control the speed of the I-beam 2514. The controller 1104 may be configured to predict the speed of the I-beam 2514 based on various parameters of the power supplied to the electric motor 1122, such as voltage and/or current, for example, and/or other operating parameters of the electric motor 1122 or external influences. The controller 1104 may be configured to predict the current speed of the I-beam 2514 based on the previous values of the current and/or voltage supplied to the electric motor 1122, and/or previous states of the system like velocity, acceleration, and/or position. The controller 1104 may be configured to sense the speed of the I-beam 2514 utilizing the absolute positioning sensor system described herein. The controller can be configured to compare the predicted speed of the I-beam 2514 and the sensed speed of the I-beam 2514 to determine whether the power to the electric motor 1122 should be increased in order to increase the speed of the I-beam 2514 and/or decreased in order to decrease the speed of the I-beam 2514. U.S. Pat. No. 8,210,411, entitled MOTOR-DRIVEN SURGICAL CUTTING INSTRUMENT, which is incorporated herein by reference in its entirety. U.S. Pat. No. 7,845,537, entitled SURGICAL INSTRUMENT HAVING RECORDING CAPABILITIES, which is incorporated herein by reference in its entirety.

Force acting on the I-beam 2514 may be determined using various techniques. The I-beam 2514 force may be determined by measuring the motor 2504 current, where the motor 2504 current is based on the load experienced by the I-beam 2514 as it advances distally. The I-beam 2514 force may be determined by positioning a strain gauge on the drive member 120 (FIG. 2), the firing member 220 (FIG. 2), I-beam 2514 (I-beam 178, FIG. 20), the firing bar 172 (FIG. 2), and/or on a proximal end of the cutting edge 2509. The I-beam 2514 force may be determined by monitoring the actual position of the I-beam 2514 moving at an expected velocity based on the current set velocity of the motor 2504 after a predetermined elapsed period $T_1$ and comparing the actual position of the I-beam 2514 relative to the expected position of the I-beam 2514 based on the current set velocity of the motor 2504 at the end of the period $T_1$. Thus, if the actual position of the I-beam 2514 is less than the expected position of the I-beam 2514, the force on the I-beam 2514 is greater than a nominal force. Conversely, if the actual position of the I-beam 2514 is greater than the expected position of the I-beam 2514, the force on the I-beam 2514 is less than the nominal force. The difference between the actual and expected positions of the I-beam 2514 is proportional to the deviation of the force on the I-beam 2514 from the nominal force. Such techniques are described in U.S. Pat. No. 10,624,633, which is incorporated herein by reference in its entirety.

Figure 14:
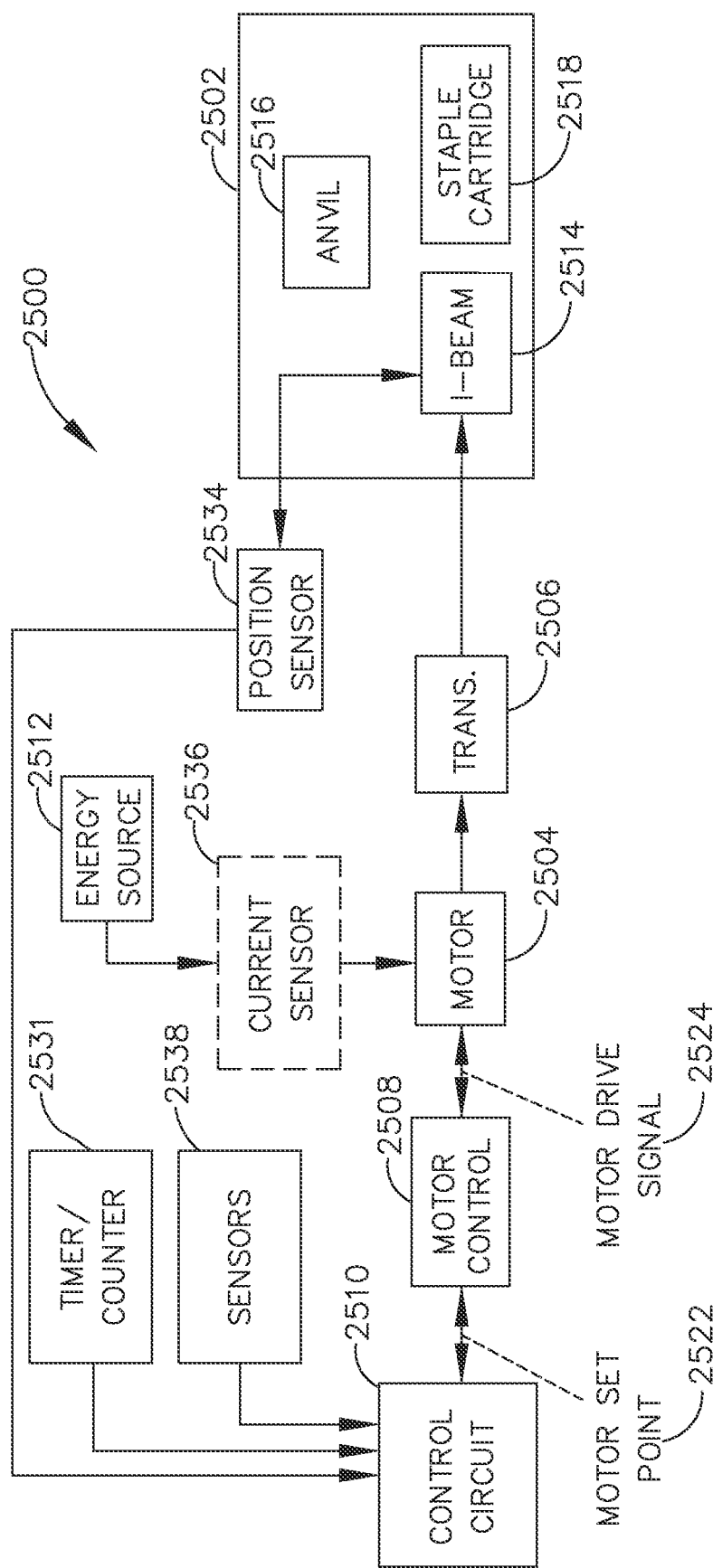
FIG. 14 illustrates a block diagram of a surgical instrument programmed to control distal translation of a displacement member according to one aspect of this disclosure.

FIG. 14 illustrates a block diagram of a surgical instrument 2500 programmed to control distal translation of a displacement member according to one aspect of this disclosure. In one aspect, the surgical instrument 2500 is programmed to control distal translation of a displacement member 1111 such as the I-beam 2514. The surgical instrument 2500 comprises an end effector 2502 that may comprise an anvil 2516, an I-beam 2514 (including a sharp cutting edge 2509), and a removable staple cartridge 2518. The end effector 2502, anvil 2516, I-beam 2514, and staple cartridge 2518 may be configured as described herein, for example, with respect to FIGS. 1-13.

The position, movement, displacement, and/or translation of a liner displacement member 1111, such as the I-beam 2514, can be measured by the absolute positioning system 1100, sensor arrangement 1102, and position sensor 1200 as shown in FIGS. 10-12 and represented as position sensor 2534 in FIG. 14. Because the I-beam 2514 is coupled to the longitudinally movable drive member 120, the position of the I-beam 2514 can be determined by measuring the position of the longitudinally movable drive member 120 employing the position sensor 2534. Accordingly, in the following description, the position, displacement, and/or translation of the I-beam 2514 can be achieved by the position sensor 2534 as described herein. A control circuit 2510, such as the control circuit 700 described in FIGS. 5A and 5B, may be programmed to control the translation of the displacement member 1111, such as the I-beam 2514, as described in connection with FIGS. 10-12. The control circuit 2510, in some examples, may comprise one or more microcontrollers, microprocessors, or other suitable processors for executing instructions that cause the processor or processors to control the displacement member, e.g., the I-beam 2514, in the manner described. In one aspect, a timer/counter circuit 2531 provides an output signal, such as elapsed time or a digital count, to the control circuit 2510 to correlate the position of the I-beam 2514 as determined by the position sensor 2534 with the output of the timer/counter circuit 2531 such that the control circuit 2510 can determine the position of the I-beam 2514 at a specific time (t) relative to a starting position. The timer/counter circuit 2531 may be configured to measure elapsed time, count external evens, or time external events.

The control circuit 2510 may generate a motor set point signal 2522. The motor set point signal 2522 may be provided to a motor controller 2508. The motor controller 2508 may comprise one or more circuits configured to provide a motor drive signal 2524 to the motor 2504 to drive the motor 2504 as described herein. In some examples, the motor 2504 may be a brushed DC electric motor, such as the motor 82, 714, 1120 shown in FIGS. 1, 5B, 10. For example, the velocity of the motor 2504 may be proportional to the motor drive signal 2524. In some examples, the motor 2504 may be a brushless direct current (DC) electric motor and the motor drive signal 2524 may comprise a pulse-width-modulated (PWM) signal provided to one or more stator windings of the motor 2504. Also, in some examples, the motor controller 2508 may be omitted and the control circuit 2510 may generate the motor drive signal 2524 directly.

The motor 2504 may receive power from an energy source 2512. The energy source 2512 may be or include a battery, a super capacitor, or any other suitable energy source 2512. The motor 2504 may be mechanically coupled to the I-beam 2514 via a transmission 2506. The transmission 2506 may include one or more gears or other linkage components to couple the motor 2504 to the I-beam 2514. A position sensor 2534 may sense a position of the I-beam 2514. The position sensor 2534 may be or include any type of sensor that is capable of generating position data that indicates a position of the I-beam 2514. In some examples, the position sensor 2534 may include an encoder configured to provide a series of pulses to the control circuit 2510 as the I-beam 2514 translates distally and proximally. The control circuit 2510 may track the pulses to determine the position of the I-beam 2514. Other suitable position sensor may be used, including, for example, a proximity sensor. Other types of position sensors may provide other signals indicating motion of the I-beam 2514. Also, in some examples, the position sensor 2534 may be omitted. Where the motor 2504 is a stepper motor, the control circuit 2510 may track the position of the I-beam 2514 by aggregating the number and direction of steps that the motor 2504 has been instructed to execute. The position sensor 2534 may be located in the end effector 2502 or at any other portion of the instrument.

The control circuit 2510 may be in communication with one or more sensors 2538. The sensors 2538 may be positioned on the end effector 2502 and adapted to operate with the surgical instrument 2500 to measure the various derived parameters such as gap distance versus time, tissue compression versus time, and anvil strain versus time. The sensors 2538 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 2502. The sensors 2538 may include one or more sensors.

The one or more sensors 2538 may comprise a strain gauge, such as a micro-strain gauge, configured to measure the magnitude of the strain in the anvil 2516 during a clamped condition. The strain gauge provides an electrical signal whose amplitude varies with the magnitude of the strain. The sensors 2538 may comprise a pressure sensor configured to detect a pressure generated by the presence of compressed tissue between the anvil 2516 and the staple cartridge 2518. The sensors 2538 may be configured to detect impedance of a tissue section located between the anvil 2516 and the staple cartridge 2518 that is indicative of the thickness and/or fullness of tissue located therebetween.

The sensors 2538 may be is configured to measure forces exerted on the anvil 2516 by the closure drive system 30. For example, one or more sensors 2538 can be at an interaction point between the closure tube 260 (FIG. 3) and the anvil 2516 to detect the closure forces applied by the closure tube 260 to the anvil 2516. The forces exerted on the anvil 2516 can be representative of the tissue compression experienced by the tissue section captured between the anvil 2516 and the staple cartridge 2518. The one or more sensors 2538 can be positioned at various interaction points along the closure drive system 30 (FIG. 2) to detect the closure forces applied to the anvil 2516 by the closure drive system 30. The one or more sensors 2538 may be sampled in real time during a clamping operation by a processor as described in FIGS. 5A-5B. The control circuit 2510 receives real-time sample measurements to provide analyze time based information and assess, in real time, closure forces applied to the anvil 2516.

A current sensor 2536 can be employed to measure the current drawn by the motor 2504. The force required to advance the I-beam 2514 corresponds to the current drawn by the motor 2504. The force is converted to a digital signal and provided to the control circuit 2510.

Using the physical properties of the instruments disclosed herein in connection with FIGS. 1-14, and with reference to FIG. 14, the control circuit 2510 can be configured to simulate the response of the actual system of the instrument in the software of the controller. A displacement member can be actuated to move an I-beam 2514 in the end effector 2502 at or near a target velocity. The surgical instrument 2500 can include a feedback controller, which can be one of any feedback controllers, including, but not limited to a PID, a State Feedback, LQR, and/or an Adaptive controller, for example. The surgical instrument 2500 can include a power source to convert the signal from the feedback controller into a physical input such as case voltage, pulse width modulated (PWM) voltage, frequency modulated voltage, current, torque, and/or force, for example.

The actual drive system of the surgical instrument 2500 is configured to drive the displacement member, cutting member, or I-beam 2514, by a brushed DC motor with gearbox and mechanical links to an articulation and/or knife system. Another example is the electric motor 2504 that operates the displacement member and the articulation driver, for example, of an interchangeable shaft assembly. An outside influence is an unmeasured, unpredictable influence of things like tissue, surrounding bodies and friction on the physical system. Such outside influence can be referred to as drag which acts in opposition to the electric motor 2504. The outside influence, such as drag, may cause the operation of the physical system to deviate from a desired operation of the physical system.

Before explaining aspects of the surgical instrument 2500 in detail, it should be noted that the example aspects are not limited in application or use to the details of construction and arrangement of parts illustrated in the accompanying drawings and description. The example aspects may be implemented or incorporated in other aspects, variations and modifications, and may be practiced or carried out in various ways. Further, unless otherwise indicated, the terms and expressions employed herein have been chosen for the purpose of describing the example aspects for the convenience of the reader and are not for the purpose of limitation thereof. Also, it will be appreciated that one or more of the following-described aspects, expressions of aspects and/or examples, can be combined with any one or more of the other following-described aspects, expressions of aspects and/or examples.

Various example aspects are directed to a surgical instrument 2500 comprising an end effector 2502 with motor-driven surgical stapling and cutting implements. For example, a motor 2504 may drive a displacement member distally and proximally along a longitudinal axis of the end effector 2502. The end effector 2502 may comprise a pivotable anvil 2516 and, when configured for use, a staple cartridge 2518 positioned opposite the anvil 2516. A clinician may grasp tissue between the anvil 2516 and the staple cartridge 2518, as described herein. When ready to use the instrument 2500, the clinician may provide a firing signal, for example by depressing a trigger of the instrument 2500. In response to the firing signal, the motor 2504 may drive the displacement member distally along the longitudinal axis of the end effector 2502 from a proximal stroke begin position to a stroke end position distal of the stroke begin position. As the displacement member translates distally, an I-beam 2514 with a cutting element positioned at a distal end, may cut the tissue between the staple cartridge 2518 and the anvil 2516.

In various examples, the surgical instrument 2500 may comprise a control circuit 2510 programmed to control the distal translation of the displacement member, such as the I-beam 2514, for example, based on one or more tissue conditions. The control circuit 2510 may be programmed to sense tissue conditions, such as thickness, either directly or indirectly, as described herein. The control circuit 2510 may be programmed to select a firing control program based on tissue conditions. A firing control program may describe the distal motion of the displacement member. Different firing control programs may be selected to better treat different tissue conditions. For example, when thicker tissue is present, the control circuit 2510 may be programmed to translate the displacement member at a lower velocity and/or with lower power. When thinner tissue is present, the control circuit 2510 may be programmed to translate the displacement member at a higher velocity and/or with higher power.

In some examples, the control circuit 2510 may initially operate the motor 2504 in an open-loop configuration for a first open-loop portion of a stroke of the displacement member. Based on a response of the instrument 2500 during the open-loop portion of the stroke, the control circuit 2510 may select a firing control program. The response of the instrument may include, a translation distance of the displacement member during the open-loop portion, a time elapsed during the open-loop portion, energy provided to the motor 2504 during the open-loop portion, a sum of pulse widths of a motor drive signal, etc. After the open-loop portion, the control circuit 2510 may implement the selected firing control program for a second portion of the displacement member stroke. For example, during the closed loop portion of the stroke, the control circuit 2510 may modulate the motor 2504 based on translation data describing a position of the displacement member in a closed-loop manner to translate the displacement member at a constant velocity.

FIG. 15 illustrates a diagram 2580 plotting two example displacement member strokes executed according to one aspect of this disclosure. The diagram 2580 comprises two axes. A horizontal axis 2584 indicates elapsed time. A vertical axis 2582 indicates the position of the I-beam 2514 between a stroke begin position 2586 and a stroke end position 2588. On the horizontal axis 2584, the control circuit 2510 may receive the firing signal and begin providing the initial motor setting at $t_0$. The open-loop portion of the displacement member stroke is an initial time period that may elapse between $t_0$ and $t_1$.

A first example 2592 shows a response of the surgical instrument 2500 when thick tissue is positioned between the anvil 2516 and the staple cartridge 2518. During the open-loop portion of the displacement member stroke, e.g., the initial time period between $t_0$ and $t_1$, the I-beam 2514 may traverse from the stroke begin position 2586 to position 2594. The control circuit 2510 may determine that position 2594 corresponds to a firing control program that advances the I-beam 2514 at a selected constant velocity (Vslow), indicated by the slope of the example 2592 after $t_1$ (e.g., in the closed loop portion). The control circuit 2510 may drive I-beam 2514 to the velocity Vslow by monitoring the position of I-beam 2514 and modulating the motor set point 2522 and/or motor drive signal 2524 to maintain Vslow. A second example 2590 shows a response of the surgical instrument 2500 when thin tissue is positioned between the anvil 2516 and the staple cartridge 2518.

During the initial time period (e.g., the open-loop period) between $t_0$ and $t_1$, the I-beam 2514 may traverse from the stroke begin position 2586 to position 2596. The control circuit may determine that position 2596 corresponds to a firing control program that advances the displacement member at a selected constant velocity (Vfast). Because the tissue in example 2590 is thinner than the tissue in example 2592, it may provide less resistance to the motion of the I-beam 2514. As a result, the I-beam 2514 may traverse a larger portion of the stroke during the initial time period. Also, in some examples, thinner tissue (e.g., a larger portion of the displacement member stroke traversed during the initial time period) may correspond to higher displacement member velocities after the initial time period.

Figure 19:
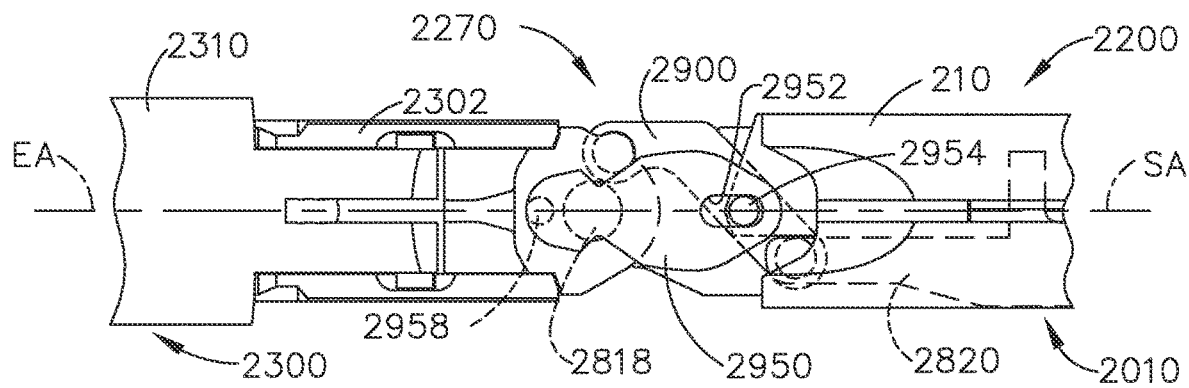
FIG. 19 is a top view of the end effector of FIG. 16 showing the elongate shaft assembly in an unarticulated orientation, according to one aspect of this disclosure.
Figure 20:
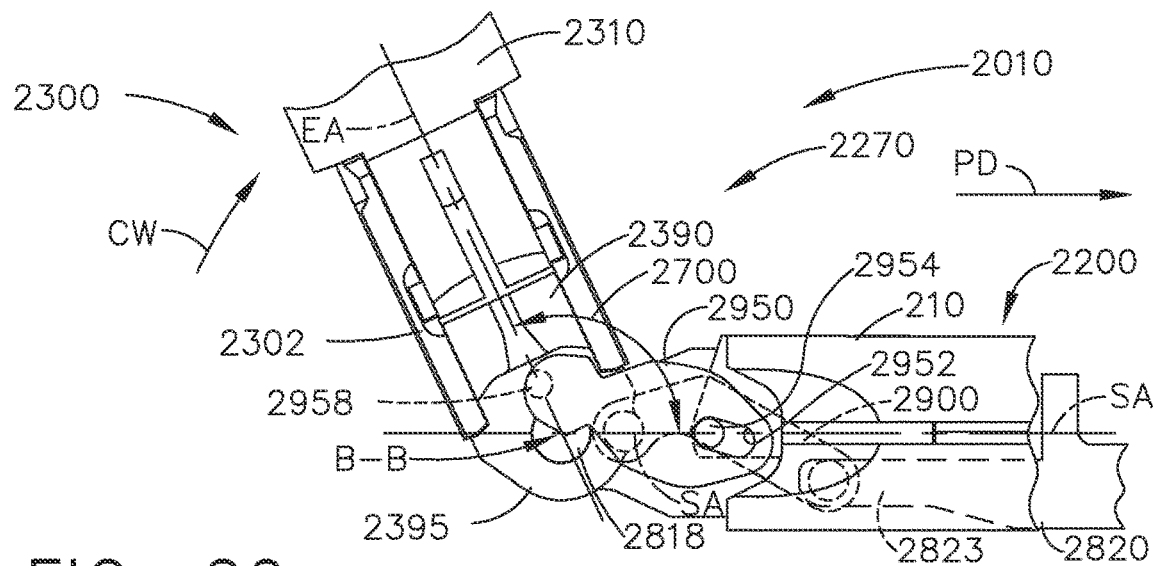
FIG. 20 is another top view of the end effector of FIG. 16 showing the elongate shaft assembly in a first articulated orientation, according to one aspect of this disclosure.
Figure 21:
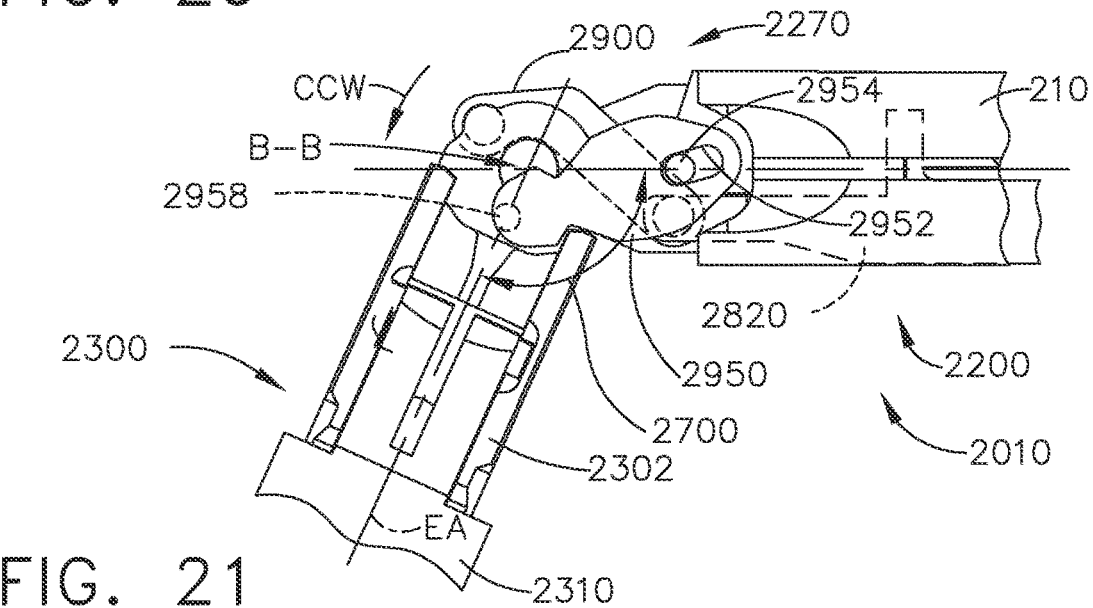
FIG. 21 is another top view of the end effector of FIG. 16 showing the elongate shaft assembly in a second articulated orientation, according to one aspect of this disclosure.

FIGS. 16-21 illustrate an end effector 2300 of a surgical instrument 2010 showing how the end effector 2300 may be articulated relative to the elongate shaft assembly 2200 about an articulation joint 2270 according to one aspect of this disclosure. FIG. 16 is a partial perspective view of a portion of the end effector 2300 showing an elongate shaft assembly 2200 in an unarticulated orientation with portions thereof omitted for clarity. FIG. 17 is a perspective view of the end effector 2300 of FIG. 16 showing the elongate shaft assembly 2200 in an unarticulated orientation. FIG. 18 is an exploded assembly perspective view of the end effector 2300 of FIG. 16 showing the elongate shaft assembly 2200. FIG. 19 is a top view of the end effector 2300 of FIG. 16 showing the elongate shaft assembly 2200 in an unarticulated orientation. FIG. 20 is a top view of the end effector 2300 of FIG. 16 showing the elongate shaft assembly 2200 in a first articulated orientation. FIG. 21 is a top view of the end effector 2300 of FIG. 16 showing the elongate shaft assembly 2200 in a second articulated orientation.

With reference now to FIGS. 16-21, the end effector 2300 is adapted to cut and staple tissue and includes a first jaw in the form of an elongate channel 2302 that is configured to operably support a surgical staple cartridge 2304 therein. The end effector 2300 further includes a second jaw in the form of an anvil 2310 that is supported on the elongate channel 2302 for movement relative thereto. The elongate shaft assembly 2200 includes an articulation system 2800 that employs an articulation lock 2810. The articulation lock 2810 can be configured and operated to selectively lock the surgical end effector 2300 in various articulated positions. Such arrangement enables the surgical end effector 2300 to be rotated, or articulated, relative to the shaft closure sleeve 260 when the articulation lock 2810 is in its unlocked state. Referring specifically to FIG. 18, the elongate shaft assembly 2200 includes a spine 210 that is configured to (1) slidably support a firing member 220 therein and, (2) slidably support the closure sleeve 260 (FIG. 16), which extends around the spine 210. The shaft closure sleeve 260 is attached to an end effector closure sleeve 272 that is pivotally attached to the closure sleeve 260 by a double pivot closure sleeve assembly 271.

The spine 210 also slidably supports a proximal articulation driver 230. The proximal articulation driver 230 has a distal end 231 that is configured to operably engage the articulation lock 2810. The articulation lock 2810 further comprises a shaft frame 2812 that is attached to the spine 210 in the various manners disclosed herein. The shaft frame 2812 is configured to movably support a proximal portion 2821 of a distal articulation driver 2820 therein. The distal articulation driver 2820 is movably supported within the elongate shaft assembly 2200 for selective longitudinal travel in a distal direction DD and a proximal direction PD along an articulation actuation axis AAA that is laterally offset and parallel to the shaft axis SA-SA in response to articulation control motions applied thereto.

In FIGS. 17 and 18, the shaft frame 2812 includes a distal end portion 2814 that has a pivot pin 2818 formed thereon. The pivot pin 2818 is adapted to be pivotally received within a pivot hole 2397 formed in pivot base portion 2395 of an end effector mounting assembly 2390. The end effector mounting assembly 2390 is attached to the proximal end 2303 of the elongate channel 2302 by a spring pin 2393 or equivalent. The pivot pin 2818 defines an articulation axis B-B transverse to the shaft axis SA-SA to facilitate pivotal travel (i.e., articulation) of the end effector 2300 about the articulation axis B-B relative to the shaft frame 2812.

As shown in FIG. 18, a link pin 2825 is formed on a distal end 2823 of the distal articulation link 2820 and is configured to be received within a hole 2904 in a proximal end 2902 of a cross link 2900. The cross link 2900 extends transversely across the shaft axis SA-SA and includes a distal end portion 2906. A distal link hole 2908 is provided through the distal end portion 2906 of the cross link 2900 and is configured to pivotally receive therein a base pin 2398 extending from the bottom of the pivot base portion 2395 of the end effector mounting assembly 2390. The base pin 2395 defines a link axis LA that is parallel to the articulation axis B-B. FIGS. 17 and 20 illustrate the surgical end effector 2300 in an unarticulated position. The end effector axis EA is defined by the elongate channel 2302 is aligned with the shaft axis SA-SA. The term "aligned with" may mean "coaxially aligned" with the shaft axis SA-SA or parallel with the shaft axis SA-SA. Movement of the distal articulation driver 2820 in the proximal direction PD will cause the cross link 2900 to draw the surgical end effector 2300 in a clockwise CW direction about the articulation axis B-B as shown in FIG. 19. Movement of the distal articulation driver 2820 in the distal direction DD will cause the cross link 2900 to move the surgical end effector 2300 in the counterclockwise CCW direction about the articulation axis B-B as shown in FIG. 21. As shown in FIG. 21, the cross link 2900 has a curved shape that permits the cross-link 2900 to curve around the articulation pin 2818 when the surgical end effector 2300 is articulated in that direction. When the surgical end effector 2300 is in a fully articulated position on either side of the shaft axis SA-SA, the articulation angle 2700 between the end effector axis EA and the shaft axis SA-SA is approximately sixty-five degrees (65°). Thus, the range of articulation on either said of the shaft axis is from one degree (1°) to sixty-five degrees (65°).

FIG. 19 shows the articulation joint 2270 in a straight position, i.e., at a zero angle $\theta_0$ relative to the longitudinal direction depicted as shaft axis SA, according to one aspect. FIG. 20 shows the articulation joint 2270 of FIG. 19 articulated in one direction at a first angle $\theta_1$ defined between the shaft axis SA and the end effector axis EA, according to one aspect. FIG. 21 illustrates the articulation joint 2270 of FIG. 19 articulated in another direction at a second angle $\theta_2$ defined between the shaft axis SA and the end effector axis EA.

The surgical end effector 2300 in FIGS. 16-21 comprises a surgical cutting and stapling device that employs a firing member 220 of the various types and configurations described herein. However, the surgical end effector 2300 may comprise other forms of surgical end effectors that do not cut and/or staple tissue. A middle support member 2950 is pivotally and slidably supported relative to the spine 210. In FIG. 18, the middle support member 2950 includes a slot 2952 that is adapted to receive therein a pin 2954 that protrudes from the spine 210. This enables the middle support member 2950 to pivot and translate relative to the pin 2954 when the surgical end effector 2300 is articulated. A pivot pin 2958 protrudes from the underside of the middle support member 2950 to be pivotally received within a corresponding pivot hole 2399 provided in the base portion 2395 of the end effector mounting assembly 2390. The middle support member 2950 further includes a slot 2960 for receiving a firing member 220 there through. The middle support member 2950 serves to provide lateral support to the firing member 220 as it flexes to accommodate articulation of the surgical end effector 2300.

The surgical instrument can additionally be configured to determine the angle at which the end effector 2300 is oriented. In various aspects, the position sensor 1112 of the sensor arrangement 1102 may comprise one or more magnetic sensors, analog rotary sensors (such as potentiometers), arrays of analog Hall effect sensors, which output a unique combination of position signals or values, among others, for example. In one aspect, the articulation joint 2270 of the aspect illustrated in FIGS. 16-21 can additionally comprise an articulation sensor arrangement that is configured to determine the angular position, i.e., articulation angle, of the end effector 2300 and provide a unique position signal corresponding thereto.

The articulation sensor arrangement can be similar to the sensor arrangement 1102 described above and illustrated in FIGS. 10-12. In this aspect, the articulation sensor arrangement can comprise a position sensor and a magnet that is operatively coupled to the articulation joint 2270 such that it rotates in a manner consistent with the rotation of the articulation joint 2270. The magnet can, for example, be coupled to the pivot pin 2818. The position sensor comprises one or more magnetic sensing elements, such as Hall effect sensors, and is placed in proximity to the magnet, either within or adjacent to the articulation joint 2270. Accordingly, as the magnet rotates, the magnetic sensing elements of the position sensor determine the magnet's absolute angular position. As the magnet is coupled to the articulation joint 2270, the angular position of the magnet with respect to the position sensor corresponds to the angular position of the end effector 2300. Therefore, the articulation sensor arrangement is able to determine the angular position of the end effector as the end effector articulates.

In another aspect, the surgical instrument is configured to determine the angle at which the end effector 2300 is positioned in an indirect manner by monitoring the absolute position of the articulation driver 230 (FIG. 3). As the position of the articulation driver 230 corresponds to the angle at which the end effector 2300 is oriented in a known manner, the absolute position of the articulation driver 230 can be tracked and then translated to the angular position of the end effector 2300. In this aspect, the surgical instrument comprises an articulation sensor arrangement that is configured to determine the absolute linear position of the articulation driver 230 and provide a unique position signal corresponding thereto. In some aspects, the articulation sensor arrangement or the controller operably coupled to the articulation sensor arrangement is configured additionally to translate or calculate the angular position of the end effector 2300 from the unique position signal.

The articulation sensor arrangement in this aspect can likewise be similar to the sensor arrangement 1102 described above and illustrated in FIGS. 10-12. In one aspect similar to the aspect illustrated in FIG. 10 with respect to the displacement member 1111, the articulation sensor arrangement comprises a position sensor and a magnet that turns once every full stroke of the longitudinally-movable articulation driver 230. The position sensor comprises one or more magnetic sensing elements, such as Hall effect sensors, and is placed in proximity to the magnet. Accordingly, as the magnet rotates, the magnetic sensing elements of the position sensor determine the absolute angular position of the magnet over one revolution.

In one aspect, a single revolution of a sensor element associated with the position sensor is equivalent to a longitudinal linear displacement d1 of the of the longitudinally-movable articulation driver 230. In other words, d1 is the longitudinal linear distance that the longitudinally-movable articulation driver 230 moves from point "a" to point "b" after a single revolution of a sensor element coupled to the longitudinally-movable articulation driver 230. The articulation sensor arrangement may be connected via a gear reduction that results in the position sensor completing only one revolution for the full stroke of the longitudinally-movable articulation driver 230. In other words, d1 can be equal to the full stroke of the articulation driver 230. The position sensor is configured to then transmit a unique position signal corresponding to the absolute position of the articulation driver 230 to the controller 1104, such as in those aspects depicted in FIG. 10 Upon receiving the unique position signal, the controller 1104 is then configured execute a logic to determine the angular position of the end effector corresponding to the linear position of the articulation driver 230 by, for example, querying a lookup table that returns the value of the pre-calculated angular position of the end effector 2300, calculating via an algorithm the angular position of the end effector 2300 utilizing the linear position of the articulation driver 230 as the input, or performing any other such method as is known in the field.

In various aspects, any number of magnetic sensing elements may be employed on the articulation sensor arrangement, such as, for example, magnetic sensors classified according to whether they measure the total magnetic field or the vector components of the magnetic field. The number of magnetic sensing elements utilized corresponds to the desired resolution to be sensed by the articulation sensor arrangement. In other words, the larger number of magnetic sensing elements used, the finer degree of articulation that can be sensed by the articulation sensor arrangement. The techniques used to produce both types of magnetic sensors encompass many aspects of physics and electronics. The technologies used for magnetic field sensing include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber optic, magnetooptic, and microelectromechanical systems-based magnetic sensors, among others.

In one aspect, the position sensor of the various aspects of the articulation sensor arrangement may be implemented in a manner similar to the positioning system illustrated in FIG. 12 for tracking the position of the displacement member 1111. In one such aspect, the articulation sensor arrangement may be implemented as an AS5055EQFT single-chip magnetic rotary position sensor available from Austria Microsystems, AG. The position sensor is interfaced with the controller to provide an absolute positioning system for determining the absolute angular position of the end effector 2300, either directly or indirectly. The position sensor is a low voltage and low power component and includes four Hall-effect elements 1228A, 1228B, 1228C, 1228D in an area 1230 of the position sensor 1200 that is located above the magnet 1202 (FIG. 11). A high resolution ADC 1232 and a smart power management controller 1238 are also provided on the chip. A CORDIC processor 1236 (for Coordinate Rotation Digital Computer), also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits and magnetic field information are transmitted over a standard serial communication interface such as an SPI interface 1234 to the controller 1104. The position sensor 1200 provides 12 or 14 bits of resolution. The position sensor 1200 may be an AS5055 chip provided in a small QFN 16-pin 4×4×0.85 mm package.

With reference to FIGS. 1-4 and 10-21, the position of the articulation joint 2270 and the position of the I-beam 178 (FIG. 4) can be determined with the absolute position feedback signal/value from the absolute positioning system 1100. In one aspect, the articulation angle can be determined fairly accurately based on the drive member 120 of the surgical instrument 10. As described above, the movement of the longitudinally movable drive member 120 (FIG. 2) can be tracked by the absolute positioning system 1100 wherein, when the articulation drive is operably coupled to the firing member 220 (FIG. 3) by the clutch assembly 400 (FIG. 3), for example, the absolute positioning system 1100 can, in effect, track the movement of the articulation system via the drive member 120. As a result of tracking the movement of the articulation system, the controller of the surgical instrument can track the articulation angle θ of the end effector 2300, such as the end effector 2300, for example. In various circumstances, as a result, the articulation angle θ can be determined as a function of longitudinal displacement DL of the drive member 120. Since the longitudinal displacement DL of the drive member 120 can be precisely determined based on the absolute position signal/value provided by the absolute positioning system 1100, the articulation angle θ can be determined as a function of longitudinal displacement DL.

In another aspect, the articulation angle θ can be determined by locating sensors on the articulation joint 2270. The sensors can be configured to sense rotation of the articulation joint 2270 using the absolute positioning system 1100 adapted to measure absolute rotation of the articulation joint 2270. For example, the sensor arrangement 1102 comprises a position sensor 1200, a magnet 1202, and a magnet holder 1204 adapted to sense rotation of the articulation joint 2270. The position sensor 1200 comprises one or more than one magnetic sensing elements such as Hall elements and is placed in proximity to the magnet 1202. The position sensor 1200 described in FIG. 12 can be adapted to measure the rotation angle of the articulation joint 2270. Accordingly, as the magnet 1202 rotates, the magnetic sensing elements of the position sensor 1200 determine the absolute angular position of the magnet 1202 located on the articulation joint 2270. This information is provided to the microcontroller 1104 to calculate the articulation angle of the articulation joint 2270. Accordingly, the articulation angle of the end effector 2300 can be determined by the absolute positioning system 1100 adapted to measure absolute rotation of the articulation joint 2270.

In one aspect, the firing rate or velocity of the I-beam 178 may be varied as a function of end effector 2300 articulation angle to lower the force-to-fire on the firing drive system 80 and, in particular, the force-to-fire of the I-beam 178, among other components of the firing drive system 80 discussed herein. To adapt to the variable firing force of the I-beam 178 as a function of end effector 2300 articulation angle, a variable motor control voltage can be applied to the motor 82 to control the velocity of the motor 82. The velocity of the motor 82 may be controlled by comparing the I-beam 178 firing force to different maximum thresholds based on articulation angle of the end effector 2300. The velocity of the electric motor 82 can be varied by adjusting the voltage, current, pulse width modulation (PWM), or duty cycle (0-100%) applied to the motor 82, for example.

Control of Motor Velocity of a Surgical Stapling and Cutting Instrument Based on Angle of Articulation During use of a motorized surgical stapling and cutting instrument it is possible that the end effector may articulate or further articulate undesirably due to externally applied loads. Therefore, it may be desirable to maintain the articulation of the end effector stationary and prevent articulation or further articulation of the end effector due to the externally applied loads.

Various aspects described herein are directed to surgical instruments comprising distally positioned, rotatable and articulatable jaw assemblies. The jaw assemblies may be utilized in lieu of or in addition to shaft articulation. For example, the jaw assemblies may be utilized to grasp, staple, and cut tissue.

With reference to FIGS. 13 and 14, in one aspect, a surgical instrument 2500 may comprise an end effector 2502 comprising a staple cartridge 2518 and anvil 2516 at a distal end and an I-beam 2514 comprising a cutting edge 2509 to sever tissue. The jaw assembly may be articulatable and may pivot about a longitudinal axis of the instrument shaft. The jaw assembly may pivot about a wrist pivot axis from a first position where the jaw assembly is substantially parallel to the staple cartridge 2518 to a second position where the jaw assembly is not substantially parallel to the staple cartridge 2518. In addition, the jaw assembly may comprise first and second jaw members that are pivotable about a second axis or jaw pivot axis. The jaw pivot axis may be substantially perpendicular to the wrist pivot axis. In some aspects, the jaw pivot axis itself may pivot as the jaw assembly pivots about the wrist pivot axis. The first and second jaw members may be pivotably relative to one another about the jaw pivot axis such that the first and second jaw members may "open" and "close." Additionally, in some aspects, the first and second jaw members are also pivotable about the jaw pivot axis together such that the direction of the first and second jaw members may change.

In one aspect, a surgical instrument 2500 may include an end effector 2502, an articulation joint and an articulation member. The articulation member may be translatable relative to the end effector 2502 a distance from a proximal position to a distal position, wherein the translation of the articulation member causes the articulation joint to articulate. The surgical instrument 2500 may include a motor 2504 operable to translate the articulation member along the distance from the proximal position to the distal position. The motor 2504 may include an engaged condition, a disengaged condition, and a hold condition. The surgical instrument 2500 may further include a control circuit 2510 coupled to the motor 2504 and a position sensor 2534 coupled to the control circuit 2510. The position sensor 2534 may be configured to detect a position of the articulation member along at least a portion of the distance. The control circuit 2510 may be configured to receive position input from the position sensor 2534 indicative of an articulation position of the articulation member. The control circuit 2510 may identify a predetermined threshold corresponding to the articulation position of the articulation member. The control circuit 2510 may determine a control action of the motor 2504, when the motor 2504 is in the disengaged condition, in response to a movement of the articulation member that exceeds the predetermined threshold. The control circuit 2510 may control the movement of the articulation member, wherein controlling the movement of the articulation member comprises engaging the motor 2504 to the hold condition.

One or more of the following features may be included. The control circuit 2510 may be configured to maintain the articulation position in response to the movement of the articulation member that exceeds the predetermined threshold. In maintaining the articulation position, the control circuit may supply pulse width modulation (PWM) of the current (e.g., the motor drive signal 2514) to the motor 2504 in the hold condition to resist the movement of the articulation member. The motor 2504 may include a DC brushed motor. The control circuit 2510 may be configured to inner connect leads to the DC brushed motor when the motor 2504 is in the hold condition. The control circuit 2510 may include a forward condition, a coast condition, and a brake condition. When the control circuit 2510 is in the forward condition, the DC motor is in the engaged condition. When the control circuit 2510 is in the coast condition, the DC motor is in the disengaged condition. When the control circuit 2510 is in the brake condition, the DC motor is in the hold condition. The control circuit 2510 may include a first switch, a second switch, a third switch, and a fourth switch. When the control circuit 2510 is in the forward condition, the second switch and the third switch are in a closed configuration and the first switch and the fourth switch are in an open configuration. When the control circuit is in the brake condition, the first switch and the second switch are in a closed configuration and the third switch and the fourth switch are in an open configuration. When the control circuit 2510 is in the coast condition, the first switch, the second switch, the third switch, and the fourth switch are in an open configuration.

In one aspect, a surgical instrument 2500 may include an end effector 2502 and a rotatable shaft assembly. The rotatable shaft assembly may include a longitudinal axis, a rotational position sensor 2534, and a gear assembly. The rotational position sensor 2534 may be configured to measure the rotation of the rotatable shaft assembly around the longitudinal axis. The surgical instrument 2500 may include a motor 2504 operably connected to the gear assembly of the rotatable shaft assembly. The motor 2504 may be configured to apply a rotary force to rotate the gear assembly. The rotation of the gear assembly rotates the rotatable shaft assembly around the longitudinal axis. The surgical instrument 2500 may further include a control circuit 2510 coupled to the motor 2504. The control circuit 2510 may be configured to monitor a rotational position of the rotatable shaft assembly based on a signal from the rotational position sensor 2534. The control circuit 2510 may also identify a predetermined threshold corresponding to the rotational position of the rotatable shaft assembly. The control circuit 2510 may further determine a control action of the motor 2504 in response to rotational movement of the rotatable shaft assembly that exceeds the predetermined threshold. The control circuit 2510 may control the rotation of the rotatable shaft assembly, wherein controlling the rotation of the rotatable shaft assembly may include resisting the rotation of the rotatable shaft assembly around the longitudinal axis.

One or more of the following features may be included. The control circuit may be configured to maintain a rotational position of the rotatable shaft assembly in response to rotation of the rotatable shaft assembly around the longitudinal axis that exceeds the predetermined threshold. Maintaining the rotational position may include suppling PWM of the current to the motor 2504 to resist the rotation of the rotatable shaft assembly. The motor 2504 may include a DC brushed motor. The control circuit 2510 may be configured to inner connect leads to the DC brushed motor when the motor 2504 to resist the rotation of the rotatable shaft assembly beyond the predetermined threshold.

In one aspect, a surgical instrument 2500 may include a longitudinal shaft assembly. The longitudinal shaft assembly may include a rotatable shaft portion comprising a longitudinal axis and a drive gear and an articulation joint. The drive gear may be configured to rotate about the longitudinal axis. The articulation joint may include an articulation gear. The surgical instrument 2500 may further include a drive assembly. The drive assembly may include a motor 2504, a control circuit 2510 and a drive member. The motor 2504 may include a drive output. The control circuit 2510 may be configured to control the motor 2504. The drive member may be operably connected to the drive output. When the control circuit 2510 is in a rotational condition, the drive member is operably connected to the drive gear of the rotatable shaft portion. When the control circuit 2510 is in an articulation condition, the drive member is operably connected to the articulation gear of the articulation joint. The surgical instrument 2500 may further include an energy source 2512. The control circuit 2510 may comprise an engaged condition, a disengaged condition, and a dynamic brake condition. When the control circuit 2510 is in the engaged condition, the control circuit 2510 supplies the energy source 2512 to the motor 2504 in a series circuit configuration. When the control circuit 2510 is in the disengaged condition, the control circuit 2510 disconnects the energy source 2512 from the motor 2504. When the control circuit 2510 is in the dynamic brake condition, the control circuit 2510 places the energy source 2512 in a parallel circuit condition with the motor 2504.

One or more of the following features may be included. When the control circuit 2510 is in the rotational condition and the dynamic brake condition, the control circuit 2510 may be configured to monitor a rotational position of the rotatable shaft portion based on a signal from a rotational position sensor 2534. The control circuit 2510 may identify a predetermined threshold corresponding to a rotational position of the rotatable shaft portion. The control circuit 2510 may determine a control action of the motor 2504 in response to rotational movement of the rotatable shaft portion that exceeds the predetermined threshold. The control circuit 2510 may control the rotation of the rotatable shaft portion, wherein controlling the rotation of the rotatable shaft portion comprises resisting the rotation of the rotatable shaft portion around the longitudinal axis. When the control circuit 2510 is in the articulation condition and the dynamic brake condition, the control circuit may be configured to monitor an articulation position of the articulation joint based on a signal from an articulation position sensor 2534. The control circuit 2510 may identify a predetermined threshold corresponding to an articulation position of the articulation joint. The control circuit 2510 may determine a control action of the motor 2504 in response to articulation of the articulation joint that exceeds the predetermined threshold. The control circuit 2510 may control the articulation of the articulation joint, wherein controlling the articulation of the articulation joint comprises resisting the articulation of the articulation joint. The motor 2504 may include a DC brushed motor, and the energy source 2512 may include a battery.

In various aspects, the surgical instrument 2500 can include a single motor 2504 and a clutch or gear assembly. The single motor 2504 can be configured to articulate the end effector 2502, rotate the shaft of the surgical instrument 2500, and translate the firing member of the surgical instrument 2500. A gear or clutch system permits the motor 2504 to transfer its power to the various functions of the surgical instrument 2500. In one aspect, the motor 2504 and the clutch assembly may be configured to engage multiple surgical instrument 2500 functions at the same time. This permits, for example, the surgical instrument 2500 to maintain a dynamic hold or resistance condition with regard to the articulation or rotation of the end effector 2502 and shaft, while allowing the firing of the firing member. In another aspect, the surgical instrument 2500 can include separate motors 2504 for articulation of the end effector 2502, rotation of the shaft, and firing of the end effector 2502.

Reference will now be made in detail to several aspects, including aspects showing example implementations of manual and robotic surgical instruments 2500 with end effectors 2502 comprising sealing and cutting elements. Wherever practicable similar or like reference numbers may be used in the figures and may indicate similar or like functionality. The figures depict example aspects of the disclosed surgical instruments and/or methods of use for purposes of illustration only. Alternative example aspects of the structures and methods illustrated herein may be employed without departing from the scope of this disclosure.

Figure 22:
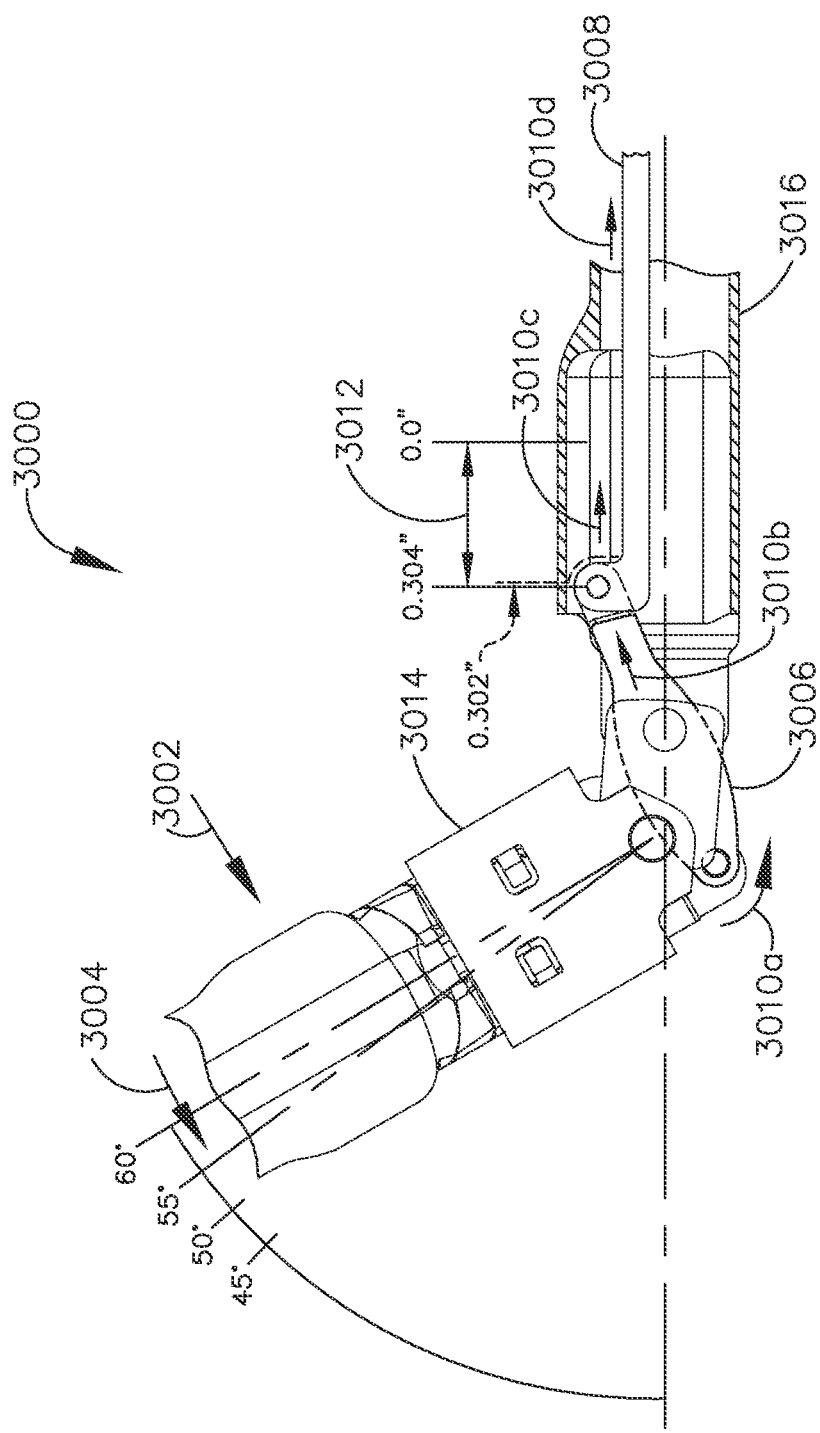
FIG. 22 depicts an example of an articulation mechanism for articulating an end effector of a surgical instrument according to one aspect of this disclosure.

FIG. 22 depicts an example of an articulation mechanism 3000 for articulating an end effector of a surgical instrument according to one aspect of this disclosure. With reference also to FIG. 14, the articulation mechanism 3000 includes an articulation joint 3006 which permits a distal arm 3014 of the surgical instrument 2500 to articulate or pivot with respect to a proximal arm 3016 of the surgical instrument 2500. The articulation joint 3006 may be articulated through the actuation of the articulation rod/member 3008. The articulation rod/member 3008 can have a degree of displacement 3012. In one aspect, the overall degree of displacement can be 0.304". However, in other aspects the degree of displacement 3012 can be greater or less. The articulation rod/member 3008 may be operably coupled to a motor 2504 or actuator which is controlled by a control circuit 2510. In controlling the desired articulation of the distal arm 3014 relative to the proximal arm 3016 of the surgical instrument 2500, the surgical instrument 2500 may include sensors 2534 to detect the articulational movement. In one aspect, a distal arm sensor may detect the angle of articulation of the distal arm 3014 relative to the proximal arm 3016 of the surgical instrument 2500. The distal arm sensor may communicate to the control circuit 2510 through various communications means, for example, wired or wireless means, the location of the distal arm 3014 relative to the proximal arm 3016 of the surgical instrument 2500. In addition, or in the alternative, the surgical instrument 2500 may include an articulation joint sensor 2534 that detects and communicates the articulated position of the distal arm 3014 relative to the proximal arm 3016 to the control circuit 2510. Additionally, or in the alternative, the surgical instrument 2500 may include an articulation rod sensor that measures and detects the displacement of the articulation member 3008 as discussed in reference with FIGS. 16-21. The displacement measured by the articulation sensor 2534 can be related to the articulation displacement of the distal arm 3014 and communicated to the control circuit 2510.

In operation, the articulation mechanism 3000 of the surgical instrument 2500 can be articulated by a technician to permit the end effector 2502 of the surgical instrument 2500 to reach a desired location within a patient. Once the desired articulation is achieved, the motor 2504 can be deactivated and placed into a hold condition by the control circuit 2510 to allow the articulation mechanism 3000 to maintain its articulated position. During surgery, outside resistance or force 3002 may act upon the end effector or the distal arm 3014 of the surgical instrument. With the motor in the hold condition, the control circuit 2510 can monitor the articulation angle 3004 of the end effector 2502 and distal arm 3014 via the various sensors described above. If the change in the articulation angle 3004 exceeds a predetermined threshold of articulation, the control circuit 2510 can activate a holding feature of the motor 2504 to proportionally resist the translated forces 3010*a-d* acting on the surgical instrument 2500.

Figure 23:
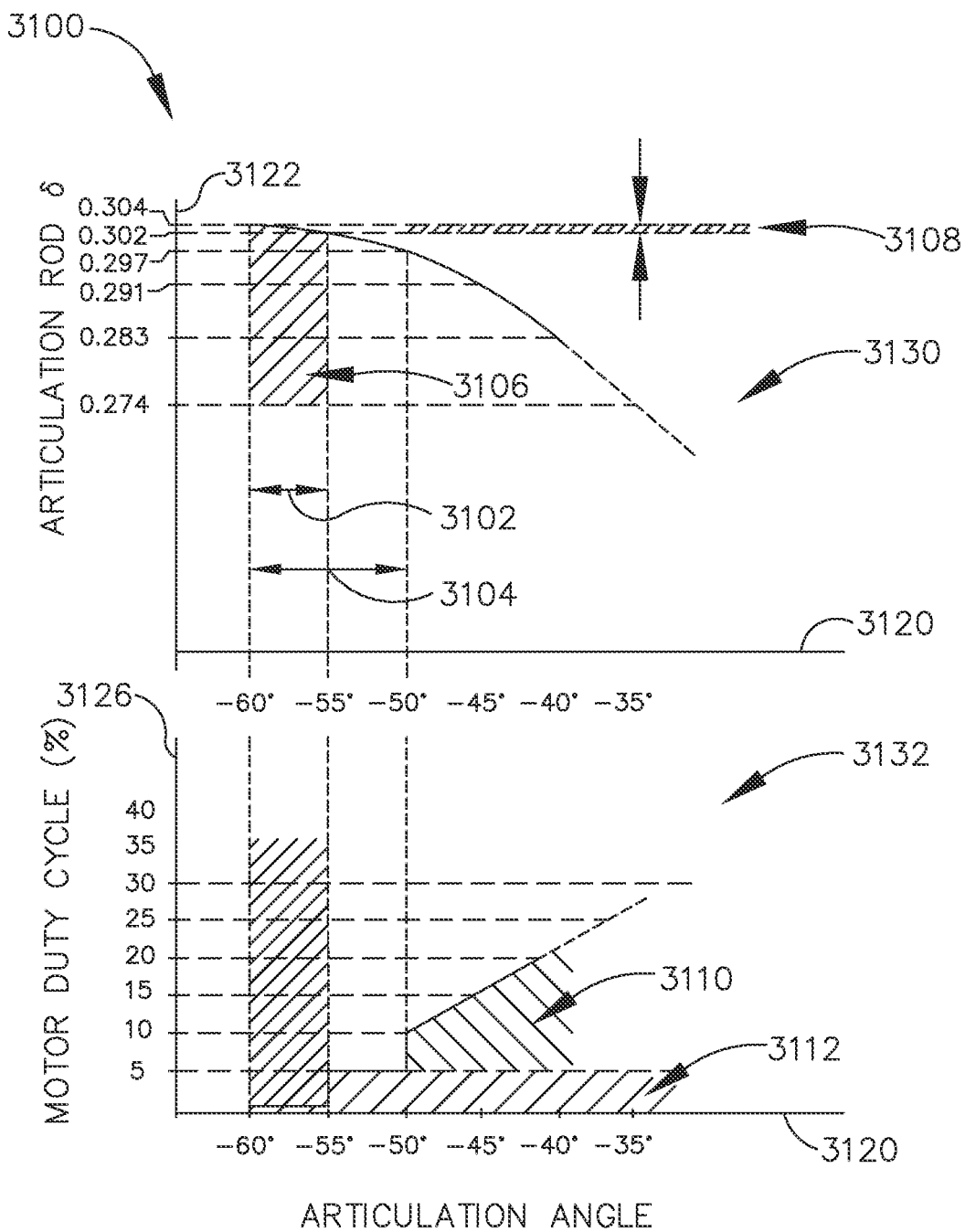
FIG. 23 is a graph of firing rod angle and motor duty cycle as a function of the articulation angle of the end effector according to one aspect of this disclosure.

FIG. 23 illustrates a graph 3100 of firing rod angle and motor duty cycle as a function of the articulation angle of the end effector according to one aspect of this disclosure. The top graph 3130 depicts firing rod displacement ($\delta$) along the vertical axis 3122 as a function of articulation angle in degrees (°) along the horizontal axis 3120. With reference also to FIG. 14, when the articulation rod/member 3008 is within a predetermined range of displacement 3108, the control circuit 2510 triggers a deactivated condition of the motor 2504. The predetermined range of displacement 3108 of the articulation rod 3008 corresponds to an allowable range of articulation angles 3102 for articulation of the distal arm 3014. When the predetermined range 3108 and/or the allowable range 3102 are exceeded, the control circuit 2510 activates a resistive hold mode of the motor 2504 to resist or counteract forces being applied to the distal arm 3014 and holds the distal arm 3014 and articulation rod 3018 within the predetermined/allowable ranges 3108, 3102.

The bottom graph 3132 in FIG. 23 depicts motor duty cycle (%) along the vertical axis 3126 as a function of articulation angle in degrees (°) along the horizontal axis 3120. As the degree of the articulation angle of the distal arm 3104 increasingly departs the predetermined threshold of articulation angles 3102 due to externally applied forces, the motor 2504 applies a force to resist the undesired articulation for an extended duration. In other word, the motor duty cycle increases as the articulation angle increasingly departs from predetermined threshold 3102. By way of example, the bottom graph 3132 in FIG. 23 represents an end effector 2502 with a desired articulation angle of −60°. The allowable range 3102 of articulation angles extends to −55°. When the end effector 2502 is articulated to a degree that falls within the allowable range 3102, the motor duty cycle is minimal. However, as the articulation angle exceeds the boundaries of the allowable range 3102, the control circuit 2510 begins to respond in a more vigorous fashion by activating the resistive hold mode of the motor 2504, thereby increasing the motor duty cycle. In addition to increasing the motor duty cycle, articulating an end effector 2502 to a degree that departs from the allowable range 3102 can increase the driving force, or torque, of the motor 2504. Shaded region 3112 indicates an initial restraint required of the motor 2504 as the articulation angle begins to exceed the boundaries of the allowable range 3102. Shaded region 3110 indicates a progressive restraint required of the motor 2504 as the articulation angle continues to exceed the boundaries of the allowable range 3102. In one aspect, the energy applied to the motor 2504 to resist the externally applied forces does not induce further articulation and/or movement of the end effector 2502, but prevents any additional undesired movement outside of the predetermined range 3102. In other aspects of this disclosure, the energy applied to the motor 2504 to resist the externally applied force can cause the end effector 2502 to articulate or rotate back to the previously set position.

Figure 24:
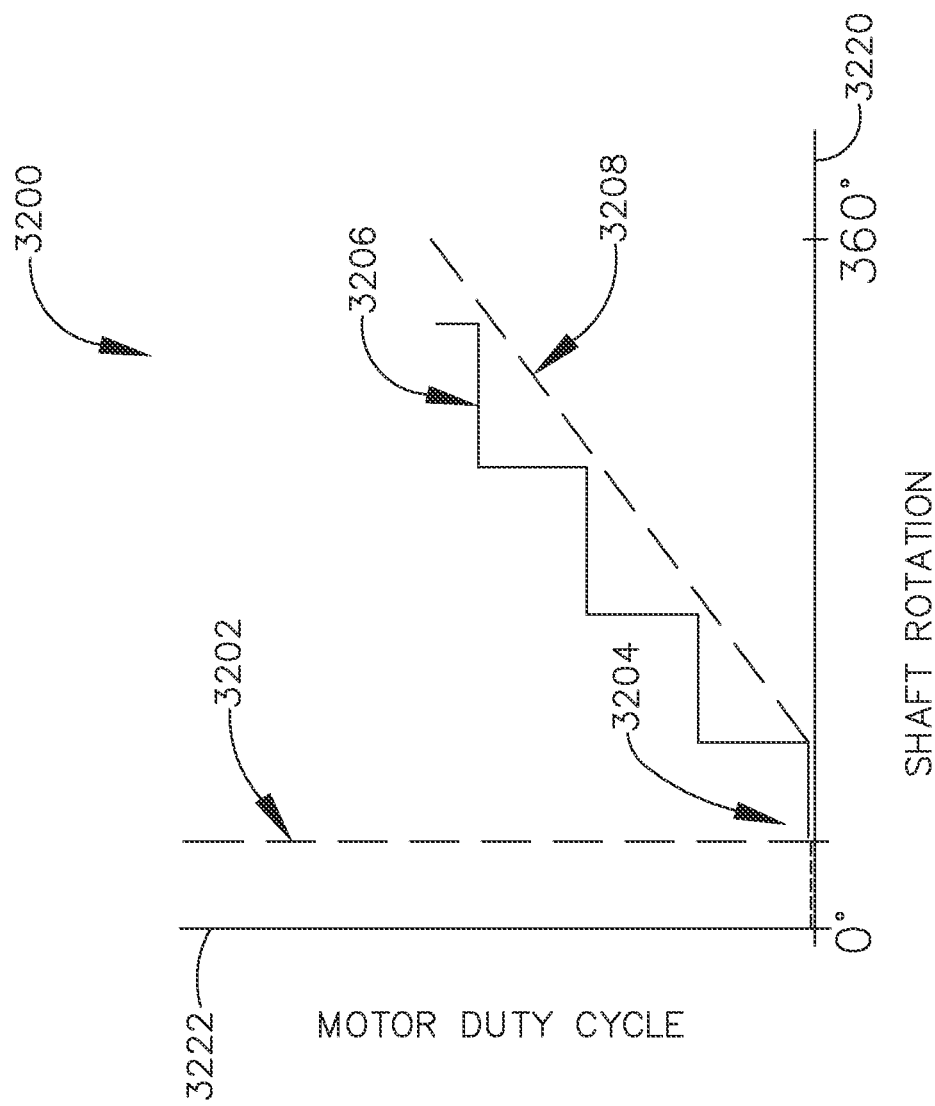
FIG. 24 is a graph of motor duty cycle as a function of the shaft rotation of a surgical instrument according to one aspect of this disclosure.

FIG. 24 illustrates a graph 3200 of motor duty cycle as a function of shaft rotation according to one aspect of this disclosure according to one aspect of this disclosure. The graph 3200 depicts motor duty cycle along the vertical axis 3222 as a function of shaft rotation in degrees (°) along the horizontal axis 3220. With reference also to FIG. 14, the control circuit 2510 permits an initial rotation threshold 3202 before activating the hold features of the motor 2504. In one aspect, the hold features include current modulation proportional to the resistance required to restrict or limit the shaft rotation. As the required motor resistance 3208 increases along with the displacement of the shaft rotation, the current 3204 can be increased. Thus the motor resistance can be increased in a stepwise 3206 fashion.

In one aspect, the leads to a DC motor of the surgical instrument 2500, when in the disengaged condition, can be inner connected. The inner connection of the DC motor leads can result in an internal magnetic resistance within the motor to prevent inadvertent back driving of the motor 2504 by externally applied forces applied to the end effector 2502. Dynamic and regenerative braking can be achieved with PWM DC motor, brushed, brushless, and/or stepper motors to hold the portions of articulation of the desired location of the end effector 2502. Additionally, or in the alternative, the various dynamic braking mechanisms can be combined with mechanical locks to maintain the desired articulational or rotational position of the end effector. In addition, or in the alternative, the natural resistance of a motor 2504 with shorted coils can be combined with a mechanical brake or lock as a passive method to perform a station keeping function of an articulated or rotated system.

Figure 25:
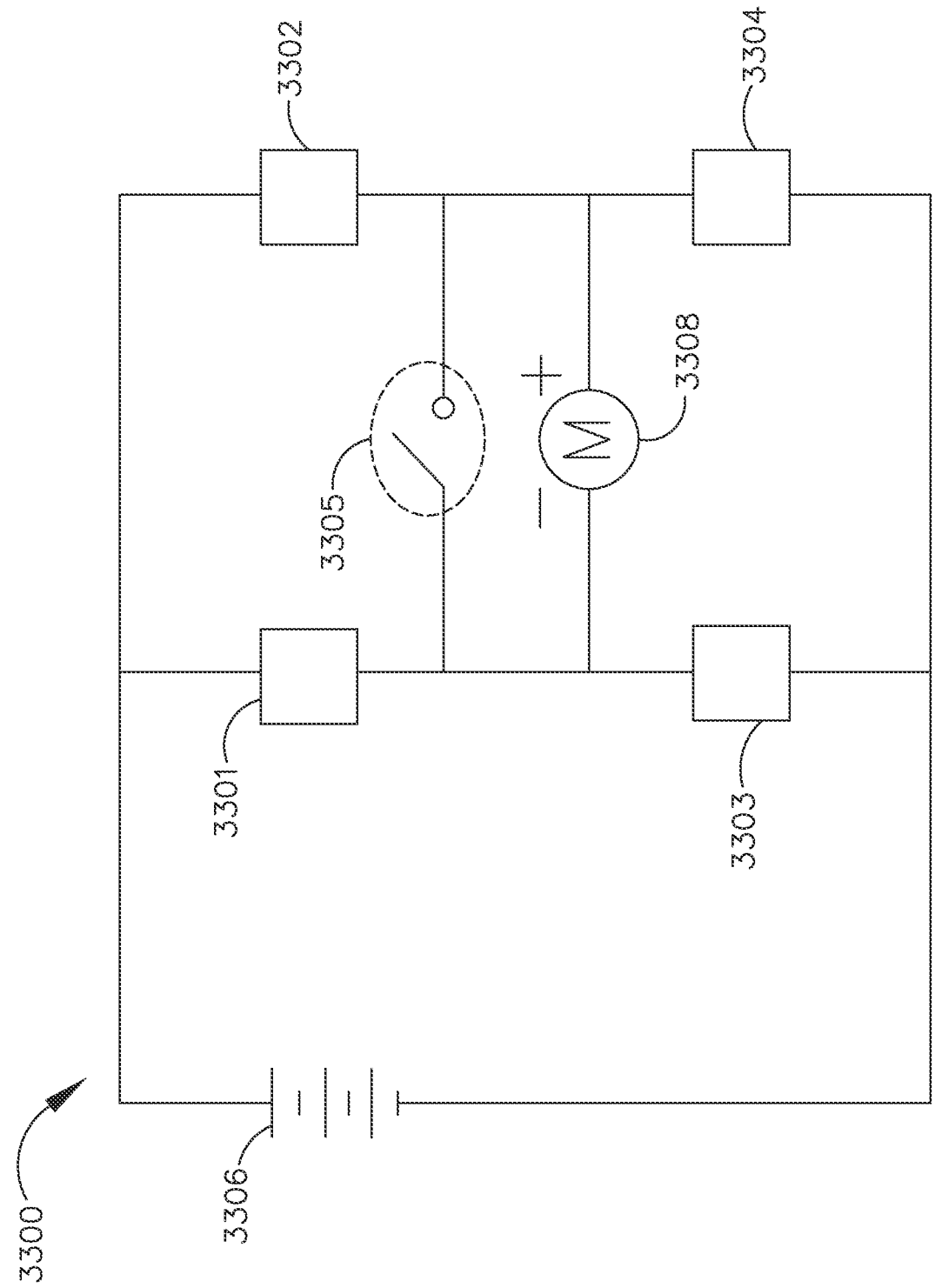
FIG. 25 is a circuit diagram and chart illustrating the circuit configurations of a dynamic motor braking system of a surgical instrument according to one aspect of this disclosure.

FIG. 25 illustrates a control circuit 3300 in accordance with the various aspects discussed above according to one aspect of this disclosure. The circuit 3300 includes a power source 3306, a motor 3308, and a plurality of switches 3301, 3302, 3303, 3304. The circuit can further include alternative switch 3305. The switches 3301-3305 each permit the circuit 3300 to be configured to operate the motor 3308 in a forward mode, a reverse mode, a resistance or brake mode, and a coast mode. When the circuit 3300 is in the forward mode, the switches 3301, 3304, and 3305 may be in the open condition while the switches 3302 and 3303 may be in the closed condition. The forward mode allows the motor 3308 and the power source 3306 to be operated in a series configuration with the motor 3308 operating in the forward direction. When the circuit 3300 is in the reverse mode, the switches 3302, 3303, and 3305 may be in the open condition while the switches 3301 and 3304 may be in the closed condition. The reverse mode allows the motor 3308 and the power source 3306 to be operated in a series configuration with the motor 3308 operating in the reverse direction. Table 1, below, illustrates the various circuit 3300 configurations discussed herein.

TABLE 1

Various Circuit Configurations.

| 1 | 2 | 3 | 4 | |
|---|---|---|---|---|
| 0 | 1 | 1 | 0 | Forward |
| 1 | 0 | 0 | 1 | Reverse |
| 0 | 0 | 1 | 1 | Brake (Static Holding Load) |
| 0 | 0 | 0 | 0 | Brake (Switch3305 Closed) |
| 1 | 1 | 0 | 0 | Brake |
| 0 | 0 | 0 | 0 | Coast (Switch 3305 Open) |

1 = Closed; 0 = Open.

In one aspect, the brake mode can use static holding load to provide resistance to outside forces on the articulation or rotation of the distal portion of a surgical instrument. When the circuit 3300 is in the brake mode that provides a static holding load, the switches 3301, 3302, and 3305 may be in the open condition while the switches 3303 and 3304 may be in the closed condition. This brake mode allows the motor 3308 and the power source 3306 to be operated in a static configuration with the circuit configuration creating a static hold. In another aspect, the brake mode can use static holding load to provide resistance to outside forces on the articulation or rotation of the distal portion of a surgical instrument. When the circuit 3300 is in the brake mode that provides a static holding load, the switches 3301, 3302, 3303, 3305 may be in the open condition while the switch 3305 may be in the closed condition. This brake mode allows the motor 3308 to be isolated from the power source 3306. While in this brake mode, the motor 3308 is in a closed loop configuration isolated from the power source with the circuit configuration creating a static hold.

In another aspect, the brake mode can use a dynamic holding load to provide resistance to outside forces on the articulation or rotation of the distal portion of a surgical instrument. When the circuit 3300 is in the dynamic brake mode, the switches 3303, 3304, and 3305 may be in the open condition while the switches 3301 and 3302 may be in the closed condition. This dynamic brake mode allows the motor 3308 and the power source 3306 to be operated in a parallel configuration with the circuit configuration creating a dynamic hold. When forces act upon the motor while in the dynamic brake mode, the parallel configuration of the circuit creates resistance in output of the motor to resist any outside force operating on the motor. In another aspect, the coast mode can allow the motor to freely rotate without any resistance from the circuit. When the circuit 3300 is in the coast mode, the switches 3301, 3302, 3303, 3304, 3305 may be in the open condition. This coast mode allows the motor 3308 and the power source 3306 to be completely disconnect from one another without any resistance created in the motor 3308.

Figure 26:
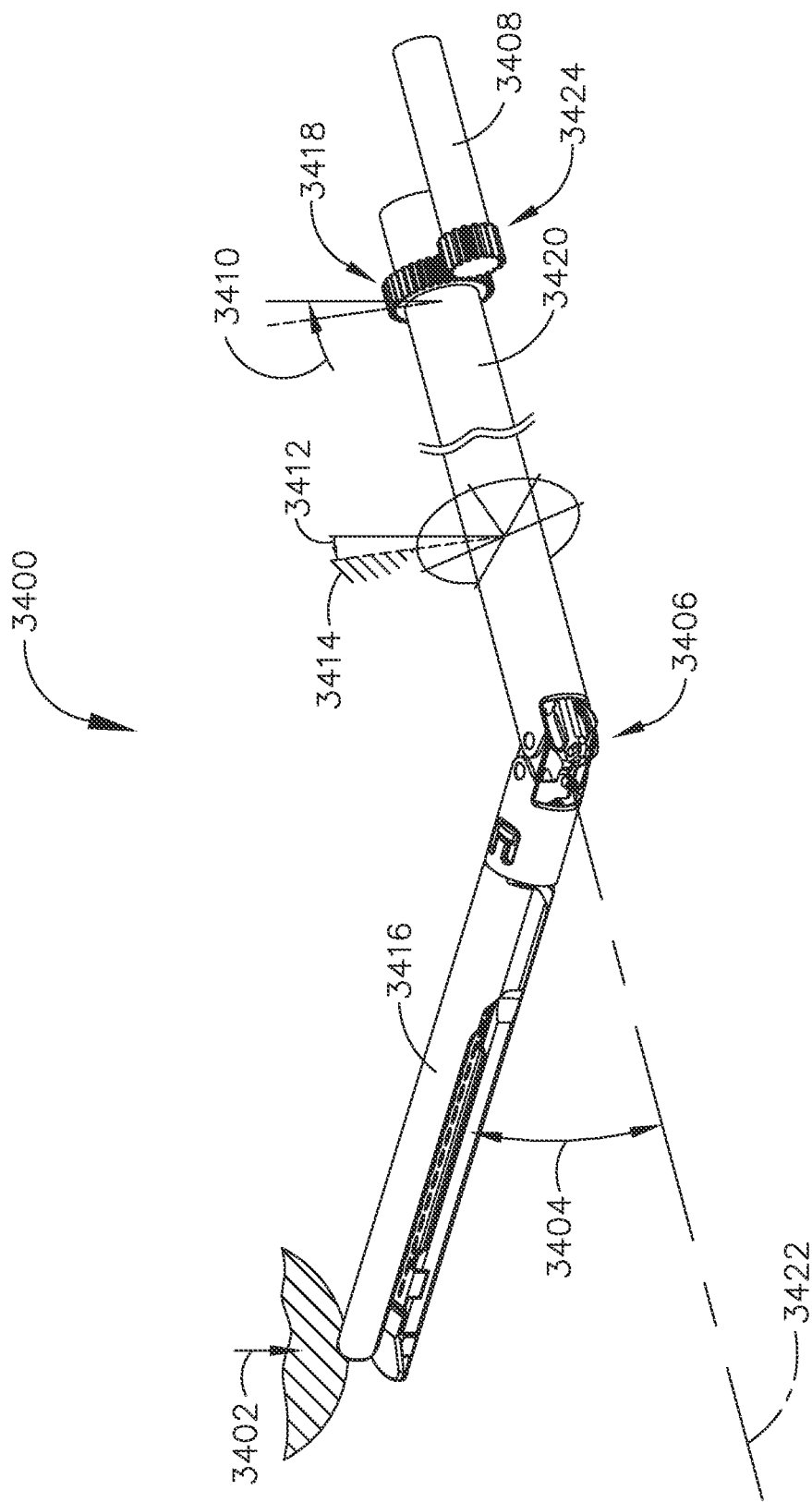
FIG. 26 depicts an example of an articulation mechanism for articulating an end effector of a surgical instrument according to one aspect of this disclosure.

FIG. 26 illustrates a rotatable and articulatable shaft assembly 3400 of a surgical instrument according to one aspect of this disclosure. With reference also to FIG. 25, the shaft assembly 3400 includes a distal end effector portion 3416, a proximal portion 3420, and an articulation mechanism 3406 connecting the distal end effector portion 3416 and the proximal portion 3420. The proximal portion 3420 defines a longitudinal axis 3422. The proximal portion 3420 is configured to rotate about the longitudinal axis 3422. The output of the motor 3308 of the surgical instrument is configured to rotate a rotational drive shaft 3408. The rotational drive shaft includes a drive gear 3424 which operably interfaces with a driven gear 3418 of the proximal portion 3420. As discussed with reference to FIG. 14, the control circuit 2510 can be connected to a rotational sensor 2534 that detects the rotation of the shaft assembly 3400. The shaft assembly 3400 may be permitted to be rotated within a float or gap threshold 3412. However, when an outside force 3402 causes the shaft assembly 3400 to rotate beyond a rotational threshold 3414, the control circuit 2510 can activate a resistance or hold condition on the motor 3308 (2504) as discussed above with respect to FIGS. 22-25. When the control circuit 2510 activates the hold condition, the motor 3308 (2504) may be energized and apply a force 3410 to oppose the outside rotation force 3402. The force 3410 applied by the motor 3308 (2504) may include a passive or active resistance force as discussed above with respect to FIGS. 22-25.

Through the active PWM and current step resistance of the control circuit 2510 and the dynamic and passive resistance of the control circuit configurations, the control circuit 2510 can resist unwanted rotation or articulation of an end effector from outside forces. These hold conditions of the control circuit 2510 permit the end effector to remain within a desired position during a surgical procedure.

Figure 27:
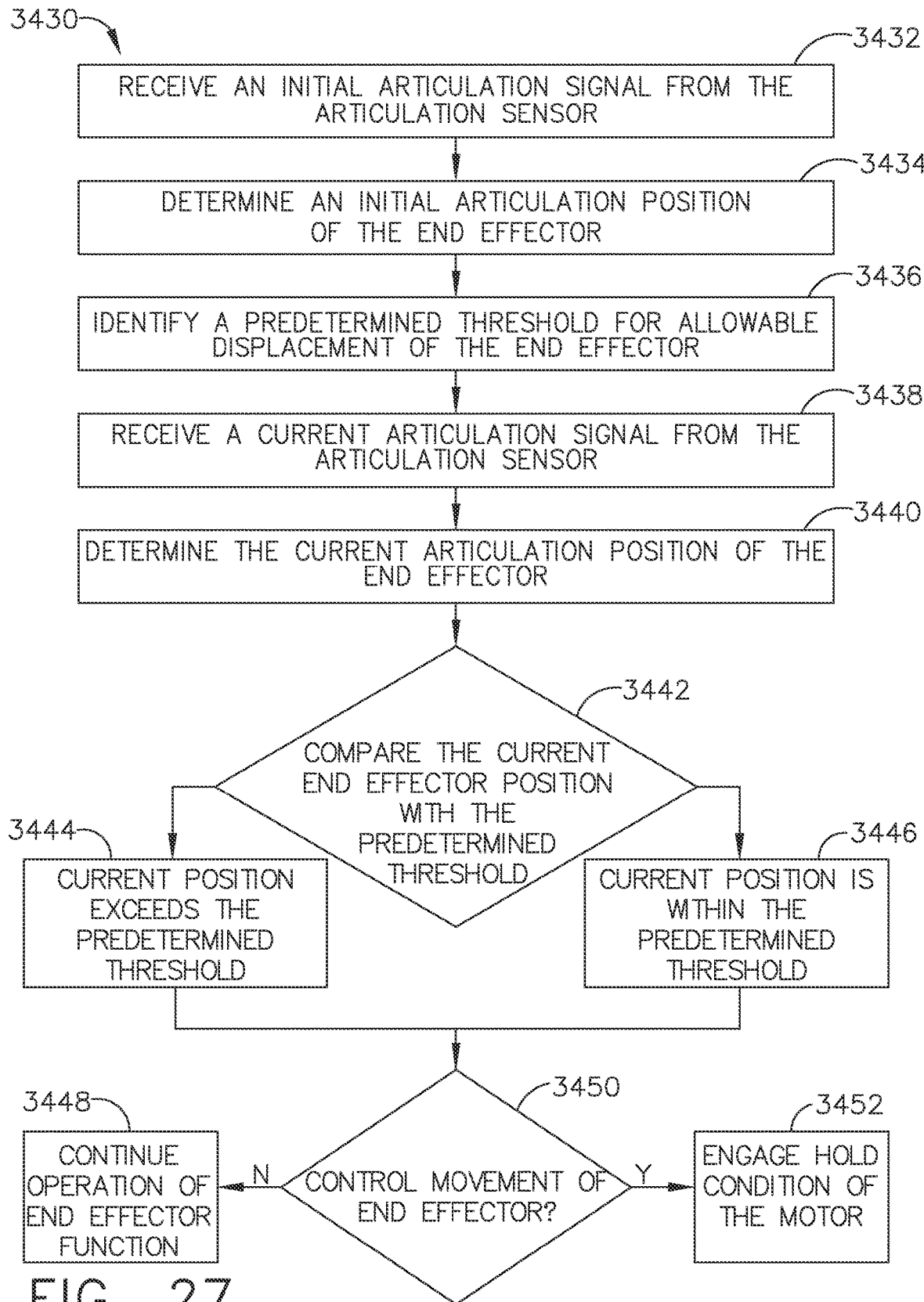
FIG. 27 is a logic flow diagram of a process depicting a control program or logic configuration representing an articulation control program according to one aspect of this disclosure.

FIG. 27 illustrates a logic flow diagram showing one example of a process 3430 that may be executed by the surgical instrument 2500 (e.g., the control circuit 2510) to resist and control the articulation of the end effector 2502 from outside forces. The control circuit 2510 may receive 3432 an initial articulation signal. The initial articulation signal may be received 3432 from the articulation sensor once the end effector 2502 is in a desired articulation position. For example, a clinician may place the end effector 2502 in a desired position and then clamp tissue between the anvil 2516 and staple cartridge 2518, and then actuate the trigger 32 to begin a firing stroke. The trigger 32 may be configured to provide the firing signal to the control circuit 2510 upon actuation.

Once the end effector 2502 is placed in the desired position, the control circuit 2510, in response to the initial articulation signal, may determine 3434 an initial articulation position of the end effector 2502 from the articulation signal. Upon determining 3434 the initial position, the control circuit 2510 may identify 3436 a predetermined threshold for allowable displacement of the end effector 2502. For example, the surgical instrument 2500 may transition from the articulation mode to the firing mode via the transmission 2506. When in the firing mode, the control circuit 2510 can monitor the articulation position of the end effector 2502.

The control circuit 2510 may receive 3438 a current articulation signal. The current articulation signal may be received 3438 from the articulation sensor once the end effector 2502 is in the firing mode to monitor the position of the end effector 2502 during the firing mode. The current articulation signal may be received 3438 from the articulation sensor. The control circuit 2510, in response to the current articulation signal, may determine 3440 a current articulation position of the end effector 2502 from the current articulation signal. The control circuit 2510 may compare 3442 the current articulation position of the end effector 2502 against the initial articulation position and the predetermined threshold for allowable displacement of the end effector 2502. If the current position exceeds the predetermined threshold 3444, then the control circuit 2510 controls 3452 the movement of the end effector 2502 by engaging 3452 the hold condition of the motor 3308 (2504). For example, when the control circuit compares 3512 the current position of the end effector 2502 against the predetermined threshold and the current position exceeds the predetermined threshold, the control circuit 2510 may switch the transmission 2506 from the firing mode to the control mode. When the control circuit 2510 switches into the control mode, the control circuit 2510 engages 3452 the hold condition of the motor 3308 (2504) to resist unwanted movement of the end effector 2502. The hold condition may include any of the hold conditions as discussed above with respect to FIGS. 22-25. When the control circuit 2502 compares 3512 the current position of the end effector 2502 against the predetermined threshold and the current position is within the predetermined threshold 3446, the control circuit 2510 continues 3448 operation of the end effector function, for example, continues operating in the firing mode.

In another aspect, the surgical instrument 2500 may have a second motor. The original motor 3308 (2504) may be configured to operate the articulation of the end effector 2502. The second motor may be configured to operate the firing drive of the end effector 2502. When the surgical instrument comprises two motors, the controlling 3450 can be completed independently of the firing mode.

In another aspect, the surgical instrument 2500 may have a manual firing drive. Where the surgical instrument has a manual firing drive, the motor 3308 (2504) may remain engaged with the articulation mechanism during the firing mode. The motor 3308 (2504) may be configured to operate the articulation of the end effector 2502. When the surgical instrument comprises a manual firing drive, the controlling 3450 can be completed independently of the firing mode.

Figure 28:
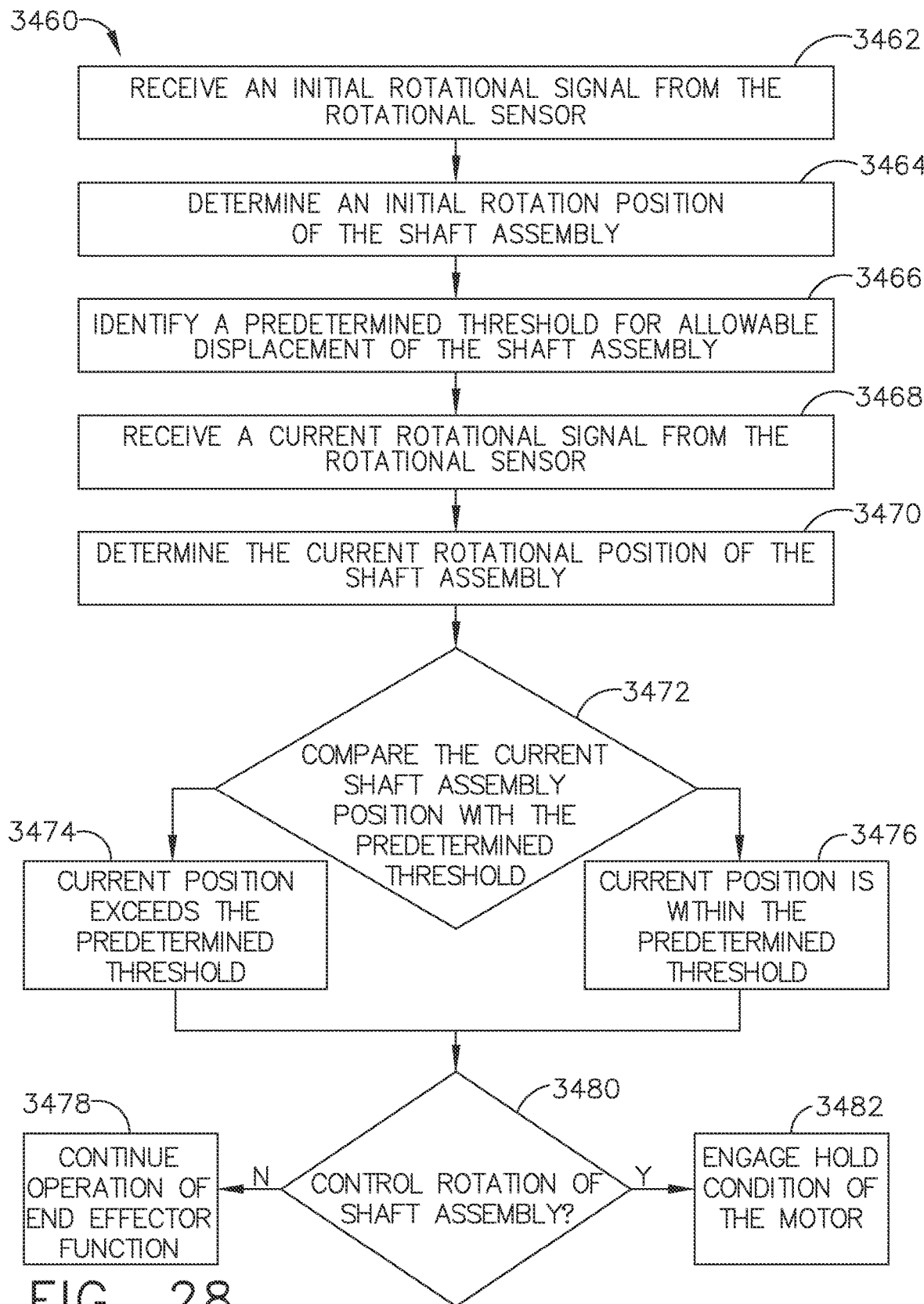
FIG. 28 is a logic flow diagram of a process depicting a control program or logic configuration representing a rotational control program according to one aspect of this disclosure.

FIG. 28 illustrates a logic flow diagram showing one example of a process 3460 that may be executed by the surgical instrument 2500 (e.g., the control circuit 2510) to resist and control the rotation of the shaft assembly 200 from outside forces. The control circuit 2510 may receive an initial rotational signal 3462. The initial rotational signal may be received 3462 from the rotation sensor once the shaft assembly 200 is in a desired rotational position. For example, a clinician may place the shaft assembly 200 in a desired rotational position and then clamp tissue between the anvil 2516 and staple cartridge 2518, and then actuate the trigger 32 to begin a firing stroke. The trigger 32 may be configured to provide the firing signal to the control circuit 2510 upon actuation.

Once the shaft assembly 200 is placed in the desired rotational position, the control circuit 2510, in response to the initial rotational signal, may determine 3464 an initial rotational position of the shaft assembly 200 from the rotational signal. Upon determining 3464 the initial rotational position, the control circuit 2510 may identify 3466 a predetermined threshold for allowable displacement of the shaft assembly 200. For example, the surgical instrument 2500 may transition from the rotational mode to the firing mode via the transmission 2506. When in the firing mode, the control circuit 2510 can monitor the rotational position of the shaft assembly 200.

The control circuit 2510 may receive 3468 a current rotational signal. The current rotational signal may be received 3468 from the rotation sensor once the shaft assembly 200 is in the firing mode to monitor the position of the shaft assembly 200 during the firing mode. The current rotational signal may be received 3468 from a rotation sensor. The control circuit 2510, in response to the current rotational signal, may determine 3470 a current rotational position of the shaft assembly 200 from the current rotational signal. The control circuit 2510 may compare 3472 the current rotational position of the shaft assembly 200 against the initial rotational position and the predetermined threshold for allowable rotational displacement of the shaft assembly 200. If the current rotational position of the shaft assembly 200 exceeds the predetermined threshold 3474, then the control circuit 2510 will control 3480 the rotation of the shaft assembly 200 by engaging 3482 the hold condition of the motor 3308 (2504). For example, when the control circuit compares 3472 the current position of the shaft assembly 200 against the predetermined threshold and the current position exceeds a boundary of the predetermined threshold, the control circuit 2510 may switch the transmission 2506 from the firing mode to the control mode. When the control circuit 2510 switches into the control mode, the control circuit 2510 then engages 3482 the hold condition of the motor 3308 (2504) to resist unwanted rotation of the shaft assembly 200. The hold condition may include any of the hold conditions as discussed above with respect to FIGS. 22-25 and with respect to articulation of the end effector 2502. When the control circuit 2510 compares 3472 the current rotational position of the shaft assembly 200 against the predetermined threshold and the current rotational position is within the predetermined threshold 3476, the control circuit 2510 continues 3478 operation of the end effector function, for example, continues operating in the firing mode.

In another aspect, the surgical instrument 2500 may have a second motor. The original motor 3308 (2504) may be configured to operate the rotation of the shaft assembly 200. The second motor may be configured to operate the firing drive of the end effector 2502. When the surgical instrument comprises two motors, the controlling 3480 can be completed independently of the firing mode.

In another aspect, the surgical instrument 2500 may have a manual firing drive. Where the surgical instrument has a manual firing drive, the motor 3308 (2504) may remain engaged with the transmission 2506 during the firing mode. The motor 3308 (2504) may be configured to operate the rotation of the shaft assembly 200. When the surgical instrument comprises a manual firing drive, the controlling 3480 can be completed independently of the firing mode.

In another aspect, control circuit 2510 of the surgical instrument 2500 may be configured to resist and control the articulation of the articulation mechanism and resist and control the rotation of the shaft assembly 200. The resistance and hold functions of the articulation control and the rotational control may operate independently or cooperate to control the overall spatial position of the end effector 2502.

Various aspects of the subject matter described herein are set out in the following numbered examples:

Example 1. A surgical instrument, comprising: a motor operable to translate an articulation member along a distance from a proximal position to a distal position, wherein the articulation member is translatable relative to an end effector a distance from a proximal position to a distal position, wherein the translation of the articulation member causes an articulation joint to articulate, and wherein the motor comprises an engaged condition, a disengaged condition, and a hold condition; a control circuit coupled to the motor; a position sensor coupled to the control circuit, the position sensor configured to detect a position of the articulation member along at least a portion of the distance; and wherein the control circuit is configured to: receive position input from the position sensor indicative of an articulation position of the articulation member; identify a predetermined threshold corresponding to the articulation position of the articulation member; determine a control action of the motor, when the motor is in the disengaged condition, in response to a movement of the articulation member that exceeds the predetermined threshold; and control the movement of the articulation member, wherein controlling the movement of the articulation member comprises engaging the motor to the hold condition.

Example 2. The surgical instrument of Example 1, wherein the control circuit is configured to maintain the articulation position in response to the movement of the articulation member that exceeds the predetermined threshold.

Example 3. The surgical instrument of Example 2, wherein the control circuit is configured to apply pulse width modulated (PWM) current to the motor in the hold condition to resist the movement of the articulation member.

Example 4. The surgical instrument of Example 1 through Example 3, wherein the motor comprises a DC brushed motor.

Example 5. The surgical instrument of Example 4, wherein the control circuit is configured to inner connect leads to the direct current (DC) brushed motor when the motor is in the hold condition.

Example 6. The surgical instrument of Example 4 through Example 5, wherein the control circuit comprises a forward condition, a coast condition, and a brake condition, wherein when the control circuit is in the forward condition, the DC motor is in the engaged condition, wherein when the control circuit is in the coast condition, the DC motor is in the disengaged condition, and wherein when the control circuit is in the brake condition, the DC motor is in the hold condition.

Example 7. The surgical instrument of Example 6, wherein the control circuit comprises a first switch, a second switch, a third switch and a fourth switch, wherein when the control circuit is in the forward condition, the second switch and the third switch are in a closed configuration and the first switch and the fourth switch are in an open configuration.

Example 8. The surgical instrument of Example 7, wherein when the control circuit is in the brake condition, the first switch and the second switch are in a closed configuration and the third switch and the fourth switch are in an open configuration.

Example 9. The surgical instrument of Example 8, wherein when the control circuit is in the coast condition, the first switch, the second switch, the third switch, and the fourth switch are in an open configuration.

Example 10. A surgical instrument, comprising: a motor configured to couple to a gear assembly of a rotatable shaft assembly, wherein the a rotatable shaft assembly, comprises a longitudinal axis, a rotational position sensor configured to measure the rotation of the rotatable shaft assembly around the longitudinal axis, wherein the motor is configured to apply a rotary force to rotate the gear assembly, and wherein the rotation of the gear assembly rotates the rotatable shaft assembly around the longitudinal axis; a control circuit coupled to the motor, wherein the control circuit is configured to: monitor a rotational position of the rotatable shaft assembly based on a signal from the rotational position sensor; identify a predetermined threshold corresponding to the rotational position of the rotatable shaft assembly; determine a control action of the motor in response to rotational movement of the rotatable shaft assembly that exceeds the predetermined threshold; and control the rotation of the rotatable shaft assembly, wherein controlling the rotation of the rotatable shaft assembly comprises resisting the rotation of the rotatable shaft assembly around the longitudinal axis.

Example 11. The surgical instrument of Example 10, wherein the control circuit is configured to maintain a rotational position of the rotatable shaft assembly in response to rotation of the rotatable shaft assembly around the longitudinal axis that exceeds the predetermined threshold.

Example 12. The surgical instrument of Example 11, wherein the control circuit is configured to apply pulse width modulated (PWM) current to the motor to resist the rotation of the rotatable shaft assembly.

Example 13. The surgical instrument of Example 10 through Example 12, wherein the motor comprises a direct current (DC) brushed motor.

Example 14. The surgical instrument of Example 13, wherein the control circuit is configured to inner connect leads to the DC brushed motor when the motor to resist the rotation of the rotatable shaft assembly beyond the predetermined threshold.

Example 15. A surgical instrument, comprising: a longitudinal shaft assembly, comprising: a rotatable shaft portion comprising a longitudinal axis and a drive gear, wherein the rotatable shaft portion is configured to rotate about the longitudinal axis; and an articulation joint comprising an articulation gear; a drive assembly, comprising: a motor comprising a drive output; a control circuit configured to control the motor; and a drive member operably connected to the drive output, wherein when the control circuit is in a rotational condition, the drive member is operably connected to the drive gear of the rotatable shaft portion, and wherein when the control circuit is in an articulation condition, the drive member is operably connected to the articulation gear of the articulation joint; and a power source; wherein the control circuit comprises an engaged condition, a disengaged condition, and a dynamic brake condition, wherein when the control circuit is in the engage condition, the control circuit supplies the power source to the motor in a series circuit configuration, wherein when the control circuit is in the disengaged condition, the control circuit disconnects the power source from the motor, and wherein when the control circuit is in the dynamic brake condition, the control circuit places the power source in a parallel circuit condition with the motor.

Example 16. The surgical instrument of Example 15, wherein when the control circuit is in the rotational condition and the dynamic brake condition, the control circuit is configured to: monitor a rotational position of the rotatable shaft portion based on a signal from a rotational position sensor; identify a predetermined threshold corresponding to a rotational position of the rotatable shaft portion; determine a control action of the motor in response to rotational movement of the rotatable shaft portion that exceeds the predetermined threshold; control the rotation of the rotatable shaft portion, wherein controlling the rotation of the rotatable shaft portion comprises resisting the rotation of the rotatable shaft portion around the longitudinal axis.

Example 17. The surgical instrument of Example 16, wherein the motor comprises a DC brushed motor, and wherein the power supply comprises a battery.

Example 18. The surgical instrument of Example 15 through Example 17, wherein when the control circuit is in the articulation condition and the dynamic brake condition, the control circuit is configured to: monitor an articulation position of the articulation joint based on a signal from an articulation position sensor; identify a predetermined threshold corresponding to an articulation position of the articulation joint; determine a control action of the motor in response to articulation of the articulation joint that exceeds the predetermined threshold; control the articulation of the articulation joint, wherein controlling the articulation of the articulation joint comprises resisting the articulation of the articulation joint.

Example 19. The surgical instrument of Example 18, wherein the motor comprises a DC brushed motor, and wherein the power supply comprises a battery.

Example 20. The surgical instrument of Example 16 through Example 19, wherein when the control circuit is in the articulation condition and the dynamic brake condition, the control circuit is configured to: monitor an articulation position of the articulation joint based on a signal from an articulation position sensor; identify a predetermined threshold corresponding to an articulation position of the articulation joint; determine a control action of the motor in response to articulation of the articulation joint that exceeds the predetermined threshold; control the articulation of the articulation joint, wherein controlling the articulation of the articulation joint comprises resisting the articulation of the articulation joint.

Surgical Instrument with Variable Duration Trigger Arrangement

During use of a motorized surgical stapling and cutting instrument it is possible that maximum current could be triggered by an instantaneous exceeding of a current limit during a predefined zone of a firing stroke of the cutting member or a closure stroke of an anvil. Nevertheless, outside of the predefined zone the current limit may be exceeded over a predefined period to minimize the likelihood that noise within a measurement inadvertently triggers the that maximum current event. Therefore, it may be desirable to set a predefined time period for a triggering event to cause a motor control program to change based on the location of the cutting member or anvil within a firing stroke or a closure stroke.

As described above in connection with FIG. 13-15, a control circuit 2510 may be programmed to control the translation of the I-beam 2514. As the I-beam 2514 translates distally, the knife 2509 contacts and may cut tissue between the anvil 2516 and the staple cartridge 2518. Also, the I-beam 2514 contacts the wedge sled 2513 and pushes it distally, causing the wedge sled 2513 to contact staple drivers 2511. The staple drivers 2511 may be driven up into staples 2505, causing the staples 2505 to advance through tissue and into pockets 2507 defined in the anvil 2516, which shape the staples 2505. The I-beam stroke may comprise a stroke begin position 2527 and a stroke end position 2528. During an I-beam firing stroke, the I-beam 2514 may be advanced distally from the stroke begin position 2527 to the stroke end position 2528.

The control circuit 2510 may generate a motor set point signal 2522. The motor set point signal 2522 may be provided to a motor controller 2508. The motor controller 2508 may comprise one or more circuits configured to provide a motor drive signal 2524 to a motor 2504 to drive the motor 2504. The motor 2504 may receive power from an energy source 2512. The motor 2504 may be mechanically coupled to the I-beam 2514 via a transmission 2506. The transmission 2506 may include one or more gears or other linkage components to couple the motor 2504 to the I-beam 2514.

Force acting on the I-beam 2514, the force to fire (FTF), may be determined using various techniques. In one aspect, the I-beam 2514 force may be determined by measuring the motor 2504 current, where the motor 2504 current is based on the load experienced by the I-beam 2514 as it advances distally. As illustrated in FIG. 14, a current sensor 2536 can be included to measure energy provided to the motor 2504. The current sensor 2536 may be positioned between the energy source 2512 and the motor 2504 to measure energy provided by the energy source 2512 to the motor 2504. The Current sensor 2536 may monitor current drawn by the motor 2504 and may provide data describing the current drawn by the motor 2504 to the control circuit 2510. Any suitable current sensor may be used such as, for example, a coulomb sensor. Alternatively, in some examples, the control circuit 2510 may determine the current drawn by the motor 2504 indirectly.

In another aspect, the I-beam 2514 force may be determined by positioning a strain gauge on the drive member 120 (FIG. 2), the firing member 220 (FIG. 2), I-beam 2514 (FIGS. 13 and 14), the firing bar 172 (FIG. 2), and/or on a proximal end of the cutting edge 2509. In yet another aspect, the I-beam 2514 force may be determined by monitoring the actual position of the I-beam 2514 moving at an expected velocity based on the current set velocity of the motor 2504 after a predetermined elapsed period T1 and comparing the actual position of the I-beam 2514 relative to the expected position of the I-beam 2514 based on the current set velocity of the motor 2504 at the end of the period T1, as described in detail in commonly owned U.S. Pat. No. 10,624,633, filed on Jun. 20, 2017, which is incorporated herein by reference in its entirety.

Figure 29:
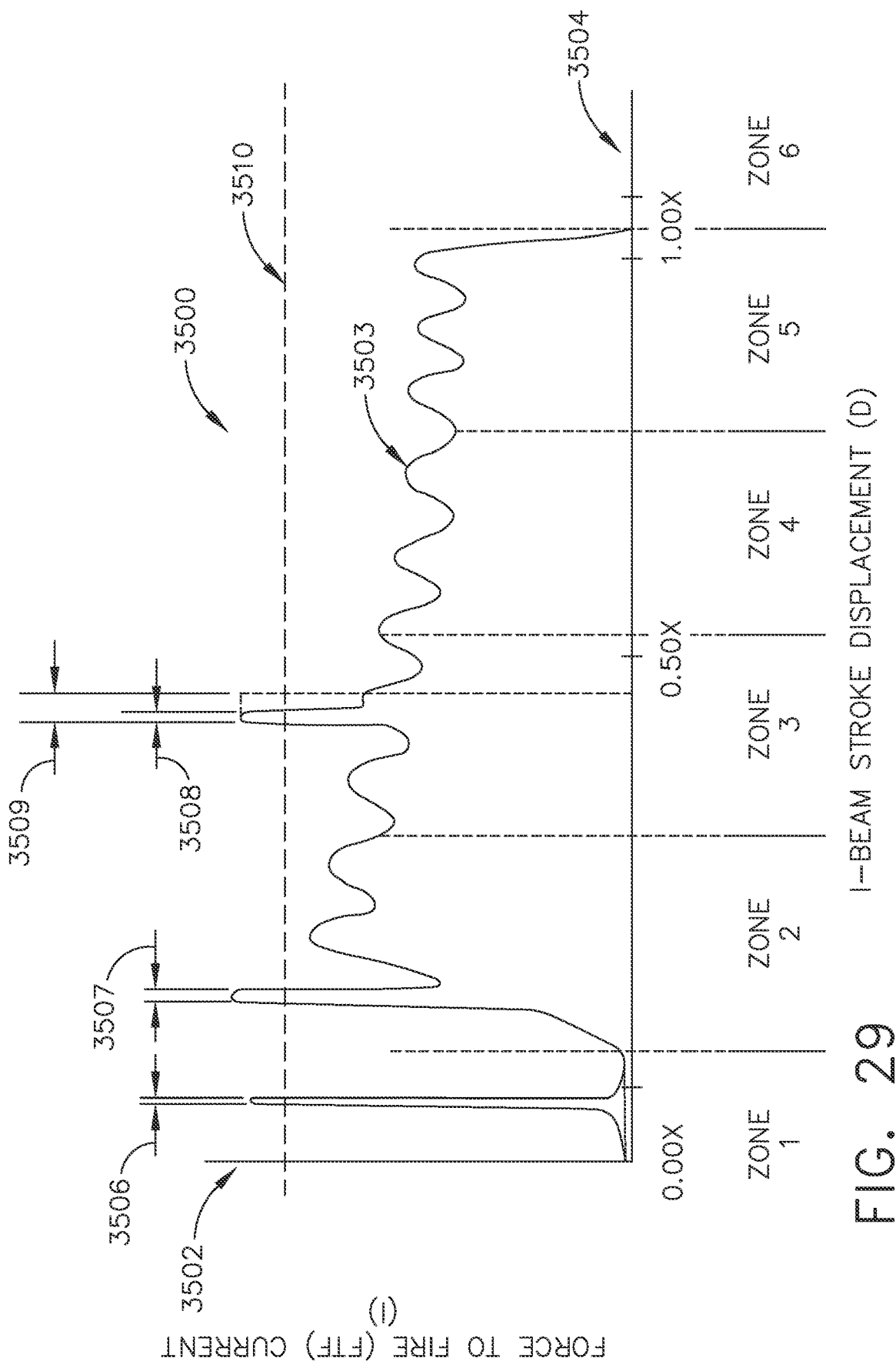
FIG. 29 is a diagram of current (I) drawn by a motor to translate an I-beam of the surgical instrument of FIG. 1 in a firing stroke, which represents the force to fire (FTF) the surgical instrument, as a function of the distance traveled by the I-beam during the firing stroke according to one aspect of this disclosure.

Referring to FIG. 29, a diagram 3500 plots an example 3503 of the force applied to fire (FTF) the surgical instrument 2500, the force to fire (FTF) represented by current (I) drawn by the motor 2504. The force to fire (FTF) can be applied to advance the I-beam 2514 during a firing stroke of the surgical instrument 2500. In the diagram 3500, current (I) drawn by the motor 2504 is plotted as a function of the distance traveled by the I-beam 2514 during a firing stroke. The diagram 3500 comprises two axes. A vertical axis 3502 indicates the current (I) in milliamps, which corresponds to the force to fire (FTF). A horizontal axis 3504 represents I-beam stroke displacement (d) in millimeters.

In some examples, the control circuit 2510 employs a current sensor 2536 to sample the current (I) drawn by the motor 2504 at predetermined intervals along the distance traveled by the I-beam 2514 during the firing stroke. In at least one example, the current (I) is sampled in 1 mm intervals. In other examples, the current (I) drawn by the motor 2504 can be sampled in suitable time intervals during a firing stroke. The control circuit 2510 may develop a digital current signal based on the sampled current (I) data. In various aspects, the sampled current (I) defines data points, wherein each data point constitutes a current (I) value greater than or equal to a predetermined threshold at a predetermined interval.

Spikes in the current (I) signal can be treated as triggering events for various control actions of the surgical instrument 2500. In some examples, current (I) spikes may indicate malfunctions during a firing stroke that require one or more motor control actions. For example, certain current (I) spikes may be triggering events for motor control actions that include dynamic braking and/or retracting of the I-beam 2514. Furthermore, current (I) spikes occurring in particular portions or zones of the firing stroke may trigger a lockout of the surgical instrument 2500, for example. That said, noise in the current (I) signal may trigger unnecessary control actions during a firing stroke. Accordingly, discerning between signal noise and event-triggering current spikes improves the operation of the surgical instrument 2500.

Figure 30:
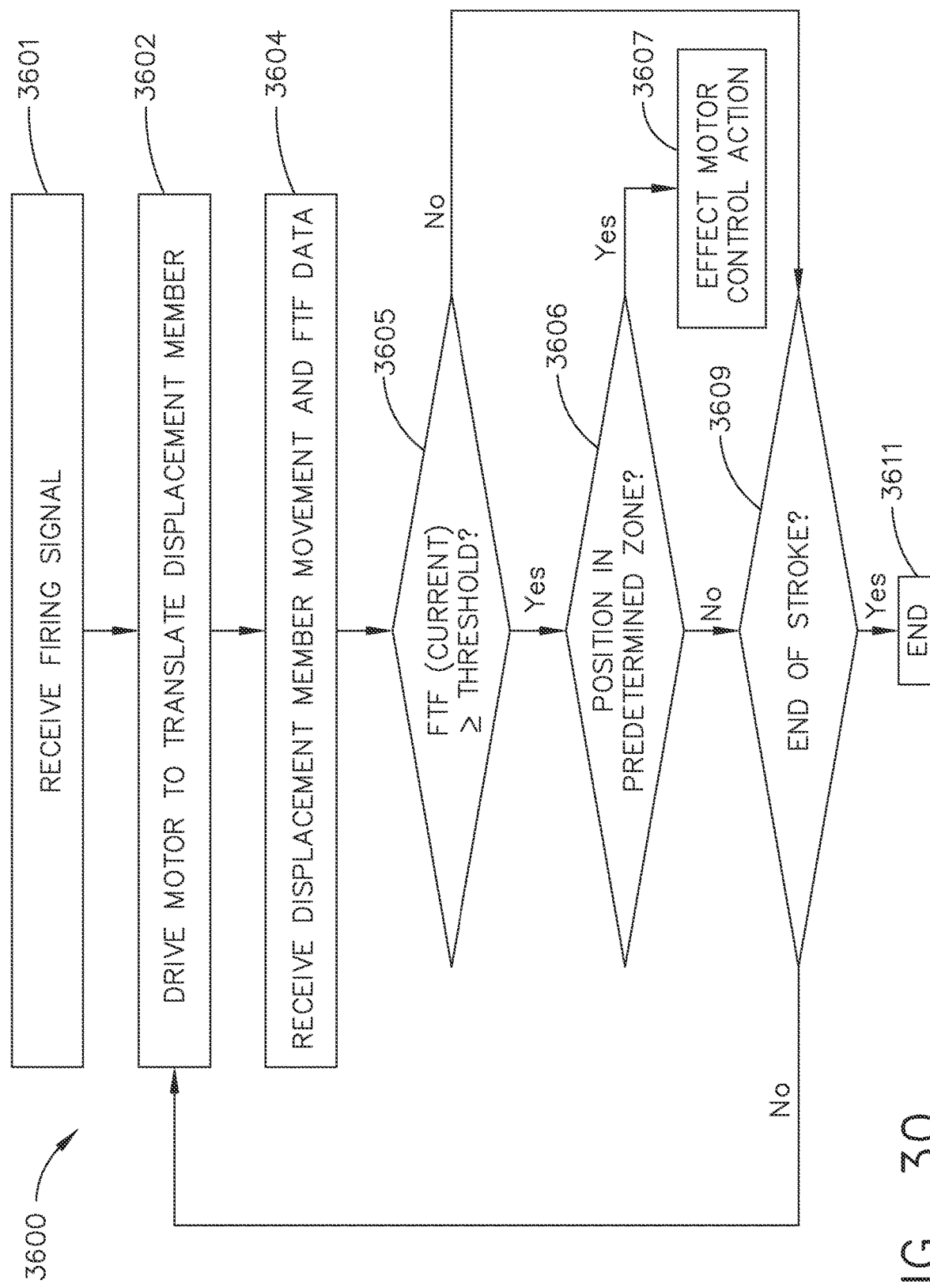
FIG. 30 is a logic flow diagram of a process depicting a control program or logic configuration representing a firing control program according to one aspect of this disclosure.

FIG. 30 is a logic flow diagram of a process 3600 depicting a control program or logic configuration representing a firing control program according to one aspect of this disclosure. The process 3600 may be executed by the surgical instrument 2500 (e.g., the control circuit 2510) to implement an I-beam stroke responsive to tissue conditions and/or staple cartridge type. The control circuit 2510 may receive 3601 a firing signal. The firing signal may be received from the trigger 32 (FIG. 1) or other suitable actuation device. For example, a clinician may place the end effector 2502, clamp tissue between the anvil 2516 and staple cartridge 2518 and then actuate the trigger 32 to begin a I-beam stroke. The trigger 32 may be configured to provide the firing signal to the control circuit 2510 upon actuation.

The control circuit 2510, in response to the firing signal, may provide a motor setting. For example, the motor setting may be a motor set point 2522 provided to the motor controller 2508. The motor controller 2508 may translate the motor set point 2522 into a PWM signal, voltage signal, or other suitable motor drive signal to drive 3602 the motor 2504 to translate the displacement member such as, for example, the I-beam 2414. In some examples, (e.g., when the control circuit 2510 directly generates the motor drive signal 2524), the motor setting may be a motor drive signal 2524 provided directly to the motor 2504. The motor setting may correspond to a particular motor velocity, power, or other suitable variable. In some examples where the motor 2504 is a brushed DC motor, the initial motor setting may be a signal having a constant voltage. In some examples where the motor is a brushless DC motor, the initial motor setting may be a signal or set of signals having a constant phase, duty cycle, etc.

In the example where the displacement member is the I-beam 2514, the control circuit 2510 may receive 3604 I-beam movement data. I-beam movement data may comprise information (e.g., from the position sensor 2534) that describes the position and/or movement of the I-beam 2514. Although receiving I-beam movement data is displayed as a distinct box in the process 3600, the control circuit 2510 may receive I-beam movement data while the I-beam 2514 is in motion. For example, when the position sensor 2534 is an encoder, the control circuit 2510 may receive pulse signals from the encoder while the I-beam 2514 is moving with each pulse signal representing a quantum of motion. Also, in examples where the motor 2504 is a stepper motor, the control circuit 2510 may derive I-beam movement data based on the total number of steps that the control circuit 2510 instructs the motor 2504 to execute.

I-beam movement data may indicate a distance that the I-beam 2514 moved during the initial time period, which may reflect the tissue conditions such as the thickness and/or toughness of the tissue present between the anvil 2516 and the staple cartridge 2518 because different types of tissue will offer different levels of resistance. For example, thicker or tougher tissue may provide more mechanical resistance to the knife and staples. More mechanical resistance may cause the motor 2504 to run more slowly while the initial motor setting is held substantially constant. Similarly, thinner or weaker tissue may provide less mechanical resistance to the knife and staples. This may cause the motor to run faster and traverse more distance while the initial motor setting is held substantially constant.

In some examples, the distance traveled by the I-beam 2514 during a firing stroke is divided into a plurality of zones. In the example 3503 of the diagram 3500, the distance is divided into six zones. In other examples, the distance can be divided into more or less than six zones. In the example 3503 the zones are equal, or at least substantially equal, in length. In other examples, the zones may comprise different lengths.

The control circuit 2510 may also receive 3604 force to fire (FTF) data. Although receiving force to fire (FTF) data is depicted as a distinct function of the process 3600, the control circuit 2510 may receive 3604 the force to fire (FTF) data while the I-beam 2514 is in motion. For example, as described above, the force to fire (FTF) data can be in the form of current (I) drawn by the motor, sampled at predetermined intervals.

The control circuit 2510 determines 3605 whether the force to fire (FTF) is greater than or equal to a fault threshold. As described above, the current (I) drawn by the motor 2504 may represent the force to fire (FTF) applied to the I-beam 2514 during a firing stroke. Through the sampled current (I) values provided by the current sensor 2536, the control circuit 2510 detects current (I) spikes that are greater than or equal to a predetermined threshold 3510 (FIG. 29), which correspond to force to fire (FTF) values above the fault threshold. In the example 3503, one threshold is assigned to all the zones. In some examples, different zones may be assigned the same or different thresholds. If the force to fire (FTF) is greater than or equal to the threshold, the process 3600 continues along the YES branch and the control circuit 2510 determines 3606 whether the position of the I-beam 2514 corresponding to the current (I) spike is in a predetermined zone or zones. If the force to fire (FTF) is less than the threshold, the process 3600 continues along the NO branch and the control circuit 2510 determines 3609 if the I-beam 2514 is at the end of stroke.

The control circuit 2510 may include a memory storing the value or values of the predetermined thresholds. If the control circuit 2510 determines that a current (I) spike is greater than or equal to the predetermined threshold, the control circuit 2510 further determines 3606 whether the position of the I-beam 2514 corresponding to the current (I) spike is in a predetermined zone or zones. If the control circuit 2510 determines 3606 that a current (I) spike greater than or equal to the predetermined threshold is detected in a predetermined zone or zones, the control circuit 2510 proceeds along the YES branch and effects 3607 a motor control action. If, however, no current (I) spikes greater than or equal to the predetermined threshold 3510 are detected in the predetermined zone or zones, or a current (I) spike greater than or equal to the predetermined threshold 3510 are detected outside the predetermined zone or zones, the control circuit 2510 determines 3609 whether the I-beam 2514 has reached the end of stroke. If the I-beam 2514 is at the end of the firing stroke, the process 3600 proceeds along the YES branch and ends 3611. If the I-beam 2514 is not at the end of the firing stroke, the process 3600 proceeds along the NO branch and continues to drive 3602 the motor to translate the I-beam 2514. The process 3600 continues until the I-beam 2514 reaches the end of stroke.

The control circuit 2510 may determine whether a present position of the I-beam 2514 is in a predetermined zone or zones based on the movement data delivered by the position sensor 2534 (FIG. 14). The control circuit 2510 may include a memory storing positions of the I-beam 2514 and corresponding zones. The control circuit 2510 may compare a current position of the I-beam 2514 against the data stored in the memory. In some examples, current (I) spikes may be treated differently in different zones. As illustrated in FIG. 29, a current (I) spike 3506 in an initial portion of the firing stroke such as, for example, zone 1 may be a triggering event for the control circuit 2510 to effect 3607 a motor control action. Example motor control actions include dynamic braking and/or retracting of the I-beam 2514. In one example, a suitable motor control action may involve slowing the motor 2504 to a predetermined velocity until the current (I) drawn by the motor 2504 drops below the predetermined threshold.

In some examples, the control circuit 2510 can be configured to perform other suitable control actions of the surgical instrument 2500 in response to a current (I) spike occurring in a predetermined zone such as, for example, zone 1. Other suitable control actions of the surgical instrument 2500 may include alerting a user as to the status of the surgical instrument 2500.

Figure 31:
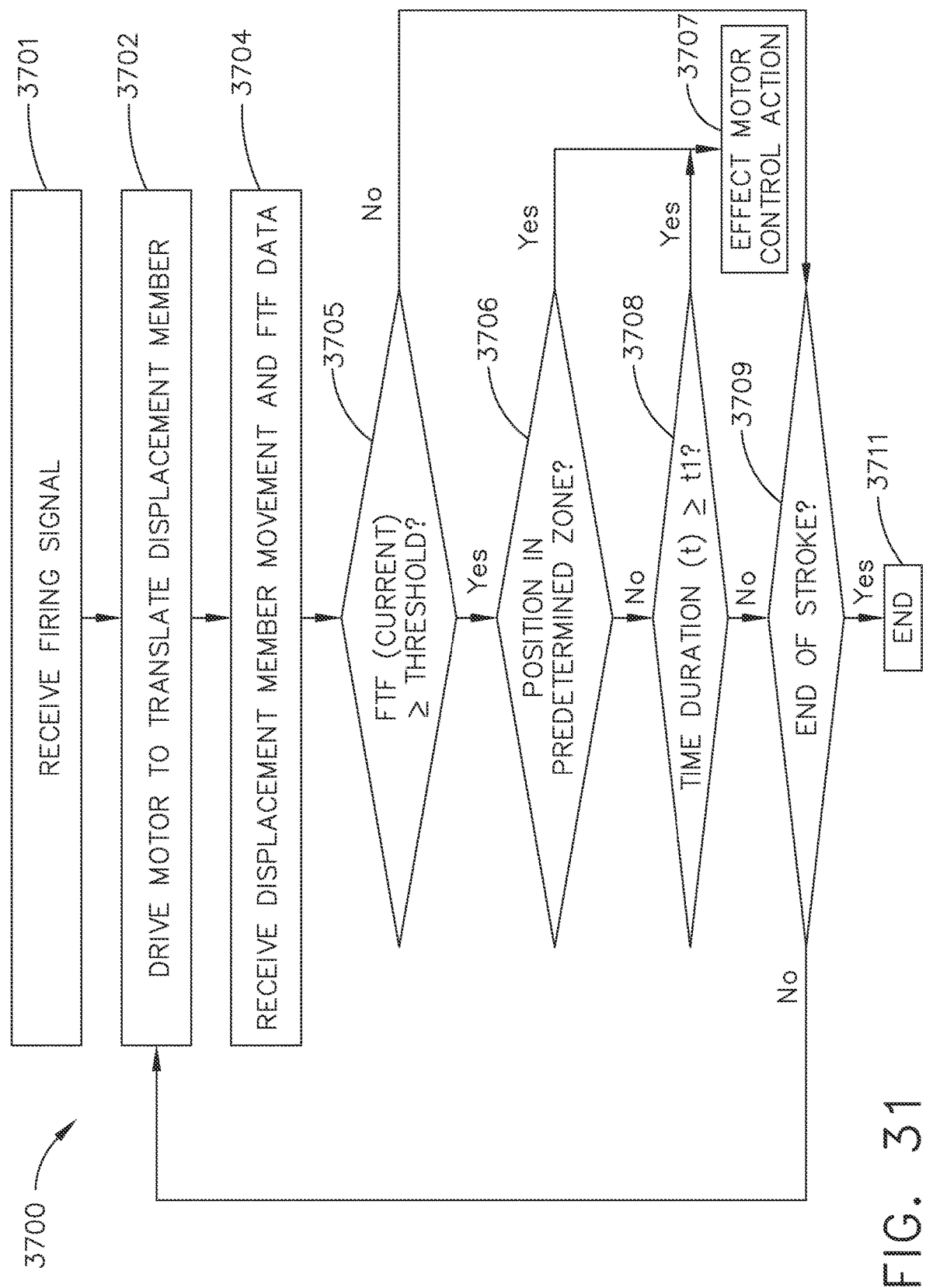
FIG. 31 is a logic flow diagram of a process depicting a control program or logic configuration representing a firing control program according to one aspect of this disclosure.

Referring to FIG. 31, in various examples, the duration during which the force to fire (FTF) is maintained at a value greater than or equal to the predetermined threshold 3510 can aid in discerning between signal noise and event-triggering spikes improves the operation of the surgical instrument 2500. FIG. 31 illustrates an alternative logic flow diagram of another example of a process 3700 depicting a control program that may be executed by the surgical instrument 2500 (e.g., the control circuit 2510) or a logic configuration to implement an I-beam stroke responsive to tissue conditions and/or staple cartridge type. The process 3700 is similar in many respects to the process 3600 (FIG. 30). Like the process 3600, in accordance with the process 3700, the control circuit 2510 receives 3701 a firing signal, drives 3702 the motor 2504 to translate the displacement member such as, for example, the I-beam 2514, receives 3704 I-beam movement and force to fire (FTF) data, determines 3705 whether the force to fire (FTF) at a present position of the I-beam 2514 is greater than or equal to a predetermined threshold 3510, and determines 3706 whether the present position of the I-beam 2514 is within a predetermined zone or zones. If the force to fire (FTF) at a present position of the I-beam 2514 is greater than or equal to a predetermined threshold 3510, the process 3700 proceeds along the YES branch and the control circuit 2510 determines 3708 if the time duration (t) is greater than or equal to (t1). Otherwise, if the force to fire (FTF) is less than the threshold, the process 3700 continues along the NO branch and the control circuit 2510 determines 3709 if the I-beam 2514 is at the end of stroke.

The process 3700, however, differs from the process flow 3600 in that the process flow 3700 further considers the duration during which a spike of current (I) drawn by the motor 2504, as a representative of the force to fire (FTF), is maintained at a value greater than or equal to the predetermined threshold 3510 in determining whether the current (I) spike constitutes a triggering event. Outside of the predetermine zone or zones the current (I) trigger must be greater than or equal to the predetermined threshold 3510 by a predefined number of milliseconds in order to minimize the likelihood that noise within the measurement inadvertently become a triggering event.

If the control circuit 2510 determines 3708 that such time duration (t) is greater than or equal to a predetermined time period (t1), the process 3700 proceeds along the YES branch and the control circuit 2510 effects 3707 a motor control action, as discussed above in connection with 3607. Otherwise, the process 3700 proceeds along the NO branch and the control circuit 2510 determines 3709 if the I-beam 2514 is at the end of stroke. If the I-beam 2514 is at the end of stroke the process continues along the YES branch and the process 3700 ends 3711. Otherwise, the process 3700 proceeds along the NO branch and drives 3702 the motor 2504 to translate the displacement member such as, for example, the I-beam 2514. The process continues until the I-beam 2514 reaches the end of the firing stroke. In other words, a current (I) spike is only considered an event triggering spike if it maintained at a value greater than or equal to the predetermined threshold 3510 for a time duration (t) that is greater than or equal to the predetermined time period (t1). Spikes 3507 and 3508 of the example 3503 of the diagram 3500 (FIG. 29) represent example current (I) spikes that exceed the predetermined threshold 3510 but are outside a predetermined zone or zones and are only maintained above the predetermined threshold 3510 for time periods that are less than the predetermined time period (t1). Accordingly, under the process flow 3700 the current (I) spikes 3507 and 3508 are not event triggering spikes.

In comparison, an alternative current (I) spike 3509 constitutes an event triggering spike in accordance with the process flow 3700 even though the current (I) spike 3509 is outside the predetermined zone or zones because the current (I) spike 3509 is maintained above the predetermined threshold 3510 for a time duration (t) that is greater than the predetermined time period (t1). In some examples, the predetermined time period (t1) can be selected from a range of about 1 millisecond to about 1 second. In some examples, the predetermined time period (t1) can be selected from a range of about 1 millisecond to about 500 milliseconds. In some examples, the predetermined time period (t1) can be selected from a range of about 1 millisecond to about 100 milliseconds. Other suitable values for the predetermined time period (t1) can be utilized.

In some examples, the control circuit 2510 determines the time duration (t) by maintaining a running counter or timer 2531 (FIG. 29) upon detection of a current (I) value greater than or equal to the predetermined threshold 3510. The control circuit 2510 maintains the running counter or timer 2531 as long as subsequent current (I) values are also greater than or equal to the predetermined threshold 3510. The control circuit 2510 may stop or reset the timer 2531 when a subsequent current (I) value is less than the predetermined threshold 3510 indicating an end of the time duration (t). In some examples, the control circuit 2510 comprises a processor which may perform the function of the timer 2531.

Figure 32:
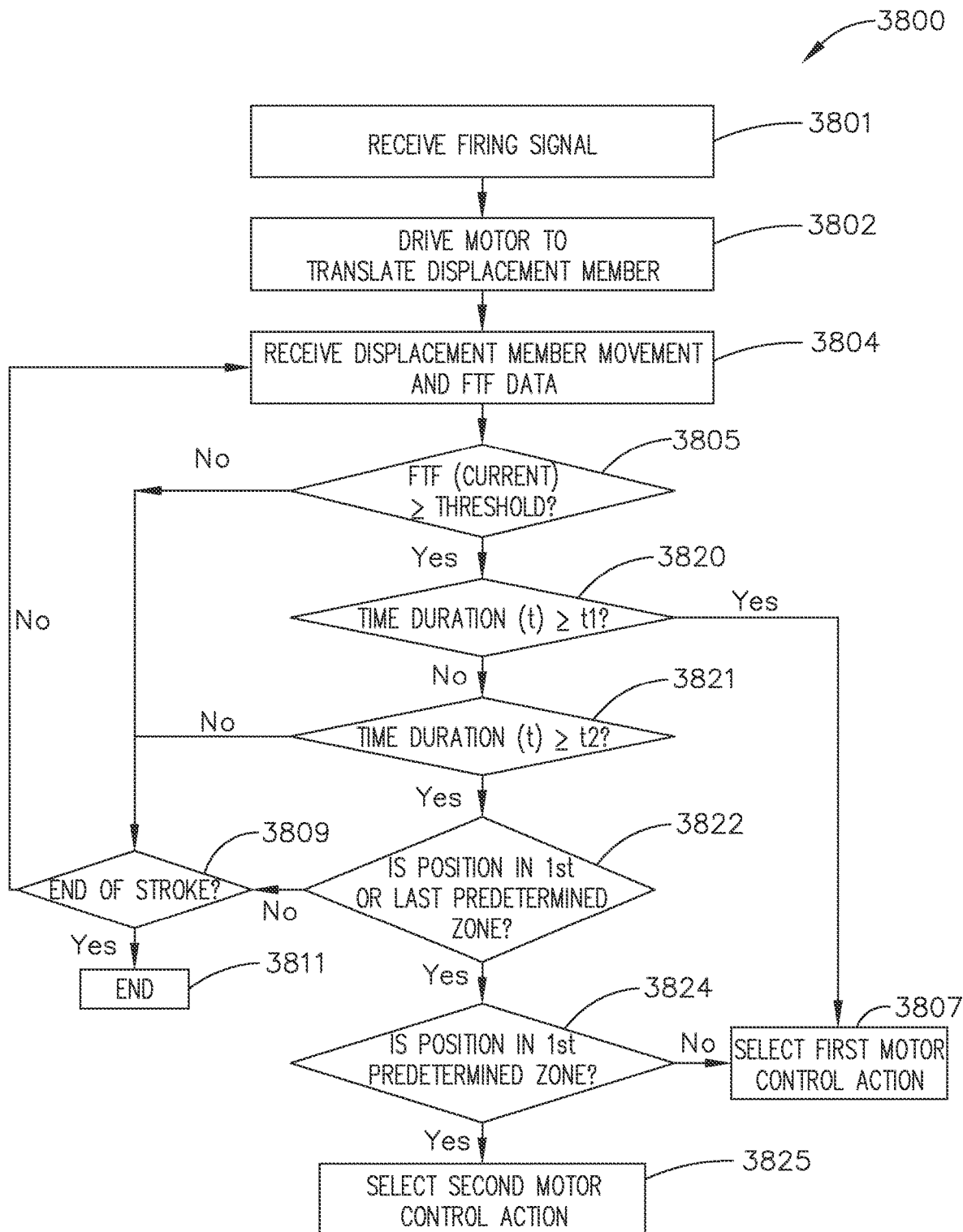
FIG. 32 is a logic flow diagram of a process depicting a control program or logic configuration representing a firing control program according to one aspect of this disclosure.

Referring to FIG. 32, in various examples, current (I) spikes in different zones along the distance traveled by the I-beam 2514 constitute triggering events for different motor control actions. FIG. 32 illustrates an alternative logic flow diagram of a process 3800 depicting a control program that may be executed by the surgical instrument 2500 (e.g., the control circuit 2510) or a logic configuration to implement an I-beam stroke responsive to tissue conditions and/or staple cartridge type. The process 3800 is similar in many respects to the process 3600 (FIG. 30). Like the process 3600, in accordance with the process 3800 the control circuit 2510 receives 3801 a firing signal, drives 3802 the motor 2504 to translate the displacement member such as, for example, the I-beam 2514, receives 3804 I-beam movement and force to fire (FTF) data, determines 3805 whether the force to fire (FTF) at a present position of the I-beam 2514 is greater than or equal to a predetermined threshold 3510, and determines whether the present position of the I-beam 2514 is within a predetermined zone. If the force to fire (FTF) at a present position of the I-beam 2514 is greater than or equal to a predetermined threshold 3510, the process 3800 proceeds along the YES branch and the control circuit 2510 determines 3820 if the time duration (t) is greater than or equal to (t1). Otherwise, if the force to fire (FTF) at a present position of the I-beam 2514 is less than a predetermined threshold 3510, the process 3800 proceeds along the NO branch and the control circuit 2510 determines 3809 if the I-beam 2514 is at the end of stroke. If the I-beam 2514 is the end of stroke, the process 3800 continues along the YES branch and ends 3811. Otherwise, the process 3800 continues along the NO branch and the control circuit 2510 receives 3804 the I-beam movement and force to fire (FTF) data. The process 3800 continues until the displacement member such as, for example, the I-beam 2514 reaches the end of stroke.

The process 3800, however, differs from the process 3600 in that the process 3800 further considers the time duration (t) during which a spike of current (I) drawn by the motor 2504, as a representative of the force to fire (FTF), is maintained at a value greater than or equal to the predetermined threshold 3510 in determining whether the current (I) spike constitutes a triggering event. The process 3800 further selects between different motor control actions.

Accordingly, the control circuit 2510 determines 3820 whether the time duration (t) during which the current (I) spike is maintained at a value greater than or equal to the predetermined threshold 3510 is greater than or equal to a first time period (t1). The process 3800 proceeds along the YES branch and further selects 3807 a first motor control action in response to a current (I) spike if the time duration (t) during which the current (I) spike is maintained at a value greater than or equal to the predetermined threshold 3510 is greater than or equal to a first time period (t1). If, however, the time duration (t) is less is less than the first time period (t1), the control circuit 2510 proceeds along the NO branch and further determines 3821 if the time duration (t) is greater than or equal than a second time period (t2). The second time period (t2) is less than the first time period (t1). If the time duration (t) is less than the first duration (t1) and the second duration (t2), the I-beam 2514 proceeds along the NO branch and the control circuit 2510 determines 3809 if the I-beam 2514 is a the end stroke 3811 and is allowed to continue to the end of the stroke 3811 unless it is determined 3822 that the position of the I-beam 2514 where the current (I) spike occurred is in either an initial zone such as, for example, zone 1 or a final zone such as, for example, zone 6. If the I-beam 2514 is not at the end of stroke, the process 3800 continues along the NO branch and the control circuit 2510 receives 3804 I-beam movement and force to fire (FTF) data. In some examples, the current (I) spikes in initial and final portions of the firing stroke are less tolerated than current (I) spikes in an intermediate portion of the firing stroke.

If the time duration (t) during which the current (I) spike is maintained at a value greater than or equal to the predetermined threshold 3510 is greater than or equal to a second time period (t2), the process continues along the YES branch and the control circuit 2510 further determines 3822 whether the current (I) spike occurred in the initial zone or the final zone. If the position is outside the initial and final predetermined zone the process 3800 proceeds along the NO branch to determine 3809 if the I-beam 2514 is at the end of stroke. If the current (I) spike occurred in the initial zone or the final predetermined zone, the process 3800 continues along the YES branch and determines 3824 if the position is in the initial predetermined zone and if not true, the process 3800 proceeds along the NO branch and the control circuit 2510 selects 3807 a first motor control action. If, however, the control circuit 2510 determines that the current (I) spike occurred in an initial zone, the process 3800 continues along the YES branch and the control circuit 2510 selects 3825 a second motor control action different from the first motor control action. Examples of suitable first control actions may include dynamic braking and/or retracting of the I-beam 2514. In one example, a suitable first motor control action may involve slowing the motor 2504 to a predetermined velocity until the current (I) drawn by the motor 2504 drops below the predetermined threshold. An example of a suitable second motor control action may include dynamic braking and/or retracting of the I-beam 2514. In one example, the first or initial zone of the firing stroke may be a lockout zone, and the second motor control action may include entering a lockout state then retracting the I-beam 2514. In the lockout zone, the second motor control action may be triggered by any current (I) spike instantaneously exceeding the predetermined threshold 3510.

In various examples, the current (I) is sampled in discrete data points, as described above. In such examples, the number of data points above the predetermined threshold 3510 can be used with or instead of the time duration (t), in the process 3700 and/or the process 3800, to determine triggering events that cause the control circuit 2510 to effect specified motor control actions. In some examples, the time duration (t) a current spike is maintained above the predetermined threshold can be substituted with the number of data points above the predetermined threshold 3510 in connection with the process 3700 and/or the process 3800.

In at least one example pertaining to the process 3700, the determination 3708 (FIG. 31) of whether the time duration (t) is greater than or equal a predetermined time threshold t1 is substituted with a determination of whether the number of data points above the predetermined threshold 3510 is greater than or equal to a predetermined number N1. In another example, pertaining to the process 3800, the determination 3820 (FIG. 32) of whether the time duration (t) is greater than or equal a predetermined time threshold $t_1$ is substituted with a determination of whether the number of data points above the predetermined threshold 3510 is greater than or equal to a predetermined number N1. In addition, the determination 3821 (FIG. 32) of whether the time duration (t) is further greater than or equal a predetermined time threshold $t_2$ is substituted with a determination of whether the number of data points above the predetermined threshold 3510 is further greater than or equal to a predetermined number N2 greater than the predetermined number N1.

In various examples, the number of data points above the predetermined threshold 3510 that are counted can be the number consecutive data points above the predetermined threshold 3510. In some examples, every occurrence of a data point below the predetermined threshold 3510 resets the count. In some examples, the number of data points above the predetermined threshold 3510 that are counted can be the number of data points occurring in a predetermined time period. At the end of the predetermined time period, the count is reset.

Various aspects of the subject matter described herein are set out in the following numbered examples:

Example 1. A surgical instrument, comprising: a displacement member; a motor coupled to displacement member, the motor operable to translate the displacement member; a control circuit coupled to the motor; a parameter sensor coupled to the control circuit; and a position sensor coupled to the control circuit, wherein the control circuit is configured to: receive a parameter output of the parameter sensor indicative of a force applied to translate the displacement member; determine a duration during which the parameter output is maintained at or above a predetermined fault threshold; receive a position output of the position sensor indicative of at least one position of the displacement member during the duration; and effect a motor control action based on the duration and the at least one position.

Example 2. The surgical instrument of Example 1, wherein the motor control action comprises a dynamic brake.

Example 3. The surgical instrument of Example 1 through Example 2 wherein the motor control action comprises retracting the displacement member.

Example 4. The surgical instrument of Example 1 through Example 3, wherein the motor control action comprises changing velocity of the motor.

Example 5. The surgical instrument of Example 1 through Example 4, further comprising a timer circuit coupled to the control circuit, wherein the timer circuit is configured to measure the duration.

Example 6. The surgical instrument of Example 1 through Example 5, wherein the control circuit is configured to effect the motor control action when the duration is equal to or exceeds a predetermined time period.

Example 7. The surgical instrument of Example 6, wherein the predetermined time period is a first predetermined time period, wherein the control circuit is configured to effect the motor control action when the time period is less than the first predetermined time period but greater than a second predetermined time period, and when the at least one position is in a predetermined zone along the distance.

Example 8. The surgical instrument of Example 1 through Example 7, further comprising and end effector coupled to the displacement member.

Example 9. The surgical instrument of Example 8, wherein the end effector comprises a staple cartridge housing a plurality of staples, and wherein translation of the displacement member causes the staples to be deployed form the staple cartridge.

Example 10. A surgical instrument, comprising: a displacement member; a motor coupled to the displacement member; a current sensor coupled to the motor, the current sensor configured to measure current drawn by the motor while translating the displacement member; a position sensor; and a control circuit coupled to the motor, the current sensor, and the position sensor, wherein the control circuit is configured to: determine a duration during which the current drawn by the motor is maintained at or above a predetermined fault threshold; receive a position output of the position sensor indicative of at least one position of the displacement member during the duration; and effect a motor control action based on the duration and the at least one position.

Example 11. The surgical instrument of Example 10, wherein the motor control action comprises a dynamic brake.

Example 12. The surgical instrument of Example 10 through Example 11, wherein the motor control action comprises retracting the displacement member.

Example 13. The surgical instrument of Example 10 through Example 12, wherein the motor control action comprises changing velocity of the motor.

Example 14. The surgical instrument of Example 10 through Example 13, further comprising a timer circuit coupled to the control circuit, wherein the timer circuit is configured to measure the duration.

Example 15. The surgical instrument of Example 10 through Example 14, wherein the control circuit is configured to effect the motor control action when the duration is equal to or exceeds a predetermined time period.

Example 16. The surgical instrument of Example 15, wherein the predetermined time period is a first predetermined time period, wherein the control circuit is configured to effect the motor control action when the duration is less than the first predetermined time period but greater than a second predetermined time period, and when the at least one position is in a predetermined zone along the distance.

Example 17. The surgical instrument of Example 10 through Example 16, further comprising an end effector coupled to the displacement member.

Example 18. The surgical instrument of Example 17, wherein the end effector comprises a staple cartridge housing a plurality of staples, and wherein translation of the displacement member causes the staples to be deployed form the staple cartridge.

Example 19. A method of controlling a motor in a surgical instrument, the surgical instrument comprising a displacement member, a motor coupled to displacement member, the motor operable to translate the displacement member, a control circuit coupled to the motor, a parameter sensor coupled to the control circuit, and a position sensor coupled to the control circuit, the method comprising: receiving, by the control circuit, a parameter output of the parameter sensor indicative of a force applied to translate the displacement member; determining, by the control circuit, a duration during which the parameter output is maintained at or above a predetermined fault threshold; receiving, by the control circuit, a position output of the position sensor indicative of at least one position of the displacement member during the duration; and effecting, by the control circuit, a motor control action based on the duration and the at least one position.

Example 20. The method of Example 19, further comprising dynamically braking the motor by the control circuit.

Example 21. The method of Example 19 through Example 20, further comprising retracting the displacement member by the control circuit.

Example 22. The method of Example 19 through Example 21, further comprising changing velocity of the motor by the control circuit.

Example 23. The method of Example 19 through Example 22, further comprising a timer circuit coupled to the control circuit, the method comprising measuring the duration by the timer circuit.

Example 24. The method of Example 19 through Example 23, further comprising effecting the motor control action when the duration is equal to or exceeds a predetermined time period.

Example 25. The method of Example 24, wherein the predetermined time period is a first predetermined time period, the method comprising effecting the motor control action when the time period is less than the first predetermined time period but greater than a second predetermined time period, and when the at least one position is in a predetermined zone along the distance.

Example 26. A surgical instrument, comprising: a displacement member; a motor coupled to the displacement member; a current sensor coupled to the motor, the current sensor configured to measure current drawn by the motor while translating the displacement member; a position sensor; and a control circuit coupled to the motor, the current sensor, and the position sensor, wherein the control circuit is configured to: count data points representing current (t) values at or above a predetermined current threshold; receive a position output of the position sensor indicative of at least one position of the displacement member corresponding to at least one of the data points; and effect a motor control action based on the number of data points counted and the at least one position.

Example 27. The surgical instrument of Example 26, wherein the motor control action comprises a dynamic brake.

Example 28. The surgical instrument of Example 26 through Example 27, wherein the motor control action comprises retracting the displacement member.

Example 29. The surgical instrument of Example 26 through Example 28, wherein the motor control action comprises changing velocity of the motor.

Example 30. The surgical instrument of Example 26 through Example 29, further comprising a timer circuit coupled to the control circuit.

Example 31. The surgical instrument of Example 26 through Example 30, wherein the control circuit is configured to effect the motor control action if the counted number of data points is equal to or exceeds a predetermined number.

Example 32. The surgical instrument of Example 31, wherein the predetermined number is a first predetermined number, wherein the control circuit is configured to effect the motor control action when the counted number of data points is less than the first predetermined number but greater than a second predetermined number, and when the at least one position is in a predetermined zone along the distance.

Example 33. The surgical instrument of Example 26 through Example 32, further comprising an end effector coupled to the displacement member.

Example 34. The surgical instrument of Example 33, wherein the end effector comprises a staple cartridge housing a plurality of staples, and wherein translation of the displacement member causes the staples to be deployed form the staple cartridge.

Systems and Methods for Controlling Displacement Member Motion of a Surgical Stapling and Cutting Instrument During use of a motorized surgical stapling and cutting instrument it is possible that the force to fire on the cutting member and firing member may vary based on the stroke location of the cutting member during the firing process, tissue thickness encountered by the cutting member, and the overall length of the firing stroke of the cutting member. Therefore, it may be desirable to provide variable firing pauses based on the stroke location of the cutting member. Therefore, it may be desirable to provide powered firing actuation with variable automatic pauses where the pause number, pause duration, and stroke location are based on the force and the stroke location of the firing system.

Figure 33:
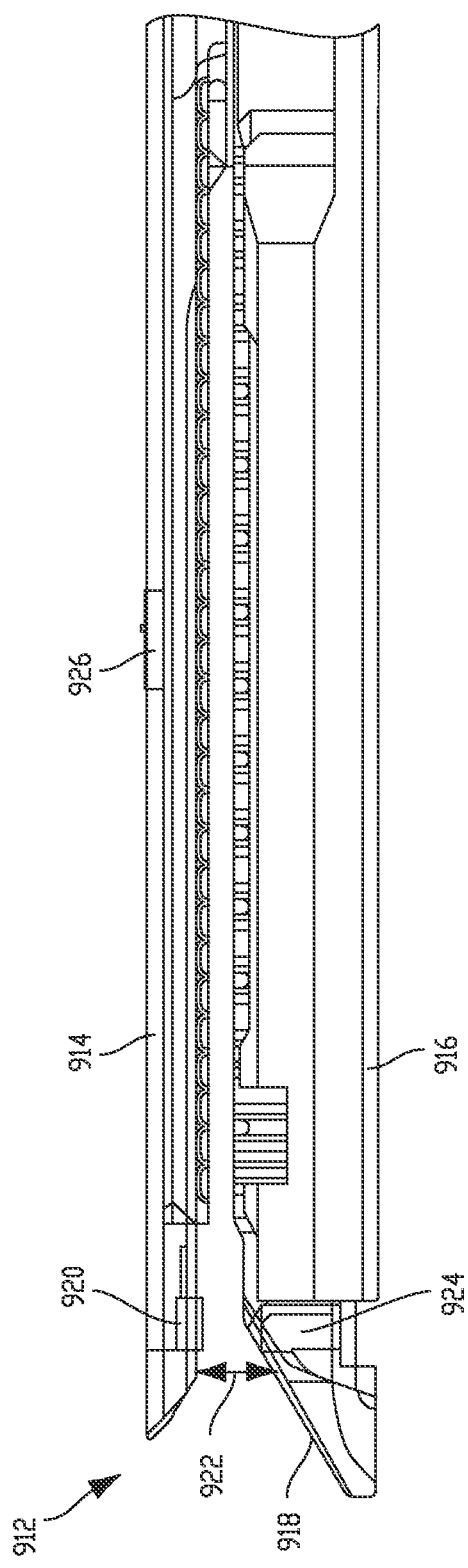
FIG. 33 illustrates a cross-sectional view of an end effector of a surgical instrument according to one or more aspects of this disclosure.

FIG. 33 illustrates a cross-sectional view of an end effector 912 of a surgical instrument according to one aspect of this disclosure. The end effector 912 is one aspect of the end effector 300 (FIGS. 1 and 4) that may be adapted to operate with surgical instrument 10 (FIG. 1) to measure the various derived parameters such as gap distance versus time, tissue compression versus time, and anvil strain versus time. Accordingly, the end effector 912 may include one or more sensors configured to measure one or more parameters or characteristics associated with the end effector 912 and/or a tissue section captured by the end effector 912. The end effector 912 may comprise a first sensor 920 and a second sensor 926. In various examples, the first sensor 920 and/or the second sensor 926 may comprise, for example, a magnetic sensor such as, for example, a magnetic field sensor, a strain gauge, a pressure sensor, a force sensor, an inductive sensor such as, for example, an eddy current sensor, a resistive sensor, a capacitive sensor, an optical sensor, and/or any other suitable sensor for measuring one or more parameters of the end effector 912. Although the illustrated end effector 912 comprises two sensors, additional or fewer sensors can be employed.

The first sensor 920 and/or the second sensor 926 may comprise, for example, a magnetic field sensor embedded in an anvil 914 and configured to detect a magnetic field generated by a magnet 924 embedded in a jaw member 916 and/or the staple cartridge 918. The anvil 914 is pivotally rotatable between open and closed positions. The strength of the detected magnetic field may correspond to, for example, the thickness and/or fullness of a bite of tissue located between the anvil 914 and the jaw member 916. In certain instances, the first sensor 920 and/or the second sensor 926 may comprise a strain gauge, such as, for example, a micro-strain gauge, configured to measure the magnitude of the strain in the anvil 914 during a clamped condition. The strain gauge provides an electrical signal whose amplitude varies with the magnitude of the strain.

In some aspects, one or more sensors of the end effector 912 such as, for example, the first sensor 920 and/or the second sensor 926 may comprise a pressure sensor configured to detect a pressure generated by the presence of compressed tissue between the anvil 914 and the jaw member 916. In some examples, one or more sensors of the end effector 912 such as, for example, the first sensor 920 and/or the second sensor 926 are configured to detect the impedance of a tissue section located between the anvil 914 and the jaw member 916. The detected impedance may be indicative of the thickness and/or fullness of tissue located between the anvil 914 and the jaw member 916.

The sensors of the end effector 912 such as, for example, the first sensor 920 may be configured to measure the gap 922 between the anvil 914 and the jaw member 916. In certain instances, the gap 922 can be representative of the thickness and/or compressibility of a tissue section clamped between the anvil 914 and the jaw member 916. The gap 922 can be representative of the force applied to the anvil 914 to compress the tissue. In one aspect, the gap 922 between the anvil 914 and the jaw member 916 can be measured by positioning a magnetic field sensor on the anvil 914 and positioning a magnet on the jaw member 916 such that the gap 922 is proportional to the signal detected by the magnetic field sensor and the signal is proportional to the distance between the magnet and the magnetic field sensor. It will be appreciated that the location of the magnetic field sensor and the magnet may be swapped such that the magnetic field sensor is positioned on the jaw member 916 and the magnet is placed on the anvil 914.

The sensors of the end effector 912 such as, for example, the first sensor 920 may be configured to measure one or more forces exerted on the anvil 914 by the closure drive system 30. For example, the first sensor 920 can be at an interaction point between the closure tube 260 (FIG. 3) and the anvil 914 to detect the closure forces applied by the closure tube 260 to the anvil 914. The forces exerted on the anvil 914 can be representative of the tissue compression experienced by the tissue section captured between the anvil 914 and the jaw member 916. In certain aspects, the first sensor 920 and/or other sensors can be positioned at various interaction points along the closure drive system 30 (FIG. 2) to detect the closure forces applied to the anvil 914 by the closure drive system 30. The first sensor 920 and/or the second sensor 926 may be sampled in real time during a clamping operation by a processor as described in FIGS. 5-10, for example, and more particularly, the system 970. The processor receives real-time sample measurements to provide analyze time based information and assess, in real time, closure forces applied to the anvil 914.

Figure 34:
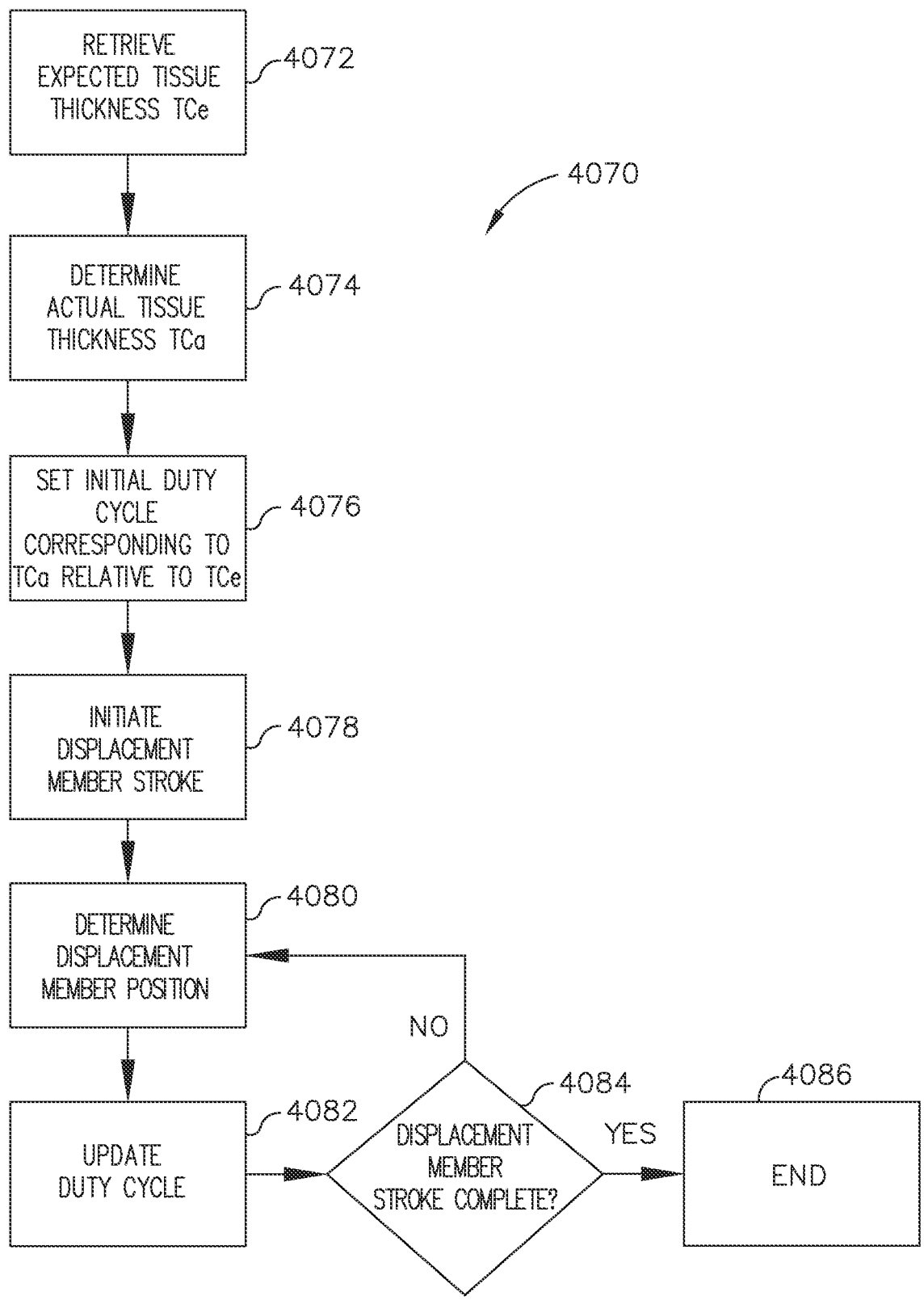
FIG. 34 is a logic flow diagram depicting a process of a control program or a logic configuration for controlling the duty cycle of the motor according to one or more aspects of this disclosure.

FIG. 34 is a logic flow diagram depicting a process 4070 of a control program or a logic configuration for controlling the duty cycle of the motor 2504 in accordance with one or more aspects of the present disclosure. In the following description of the process 4070 in FIG. 15, reference should also be made to FIG. 14 and FIG. 15. Accordingly, the control circuit 2510 retrieves 4072 the expected tissue thickness TCe of the tissue that is grasped or is to be grasped upon use of the surgical instrument 2500. The expected tissue thickness TCe can be stored, for example, in a memory of the surgical instrument 2500. The expected tissue thickness TCe can additionally be input or preprogrammed by an operator of the surgical instrument 2500 or can be downloaded, or otherwise received, by the surgical instrument 2500 from an external source prior to use. One such external source can include a staple cartridge 2518 that is configured to store the expected tissue thickness TCe with which the staple cartridge 2518 is intended to be used and then transmit the expected tissue thickness to the control circuit 2510 upon the staple cartridge 2518 being engaged with the surgical instrument 2500.

The control circuit 2510 then determines 4074 the actual thickness TCa of the tissue grasped by the surgical instrument 2500 at or by the end effector 2502. In various aspects, the actual tissue thickness can be determined 4074 either directly or via one or more proxy measurements carried out by the surgical instrument 2500 prior to or during operation. In one aspect, the surgical instrument 2500 comprises a tissue thickness sensor disposed at the distal end of the end effector 2502. The tissue thickness sensor can comprise a Hall-effect sensor, a reed switch sensor, an optical sensor, a magneto-inductive sensor, a force sensor, a pressure sensor, a piezo-resistive film sensor, an ultrasonic sensor, an eddy current sensor, an accelerometer, a pulse oximetry sensor, a temperature sensor, a sensor configured to detect an electrical characteristic of a tissue path (such as capacitance or resistance), or any combination thereof. The tissue thickness sensor can be configured to measure a thickness of a tissue located between the anvil 2516 and the staple cartridge 2518, a gap or distance between the anvil 2516 and the staple cartridge 2518, a gap or distance between the jaw members of the surgical instrument 2500, and a variety of other parameters indicating the thickness of the grasped tissue.

In another aspect, the surgical instrument 2500 can alternatively be configured to measure a proxy for the tissue thickness either prior to initiating the firing stroke or during an initial portion of the firing stroke. One such proxy can include the force on a displacement member such as the drive member 120 (FIG. 2); the firing member 220 (FIG. 3), 2520 (FIG. 13); I-beam 2514, 178 (FIG. 4); the firing bar 172 (FIG. 4); and/or on a proximal end of the cutting edge 182 (FIG. 4), 2509 (FIG. 13). For conciseness and clarity, the proxy for the tissue thickness will be described in connection with the force experienced by the I-beam 2514. Accordingly, a proxy for the tissue thickness can be determined by the I-beam 2514 force, which may be determined using various techniques. In one aspect, the I-beam 2514 force may be determined by measuring the motor 2504 current, where motor 2504 current is based on the load experienced by the I-beam 2514 as it advances distally. In another aspect, the I-beam 2514 force may be determined by way of a strain gauge positioned on the displacement member such as the drive member 120 (FIG. 2); the firing member 220 (FIG. 3), 2520 (FIG. 13); I-beam 2514, 178 (FIG. 4); the firing bar 172 (FIG. 4); and/or on a proximal end of the cutting edge 182 (FIG. 4), 2509 (FIG. 13). In yet another aspect, the I-beam 2514 force may be determined by monitoring the actual position of the I-beam 2514 moving at an expected velocity based on motor 2504 set speed after a predetermined elapsed period $t_1$ and comparing the actual position of the I-beam 2514 relative to the expected position of the I-beam 2514 based on the set velocity of the motor 2504 at time $t_1$. Thus, if the actual position of the I-beam 2514 is less than the expected position of the I-beam 2514, the I-beam 2514 is experiencing greater than a nominal force. Conversely, if the actual position of the I-beam 2514 is greater than the expected position of the I-beam 2514, the I-beam 2514 force is less than the nominal force. The difference between the actual and expected positions of the I-beam 2514 is proportional to the deviation of the I-beam 2514 force from the nominal force. The latter technique is described in detail in commonly owned U.S. Pat. No. 10,624,633, which issued on Apr. 21, 2020, which is incorporated herein by reference in its entirety.

The control circuit 2510 then provides a motor set point 2522 to the motor controller 2508, which provides the motor drive signal 2524 to set 4076 the initial duty cycle of the motor 2504 to a value corresponding to actual tissue thickness relative to the expected tissue thickness. If the actual tissue thickness TCa is greater than the expected tissue thickness TCe, then the initial duty cycle will be set to a lower value than the default duty cycle. The relative degree to which the actual tissue thickness TCa is greater than the expected tissue thickness TCe can additionally affect the value to which the initial duty cycle is set. In some aspects, the thicker the actual tissue thickness TCa is relative to the expected tissue thickness TCe, the lower the initial duty cycle will be set. Therefore, for increasingly thicker tissue, the I-beam 2514 will be initially advanced increasingly slower. If the actual tissue thickness TCa is not greater than the expected tissue thickness TCe, then the initial duty cycle will be set to a default duty cycle. The default duty cycle can be, for example, 100%.

In one aspect, the process 4070 as executed by the control circuit 2510 is configured to establish one or more discrete zones covering a range of tissue thickness values and then set 4076 the initial duty cycle of the motor 2504 according to which zone the actual tissue thickness TCa falls within. For example, if the expected tissue thickness TCe is 2 mm, then a first zone can include tissue thickness of 0-2 mm, a second zone can include tissue thickness of 2-4 mm, and a third zone can include tissue thickness of greater than 4 mm. In this example, if the actual tissue thickness TCa falls within the first zone, then the motor 2504 duty cycle is set to a default or first duty cycle. If the actual tissue thickness TCa falls within the second zone, then the motor 2504 duty cycle is set to a second duty cycle that is lower than the first duty cycle. Lastly, if the actual tissue thickness TCa falls within the third zone, then the motor 2504 duty cycle is set to a third duty cycle that is lower than the second duty cycle. The zones can be defined in terms of explicit ranges of values, ratios to the expected tissue thickness TCe, or in any other such manner according to various aspects. The number and ranges of such zones can likewise various according to various aspects. In another aspect, the process 4070 as executed by the control circuit 2510 is configured to calculate the initial duty cycle according to the actual tissue thickness TCa, the expected tissue thickness TCe, and the ratio therebetween. In this aspect, the initial duty cycle set by the control circuit 2510 is a unique value according to the inputs, rather than having a set value for a range of inputs.

Once the initial duty cycle is set 4076, the control circuit 2510 then causes the motor 2504 to initiate 4078 a firing stroke by advancing the displacement member such as, for example, the I-beam 2514 distally. In the example where the displacement member is the I-beam 2514, during the course of the firing stroke, the control circuit 2510 determines 4080 the position of the I-beam 2514 and updates 4082 the duty cycle of the motor 2504 according to the determined 4080 I-beam 2514 position. The position of the I-beam 2514 can be determined 4080 via a number of different techniques. In one aspect, the surgical instrument 2500 can comprise a position sensor 1112 (FIG. 10) that is configured to track the longitudinal displacement of the I-beam 2514, as described above. The duty cycle of the motor 2504 can be updated according to an algorithm executed by the control circuit 2510, a look-up table stored in a memory that is accessed by the control circuit 2510, or any other such technique for retrieving or calculating an updated value according to one or more inputs. In one aspect, the duty cycle of the motor 2504 is updated 4082 such that it increases over the course of the stroke of the I-beam 2514, i.e., the duty cycle directionally corresponds to the magnitude of the linear displacement of the I-beam 2514. The control circuit 2510 next determines 4084 whether the stroke of the I-beam 2514 is completed. If the firing stroke is complete, then the process 4070 proceeds along the YES branch and the process 4070 is completed 4086. If the firing stroke is not complete, then the process 4070 proceeds along the NO branch and continues a loop of determining 4080 the position of the I-beam 2514 and updating 4082 the duty cycle of the motor 2504, as described above. Stated differently, the process 4070 continues to update the duty cycle of the motor 2504 as the position of the I-beam 2514 changes throughout its firing stroke. In one aspect, the process 4070 can additionally be configured to exit the loop of determining 4080 the I-beam 2514 position and updating 4082 the duty cycle if the duty cycle reaches 100% as the duty cycle cannot exceed that value.

Figure 35:
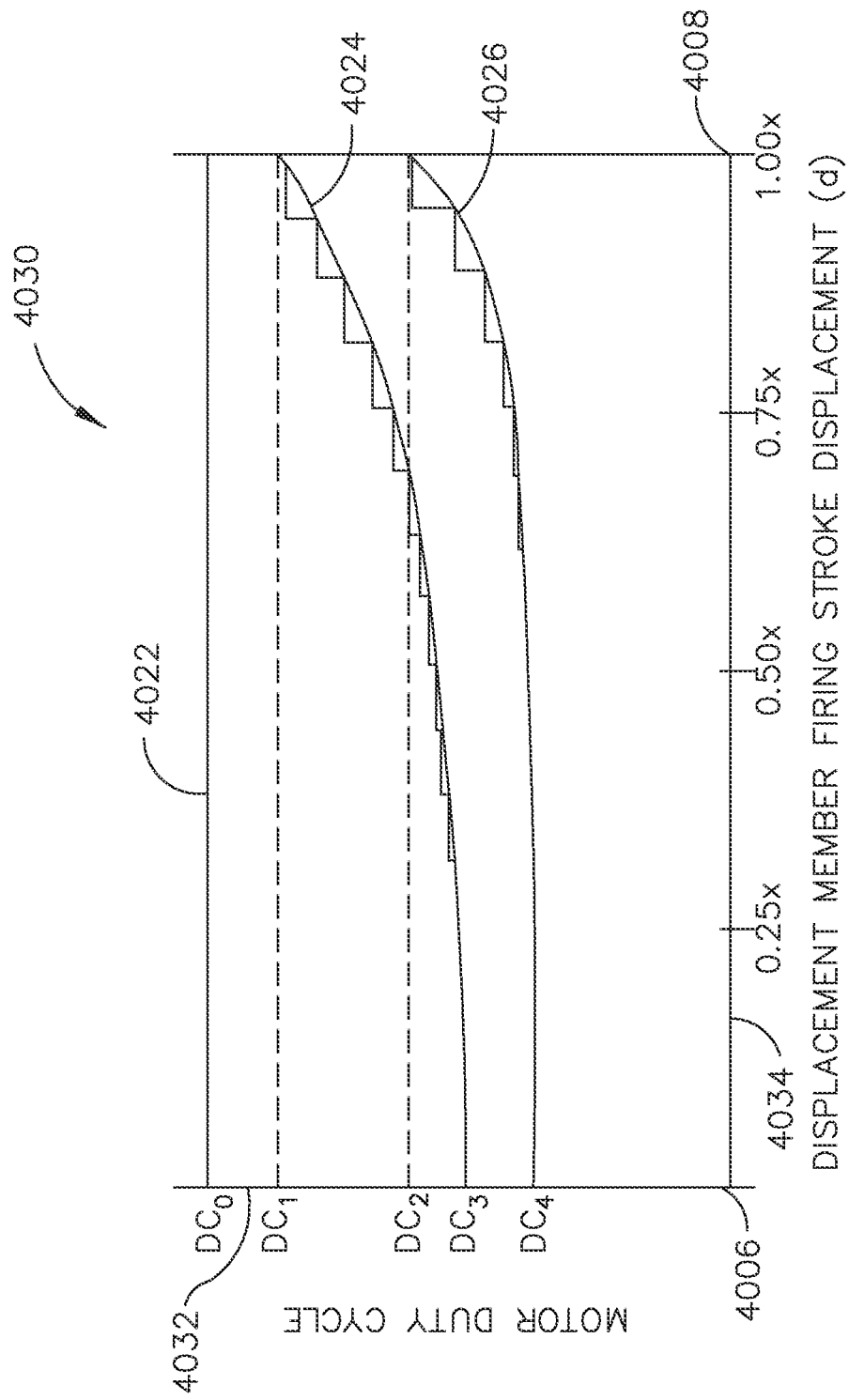
FIG. 35 is a diagram plotting three example firing member strokes executed according to the process of FIG. 34 according to one or more aspects of this disclosure.

FIG. 35 is a first diagram 4030 plotting three example firing member strokes executed according to the process 4070 of FIG. 34 according to one or more aspects of this disclosure. The first diagram 4030 includes a horizontal axis 4034 representing the displacement or position of the displacement member, e.g., the I-beam 2514, over a stroke between a stroke begin position 4006 and a stroke end position 4008 and a vertical axis 4032 representing the duty cycle of the motor 2504. The stroke end position 4008 depends, in part, upon the type of staple cartridge 2518 utilized by the surgical instrument 2500 as the staple cartridges 2518 can vary in length. In one illustrative aspect, the stroke end position 4008 is 60 mm from a stroke begin position 4006 of 0 mm.

A first example 4022 shows a response of the surgical instrument 2500 when the tissue grasped by the end effector 2502 is not greater than the expected thickness TCe. When the actual tissue thickness TCa is not greater than the expected tissue thickness TCe, then the motor 2504 drives the I-beam 2514 from the stroke begin position 4006 to the stroke end position 4008 at the default duty cycle $DC_0$ over time $t_1$. In the illustrated aspect, the default duty cycle $DC_0$ is equal to 100%. It should be noted that in alternative aspects, the default duty cycle $DC_0$ can be less than 100%. As the duty cycle $DC_0$ is 100% throughout the stroke of the I-beam 2514 in the first example 4022, there are no periods in which the motor 2504 is inactive; thus, there are no pauses in the first example 4022 from the stroke begin position 4006 to the stroke end position 4008, as there are in the second example 4024 and the third example 4026.

A second example 4024 shows a response of the surgical instrument 2500 when the tissue grasped by the end effector 2502 is greater than the expected thickness TCe. When the actual tissue thickness TCa is greater than the expected tissue thickness TCe, the control circuit 2510 causes the motor control 2508 to drive the motor 2504 at an initial duty cycle $DC_3$ that is less than the default duty cycle $DC_0$. The initial duty cycle can be a function of the degree to which the actual thickness TCa is greater than the expected thickness TCe. When the motor control 2508 drives the motor 2504 at a duty cycle that is less than 100%, the I-beam 2514 translates at a comparatively lower velocity. After the initial duty cycle is set and the I-beam 2514 begins its stroke, the control circuit 2510 updates or adjusts the duty cycle at which the motor control 2508 drives the motor 2504 over the course of the I-beam 2514 stroke. In one aspect, the control circuit 2510 is configured to increase the motor 2504 duty cycle over the course of the stroke. In the case of the second example 4024, the control circuit 2510 causes the duty cycle of the motor 2504 to increase from the initial value $DC_3$ to an ending value $DC_1$, as illustrated in the first diagram 4030. As the velocity of the I-beam 2514 corresponds to the duty cycle of the motor 2504, the velocity of the I-beam 2514 accordingly increases over the course of the firing stroke.

As with the second example 4024, the third example 4026 shows a response of the surgical instrument 2500 when the tissue grasped by the end effector 2502 is greater than the expected thickness TCe. The difference in the third example 4026 being that the actual thickness TCa of the grasped tissue is greater relative to the expected thickness TCe than in the second example 4024. In other words, the tissue is even thicker in the third example 4026 than the second example 4024. As the initial duty cycle is a function of the degree to which the actual thickness TCa is greater than the expected thickness TCe and the tissue in third example 4026 is thicker than in the second example 4024, the control circuit 2510 therefore causes the motor control 2508 to drive the motor 2504 at an initial duty cycle $DC_4$ that is less than the initial duty cycle $DC_3$ of the second example 4024.

Because the average motor 2504 duty cycles are lower over the course of the firing strokes of the second example 2024 and the third example 2026 as compared to the first example 4022, the average velocities of the I-beam 2514 over the firing strokes in the second example 4024 and the third example 4026 are likewise comparatively lower. It can be desirable to translate the I-beam 2514 at a reduced velocity when the actual thickness TCa of the tissue is greater than the expected thickness TCe to ensure proper staple formation in the tissue. Furthermore, translating the I-beam 2514 at a lower velocity can provide time for fluid in the tissue that is being cut and/or stapled to escape away from the surgical site and for the tissue itself to elastically respond to the clamping, stapling, and/or cutting operations, both of which can improve the performance of the surgical instrument 2500 and the quality of the staple formation. Additionally, it can be desirable to increase the duty cycle of the motor 2504 over the course of the stroke of the I-beam 2514 because the resistance encountered from clamped tissue decreases as the tissue is cut and/or staples are formed in the tissue by the I-beam 2514. As resistance from the tissue decreases, theI-beam 2514 can be translated at a correspondingly increased velocity without negatively impacting staple formation.

It should be noted that the various duty cycle values depicted in FIG. 35 are intended solely for illustrative purposes and no relationship between the values beyond that which is described herein should be implied. For example, although the ending duty cycle of the third example 4026 $DC_2$ is depicted as greater than the initial duty cycle of the second example 4024 $DC_3$, no such specific relationship is intended or implied. As another example, although the ending values $DC_1$ and $DC_2$ of the first example 4022 and the second example 4024, respectively, are depicted as less than the default duty cycle $DC_0$, it is not intended to be implied that in any situation wherein the actual tissue thickness is greater than the expected tissue thickness that the duty cycle of the motor 2504 will never reach the default duty cycle $DC_0$ over the course of the firing stroke. Furthermore, although the relationship between the firing stroke displacement and the motor duty cycle is depicted as roughly exponential in FIG. 37, their relationship can alternatively be linear or described via any other type of mathematical function.

Figure 36:
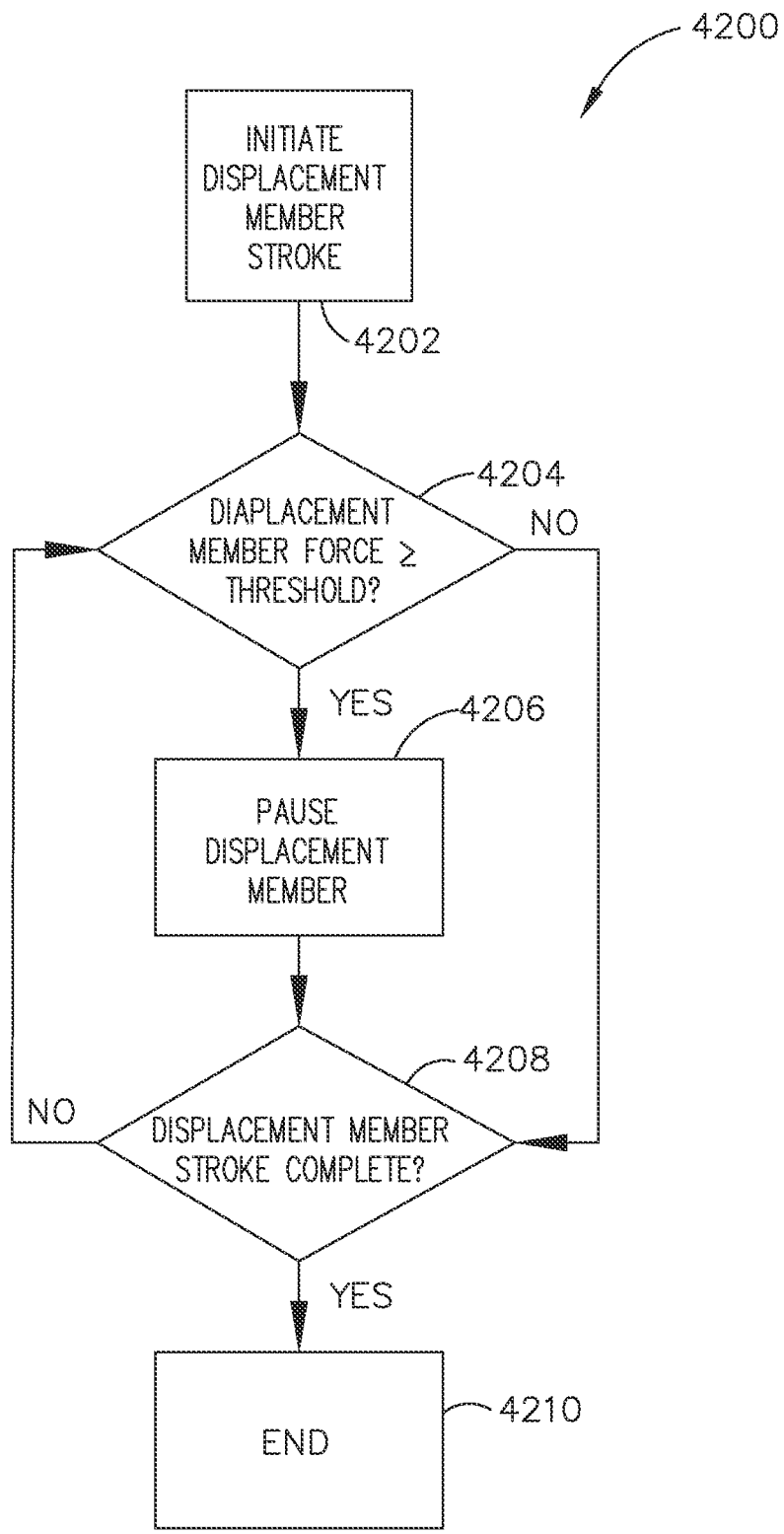
FIG. 36 is a logic flow diagram depicting a process of a control program or a logic configuration for controlling the displacement of the displacement member according to one or more aspects of this disclosure.

FIG. 36 is a logic flow diagram depicting a process 4200 of a control program or a logic configuration for controlling the displacement of the displacement member according to one or more aspects of this disclosure. In the following description of the process 4200 in FIG. 15, reference should also be made to FIG. 14 and FIG. 15. Accordingly, the control circuit 2510 initiates 4202 the stroke of the displacement member. As discussed above, the displacement member can include the drive member 120 (FIG. 2); the firing member 220 (FIG. 3), 2520 (FIG. 13); I-beam 2514, 178 (FIG. 4); the firing bar 172 (FIG. 4); and/or on a proximal end of the cutting edge 182 (FIG. 4), 2509 (FIG. 13). For conciseness and clarity, the displacement member in the process 4200 will primarily be discussed in terms of the I-beam 2514. In one aspect, the initial velocity or duty cycle at which the motor 2504 is set can vary according to the detected tissue thickness or another such tissue parameter, as discussed above with respect to the process 4070 (FIG. 34). In another aspect, the initial velocity or duty cycle at which the motor 2504 is set upon initiation 4202 of the displacement member stroke can be a fixed or default value.

After the displacement member stroke is initiated 4202, the control circuit 2510 monitors the I-beam 2514 force through the firing stroke and determines 4204 whether the force is greater than or equal to a threshold force. As discussed above, the I-beam 2514 force can be determined in several different ways in different aspects. In one aspect, the I-beam 2514 force can be determined by measuring the motor 2504 current, where motor 2504 current is based on the load experienced by the I-beam 2514 as it advances distally. In another aspect, the I-beam 2514 force can be determined by way of a strain gauge positioned on one or more components of the firing drive system. In yet another aspect, the I-beam 2514 force may be determined by monitoring the actual position of the I-beam 2514 compared to an expected position. In this aspect, when the actual position of the I-beam 2514 is less than the expected position, then the I-beam 2514 is experiencing a greater than expected force.

The threshold force can be, for example, a fixed value stored in a memory of the surgical instrument 2500. The threshold force can additionally be input or pre-programmed by an operator of the surgical instrument 2500 or can be downloaded, or otherwise received, by the surgical instrument 2500 from an external source prior to use.

If the control circuit 2510 determines 4204 that the I-beam 2514 force exceeds a threshold force, then the process 4200 proceeds down the YES branch and the control circuit 2510 pauses 4206 the I-beam 2514 for a length of time. In one aspect, the control circuit 2510 pauses 4206 the I-beam 2514 by deactivating the motor 2504. The length of time for which the I-beam 2514 is paused 4206 can be fixed or variable. In one aspect, the pause length is a fixed value that is stored in a memory of the surgical instrument 2500, input or pre-programmed by an operator of the surgical instrument 2500, or received by the surgical instrument 2500 from an external source prior to use. In another aspect, the pause length can vary according to a position of the I-beam 2514. For example, the pause length can decrease as a function of the I-beam 2514 position from the begin position 4006 to the end position 4008 of the firing stroke. In another aspect, the pause length can vary according to one or more parameters or characteristics associated with the end effector 912 and/or a tissue section captured by the end effector 2502 as measured, for example, by the sensors 920, 926 (FIG. 33) at the end effector 2502. For example, the pause length can increase as a function of the thickness of the tissue detected by the sensors 920, 926. In yet other aspects, the pause length can vary according to a combination of multiple variables.

The control circuit 2510 next determines 4208 whether the stroke of the I-beam 2514 is completed. If the firing stroke is complete, then the process 4070 proceeds along the YES branch and the process 4200 is completed 4210. If the firing stroke is not complete, then the process 4200 proceeds along the NO branch and continues a loop of determining 4204 whether I-beam 2514 force exceeds a threshold force and pausing 4206 the translation of the I-beam 2514 accordingly, as described above. Stated differently, the process 4200 continues to monitor the I-beam 2514 force throughout its firing stroke. If the control circuit 2510 determined 4204 that the I-beam 2514 force was less than a threshold force, then the process 4200 proceeds down the NO branch, which skips the pausing 4206 the translation of the I-beam 2514 and proceeds directly to determining 4208 whether the stroke of the I-beam 2514 is completed, which then proceeds as described above.

Figure 37:
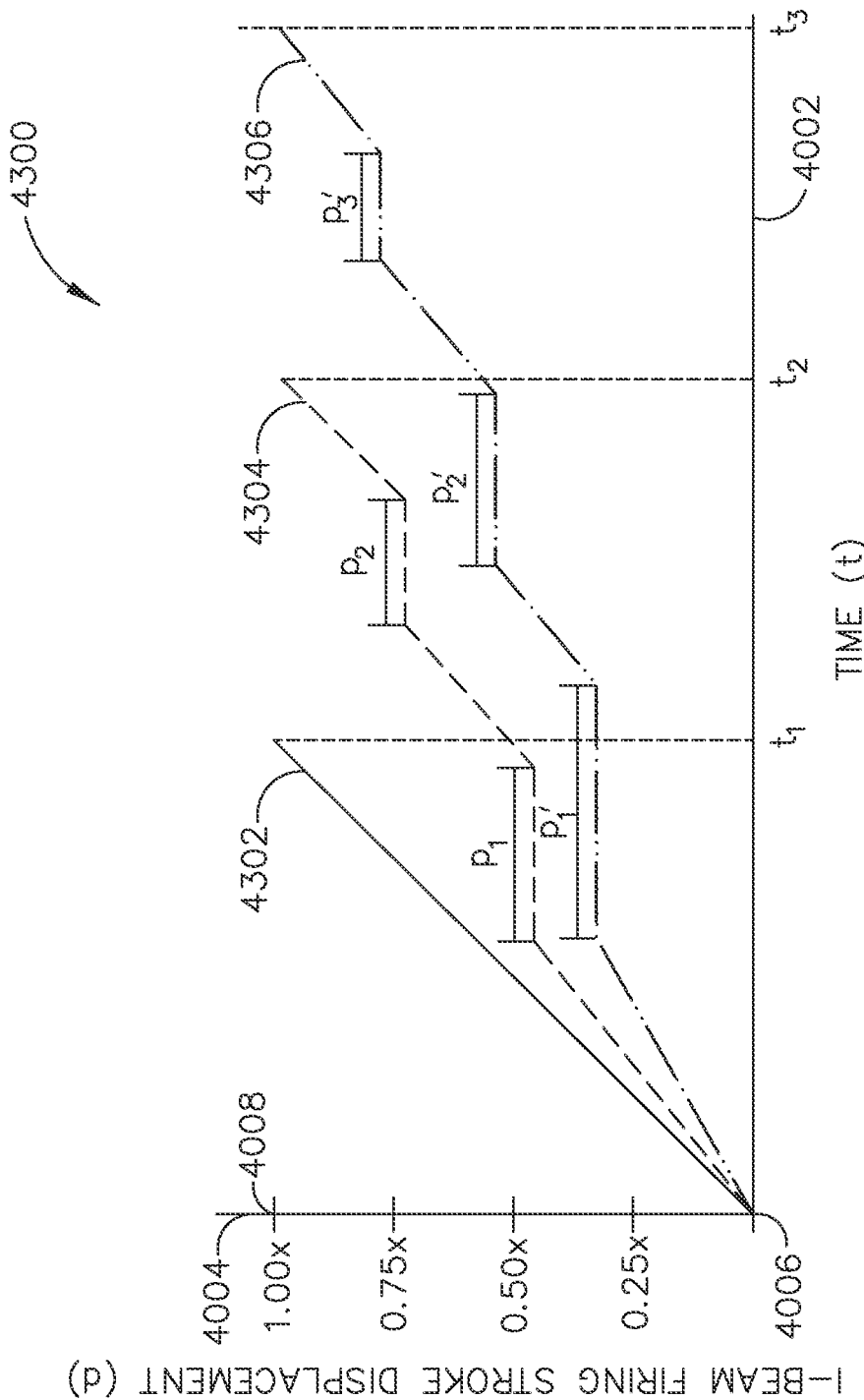
FIG. 37 is a diagram plotting three example firing member strokes executed according to the process of FIG. 36 according to one or more aspects of this disclosure.
Figure 38:
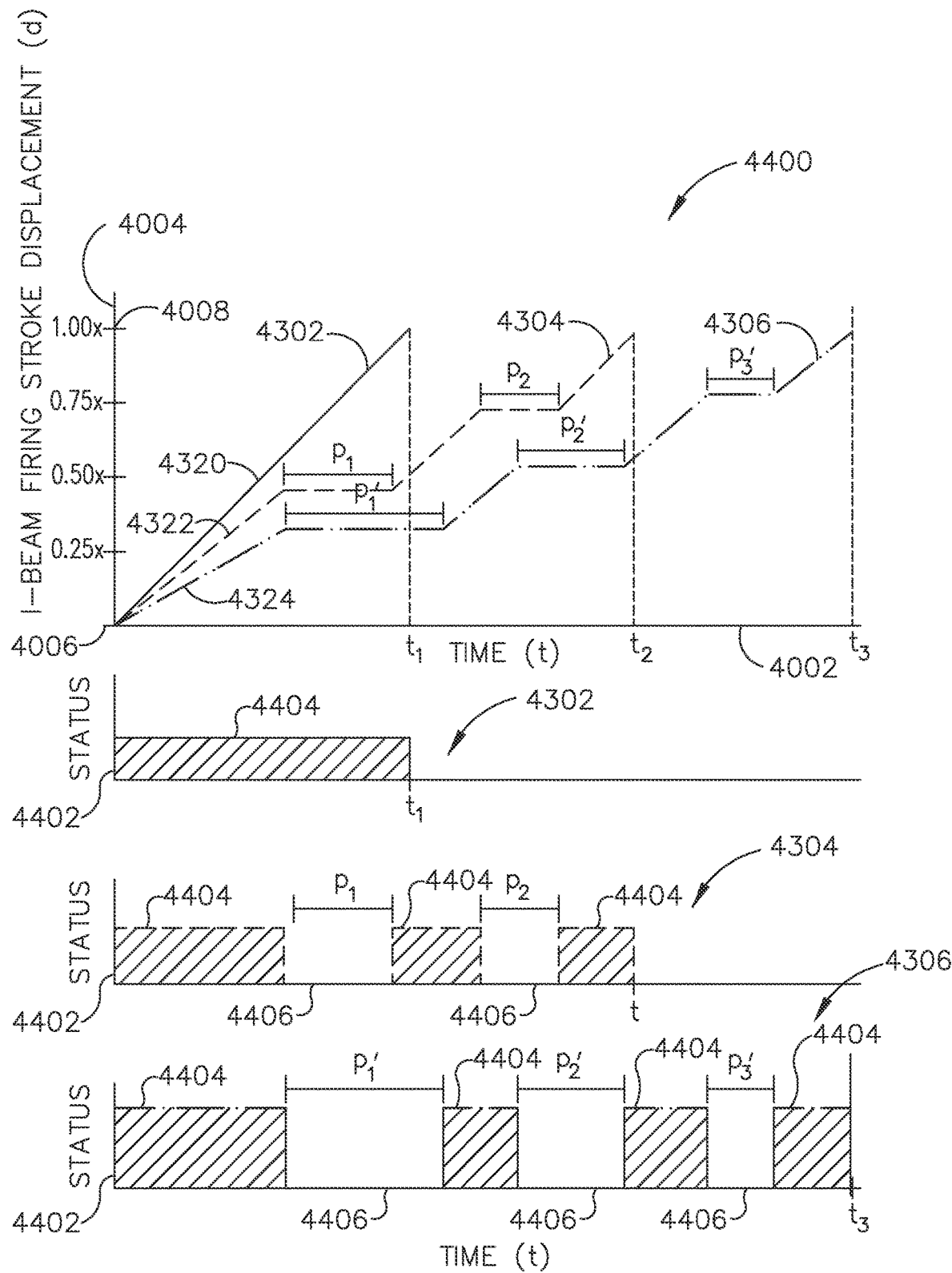
FIG. 38 is the diagram of FIG. 37 including a waveform of the motor activation of each of the three examples according to one or more aspects of this disclosure.

FIG. 37 is a second diagram 4300 plotting three examples of I-beam 2514 firing stroke displacement executed according to the process 4200 of FIG. 36 in accordance with one or more aspects of the present disclosure. For clarity, a third diagram 4400 in FIG. 38 further includes a waveform of the motor activation status 4402 of each of the three examples in FIG. 37. The second diagram 4300 includes a horizontal axis 4002 representing elapsed time and a vertical axis 4004 representing the displacement or position of the I-beam 2514 over a stroke between a stroke begin position 4006 and a stroke end position 4008. When the motor 2504 is activated 4404, the control circuit 2510 can be causing the motor control 2508 to apply a voltage or current to the motor 2504. When the motor 2504 is deactivated 4406, the control circuit 2510 can be causing the motor control 2508 to not apply a voltage or current to the motor 2504.

A first example 4302 shows a response of the surgical instrument 2500 when the I-beam 2514 force does not exceed a threshold force for the entire length of the firing stroke of the I-beam 2514. Accordingly, the process 4200 executed by the control circuit 2510 does not pause the I-beam 2514 at any point and thus the motor 2504 driving the I-beam 2514 is activated 4404 during the entire length of the firing stroke, which ends at time $t_1$.

A second example 4304 shows a response of the surgical instrument 2500 when the I-beam 2514 force exceeds a threshold force at various points. This can be visualized by the fact that the initial slope 4322 of the second example 4304 is smaller than the slope 4320 of the first example 4302. In other words, the I-beam 2514 is advancing at a lower velocity in the second example 4304 than the first example 4302. When all other factors are held constant, when the I-beam 2514 is advancing at a lower than expected velocity, the I-beam 2514 can be correspondingly experiencing a larger than expected force. Accordingly, the process 4200 executed by the control circuit 2510 pauses the I-beam 2514 when the I-beam 2514 force exceeds a threshold. The motor 2504 thus alternates between periods of activation 4404 and deactivation 4406, separated by a first pause $p_1$ and a second pause $p_2$. Note that the periods of motor activation 4404 correspond to translation of the I-beam 2514 and the periods of motor deactivation 4406 correspond to the I-beam 2514 not translating, i.e., pausing. The second example 4304 illustrates an aspect wherein the length of the pauses is a function of the displacement position of the I-beam 2514. Specifically, the lengths of the pauses decrease as the I-beam 2514 translates from the first or begin position 4006 to the second or end position 4008 of the firing stroke such that $p_2 < p_1$. The introduction of the pauses to the firing stroke decreases the average velocity of the I-beam 2514 over the course of the firing stroke, causing the firing stroke to end at time $t_2$, which is larger than $t_1$.

A third example 4306 likewise shows a response of the surgical instrument 2500 when the I-beam 2514 force exceeds a threshold force at various points. Accordingly, the process 4200 executed by the control circuit 2510 pauses the I-beam 2514 and the motor 2504 thus alternates between periods of activation 4404 and deactivation 4406, separated by a first pause $p_{1'}$, a second pause $p_{2'}$, and a third pause $p_{3'}$. The third example 4306 represents a situation wherein the I-beam 2514 force exceeds the threshold force to a greater degree than in the second example 4304. This can be visualized by the fact that the initial slope 4324 of the third example 4306 is smaller than the corresponding initial slope 4322 of the second example 4304. Therefore, the I-beam 2514 is advancing at a lower velocity in the third example 4306 than the second example 4304, which can be indicative of the thickness of the tissue being cut by the I-beam 2514 being greater in the third example 4306. The third example 4306 illustrates an aspect wherein the length of the pauses is a function of both the tissue thickness and the displacement position of the I-beam 2514. Specifically, the number of pauses increases and the pause length increases as the tissue thickness increases, such that $p_{1'} > p_1$. Furthermore, the pause length decreases as the I-beam 2514 translates from the first or begin position 4006 to the second or end position 4008 of the firing stroke such that $p_{3'} < p_{2'} < p_{1'}$. The introduction of the pauses to the firing stroke decreases the average velocity of the I-beam 2514 over the course of the firing stroke, causing the firing stroke to end at time $t_3$, which is larger than $t_1$. As the lengths of the pauses are larger and the pauses are more numerous than in the second example 4304, $t_3$ is likewise larger than $t_2$.

The functions or processes 4070, 4200 described herein may be executed by any of the processing circuits described herein, such as the control circuit 700 described in with FIGS. 5-6, the circuits 800, 810, 820 described in FIGS. 7-9, the microcontroller 1104 described in with FIGS. 10 and 12, and/or the control circuit 2510 described in FIG. 14.

Various aspects of the subject matter described herein are set out in the following numbered examples:

Example 1. A surgical instrument comprising: a displacement member configured to translate within the surgical instrument; a motor coupled to the displacement member to translate the displacement member; a sensor configured to sense a thickness of a tissue grasped by an end effector; and a control circuit coupled to the motor and the sensor, the control circuit configured to: retrieve an expected thickness of the tissue; determine the thickness of the tissue via the sensor; and set a duty cycle for driving the motor, wherein the duty cycle corresponds to the thickness of the tissue relative to the expected thickness of the tissue.

Example 2. The surgical instrument of Example 1, wherein the control circuit is configured to update the duty cycle based on a position of the displacement member.

Example 3. The surgical instrument of Example 1 through Example 2, wherein the control circuit is configured to increase the duty cycle as the displacement member is translated.

Example 4. The surgical instrument of Example 1 through Example 3, wherein the control circuit is configured to set the duty cycle to a default duty cycle when the thickness of the tissue is less than or equal to the expected thickness of the tissue.

Example 5. The surgical instrument of Example 4, wherein the control circuit is configured to set the default duty cycle to 100%.

Example 6. The surgical instrument of Example 1 through Example 5, wherein the control circuit is configured to retrieve the expected thickness of the tissue is retrieved from a memory.

Example 7. A surgical instrument comprising: a displacement member configured to translate within the surgical instrument; a motor coupled to the displacement member to translate the displacement member; and a control circuit coupled to the motor, the control circuit configured to: determine a force on the displacement member; and pause the motor according to whether the force is greater than a threshold force.

Example 8. The surgical instrument of Example 7, wherein the control circuit is configured to pause the motor for a fixed length of time.

Example 9. The surgical instrument of Example 7 through Example 8, wherein the control circuit is configured to pause the motor for a variable length of time.

Example 10. The surgical instrument of Example 9, wherein the variable length of time corresponds to a position of the displacement member.

Example 11. The surgical instrument of Example 9 through Example 10, wherein the variable length of time corresponds to the force compared to the threshold force.

Example 12. The surgical instrument of Example 9 through Example 11, further comprising: a sensor configured to detect a tissue parameter, the sensor operably coupled to the control circuit; wherein the variable length of time corresponds to the tissue parameter.

Example 13. The surgical instrument of Example 12, wherein the sensor comprises a tissue thickness sensor.

Example 14. The surgical instrument of Example 7 through Example 13, wherein the control circuit determines the force on the displacement member according to a current drawn by the motor.

Example 15. A method of controlling a motor in a surgical instrument, the surgical instrument comprising a displacement member configured to translate within the surgical instrument, a motor coupled to the displacement member to translate the displacement member, a sensor configured to sense a thickness of a tissue grasped by an end effector, and a control circuit coupled to the motor, the method comprising: retrieving, by the control circuit, an expected thickness of the tissue; determining, by the control circuit, the thickness of the tissue via the sensor; and setting, by the control circuit, a duty cycle for driving the motor, wherein the duty cycle corresponds to the thickness of the tissue relative to the expected thickness of the tissue.

Example 16. The method of Example 15, further comprising updating, by the control circuit, the duty cycle based a position of the displacement member.

Example 17. The method of Example 15 through Example 16, further comprising setting, by the control circuit, the duty cycle to a default duty cycle when the thickness of the tissue is less than or equal to the expected thickness of the tissue.

Example 18. The method of Example 17, further comprising setting, by the control circuit, the default duty cycle to 100%.

Example 19. The method of Example 15 through Example 18, further comprising retrieving, by the control circuit, the expected thickness of the tissue from a memory.

Example 20. The method of Example 15 through Example 19, further comprising detecting, by the control circuit, a position of the displacement member by another sensor.

Systems and Methods for Controlling Motor Velocity of a Surgical Stapling and Cutting Instrument According to Articulation Angle of End Effector During use of a motorized surgical stapling and cutting instrument it is possible that the force to fire or load experienced by the cutting member or the firing member will vary or increase based on the articulation angle of the end effector. Therefore, it may be desirable to vary the firing velocity the cutting member or the firing member as a function of articulation angle of the end effector to reduce the force to fire load on the cutting member or the firing member due as a function of increasing end effector articulation angle.

Having described techniques for measuring the articulation angle of the articulation joint 2270 and driving the longitudinally movable drive member 120, the firing member 220, the firing bar 172, or the I-beam 178 employing the firing drive system 80 of the surgical instrument 10 (FIGS. 1-4) the description now turns to FIGS. 13, 14, and 39-44 for a description of various techniques for controlling the firing rate or velocity of the I-beam 2514, or the firing bar 2520, based on the articulation angle of the end effector 2502.

Figures 39, 40:
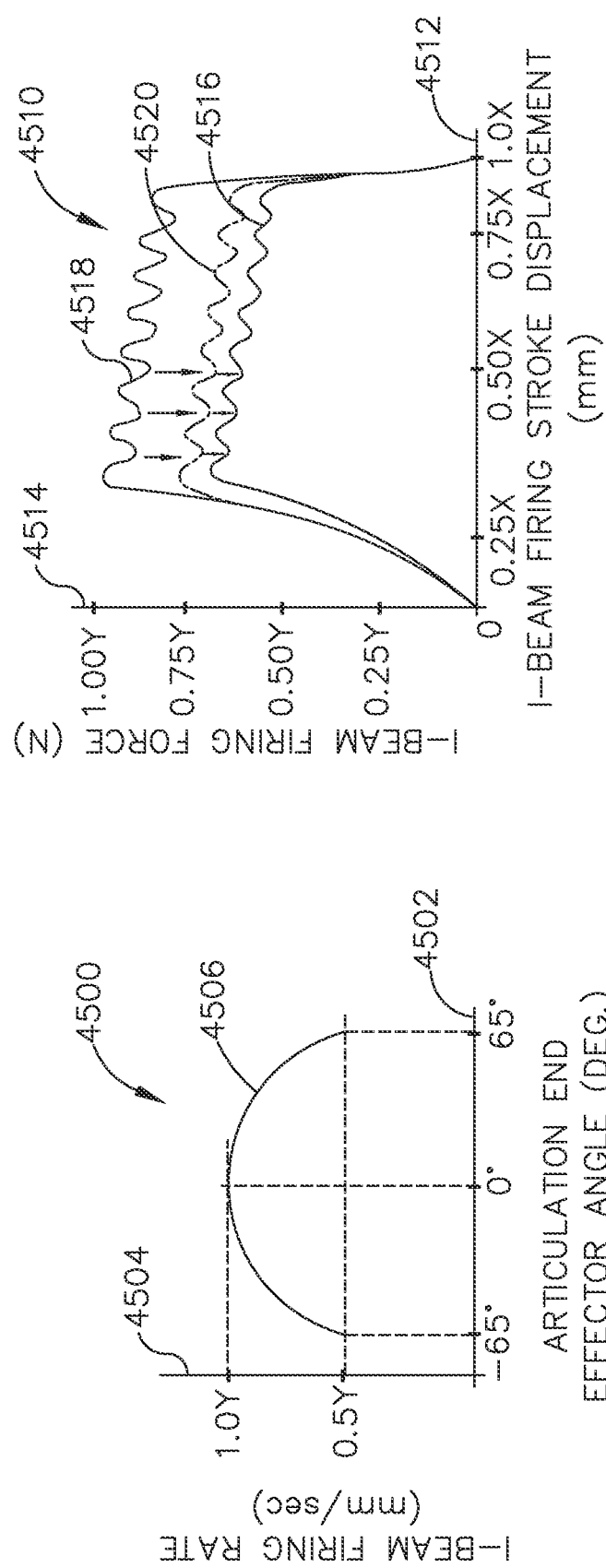
FIG. 39 is a graph of a displacement member rate (velocity) as a function of end effector articulation angle, in accordance with one or more aspects of the present disclosure.
FIG. 40 is a graph of a displacement member force as a function of firing stroke displacement of the displacement member, in accordance with one or more aspects of the present disclosure.

FIG. 39 is a graph 4500 of the I-beam 2514 firing rate (velocity) as a function of the end effector 2502 articulation angle, in accordance with one or more aspects of the present disclosure. The horizontal axis 4502 represents end effector 2502 articulation angle varying from −65° to +65° degrees, for example, and the vertical axis 4504 represents the I-beam 2514 firing rate from 0 to 1.0Y mm/sec, where Y is a scaling factor. For example, when Y=20, the vertical axis 4504 is scaled from 0 to 20 mm/sec. The curve 4506 shows that as the end effector 2502 articulation angle varies from −65° to +65° the E-bema 2514 firing rate varies nonlinearly and is symmetric about 0°. The maximum I-beam 2514 firing rate of 1.0Y occurs at an end effector 2300 articulation angle of 0°, in other words, when the end effector axis EA and the shaft axis SA are aligned. As the end effector 2502 is articulated from 0° to +65° or from or 0° to −65° the I-beam 2514 firing rate decrease nonlinearly from 1.0Y to 0.5Y.

FIG. 40 is a graph 4510 of I-beam 2514 firing force as a function of firing stroke displacement of the I-beam 2514, in accordance with one or more aspects of the present disclosure. The horizontal axis 4512 represents firing stroke displacement of the I-beam 2514 from 0 mm (the beginning of the firing stroke) to 1.0× mm (the end of the firing stroke), where X is a scaling factor associated with the nominal length of a stapler cartridge. Nominal lengths of stapler cartridges range from 10-60 mm, for example. The vertical axis 4514 represents I-beam 2514 firing force from 0-1.00Y N (Newton), where Y is a scaling factor. In one aspect, the firing member 2520 force varies from 0-900 N (0-202.328 lbs-force). The graph 4510 shows three curves 4516, 4518, 4520. The first curve 4516 represents I-beam 2514 firing force as a function of firing stroke displacement of the I-beam 2514 at an end effector 2502 articulation angle of 0° (the end effector axis EA and the shaft axis SA are aligned) as the I-beam 2514 advances distally at a constant velocity. The second curve 4518 represents I-beam 2514 firing force as a function of firing stroke displacement of the I-beam 2514 at an end effector 2502 articulation angle of ±65° as the I-beam 2514 advances distally at a constant velocity. In other words, without varying the velocity of the motor 2504 as a function of the articulation angle of the end effector 2502. As shown by the second curve 4520 relative to the first curve 4516, the I-beam 2514 force as a function of firing stroke displacement of the I-beam 2514 is greater when the I-beam 2514 advances distally at a constant velocity at an end effector 2502 articulation angle of ±65°. The third curve 4520 shows an overall lower I-beam 2514 firing force as a function of firing stroke displacement of the I-beam 2514 that is achieved by varying the velocity of the motor 2504 as a function of end effector 2502 articulation angle from ±65° as shown in FIG. 39, for example.

Force acting on the firing member 2520 may be determined using various techniques. In one aspect, the firing member force may be determined by measuring the motor 2504 current, where the motor 2504 current is based on the load experienced by the firing member 2520 as it advances distally. In another aspect, the I-beam 2514 firing force may be determined by positioning a strain gauge on the drive member 120 (FIG. 2), the firing member 220 (FIG. 2), the firing member 2520, the firing bar 172 (FIG. 2), and/or the I-beam 2514, 178 (FIG. 4). In yet another aspect, the I-beam 2514 firing force may be determined by monitoring the actual position of the I-beam 2514 moving at an expected velocity based on the current set velocity of the motor 2504 after a predetermined elapsed period $T_1$ and comparing the actual position of the I-beam 2514 relative to the expected position of the I-beam 2514 based on the current set velocity of the motor 2504 at the end of the period $T_1$. Thus, if the actual position of the I-beam 2514 is less than the expected position of the I-beam 2514, the force on the I-beam 2514 is greater than a nominal force. Conversely, if the actual position of the I-beam 2514 is greater than the expected position of the I-beam 2514, the force on the I-beam 2514 is less than the nominal force. The difference between the actual and expected positions of the I-beam 2514 is proportional to the deviation of the force on the I-beam 2514 from the nominal force. The latter technique is described in detail in U.S. Pat. No. 10,624,633, which issued on Apr. 21, 2020, which is incorporated herein by reference in its entirety. As the firing force of the I-beam 2514 varies as a function of end effector 2502 articulation angle, varying the control voltage applied to the motor 2504 to control the velocity of the motor 2504 through differing maximum current thresholds related to end effector 2502 articulation angle can be employed to reduce the firing force on the I-beam 2514 and force-to-fire the I-beam 2514 generally. This is technique is described below in connection with FIG. 40.

Figure 41:
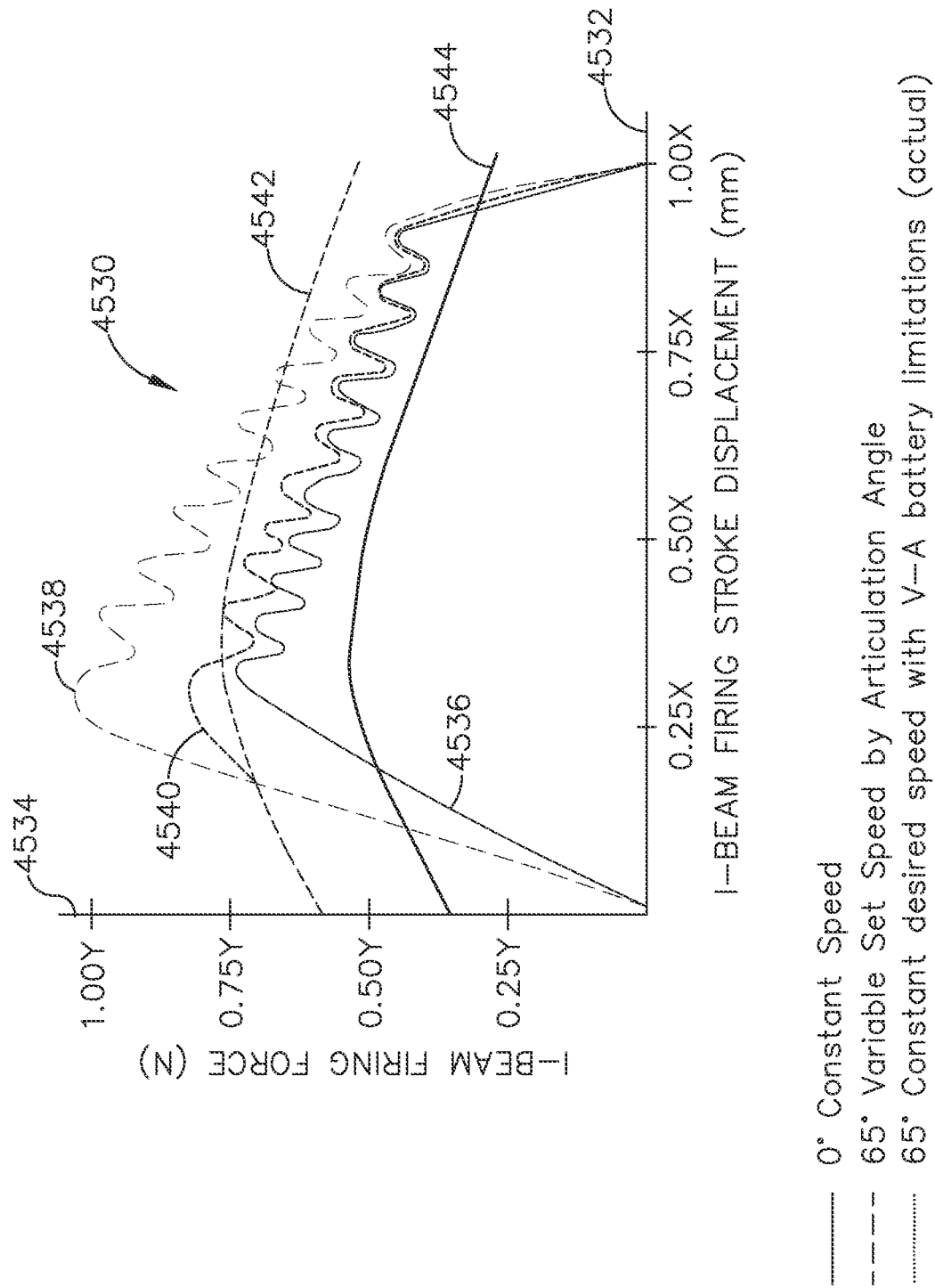
FIG. 41 is a graph of a displacement member force as a function of firing stroke displacement of the displacement member, in accordance with one or more aspects of the present disclosure.

FIG. 41 is a graph 4530 of I-beam 2514 firing force as a function of firing stroke displacement of the I-beam 2514, in accordance with one or more aspects of the present disclosure. The horizontal axis 4532 represents firing stroke displacement from 0-1.0× mm, where X is a scaling factor associated with the nominal length of a stapler cartridge. Nominal lengths of stapler cartridges range from 10-60 mm, for example. The vertical axis 4534 represents I-beam 2514 firing force from 0-1.00Y N, where Y is a scaling factor. In one aspect, the I-beam 2514 firing force varies from 0-900 N (0-202.328 lbs-force). The graph 4530 shows three curves 4536, 4538, 4540 and two thresholds 4542, 4544 based on end effector 2502 articulation angle to reduce the firing force and force-to-fire on the I-beam 2514. The first curve 4536 represents I-beam 2514 firing force as a function of firing stroke displacement at an end effector 2502 articulation angle of 0° (the end effector axis EA and the shaft axis SA are aligned) as the I-beam 2514 advances distally at a constant velocity. The second curve 4538 represents I-beam 2514 firing force as a function of firing stroke displacement of the I-beam 2514 at an end effector 2502 articulation angle of 65° as the firing member advances distally at a variable velocity set by articulation angle. The third curve 4540 represents I-beam 2514 firing force as a function of firing stroke displacement of the I-beam 2514 at an end effector 2502 articulation angle of 65° as the I-beam 2514 advances at a constant desired velocity with actual battery capacity (V-A) limitations.

The graph 4530 also shows variable I-beam 2514 firing force trigger thresholds 4542, 4544 based on the articulation angle of the end effector 2502, which results in a variable I-beam 2514 firing rate throughout the I-beam 2514 firing stroke. The upper threshold 4542 is for an end effector 2502 articulation angle of 65° and the lower threshold 4544 for an end effector 2502 articulation angle of 0°. With the end effector 2502 articulation angle set to 65° the I-beam 2514 advances at a variable velocity until the I-beam 2514 firing force crosses the upper threshold 4542, at which time, an algorithm adjusts the velocity of the motor 2504 to a desired velocity until the I-beam 2514 firing force drops below the I-beam 2514 firing force upper threshold 4542 and then holds the velocity of the motor 2054 constant. The I-beam 2514 then advances distally at the constant desired velocity. With the end effector 2502 articulation angle set to 0° the I-beam 2514 advances at a variable velocity until the I-beam 2514 firing force crosses the lower threshold 4544, at which time, an algorithm adjusts the velocity of the motor 2504 to a constant desired velocity. The I-beam 2514 advances distally at the constant desired velocity. This operation is further described below in connection with FIG. 41. The upper threshold 4542 and the lower threshold 4544 as well as intervening threshold therebetween that vary based on the articulation angle of the end effector 2502, are nonlinear across the firing stroke displacement of the stapler cartridge 2518. In other aspects, the thresholds 4542, 4544 may be a straight line constant or may be a straight line with a slope. The thresholds 4542, 4544 represent I-beam 2514 firing force regardless how the I-beam 2514 firing force is determined.

As discussed above, the I-beam 2514 firing force may be determined by motor 2504 current, strain gauge, or represented by comparing the actual position of the I-beam 2514 over a predetermined period $t_1$ relative to the expected position of the I-beam 2514 advancing distally at a set motor 2504 velocity. In the latter configuration, with reference also to FIG. 42, the surgical instrument further comprises a timer/counter circuit 2531 coupled to the control circuit 2510, where the timer/counter circuit 2531 is configured to measure elapsed time. The control circuit 2510 is configured to set the motor 2504 velocity, receive an initial position of the I-beam 2514 from the position sensor 2534, receive a reference time $t_1$ from the timer/counter circuit 2531 corresponding to the initial position of the I-beam 2514, and determine an anticipated position of the I-beam 2514 at a time $t_2$ based on the set motor 2504 velocity. The control circuit 2510 is further is configured to receive an actual position of the I-beam 2514 at the time $t_2$ from the position sensor 2534, compare the actual position of the I-beam 2514 at the time $t_2$ with the anticipated position of the I-beam 2514 at the time $t_2$, and determine the firing force on the I-beam 2514 based on a difference between the actual position of the I-beam 2514 at the time $t_2$ with the anticipated position of the I-beam 2514 at the time $t_2$.

Figure 42:
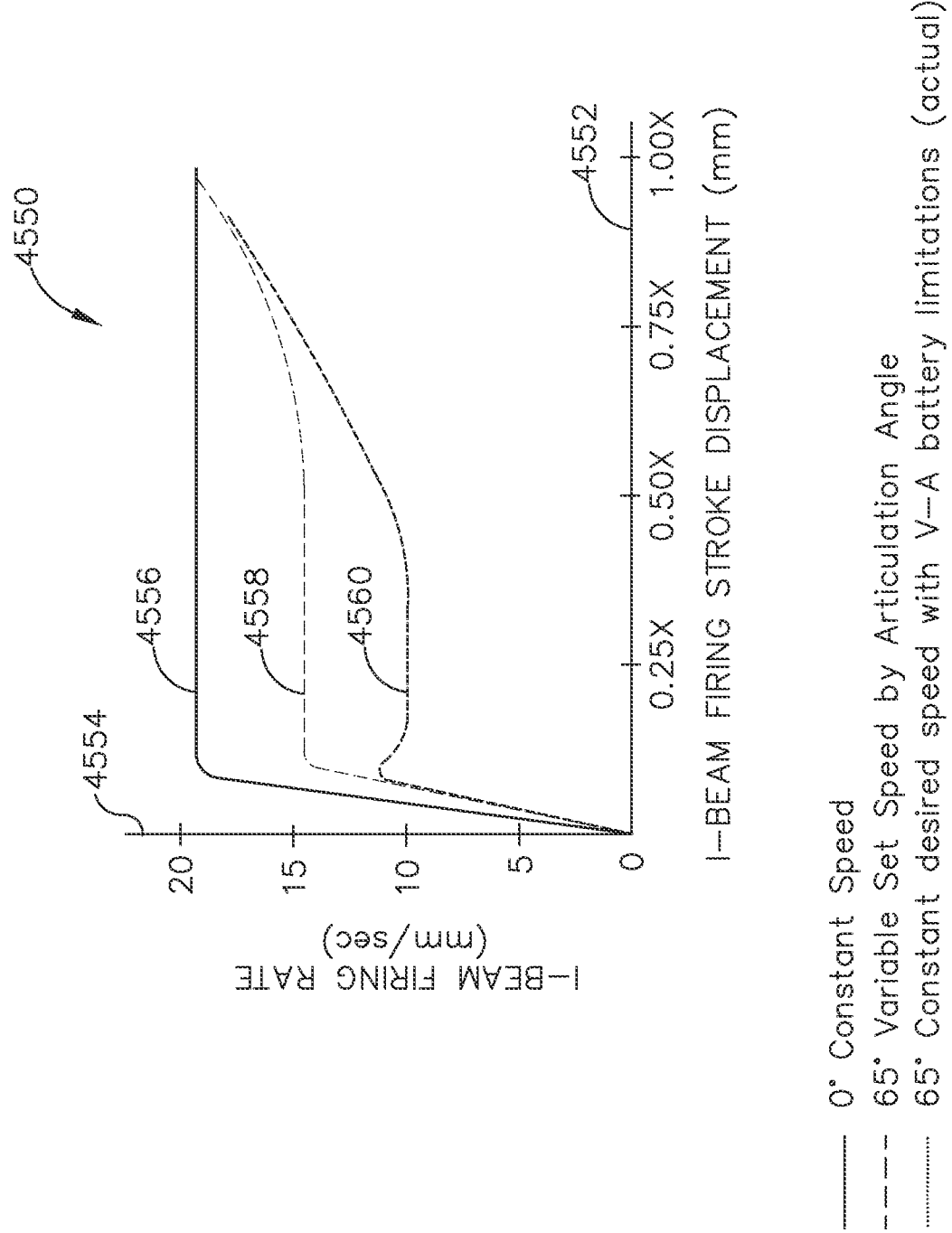
FIG. 42 is a graph of a displacement member rate as a function of a linear displacement stroke displacement of the displacement member, in accordance with one or more aspects of the present disclosure.

FIG. 42 is a graph 4550 of I-beam 2514 firing rate as a function of firing stroke displacement of the I-beam 2514, in accordance with one or more aspects of the present disclosure. The horizontal axis 4552 represents I-beam 2514 firing stroke displacement from 0-1.0× mm, where × is a scaling factor associated with the nominal length of a stapler cartridge. Nominal lengths of stapler cartridges range from 10-60 mm, for example. The vertical axis 4554 represents I-beam 2514 firing rate from 0-1.00Y N, where Y is a scaling factor. In one aspect, the I-beam 2514 force varies from 0-20 mm/sec. The graph 4550 shows three curves 4556, 4558, 4559. The first curve 4556 is the I-beam 2514 rate set at an end effector articulation angle of 0°. The firing rate of the I-beam 2514 increases over the initial displacement and remains constant throughout the remaining stroke with the motor 2504 set to a constant velocity. The second curve 4558 is the firing rate of the I-beam 2514 set at an end effector 2502 articulation angle of 65°. The I-beam 2514 firing rate increases over the initial displacement and remains constant throughout the remaining stroke with the motor 2504 set to a variable velocity based on the articulation angle of the end effector 2502. The third curve 4559 is the firing rate of the I-beam 2514 set at an end effector 2502 articulation angle of 65°. The I-beam 2514 increases over the initial displacement and varies throughout the remaining stroke with the motor 2504 set to a constant desired velocity with actual battery capacity (V-A) limitations.

Figure 43:
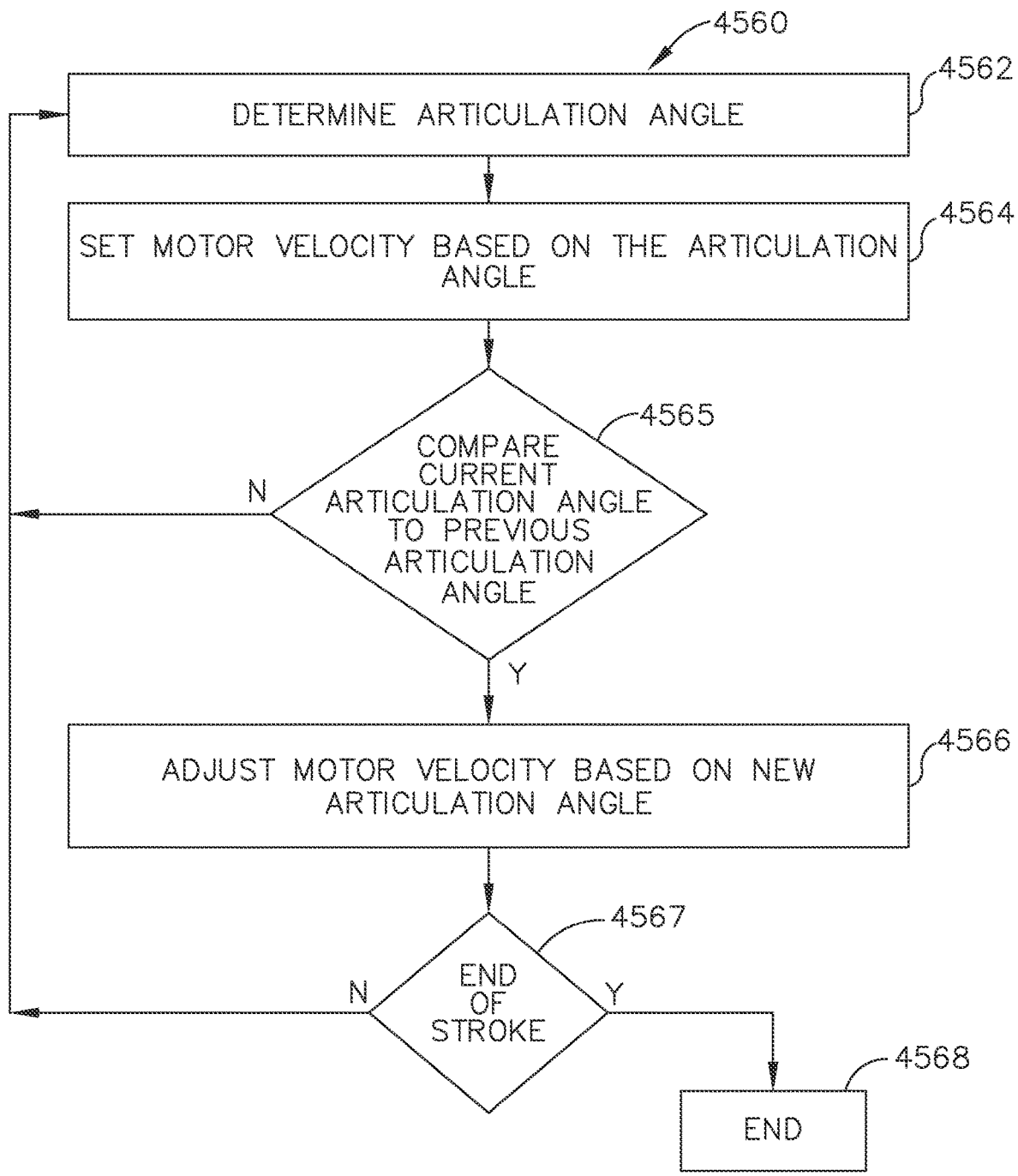
FIG. 43 is a logic flow diagram depicting a process of a control program or a logic configuration for controlling the rate of a displacement member such as an I-beam member based on articulation angle of the end effector, in accordance with one or more aspects of the present disclosure.

FIG. 43 is a logic flow diagram depicting a process 4560 of a control program or a logic configuration for controlling the rate of a displacement member such as an I-beam 2514, for example, based on articulation angle of the end effector 2502, in accordance with one or more aspects of the present disclosure. In the following description of the process 4560 in FIG. 43 reference also should be made to FIGS. 15-21 and 39-42. Accordingly, the control circuit 2510 determines 4562 the current articulation angle of the end effector 2502 based on information received from the position sensor 2534. The control circuit 2510 sets 4564 the velocity of the motor 2504 based on the articulation angle. The control circuit 2510 compares 4565 the current articulation angle to the previous articulation angle. If there is no change in articulation angle, the process 4560 continues along no branch (N) and the control circuit 2510 determines 4562 the articulation angle while maintaining the velocity of the motor 2504 constant. If there is a change in articulation angle of the end effector 2502, the process 4560 continues along yes branch (Y) and the control circuit 2501 adjusts 4566 the velocity of the motor 2504 based on the new articulation angle. The control circuit 2510 compares 4567 the actual position of the I-beam 2514 to the end of the firing stroke position. If the I-beam 2514 is at the end of the firing stroke, the process 4560 continues along the yes branch (Y) and ends 4568. If the I-beam 2514 has not reached the end of the firing stroke, the process 4560 continues along the no branch (N) and determines 4562 the articulation angle. The process 4560 continues until the position of the I-beam 2514 reaches 4569 the end of the firing stroke of the I-beam 2514.

Figure 44:
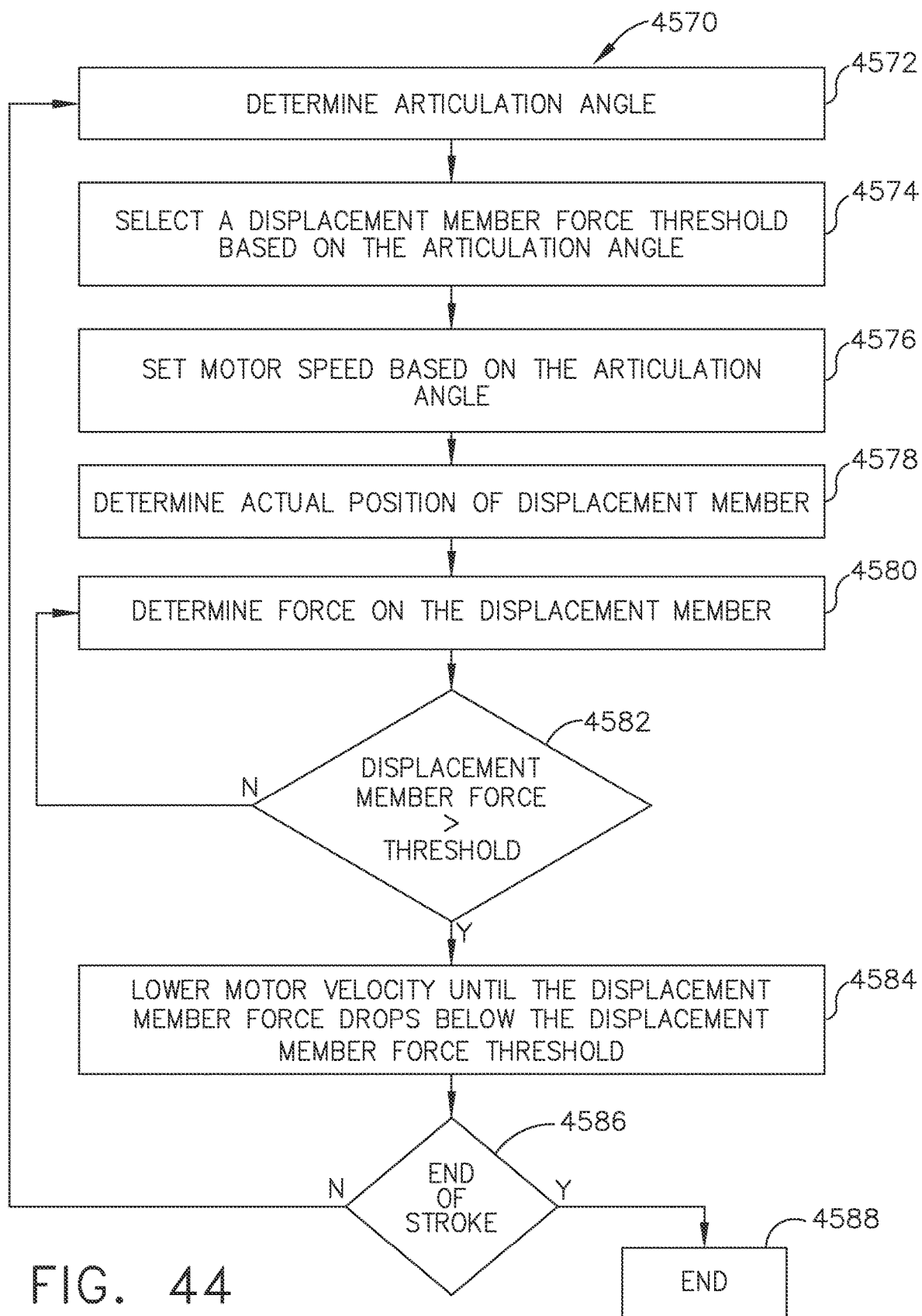
FIG. 44 is a logic flow diagram depicting a process of a control program or a logic configuration for controlling the rate of a displacement member such as a I-beam member based on articulation angle of the end effector, in accordance with one or more aspects of the present disclosure.

FIG. 44 is a logic flow diagram depicting a process 4570 of a control program or a logic configuration for controlling the rate of a displacement member such as an I-beam 2514, for example, based on articulation angle of the end effector 2502, in accordance with one or more aspects of the present disclosure. In the following description of the process 4570 in FIG. 44 reference also should be made to FIGS. 15-21 and 39-42. Accordingly, the control circuit 2510 determines 4572 the articulation angle of the end effector 2502 based on information received from the position sensor 2534. In the example where the displacement member is the I-beam 2514, the control circuit 2510 selects 4574 an I-beam 2514 force threshold based on the articulation angle of the end effector 2502. The control circuit 2510 provides a motor set point signal 2522 to the motor controller 2508, which provides the motor drive signal 2524 to set 4576 the velocity of the motor 2504 based on the articulation angle of the end effector 2502. The control circuit 2510 determines 4578 the actual position of the I-beam 2514 and determines 4580 the I-beam 2514 firing force and compares 4582 the I-beam 2514 firing force with the threshold. If the I-beam 2514 firing force exceeds the threshold, the process continues along yes (Y) branch and the lowers 4584 the velocity of the motor 2504 until the I-beam 2514 firing force drops below the I-beam 2514 firing force threshold. If the I-beam 2514 firing force is less than the threshold, the process continues along no (N) branch and continues to determine 4578 the actual position of the I-beam 2514, determine 4580 the I-beam 2514 firing force, and compare 4582 the I-beam 2514 firing force with the threshold until the I-beam 2514 firing force exceeds the threshold. The motor drive signal 2524 may be a varying voltage or current signal, a pulse-width-modulated (PWM) signal, and/or a variable duty cycle signal. The control circuit 2510 compares the actual position of the I-beam 2514 to the end of I-beam 2514 firing stroke position. If the I-beam 2514 is at the end of the firing stroke, the process 4570 continues along the yes branch (Y) and ends 4588. If the I-beam 2514 has not reached the end of the firing stroke, the process 4570 continues along the no branch (N) and determines 4572 the articulation angle of the end effector 2502. The process 4570 continues until the I-beam 2514 reaches the end of the firing stroke.

The functions or processes 4560, 4570 described herein may be executed by any of the processing circuits described herein, such as the control circuit 700 described in with FIGS. 5-6, the circuits 800, 810, 820 described in FIGS. 7-9, the microcontroller 1104 described in with FIGS. 10 and 12, and/or the control circuit 2510 described in FIG. 14.

Various aspects of the subject matter described herein are set out in the following numbered examples:

Example 1. A surgical instrument, comprising: a displacement member; a motor coupled to the displacement member to translate the displacement member; a control circuit coupled to the motor; a position sensor coupled to the control circuit, the position sensor configured to measure the position of the displacement member and configured to measure an articulation angle of an end effector relative to a longitudinally extending shaft; wherein the control circuit is configured to: determine the articulation angle between the end effector and the shaft; select a force threshold based on the articulation angle; set motor velocity based on the articulation angle; determine force on the displacement member; and adjust the motor velocity when the force on the displacement member is greater than the force threshold.

Example 2. The surgical instrument of Example 1, wherein the control circuit is configured to determine actual position of the displacement member.

Example 3. The surgical instrument of Example 1 through Example 2, wherein the control circuit is configured to determine end of firing stroke of the displacement member.

Example 4. The surgical instrument of Example 1 through Example 3, wherein the control circuit is configured to compare the force on the displacement member to the force threshold.

Example 5. The surgical instrument of Example 1 through Example 4, further comprising a timer/counter circuit coupled to the control circuit, the timer/counter circuit configured to measure elapsed time; wherein the control circuit is configured to: set the motor velocity; receive an initial position of the displacement member from the position sensor; receive a reference time $t_1$ from the timer/counter circuit corresponding to the initial position of the displacement member; and determine an anticipated position of the displacement member at a time $t_2$ based on the motor velocity.

Example 6. The surgical instrument of Example 5, wherein the control circuit is configured to: receive an actual position of the displacement member at the time $t_2$ from the position sensor; compare the actual position of the displacement member at the time $t_2$ with the anticipated position of the displacement member at the time $t_2$; and determine the force on the displacement member based on a difference between the actual position of the displacement member at the time $t_2$ and the anticipated position of the displacement member at the time $t_2$.

Example 7. The surgical instrument of Example 1 through Example 6, wherein the control circuit is configured to lower the motor velocity until the force on the displacement member is less than the force threshold.

Example 8. A surgical instrument, comprising: a displacement member; a motor coupled to a proximal end of the displacement member to translate the displacement member; a control circuit coupled to the motor; a position sensor coupled to the control circuit, the position sensor configured to measure a position of the displacement member relative to an end effector and configured to measure an articulation angle of the end effector relative to a longitudinally extending shaft; wherein the control circuit is configured to: determine the articulation angle between the end effector and the longitudinally extending shaft; and set motor velocity based on the articulation angle.

Example 9. The surgical instrument of Example 8, wherein the control circuit is configured to determine actual position of the displacement member.

Example 10. The surgical instrument of Example 8 through Example 9, wherein the control circuit is configured to determine end of firing stroke of the displacement member.

Example 11. The surgical instrument of Example 8 through Example 10, wherein the control circuit is configured to compare the articulation angle with a previous articulation angle.

Example 12. The surgical instrument of Example 11, wherein the control circuit is configured to adjust the set motor velocity based on a new articulation angle.

Example 13. The surgical instrument of Example 8 through Example 12, further comprising a timer/counter circuit coupled to the control circuit, the timer/counter circuit configured to measure elapsed time; wherein the control circuit is configured to: set the motor velocity; receive an initial position of the displacement member from the position sensor; receive a reference time $t_1$ from the timer/counter circuit corresponding to the initial position of the displacement member; and determine an anticipated position of the displacement member at a time $t_2$ based on the set motor velocity.

Example 14. The surgical instrument of Example 13, wherein the control circuit is configured to: receive an actual position of the displacement member at the time $t_2$ from the position sensor; compare the actual position of the displacement member at the time $t_2$ with the anticipated position of the I-beam member at the time $t_2$; and determine a force on the displacement member based on a difference between the actual position of the displacement member at the time $t_2$ and the anticipated position of the displacement member at the time $t_2$.

Example 15. A method of controlling motor velocity in a surgical instrument, the surgical instrument comprising a displacement member, a motor coupled to the displacement member to translate the displacement member, a control circuit coupled to the motor, and a position sensor coupled to the control circuit, the position sensor configured to measure a position of the displacement member and configured to measure an articulation angle of an end effector relative to a longitudinally extending shaft, the method comprising: determining, by the control circuit, an articulation angle between an end effector and a longitudinally extending shaft; and setting, by the control circuit, motor velocity based on the articulation angle.

Example 16. The method of Example 15, further comprising: selecting, by the control circuit, a force threshold based on the articulation angle; determining, by the control circuit, force on the displacement member; and adjusting, by the control circuit, the motor velocity when the force on the displacement member is greater than the force threshold.

Example 17. The method of Example 15 through Example 16, further comprising determining, by the control circuit, actual position of the displacement member.

Example 18. The method of Example 15 through Example 17, further comprising determining, by the control circuit, end of firing stroke of the displacement member.

Example 19. The method of Example 15 through Example 18, further comprising comparing, by the control circuit, the articulation angle with a previous articulation angle.

Example 20. The method of Example 19, further comprising adjusting, by the control circuit, the motor velocity based on a new articulation angle.

Systems and Methods for Controlling Motor Velocity of a Surgical Stapling and Cutting Instrument During use of a motorized surgical stapling and cutting instrument the force to fire load on a cutting member or a firing member may vary as a function of tissue thickness. Generally, the force to fire exerted on the cutting member or the firing member will increase as the tissue thickness increases. Therefore, it may be necessary at the initial staging of the cutting member onto a ramp of the closure anvil slot to determine the initial tissue thickness and to set the firing velocity of the cutting member based on the determined tissue thickness to reduce the force to fire load on the cutting member or the firing member. It also may be desirable to provide continuous velocity control of the firing motor based on cutting member stroke over a fixed time interval as a proxy for force to fire load on exerted on the cutting member or the firing member.

Figure 45:
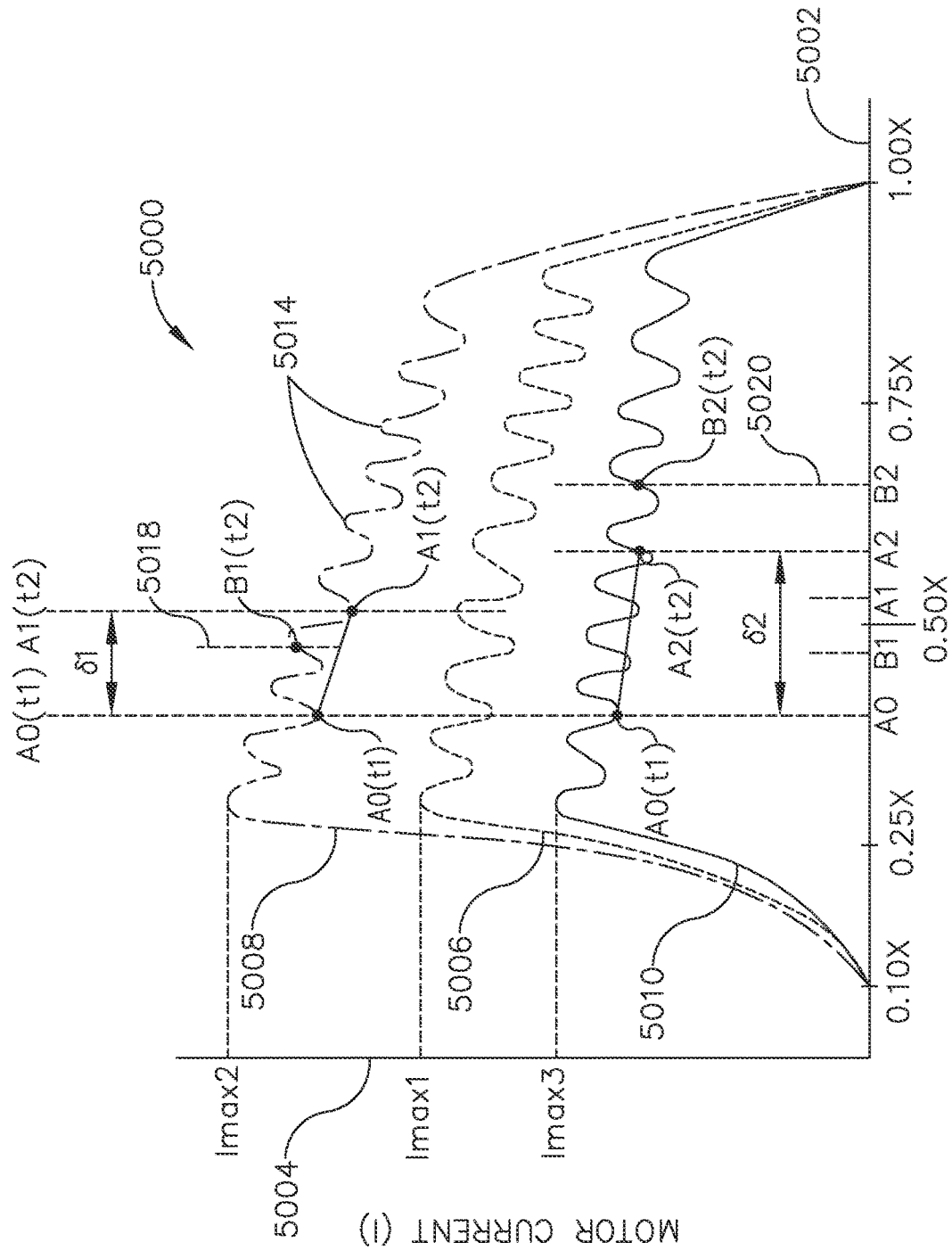
FIG. 45 is a graph depicting motor current (I) as a function of displacement member travel (d) according to one aspect of this disclosure.

FIG. 45 is a graph 5000 depicting motor current (I) as a function of displacement member travel (d) according to one aspect of this disclosure. FIG. 45 will now be described with reference also to FIGS. 10-15. In the example illustrated in FIG. 45, the horizontal axis 5002 represents the displacement of the I-beam 2514 over the length of a stapler cartridge 2518. The horizontal axis 5002 is scaled to represent the displacement of the I-beam 2514 over the length X of the stapler cartridge 2518, such as 10-60 mm stapler cartridges, for example. The horizontal axis 5002 of the graph 5000 represents travel of the I-beam 2514 and the vertical axis 5004 represents the current (I) drawn by the motor 2504.

In one aspect, the surgical instrument 2500 is programmed to control firing motor current (I) as a function of the position, displacement, or travel of the displacement member, e.g., the I-beam 2514, as it traverses the stapler cartridge 2518. The control circuit 2510 monitors the position sensor 2534 output to determine the location of the I-beam 2514. The position sensor 2534 employs the absolute positioning system 1100 described in connection with FIGS. 10-15. The displacement of the I-beam 2514 is determined over a predetermined time interval as measured by the timer/counter 2531 can be used as a proxy for the force applied to the I-beam 2514 to control the displacement rate or velocity of the I-beam 2514 to control the force-to-fire on the I-beam 2514. Accordingly, the time (t) it takes for the I-beam 2514 to get a known distance is determined by the timer/counter 2531 and the distance traveled during that time (t) is determined by the position sensor 2534, as described in connection with the absolute positioning system 1100. The time (t) it takes for the I-beam 2514 to reach a known distance and the distance traveled during that time (t) can be employed by a control algorithm or process to maximize the motor current (I) without overly elevating the force load on the I-beam 2514. This enables the proper staple formation through the tissue.

Accordingly, the surgical instrument 2500 is configured to make ongoing measurements of the expected displacement of the I-beam 2514, at its current programmed velocity, against a predefined time interval to be a proxy for the force applied to the I-beam 2514. The difference between the measured distance traveled by the I-beam 2514 and the anticipated distance traveled by the I-beam 2514 multiplied by a function (e.g., frictional coefficient of the cutting edge 2509, articulation angle, location of the cutting edge 2509 within the stroke) can be employed to calculate the load on the I-beam 2514 and provide the load as feedback to the control circuit 2510 and the motor control 2508 to adjust the motor drive signal 2524 current duty cycle (e.g., PWM) to control the velocity of the motor 2504. Accordingly, the motor 2504 can be controlled by a proxy of the load experienced by the motor 2504.

Turning back to the graph 5000 shown in FIG. 45 and with reference also to FIG. 13, FIG. 45 shows three different force-to-fire curves based on the motor current (I) as a function of the displacement of the I-beam 2514. The first curve 5006 is an ideal force-to-fire curve (shown in dashed line form) that is characteristic of good staple formation through tissue having a nominal tissue thickness. The motor current (I) initially increases rapidly to a peak current Imax1 as the displacement member advances distally through the first and second stroke regions 2517, 2519 (FIG. 13) from about 0.1× to about 0.25× and traverses the closure ramp of the anvil 2516. As the I-beam 2514 transitions to the third displacement member stroke region 2521 (FIG. 13), the I-beam 2514 may continuously contact and cut tissue 2526 and the wedge sled 2513 may repeatedly contact staple drivers 2511. As the I-beam 2514 advances distally and encounters a tissue resistance load in the third displacement member stroke region 2521, the motor current (I) steadily decreases from the peak current Imax1 as the less tissue resistance load decreases. During the third displacement member stroke region 2521, the motor current (I) exhibits ripples 5012 indicative of staples driven through the tissue and formed by the anvil 2516. By the fourth firing stroke region 2523 (FIG. 13), the force to drive the I-beam 2514 begins to steadily decline to zero and the motor current (I) decrease to zero.

The second curve 5008 is a force-to-fire curve (shown in dashed-dot line form) that is characteristic of staple formation through tissue that is thicker than the nominal tissue thickness shown in the first curve 5006. The motor current (I) rapidly increases and reaches a peak current Imax2 as it advances distally through the first and second displacement member stroke regions 2517, 2519 (FIG. 13). The motor current (I) ripples 5014 as the I-beam 2514 advances through the third displacement member stroke region 2521 (FIG. 13) and eventually drops to zero as the I-beam 2514 reaches the end of stroke.

The third curve 5010 is a force-to-fire curve (shown in solid line form) that is characteristic of staple formation through tissue that is thinner than the nominal tissue thickness shown in the first curve 5006. The motor current (I) rapidly increases and reaches a peak current Imax3 as it advances distally through the first and second displacement member stroke regions 2517, 2519 (FIG. 13). The motor current (I) ripples 5016 as the I-beam 2514 advances through the third displacement member stroke region 2521 (FIG. 13) and eventually drops to zero as the I-beam 2514 reaches the end of stroke.

With reference now to FIGS. 13, 14, and 45, a process for controlling the rate of the displacement member such as the I-beam 2514 will be described, in accordance with one aspect of the present disclosure. In one aspect, the surgical instrument 2500 is configured to make ongoing measurements of the expected position $A_1$, $A_2$ of the I-beam 2514 or the cutting edge 2509, at its current programmed velocity $V_{EXP}$, over a predefined time interval $(t_2-t_1)$ to be a proxy for the force applied to the cutting edge 2509 of the I-beam 2514, and accordingly to the I-beam 2514. The difference between the measured distance B, B' traveled by the I-beam 2514 and the anticipated position $A_1$, $A_2$ traveled by the I-beam 2514 during the predetermined period $(t_2-t_1)$ multiplied by a function (e.g., frictional coefficient of the cutting edge 2509, articulation angle, location of the I-beam 2514 within the stroke) can be employed to calculate the load on the I-beam 2514 and provide the load as feedback to adjust the current duty cycle (e.g., PWM) to control the motor 2504. Accordingly, the motor 2504 can be controlled by a proxy of the load experienced by the motor 2504.

An initial velocity $V_i$ of the motor 2504 is determined during the initial stroke regions of the I-beam 2514 by the control circuit 2510 and is set by the motor controller 2508 to set the initial velocity of the motor 2504, which, in one aspect, may be based on tissue thickness or tissue resistance to the I-beam 2514. An initial position $A_0(t_1)$ of the I-beam 2514 is determined at time $t_1$ based on the output of the position sensor 2534 and the output of the timer/counter circuit 2531. The control circuit 2510 can determine an anticipated position $A_1$ or $A_2$, depending on tissue thickness, over a predetermined period $(t_2-t_1)$ based on the current programmed velocity $V_{EXP}$ as follows:

$$A_1 = A_0 + V_{EXP}(t_2-t_1);$$

Where the difference between the initial position $A_0$ and the anticipated position $A_1$ is:

$$A_1 - A_0 = \delta = V_{EXP}(t_2-t_1).$$

If the actual displacement $B_1$ or $B_2$, depending on tissue thickness, deviates from the anticipated displacement $A_1$ or $A_2'$, the control circuit 2510 determines a motor velocity adjustment factor to velocity up or slow down the motor 2504. The motor controller 2508 applies the adjusted motor drive signal 2524 to speed up or slow down the motor 2504. The value of the current programmed velocity $V_{EXP}$ changes based on tissue thickness as the I-beam 2514 advances distally.

With reference first to the case depicted by the second curve 5008 where the tissue is thicker than expected (e.g., relative to a nominal thickness depicted in curve 5006), the actual position $B_1(t_2)$ of the I-beam 2514 as measured by the position sensor 2534 at time $t_2$ as measured by the timer/counter circuit 2531 is less than the anticipated position $A_1(t_2)$ calculated by the control circuit 2510 based upon initial expected velocity $V_{EXP}$. The control circuit 2510 determines that if the actual position of the I-beam 2514 $B_1(t_2)$ is less than the anticipated position $A_1(t_2)$ the tissue is thicker than expected and adjusts the motor velocity set point 2522 to reduce the current (I) of the motor drive signal 2524 provided to the motor 2504 by the motor controller 2508 and hence reduces the velocity of the I-beam 2514. The amount that the current (I) of the motor drive signal 2524 is reduced is proportional to the difference between the actual position $B_1(t_2)$ of the I-beam 2514 and $\delta_1 = V_{EXP}(t_2-t_1)$. In short hand notation:

If $B_1(t_2) < A_1(t_2)$, tissue is greater than expected;
Reduce motor current (I) by an amount proportional to $B_1(t_2) - \delta_2$.

With reference now to the case depicted by the third curve 5010 where the tissue is thinner than expected (e.g., relative to a nominal thickness depicted in curve 5006), the actual position $B_2(t_2)$ of the I-beam 2514 as measured by the position sensor 2534 at time $t_2$ as measured by the timer/counter circuit 2531 is greater than the anticipated position $A_2(t_2)$ calculated by the control circuit 2510 based upon initial velocity $V_{EXP}$. The control circuit 2510 determines that if the actual position of the I-beam 2514 $B_2(t_2)$ is greater than the anticipated position $A_2(t_2)$ the tissue is thinner than expected and adjusts the motor velocity set point 2522 to increase the current (I) of the motor drive signal 2524 provided to the motor 2504 by the motor controller 2508 and hence increases the velocity of the I-beam 2514. The amount that the current (I) of the motor drive signal 2524 is increased is proportional to the difference between the actual position $B_2(t_2)$ of the I-beam 2514 and $\delta_2 = V_{EXP}(t_2-t_1)$. In short hand notation:

If $B_2(t_2) > A_2(t_2)$, tissue is greater than expected;
Increase motor current (I) by an amount proportional to $B_2(t_2) - \delta_2$.

Figure 46:
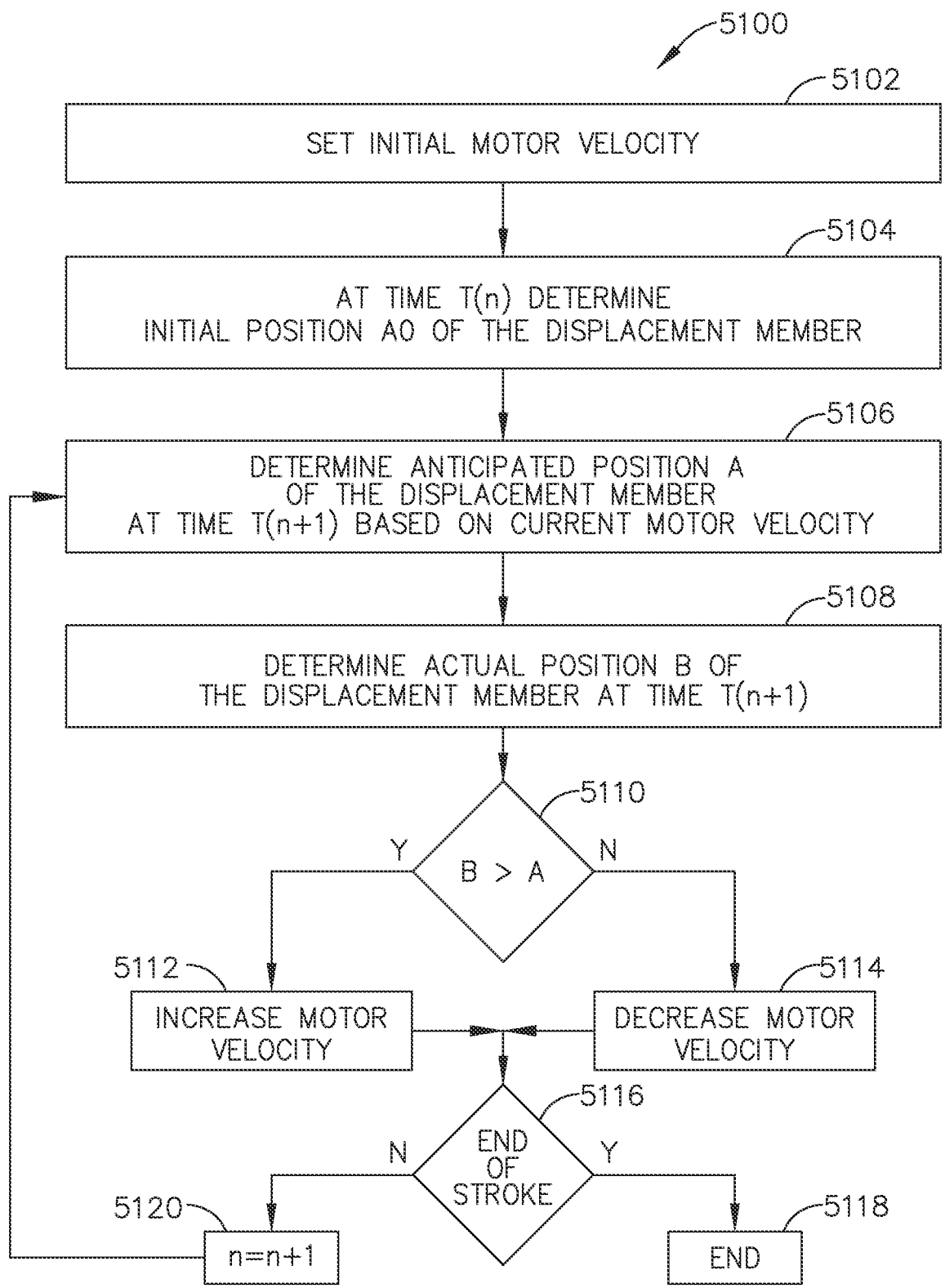
FIG. 46 is a logic flow diagram depicting a process of a control program or a logic configuration for controlling the rate of a displacement member according to one aspect of this disclosure.

FIG. 46 is a logic flow diagram depicting a process 5100 of a control program or a logic configuration for controlling the rate of a displacement member such as the I-beam 2514 according to one aspect of this disclosure. In the following desorption of the process 5100 in FIG. 46 reference also should be made to FIGS. 13, 14, and 45. Initially, the control circuit 2510 sets 5102 the initial velocity $V_{EXP}$ of the motor 2504. The control circuit 2510 then provides the motor set point 2522 to the motor controller 2508 which then applies the motor drive signal 2524 to the motor 2504. Once the motor velocity $V_{EXP}$ is set the control circuit 2510 determines 5104 the initial position $A_0$ of a displacement member, e.g., the I-beam 2514, based on the position sensor 2534 at time $t_n$ and based on the timer/counter circuit 2531. In the example where the displacement member is the I-beam 2514, upon determining 5104 the initial position $A_0$ of the I-beam 2514, the control circuit 2510 determines 5106 the anticipated position $A$ of the I-beam 2514 at time $t_{n+1}$ based on the current motor velocity $V_{EXP}$. At time $t_{n+1}$, the control circuit 2510 determines 5108 the actual position $B$ of the I-beam 2514 based on information from the timer/counter circuit 2531 and the position sensor 2534. The control circuit 2510 compares 5110 the actual position $B$ of the I-beam 2514 at $t_{n+1}$ and the anticipated position $A$ of the I-beam 2514 at $t_{n+1}$.

If the actual position $B$ of the I-beam 2514 at $t_{n+1}$ is greater than the anticipated position $A$ of the I-beam 2514 at $t_{n+1}$, the process 5100 continues along the Yes (Y) branch and the control circuit 2510 increases the velocity set point 2522 of the motor 2504. The motor velocity set point 2522 is increased proportionally to the difference between the actual position $B$ and the anticipated position $A$. The control circuit 2510 provides the new motor velocity set point 2522 to the motor controller 2508, which applies a new motor drive signal 2524 to the motor 2504 to increase the velocity of the motor 2504.

If the actual position $B$ of the I-beam 2514 at $t_{n+1}$ is less than the anticipated position $A$ of the I-beam 2514 at $t_{n+1}$, the process 5100 continues along the No (N) branch and the control circuit 2510 decreases the velocity set point 2522 of the motor 2504. The motor velocity set point 2522 is decreased proportionally to the difference between the actual position $B$ and the anticipated position $A$. The control circuit 2510 provides the new motor velocity set point 2522 to the motor controller 2508, which applies a new motor drive signal 2524 to the motor 2504 to decrease the velocity of the motor 2504.

The velocity of the motor 2504 may be maintained at the current set velocity in the event that the actual position $B$ of the I-beam 2514 at $t_{n+1}$ is equal to the anticipated position $A$ of the I-beam 2514 at $t_{n+1}$. Further, it will be appreciated that since the I-beam 2514 is an integral element of a rigid I-beam 2514, determining the position and/or translation of the I-beam 2514 can be used to determine the position and/or translation of the I-beam 2514. Accordingly, the process 5100 may be implemented by determining the position and/or translation of the I-beam 2514.

Once the new motor velocity is adjusted up or down, the position of the I-beam 2514 is compared 5116 to the end of stroke. If the I-beam 2514 has reached the end of stroke, the process 5100 ends 5118. If the I-beam 2514 has not reached the end of stroke, the process 5100 increments 5120 the counter index and continues until the I-beam 2514 reaches the end of stroke.

The function or process 5100 described herein may be executed by any of the processing circuits described herein, such as the control circuit 700 described in with FIGS. 5-6, the circuits 800, 810, 820 described in FIGS. 7-9, the microcontroller 1104 described in with FIGS. 10 and 12, and/or the control circuit 2510 described in FIG. 14.

Various aspects of the subject matter described herein are set out in the following numbered examples:

Example 1. A surgical instrument, comprising: a displacement member configured to translate within the surgical instrument; a motor coupled to the displacement member to translate the displacement member; a control circuit coupled to the motor; a position sensor coupled to the control circuit, the position sensor configured to measure the position of the displacement member; a timer circuit coupled to the control circuit, the timer/counter circuit configured to measure elapsed time; wherein the control circuit is configured to: receive the position of the displacement member from the position sensor; receive elapsed time from the timer circuit; and control velocity of the motor based on the position of the displacement member and the elapsed time.

Example 2. The surgical instrument of Example 1, wherein the control circuit is configured to: set the velocity of the motor to a first velocity; receive an initial position $A_0$ of the displacement member from the position sensor; receive a reference time $t_1$ from the timer circuit corresponding to the initial position $A_0$ of the displacement member; and determine an anticipated position $A_1$ of the displacement member at a time $t_2$ based on the first velocity.

Example 3. The surgical instrument of Example 2, wherein the control circuit is configured to: receive an actual position $B_1$ of the displacement member at the time $t_2$ from the position sensor; compare the actual position $B_1$ of the displacement member at the time $t_2$ with the anticipated position $A_1$ of the linear displacement sensor at the time $t_2$; and adjust the velocity of the motor to a second velocity based on a difference between the actual position $B_1$ of the displacement member at the time $t_2$ with the anticipated position $A_1$ of the displacement member at the time $t_2$.

Example 4. The surgical instrument of Example 3, wherein the control circuit is configured to: increase the velocity of the motor when the actual position $B_1$ of the displacement member at the time $t_2$ is greater than the anticipated position $A_1$ of the displacement member at the time $t_2$.

Example 5. The surgical instrument of Example 3 through Example 4, wherein the control circuit is configured to: decrease the velocity of the motor when the actual position $B_1$ of the displacement member at the time $t_2$ is less than the anticipated position $A_1$ of the displacement member at the time $t_2$.

Example 6. The surgical instrument of Example 3 through Example 5, wherein the control circuit is configured to: determine actual tissue thickness adjust based on a difference between the actual position $B_1$ of the displacement member at the time $t_2$ with the anticipated position $A_1$ of the displacement member at the time $t_2$.

Example 7. The surgical instrument of Example 6, wherein the control circuit is configured to: determine that the actual tissue thickness is less than anticipated when the actual position $B_1$ of the displacement member at the time $t_2$ is greater than the anticipated position $A_1$ of the displacement member at the time $t_2$.

Example 8. The surgical instrument of Example 6 through Example 7, wherein the control circuit is configured to: determine that the actual tissue thickness is greater than anticipated when the actual position $B_1$ of the displacement member at the time $t_2$ is less than the anticipated position $A_1$ of the displacement member at the time $t_2$.

Example 9. A surgical instrument, comprising: an I-beam member configured to translate within an end effector of the surgical instrument; a motor coupled to the I-beam member to translate the I-beam member within the end effector; a control circuit coupled to the motor; a position sensor coupled to the control circuit, the position sensor configured to measure the position of the I-beam member; a timer circuit coupled to the control circuit, the timer/counter circuit configured to measure elapsed time; wherein the control circuit is configured to: receive the position of the I-beam member from the position sensor; receive elapsed time from the timer circuit; and control velocity of the motor based on the position of the I-beam member and the elapsed time.

Example 10. The surgical instrument of Example 9, wherein the control circuit is configured to: set the velocity of the motor to a first velocity; receive an initial position $A_0$ of the I-beam member from the position sensor; receive a reference time $t_1$ from the timer circuit corresponding to the initial position $A_0$ of the I-beam member; and determine an anticipated position $A_1$ of the I-beam member at a time $t_2$ based on the first velocity.

Example 11. The surgical instrument of Example 10, wherein the control circuit is configured to: receive an actual position $B_1$ of the I-beam member at the time $t_2$ from the position sensor; compare the actual position $B_1$ of the I-beam member at the time $t_2$ with the anticipated position $A_1$ of the I-beam member at the time $t_2$; and adjust the velocity of the motor to a second velocity based on a difference between the actual position $B_1$ of the I-beam member at the time $t_2$ with the anticipated position $A_1$ of the I-beam member at the time $t_2$.

Example 12. The surgical instrument of Example 11, wherein the control circuit is configured to: increase the velocity of the motor when the actual position $B_1$ of the I-beam member at the time $t_2$ is greater than the anticipated position $A_1$ of the I-beam member at the time $t_2$.

Example 13. The surgical instrument of Example 11 through Example 12, wherein the control circuit is configured to: decrease the velocity of the motor when the actual position $B_1$ of the I-beam member at the time $t_2$ is less than the anticipated position $A_1$ of the I-beam member at the time $t_2$.

Example 14. The surgical instrument of Example 11 through Example 13, wherein the control circuit is configured to: determine actual tissue thickness adjust based on a difference between the actual position $B_1$ of the I-beam member at the time $t_2$ with the anticipated position $A_1$ of the I-beam member at the time $t_2$.

Example 15. The surgical instrument of Example 14, wherein the control circuit is configured to: determine that the actual tissue thickness is less than anticipated when the actual position $B_1$ of the I-beam member at the time $t_2$ is greater than the anticipated position $A_1$ of the I-beam member at the time $t_2$.

Example 16. The surgical instrument of Example 14 through Example 15, wherein the control circuit is configured to: determine that the actual tissue thickness is greater than anticipated when the actual position $B_1$ of the I-beam member at the time $t_2$ is less than the anticipated position $A_1$ of the I-beam member at the time $t_2$.

Example 17. A method of controlling motor velocity in a surgical instrument, the surgical instrument comprising a displacement member configured to translate, a motor coupled to the displacement member to translate the displacement member, a control circuit coupled to the motor, a position sensor coupled to the control circuit, the position sensor configured to measure the position of the displacement member, a timer circuit coupled to the control circuit, the timer/counter circuit configured to measure elapsed time, the method comprising: receiving, by a control circuit, a position of a displacement member from a position sensor; receiving, by the control circuit, elapsed time from a timer circuit; and controlling, by the control circuit, velocity of a motor based on the position of the displacement member and the elapsed time.

Example 18. The method of Example 17, comprising: setting, by the control circuit, the velocity of the motor to a first velocity; receiving, by the control circuit, an initial position $A_0$ of the displacement member from the position sensor; receiving, by the control circuit, a reference time $t_1$ from the timer circuit corresponding to the initial position $A_0$ of the displacement member; and determining, by the control circuit, an anticipated position $A_1$ of the displacement member at a time $t_2$ based on the first velocity.

Example 19. The method of Example 18, comprising: receiving, by the control circuit, an actual position $B_1$ of the displacement member at the time $t_2$ from the position sensor; comparing, by the control circuit, the actual position $B_1$ of the displacement member at the time $t_2$ with the anticipated position $A_1$ of the displacement member at the time $t_2$; and adjusting, by the control circuit, the velocity of the motor to a second velocity based on a difference between the actual position $B_1$ of the displacement member at the time $t_2$ with the anticipated position $A_1$ of the displacement member at the time $t_2$.

Example 20. The method of Example 19, comprising: increasing, by the control circuit, the velocity of the motor when the actual position $B_1$ of the displacement member at the time $t_2$ is greater than the anticipated position $A_1$ of the displacement member at the time $t_2$.

Example 21. The method of Example 19 through Example 20, comprising: decreasing, by the control circuit, the velocity of the motor when the actual position $B_1$ of the displacement member at the time $t_2$ is less than the anticipated position $A_1$ of the displacement member at the time $t_2$.

Example 22. The method of Example 19 through Example 21, comprising: determining, by the control circuit, actual tissue thickness adjust based on a difference between the actual position $B_1$ of the displacement member at the time $t_2$ with the anticipated position $A_1$ of the displacement member at the time $t_2$.

Example 23. The method of Example 22, comprising: determining, by the control circuit, that the actual tissue thickness is less than anticipated when the actual position $B_1$ of the displacement member at the time $t_2$ is greater than the anticipated position $A_1$ of the displacement member at the time $t_2$.

Example 24. The method of Example 22 through Example 23, comprising: determining, by the control circuit, that the actual tissue thickness is greater than anticipated when the actual position $B_1$ of the displacement member at the time $t_2$ is less than the anticipated position $A_1$ of the displacement member at the time $t_2$.

Surgical Instrument Having Controllable Articulation Velocity

During use of a motorized surgical stapling and cutting instrument it is possible that the end effector sweep rate may vary undesirably in areas of interest such as near the end of stroke or near the home position for removal from a trocar. Therefore, it may be desirable to provide articulation velocity control to improve user control. It may be desirable to vary the end effector articulation by varying the duty cycle of the motor drive signal to vary the articulation head angle rate as a function of the end effector articulation angle.

Referring now to FIGS. 47-48 and 51-57, there are shown a variety of diagrams. The axes in each of these figures are normalized such that each axis represents a ratio between a minimum value and a maximum value, rather than set values. The minimum and maximum values of the variables represented in these graphs can vary according to different aspects of the surgical instrument. For example, the minimum articulation angle of the sweep range of the end effector can in various aspects include −65°, −60°, and −45° and the maximum articulation angle of the end effector of the sweep range of the end effector can in various aspects include +45°, +60°, and +65° relative to the longitudinal axis of the elongated shaft assembly. Furthermore, it can be understood that although the above examples were discussed in terms of degrees, angular position can additionally be represented in terms of radians or any other unit of angular position. As another example, the minimum and maximum position of the articulation driver can include 0.0 m and 0.304 m, respectively. Furthermore, it can be understood that although the above example was discussed in terms of meters, linear position can additionally be represented in terms of feet, inches, or any other unit of linear position.

Figure 47:
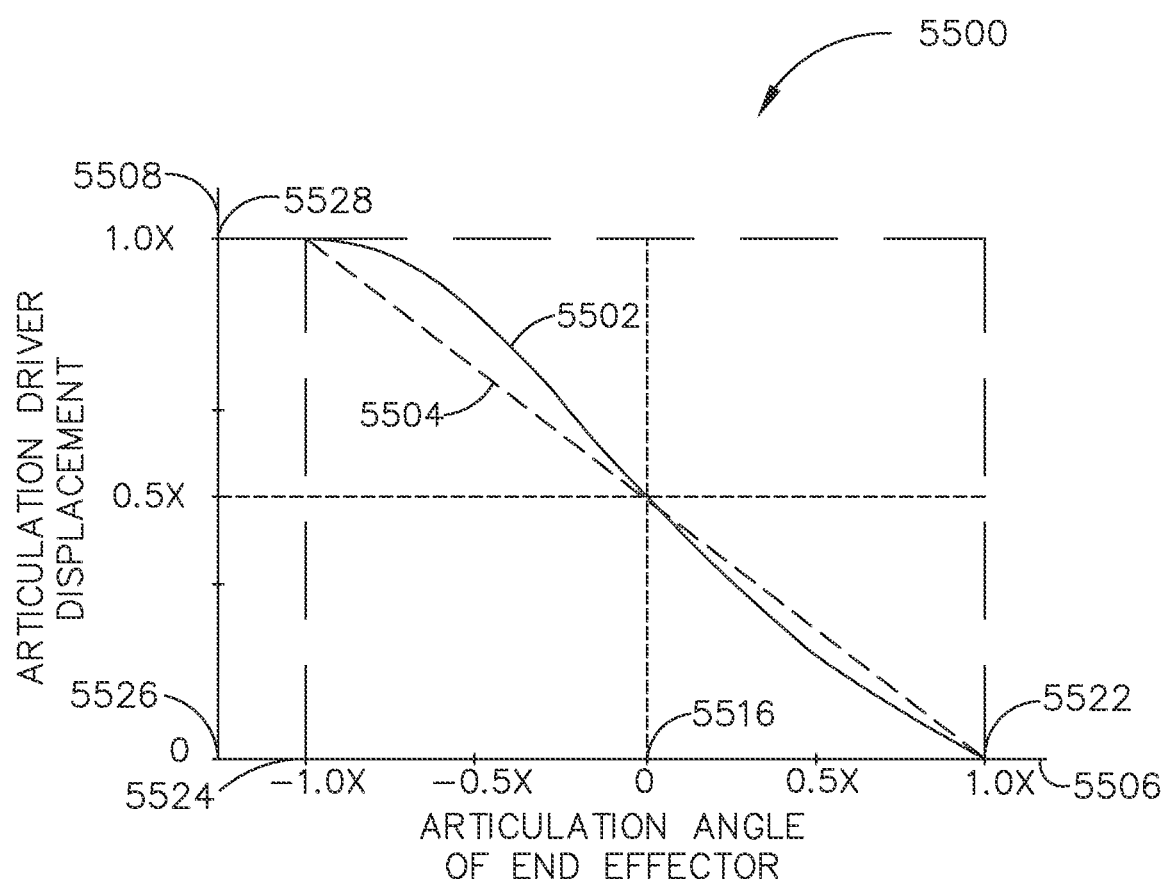
FIG. 47 is a diagram illustrating displacement of an articulation driver relative to end an effector articulation angle for constant articulation driver velocity and variable articulation drive velocity according to one aspect of this disclosure.

In some aspects of the surgical instrument wherein the angular displacement of the end effector through the articulation joint is driven by the displacement of the articulation driver, such as the aspect depicted in FIGS. 19-21, there exists a non-linear relationship between the displacement of the articulation driver 230 (FIG. 17) and the angular displacement of the end effector 2300 (FIGS. 19-21). Stated differently, there may not be a 1:1 relationship between the displacement of the articulation driver and the angular displacement of the end effector due to the kinematics of the linkage between the components. Referring specifically now to FIG. 47, there is shown a diagram 5500 illustrating articulation driver displacement 5508 relative to end an effector articulation angle 5506 for constant articulation driver velocity and variable articulation drive velocity according to one aspect of this disclosure. In some aspects of the surgical instrument, the articulation driver is driven from a first position 5526 to a second position 5528 at a constant rate, as depicted by line 5504, that is independent of the articulation angle of the end effector. In these aspects, the articulation velocity, i.e., rate of angular displacement of the end effector, varies according to the particular articulation angle of the end effector due to the non-linear relationship with the displacement of the articulation driver. Notably, the natural response of the linkage between the end effector and the articulation driver in some such aspects is to cause the articulation velocity of the end effector to increase from a midpoint 5516 towards the ends 5522, 5524 of the end effector articulation range, if the articulation driver is being translated at a constant rate. In some cases, it may be desired for the articulation velocity to remain constant throughout the entire articulation range of the end effector, i.e., from the first end 5522 to the second end 5524 of the articulation range. In such aspects where it is desired to compensate for the kinematics of the linkage between the articulation driver and the end effector, the articulation driver is driven at a variable rate, as depicted by line 5502, as a function of the articulation angle.

Figure 48:
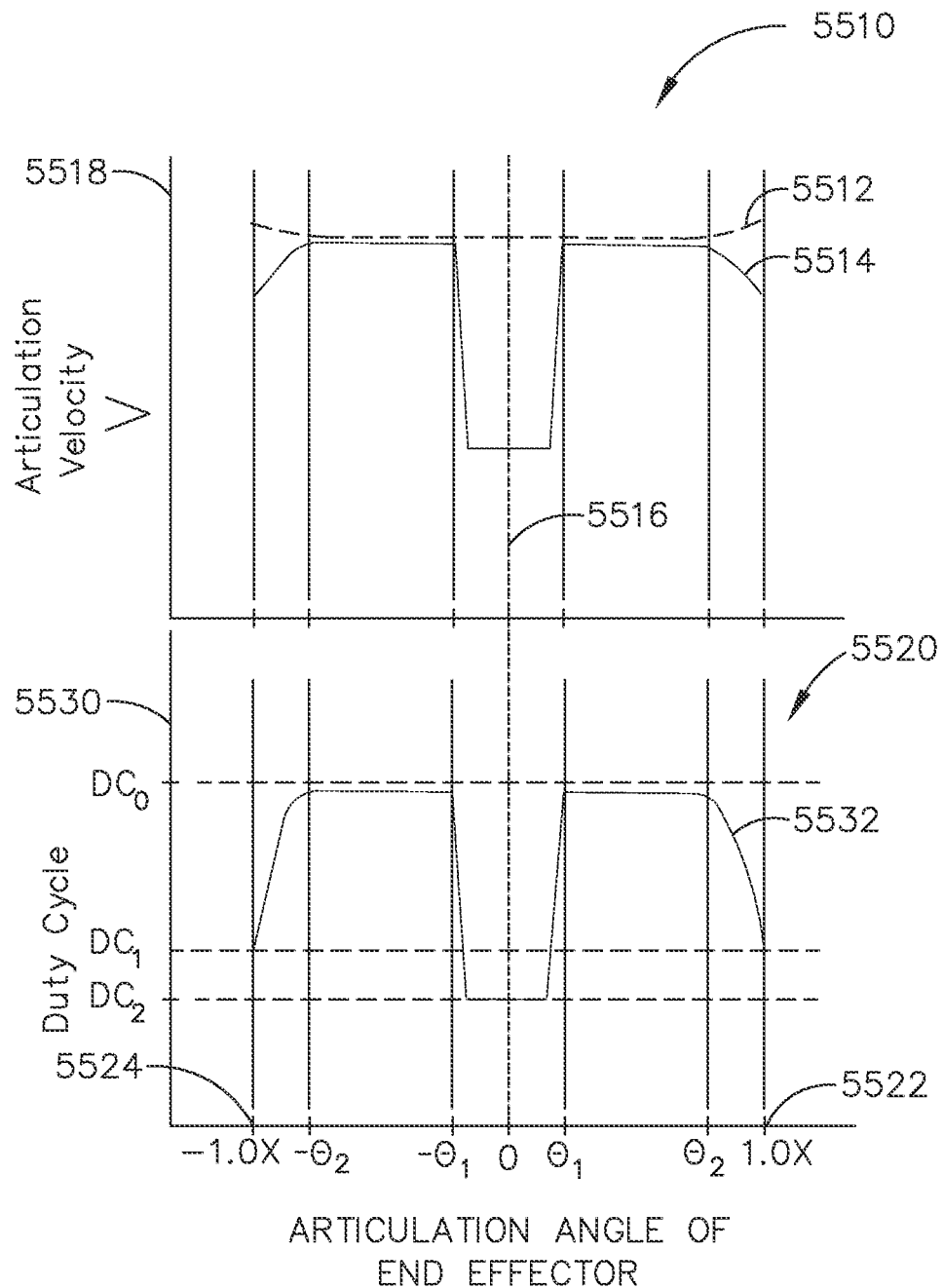
FIG. 48 is a first diagram illustrating articulation velocity relative to articulation angle of an end effector and a second diagram illustrating motor duty cycle relative to articulation angle of an end effector according to one aspect of this disclosure.

FIG. 48 depicts a first diagram 5510 illustrating articulation velocity 5518 relative to the articulation angle of the end effector 5506 and a second diagram 5520 illustrating motor duty cycle 5530 relative to the articulation angle of the end effector 5506. In addition to controlling the articulation of the end effector to provide a constant angular displacement rate over the articulation range of the end effector or a portion of the articulation range of the end effector, the articulation velocity can additionally be adjusted to a fixed value when the end effector is positioned at or near certain locations within the end effector articulation range. Stated differently, in certain aspects the articulation range can include a first zone, wherein the articulation velocity is a fixed value, and a second zone, wherein the articulation velocity is a function of the particular position or articulation angle of the end effector. Line 5514 exemplifies a control scheme for a surgical instrument that includes one or more zones wherein the articulation velocity is a fixed value. Comparatively, line 5512 exemplifies a control scheme for a surgical instrument wherein the displacement of the articulation driver is constant, as depicted by line 5504 in FIG. 47. As exemplified by line 5514, the end effector can be slowed when it reaches within a threshold distance from a predefined location. In one such aspect, the end effector is slowed to $V_2$, which is less than the default or steady state velocity, $V_0$, when the end effector falls within $\theta_1$ degrees of the home or default position. The home or default position can be, for example, the 0° position 5516, which is the position in which the end effector is aligned with the longitudinal axis of the shaft. Such an aspect wherein the end effector slows when it nears the home position can be beneficial in making it easier to remove the surgical instrument from a trocar through which the instrument is positioned. In another aspect, the end effector is slowed to $V_1$, which is less than the default or steady state velocity, $V_0$, when the end effector is positioned in excess of $\theta_2$ degrees from the default or home position. Such an aspect wherein the end effector slows near the ends 5522, 5524 of its articulation range can be useful in signaling to a user of the surgical instrument that the end effector is nearing the end of its effective range. Line 5532 in the second diagram 5520 indicating the change in the duty cycle at which the motor is driven corresponds to line 5514 in the first diagram 5510. In various aspects, the duty cycle at which the motor is driven can be adjusted according to the desired articulation velocity of the end effector. In various other aspects, the articulation velocity of the end effector can also be increased, as opposed to decreased as described above, relative to the default or steady state velocity according to the position of the end effector. Aspects utilizing combinations of positional ranges where the articulation velocity of the end effector is adjusted are also within the scope of the present disclosure.

There are several possible methods for controlling the angular velocity of the end effector by varying the velocity of the articulation driver 230 according to the articulation angle at which the end effector is positioned. One such method is varying the duty cycle of the motor driving the articulation driver 230, which is referred to as pulse width modulation (PWM). One aspect utilizing this method is illustrated as line 5532, which corresponds to line 5514 depicting the change in articulation velocity of the end effector 2502 as a function of the articulation angle. Another method is varying the magnitude of the voltage supplied to the motor driving the articulation driver. A third method is utilizing a combination of PWM and varying the magnitude of the voltage supplied to the motor. As the velocity at which the motor drives the articulation driver 230 corresponds to both the duty cycle at which the motor is operating and the magnitude of the voltage received by the motor, each of the aforementioned methods allows the surgical instrument to control the velocity of the articulation driver 230 and, thus, the angular velocity of the end effector.

Figure 49:
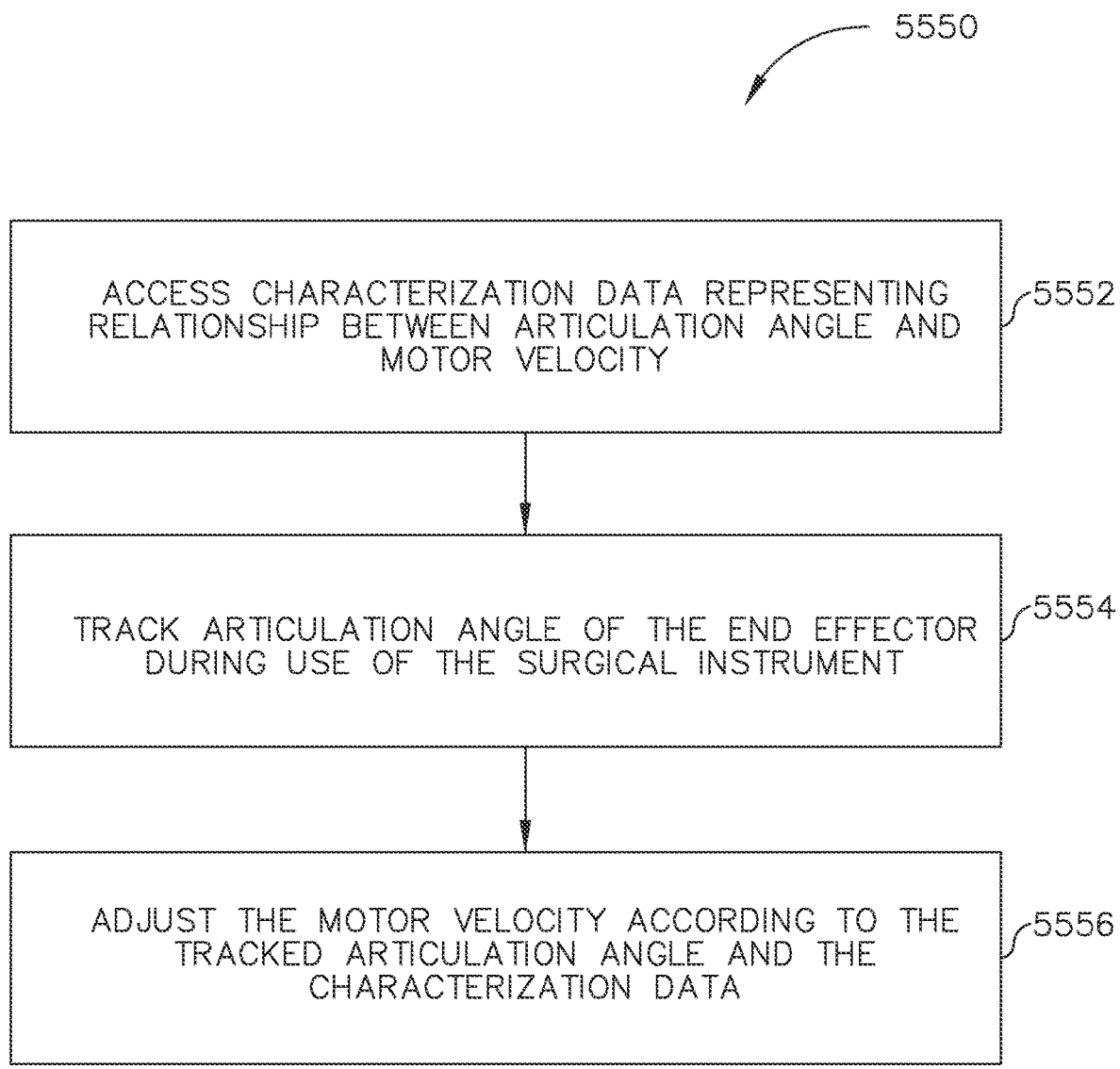
FIG. 49 is a logic flow diagram depicting a process of a control program or a logic configuration for controlling end effector articulation velocity according to one aspect of this disclosure.

FIG. 49 illustrates a logic flow diagram depicting a process of a control program or a logic configuration for controlling end effector articulation velocity according to one aspect of this disclosure. In the following description of the logic 5550 in FIG. 49, reference should also be made to FIG. 14-21. In one aspect of a logic 5550 for controlling the articulation velocity of the end effector 2502, the relationship between the articulation angle of the end effector 2502 and a property of the motor 2504 affecting the articulation velocity of the end effector 2502 is initially characterized and the characterization data is stored in the memory of the surgical instrument 2500. The property of the motor 2504 affecting the articulation velocity of the end effector 2502 can include the duty cycle of the motor, the magnitude of the voltage supplied to the motor, a combination thereof, or other such methods. In one aspect, the memory is a non-volatile memory such as flash memory, EEPROM, and the like. When the surgical instrument is being utilized, the control circuit 2510 accesses 5552 the characterization data stored in the memory. In aspects wherein the position of the articulation driver 230 is tracked by the articulation sensor arrangement as a proxy for the articulation angle of the end effector 2502, the relationship between the position of the articulation driver 230 and the property of the motor can instead be initially characterized in order to reduce the processing power that would otherwise be required to first translate the position of the articulation driver 230 to the angular position of the end effector 2502, prior to accessing 5552 the characterized data stored in the memory according to the translated angular position of the end effector 2502.

In one aspect, the output of the characterization process is an algorithm implemented in computer readable instructions stored in memory and executed by the control circuit 2510. Accordingly, in one aspect, the control circuit 2510 accesses 5552 the characterization data of the algorithm implemented in the memory, inputs either the angular position of the end effector 2502 (which is determined either directly or indirectly) or the position of the articulation driver 230, and then performs a run-time calculation to determine the output, which is the value the particular motor property is to be set at to effectuate the desired articulation velocity of the end effector 2502.

In one aspect, the output of the characterization process is a lookup table implemented in the memory. Accordingly, in one aspect, the control circuit 2510 accesses 5552 the characterization data from the lookup table implemented in the memory. In one aspect, the lookup table comprises an array that replaces runtime computation with a simpler array indexing operation. The savings in terms of processing time can be significant, since retrieving a value from the memory by the control circuit 2510 is generally faster than undergoing an "expensive" computation or input/output operation. The lookup table may be precalculated and stored in static program storage, calculated (or "pre-fetched") as part of a program's initialization phase (memoization), or even stored in hardware in application-specific platforms. In the instant application, the lookup table stores the output values of the characterization of the relationship between articulation angle of the end effector 2502 and the property of the motor 2504 dictating the articulation velocity of the end effector 2502. The lookup table stores these output values in an array and, in some programming languages, may include pointer functions (or offsets to labels) to process the matching input. Thus, for each unique value of the articulation angle of the end effector 2502 or the position of the articulation driver 230 (as a proxy for the articulation angle), there exists a corresponding motor 2504 duty cycle value. The corresponding motor 2504 duty cycle value is stored in the lookup table and is used by the control circuit 2510 to determine what duty cycle the motor 2504 should be set to according to the angular position of the end effector 2502. Other lookup table techniques are contemplated within the scope of the present disclosure.

In one aspect, the output of the characterization process is a best curve fit formula, linear or nonlinear. Accordingly, in one aspect, the control circuit 2510 is operative to execute computer readable instructions to implement a best curve fit formula based on the characterization data. Curve fitting is the process of constructing a curve, or mathematical function that has the best fit to a series of data points, possibly subject to constraints. Curve fitting can involve either interpolation, where an exact fit to the data is required. In one aspect, the curve represents the motor 2504 duty cycle at which the motor is to be set as a function of the articulation angle of the end effector 2502. The data points such as the articulation angle of the end effector 2502, the position of the articulation driver 230, and the motor 2504 duty cycle can be measured and used to generate a best fit curve in the form of an $n^{th}$ order polynomial (usually a $3^{rd}$ order polynomial would provide a suitable curve fit to the measured data). The control circuit 2510 can be programmed to implement the $n^{th}$ order polynomial. In use, the input of the $n^{th}$ order polynomial is the angular position of the end effector 2502 and/or the position of the articulation driver 230.

As the surgical instrument is operated, the surgical instrument tracks 5554 the articulation angle of the end effector 2502, either directly or indirectly, via an articulation sensor arrangement, as described above. As the articulation angle is tracked 5554, the surgical instrument adjusts 5556 one or more properties of the motor 2504, such as the duty cycle of the motor 2504, to in turn adjust the articulation velocity at which the motor 2504 drives the end effector 2502. The property (or properties) of the motor 2504 that is adjusted according to the characterization data to control the articulation velocity of the end effector 2502 includes, for example, varying the motor duty cycle, varying the magnitude of the voltage supplied to the motor, or a combination thereof. The logic 5550 therefore provides a dynamic system wherein the motor is controlled to continuously or regularly adjust the articulation velocity of the end effector 2502 according to the pre-characterized data.

In various aspects, the memory for storing the characterization may be a nonvolatile memory located on the on the shaft, the handle, or both, of the surgical instrument.

In one aspect, the characterization is utilized by control software of the microcontroller communicating with the non-volatile memory to gain access to the characterization.

Figure 50:
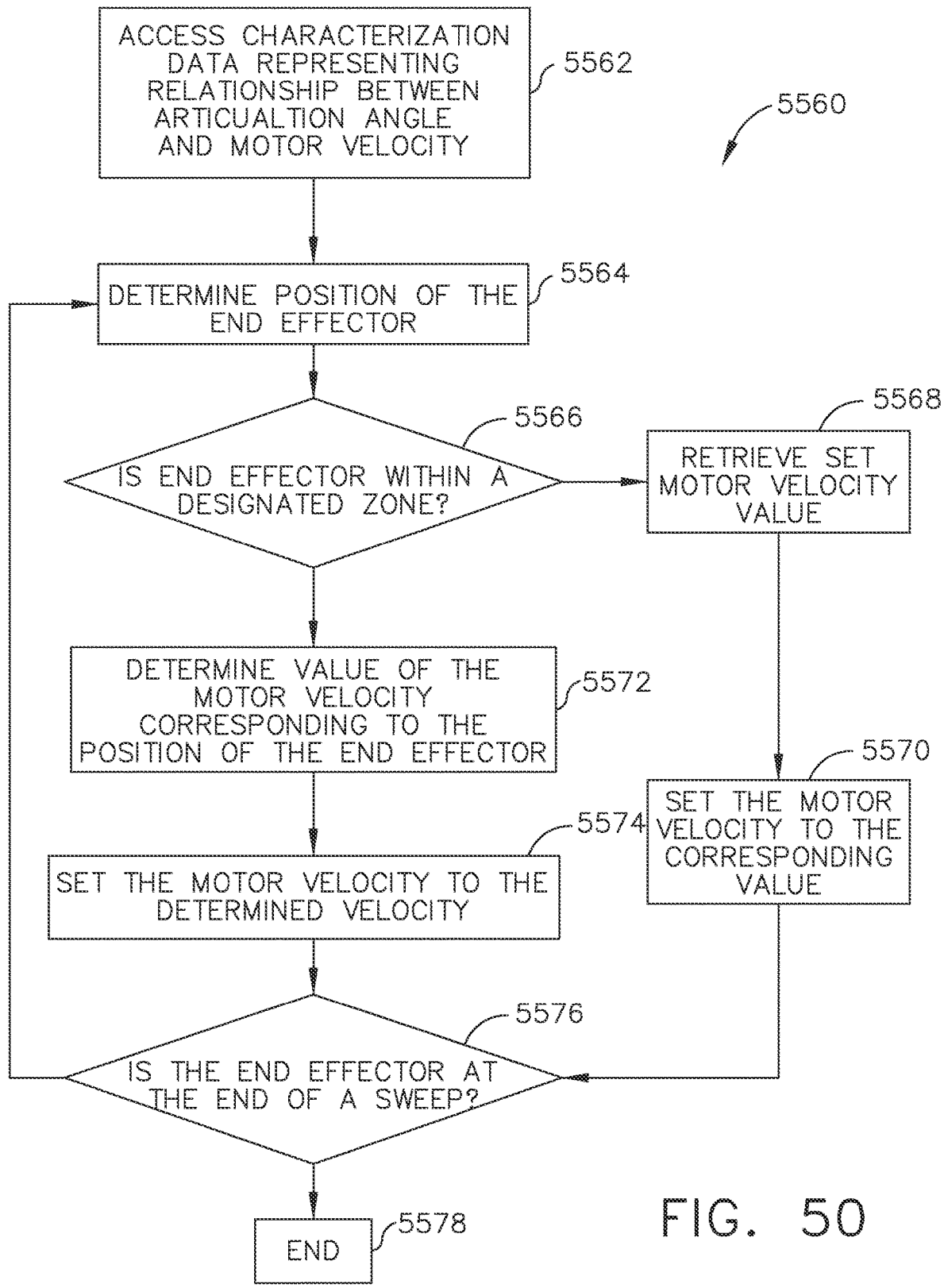
FIG. 50 is a logic flow diagram depicting a process of a control program or a logic configuration for controlling end effector articulation velocity according to one aspect of this disclosure.

FIG. 50 illustrates another aspect of a logic flow diagram depicting a process of a control program or a logic configuration for controlling the end effector articulation velocity. As above, in the following description of the logic 5560 in FIG. 50, reference should also be made to FIG. 14-21. In one aspect, the logic 5560 for controlling the articulation velocity of the end effector 2502 comprises accessing 5562 characterization data of the relationship between the articulation angle of the end effector 2502 and a property of the motor 2504 affecting the articulation velocity of the end effector 2502. The characterization data can be accessed 5562 prior to or during use of the surgical instrument 2500. The relationship between the articulation angle of the end effector 2502 and the property of the motor 2504 can initially be stored in the memory of the surgical instrument. The property of the motor 2504 affecting the articulation velocity of the end effector 2502 can include the duty cycle of the motor, the magnitude of the voltage received by the motor, and a combination thereof.

Once the characterization data is accessed 5562, the logic 5560 then determines 5564 the present position or articulation angle of the end effector 2502 via an articulation sensor arrangement. The logic 5560 then determines 5566 whether the end effector 2502 is positioned within one or more designated zones within the angular articulation range or sweep of the end effector 2502. The designated zones within the articulation range of the end effector 2502 correspond to areas where the end effector 2502 is driven at a certain fixed velocity, rather than at a velocity that corresponds to the articulation angle at which the end effector 2502 is positioned. In one aspect, a designated zone includes when the end effector 2502 is positioned within a threshold distance of a set position, as illustrated in FIG. 48. The designated zone or zones are also referred to collectively as a "first zone" and the remaining portion or portions of the articulation range of the end effector are also referred to collectively as a "second zone."

The first zone can include multiple discrete portions of the angular articulation range of the end effector 2502, as also illustrated in FIG. 48. If the end effector 2502 is within the first zone, the logic 5560 then retrieves 5568 a fixed value for the particular motor 2504 property and then sets 5570 the motor 2504 property to that value. The fixed value can be stored in, for example, a lookup table implemented in memory. In the aspect of the logic 5560 corresponding to FIG. 48, for example, if the end effector 2502 is within $\theta_1$ degrees of a position, then the logic 5560 retrieves 5568 the motor 2504 duty cycle value $DC_2$ and then sets 5570 the motor 2504 duty cycle to that value for the duration of the time that the end effector 2502 is within that particular portion of the first zone. In one aspect of the logic 5560, there can be multiple designated zones wherein a motor 2504 property, such as the duty cycle at which the motor 2504 is driven, is set to a fixed value. In the aspect of the logic 5560 corresponding to FIG. 48, for example, in addition to the motor being set to duty cycle $DC_2$ if it is within $\theta_1$ degrees of a position 5516, the sweep range can include additional zones where the motor is set to duty cycle $DC_1$ if the end effector 2502 is greater than $\theta_2$ degrees from a position 5516. If the end effector 2502 is not within the first zone, i.e., is in the second zone, the logic 5560 instead determines 5572 the value of the motor property corresponding to the particular position of the end effector 2502 and then sets 5574 the motor property to the determined value. The logic 5560 can determine 5572 the motor property value by accessing the output characterization data in a variety of manners, as described above.

Once the property of the motor 2504 has been set 5570 to a fixed value or set 5574 to a value that is a function of the position of the end effector 5572, the logic 5560 then determines 5576 whether the sweep of the end effector 2502 is completed or whether the operator is otherwise finished using the surgical instrument 2500. The logic 5560 can determine whether the end effector 2502 is no longer in use by, for example, monitoring whether the articulation lock 2810 is engaged. If the sweep of the end effector 2502 is completed, then the logic 5560 is likewise completed 5578 for the particular sweep of the end effector 2502. If the sweep of the end effector 2502 is not completed, then the logic 5560 continues monitoring the position of the end effector 2502 and adjusting the articulation velocity of the end effector 2502 until the sweep is completed 5578. In some aspects, the logic 5560 continuously monitors the position of the end effector. In other aspects, the logic 5560 implements a delay between instances of sampling the articulation angle of the end effector. The delay between instances of sampling the end effector 2502 position can be determined by, for example, a timer or counter circuit 2531.

Figure 51:
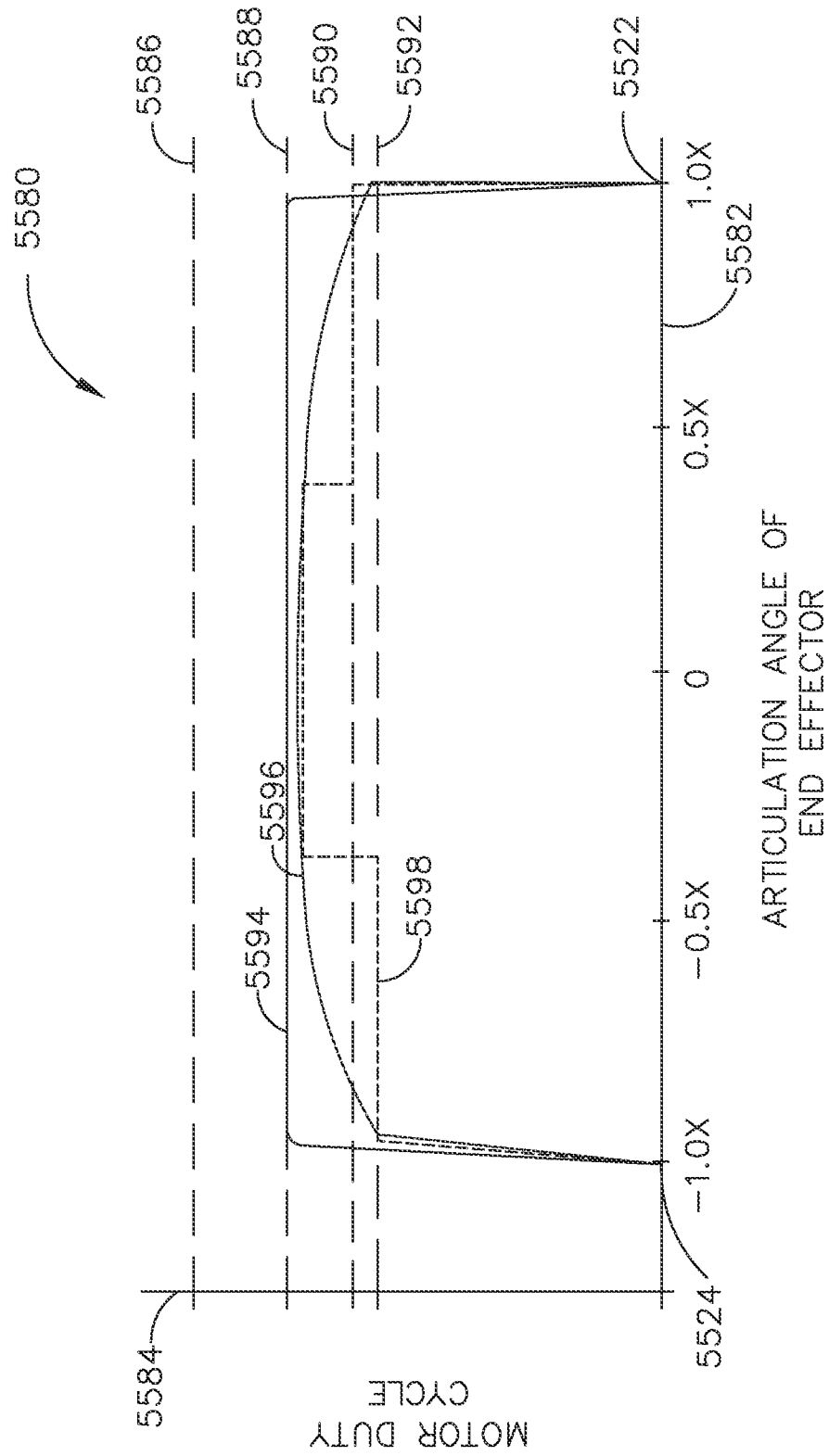
FIG. 51 is a diagram illustrating motor duty cycle relative to articulation angle of an end effector for aspects utilizing a constant motor duty cycle, a constantly variable motor duty cycle, and a discretely variable motor duty cycle according to one aspect of this disclosure.

FIG. 51 depicts a diagram 5580 illustrating the motor duty cycle 5584 relative to the articulation angle of the end effector for aspects utilizing a constant motor duty cycle, a constantly variable motor duty cycle, and a discretely variable motor duty cycle. In some aspects of the surgical instrument 2500, the duty cycle of the motor is held constant throughout the sweep of the end effector 2502, as represented by line 5594. In other words, the duty cycle of the motor 2504 is not a function of the position or articulation angle of the end effector 2502. The constant duty cycle 5588 can be less than or equal to a maximum duty cycle 5586 at which the motor 2504 can be driven. In other aspects, the motor 2504 duty cycle is varied according to the articulation angle of the end effector 2502. In one such aspect represented by line 5596, the articulation angle of the end effector 2502 is sampled continuously and the articulation sensor arrangement has a correspondingly high resolution that is able to detect the articulation angle of the end effector 2502 throughout its angular sweep. In this aspect, the motor 2504 duty cycle can be updated at a very high rate, illustrated by the smooth, continuous curvature of the line 5596. In another such aspect represented by line 5598, the articulation angle of the end effector 2502 is sampled at a relatively low rate and/or the articulation sensor arrangement has a relatively low resolution. In this aspect, the motor 2504 duty cycle is updated at discrete points, rather than continuously over the course of the angular sweep of the end effector 2502. Aspects that sample the position of the end effector 2502 at a high rate and update the motor 2504 duty cycle at a corresponding high rate can be computationally expensive, but can also produce smoother, more consistent movement for the end effector 2502 as it articulates.

Although the aspects illustrated in FIG. 51 were described in terms of the motor duty cycle, it is to be understood that the principles are equally applicable to aspects wherein either the magnitude of the voltage supplied to the motor is adjusted or a combination of the motor duty cycle and the motor duty cycle are adjusted as a function of the articulation angle of the end effector.

Figure 52:
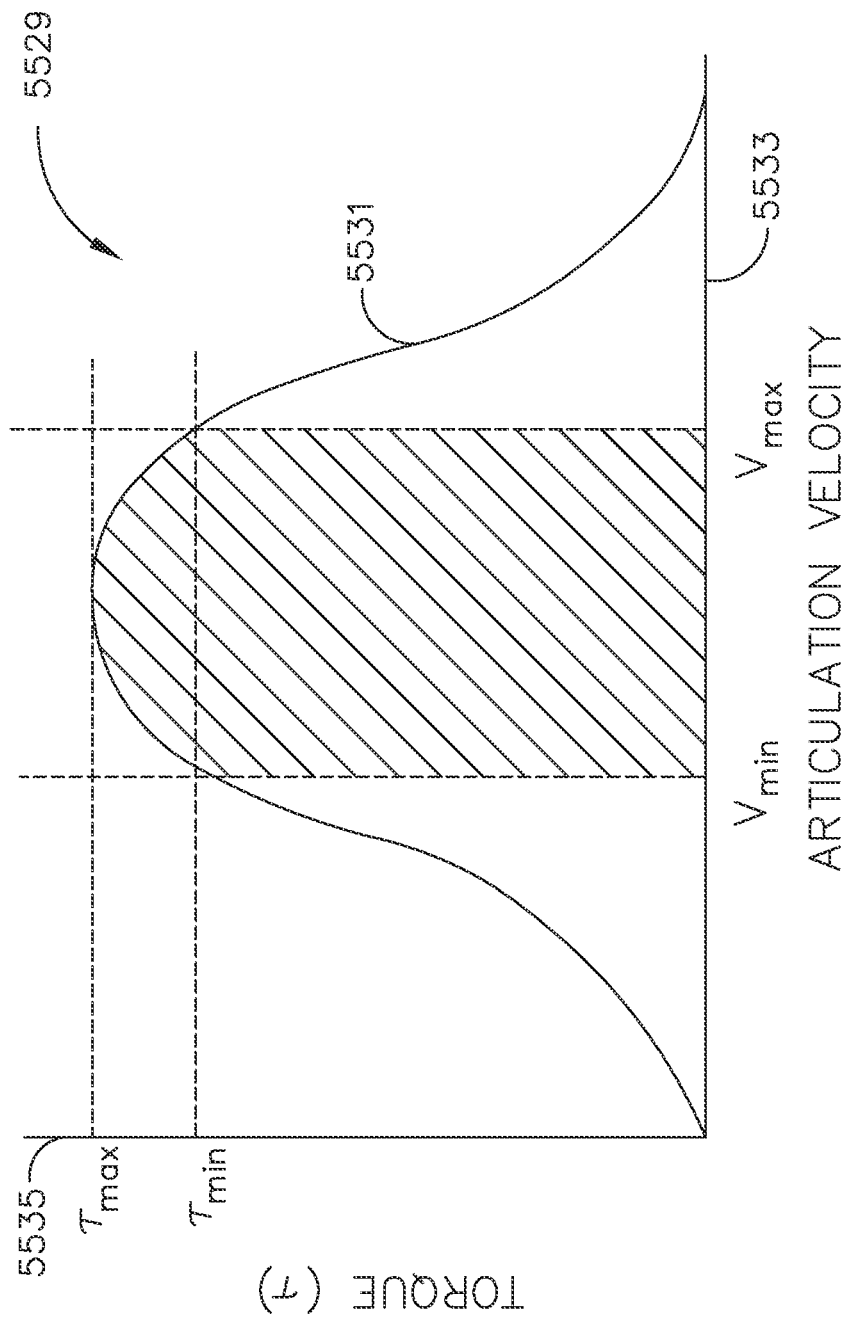
FIG. 52 is a diagram illustrating torque relative to articulation velocity of an end effector according to one aspect of this disclosure.

FIG. 52 shows a diagram 5529 illustrating torque 5535 relative to articulation velocity of an end effector 5533 according to one aspect of this disclosure. Line 5531 depicts the relationship between the articulation velocity of the end effector and the torque generated by the movement of the end effector. In some aspects, it can be beneficial to maintain the torque generated by the end effector between a first value $\tau_{min}$ and a second value $\tau_{max}$. Therefore, in order to maintain the torque generated by the articulation of the end effector between $\tau_{min}$ and $\tau_{max}$, the articulation velocity of the end effector is correspondingly maintained between a first value $V_{min}$ and a second value $V_{max}$. In such aspects, the logic executed by the surgical instrument can be configured to maintain the articulation velocity between $V_{min}$ and $V_{max}$ throughout the articulation range of the end effector. In aspects where the articulation velocity is set to certain fixed values within designated zones of the articulation range of the end effector, such as is depicted in FIG. 48, the fixed values can fall within the upper and lower bounds set by $V_{min}$ and $V_{max}$. In aspects where the end effector is articulated at a constant articulation velocity either throughout is articulation range or when the end effector is not located in one or more of the aforementioned designated zones, then the velocity at which the end effector is articulated can likewise fall within the upper and lower bounds set by $V_{min}$ and $V_{max}$.

Figure 53:
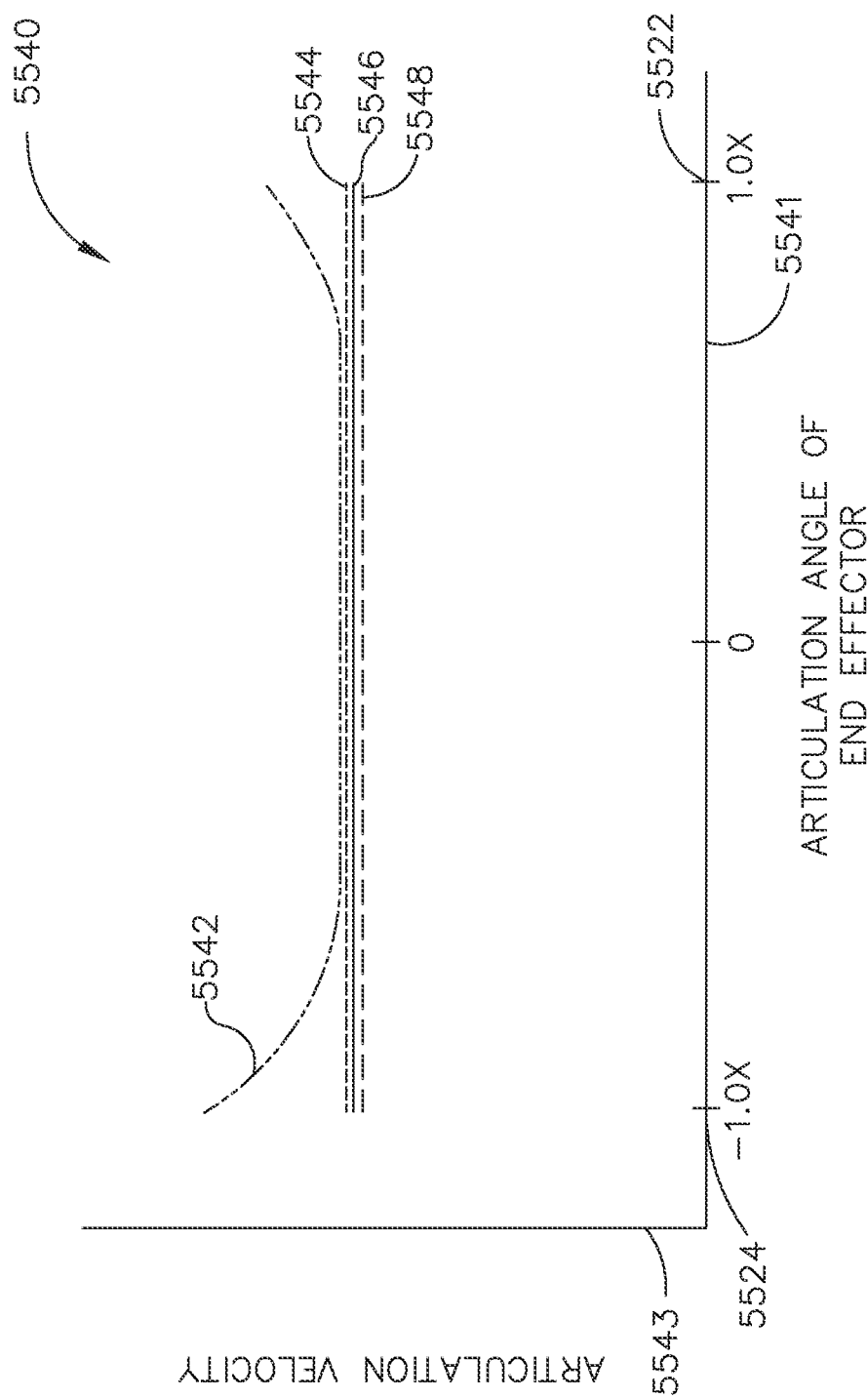
FIG. 53 is a diagram depicting articulation velocity of an end effector relative to articulation angle based on various control algorithms according to one aspect of this disclosure.
Figure 57:
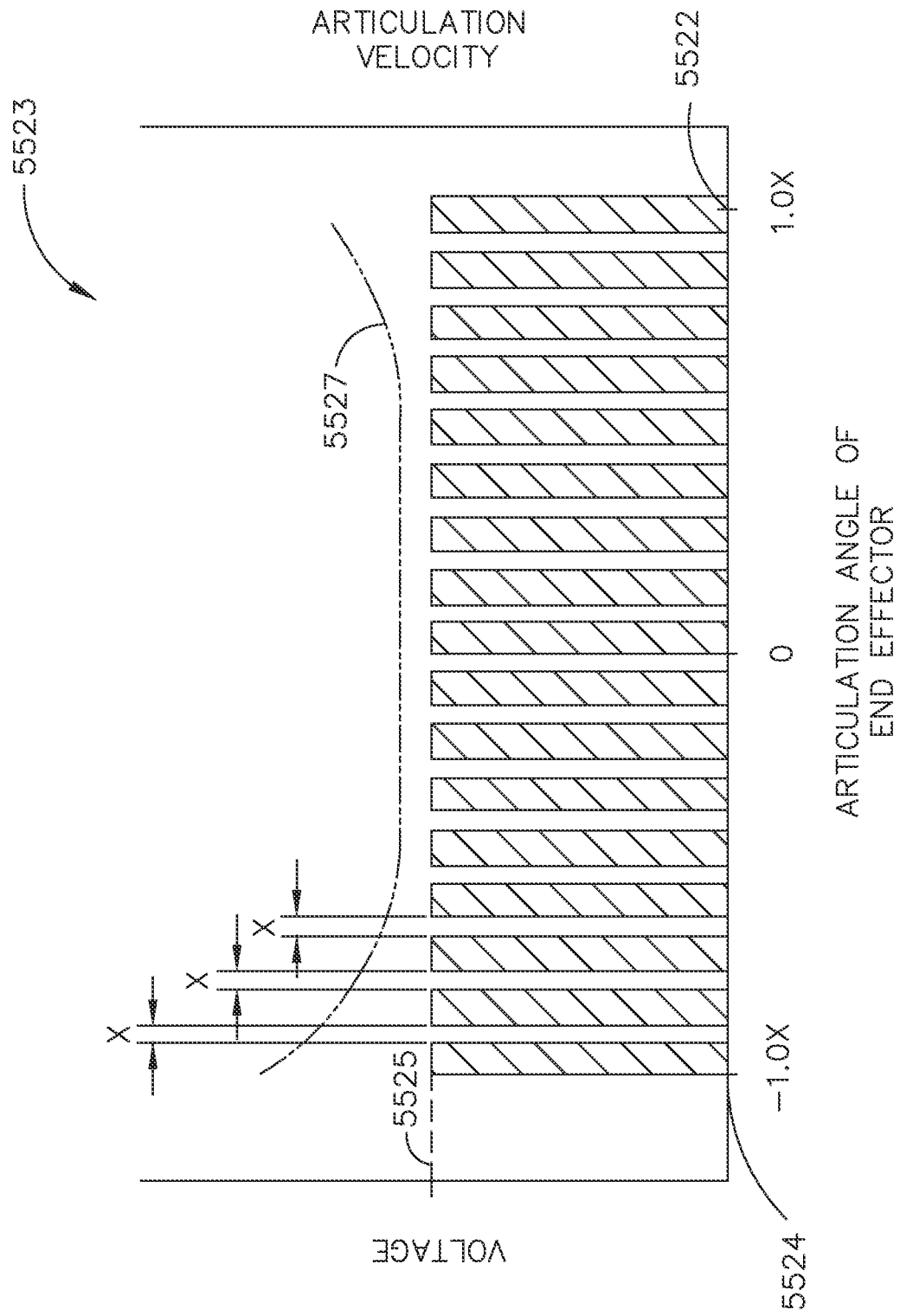

FIG. 53 shows a diagram 5540 depicting the articulation velocity 5543 of the end effector relative to the articulation angle 5541 according to various control algorithms according to one aspect of this disclosure. Line 5542 depicts an aspect of the surgical instrument wherein the articulation driver is driven by the motor at a constant rate, which causes the articulation velocity of the end effector to vary from a first end 5522 to a second end 5524 of its articulation range. In this aspect, the motor voltage and the motor duty cycle are held constant regardless of the articulation angle of the end effector, as illustrated in FIG. 57. FIG. 57 is a diagram 5523 that depicts a control algorithm for controlling an articulation velocity of an end effector utilizing constant voltage and no pulse width modulation. In this aspect, the motor is held at a constant voltage 5525, which results in the articulation velocity represented by line 5527 increasing towards the ends 5522, 5524 of the articulation range of the end effector.

Figure 54:
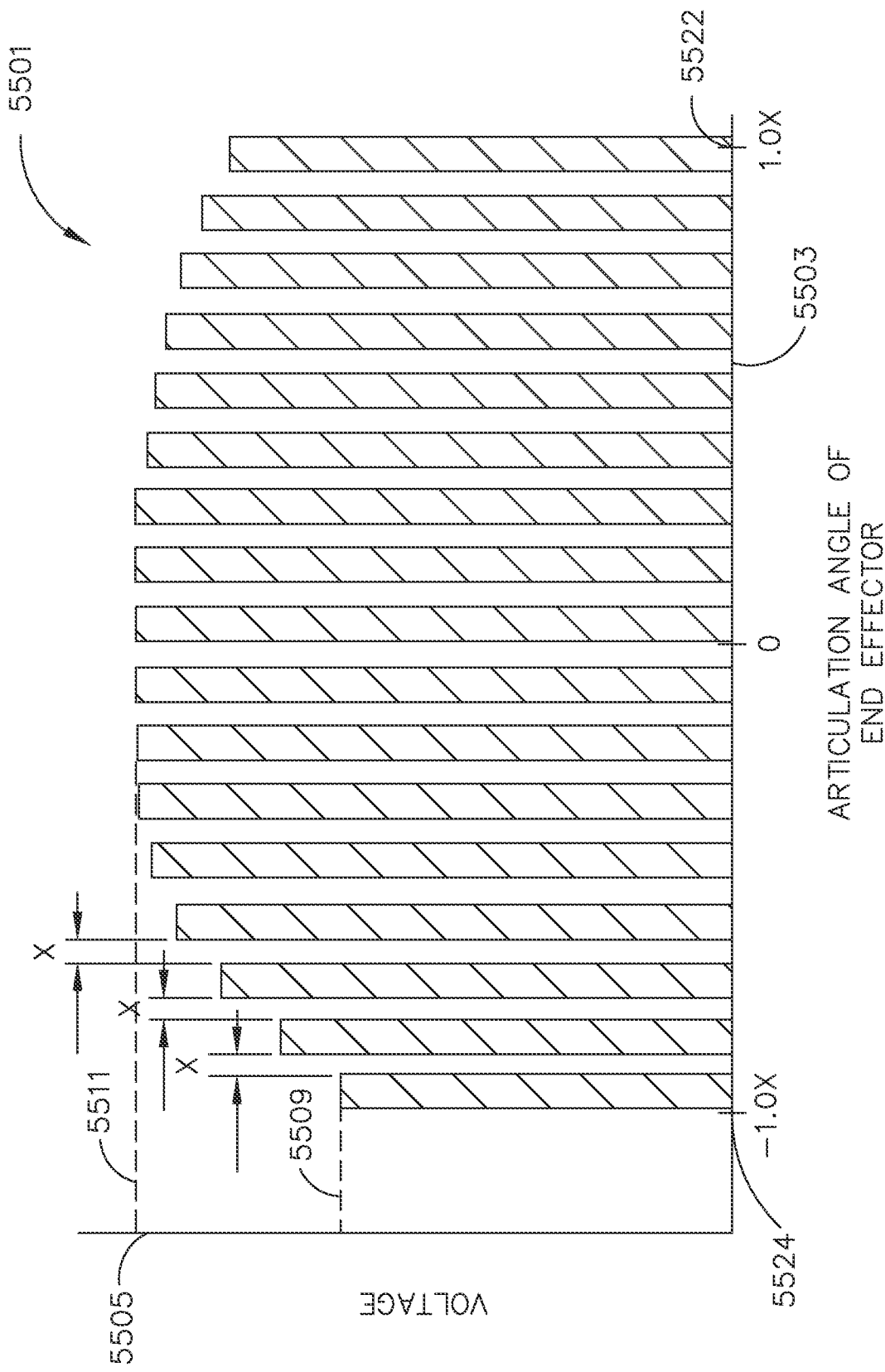
FIGS. 54-57 are diagrams depicting motor voltage and duty cycle relative to articulation angle of an end effector based on various control algorithms according to one aspect of this disclosure, where.

Conversely, lines 5544, 5546, 5548 in FIG. 53 depict aspects of the surgical instrument utilizing control algorithms, such as the logic described in FIGS. 49 and 50, to cause the end effector to have a constant articulation velocity throughout its entire range of movement. One such aspect is illustrated in FIG. 54. FIG. 54 is a diagram 5501 that depicts voltage 5505 relative to the articulation angle of the end effector 5503 for a control algorithm for controlling an articulation velocity of an end effector utilizing variable voltage and no pulse width modulation. In this aspect, the duty cycle is held constant, but the magnitude of the voltage supplied to the motor is varied as a function of the articulation angle of the end effector. For the particular linkage of the articulation pivot assembly described in FIGS. 14-21, the articulation velocity of the end effector tends to increase at the ends of the articulation range of movement. Therefore, to counteract this natural tendency and hold the articulation velocity of the end effector constant throughout the entire range of movement, the magnitude of the voltage supplied to the motor varies between a maximum voltage 5511 and a minimum voltage 5509, such that the voltage is decreased as the articulation angle of the end effector approaches the ends 5522, 5524 of the range of movement in order to slow the articulation driver and thus hold the articulation velocity constant. The voltage at each of the ends 5522, 5524 can be equal or unequal in various aspects of the surgical instrument.

Figure 55:
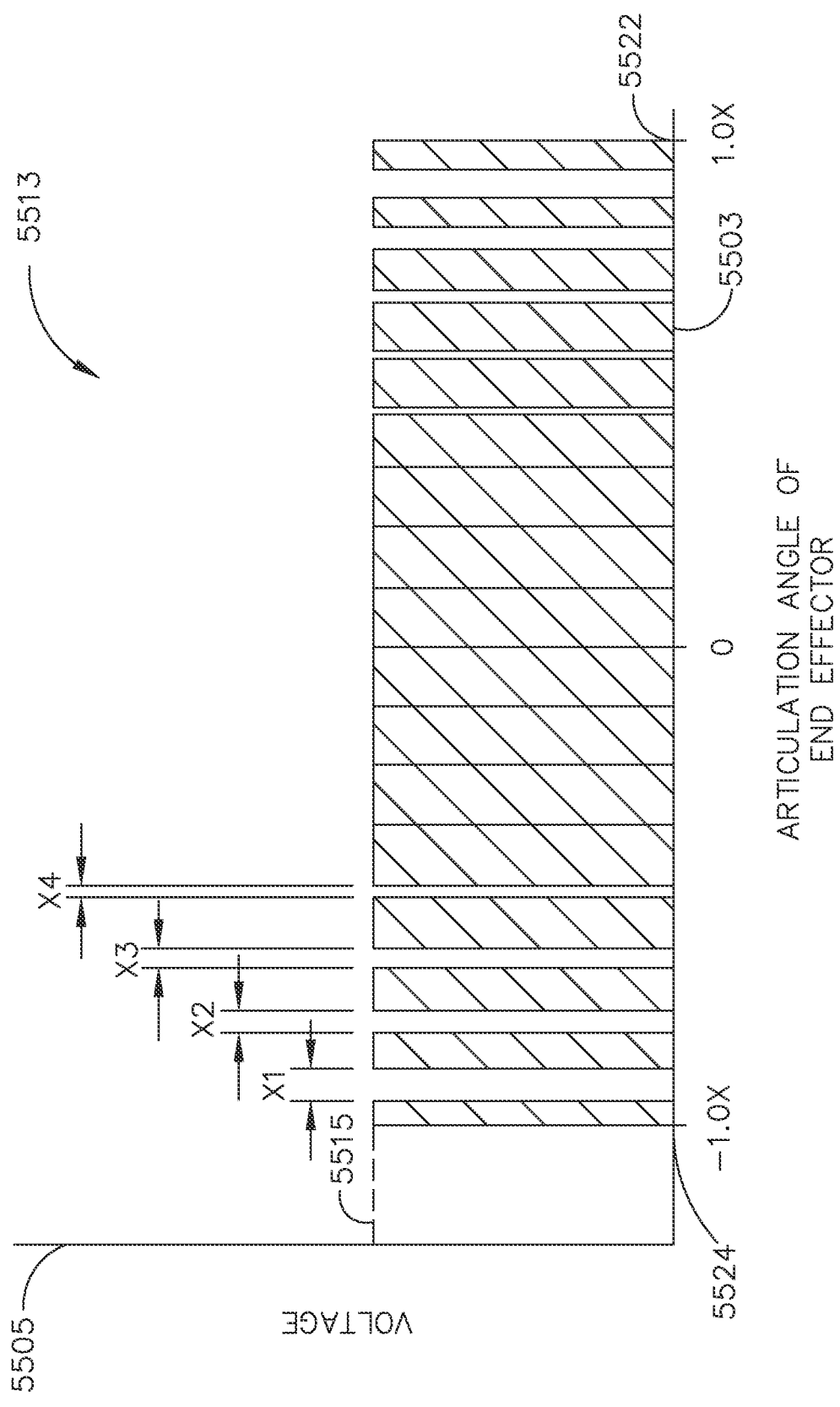
Figure 56:
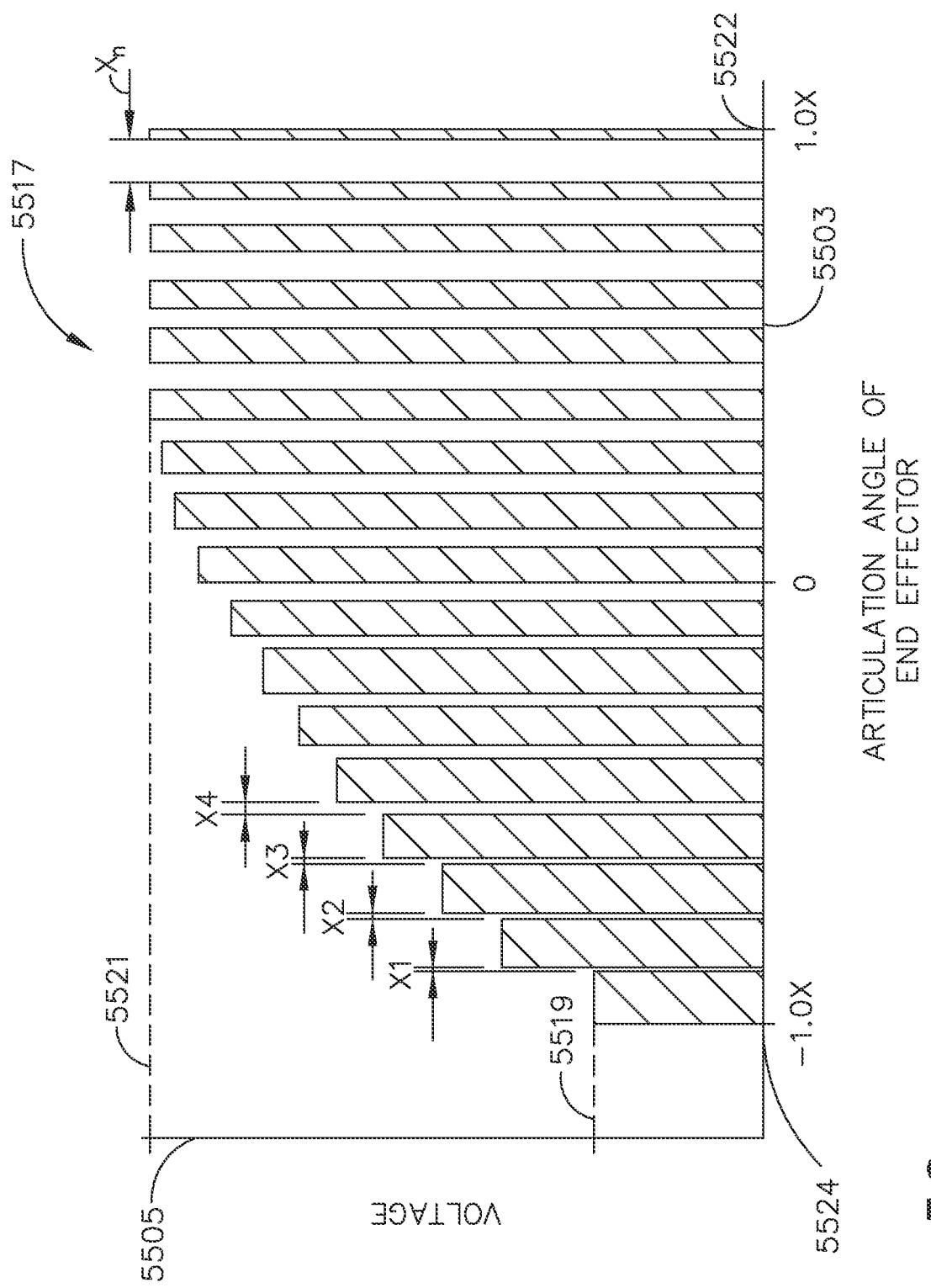

Another such aspect is illustrated in FIG. 55. FIG. 55 is a diagram 5513 that depicts voltage 5505 relative to the articulation angle of the end effector 5503 for a control algorithm for controlling an articulation velocity of an end effector utilizing constant voltage and pulse width modulation. In this aspect, the voltage supplied to the motor is held at a constant voltage 5515 and the duty cycle of the motor is decreased (such that $x_1 > x_2 > x_3$ and so on) as the articulation angle of the end effector approaches the ends 5522, 5524 of the range of movement in order to slow the articulation driver at the ends 5522, 5524 of the articulation range. Yet another such aspect is illustrated in FIG. 56. FIG. 56 is a diagram 5517 that depicts a control algorithm for controlling an articulation velocity of an end effector utilizing variable voltage and pulse width modulation. In this aspect, both the magnitude of the motor voltage and the motor duty cycle are varied as a function of the articulation angle of the end effector to the same general effect as was described with respect to FIGS. 54 and 55. The motor voltage is varied between a maximum voltage 5521 and a minimum voltage 5519. Accordingly, the duty cycle of the motor decreases (such that $x_1 < x_2 < x_3 \ldots < x_n$). The net effect between the varying motor voltage and the motor duty cycle is that the end effector is driven at a constant articulation velocity from the first end 5522 to the second end 5524 of its articulation range.

The functions or processes 5550, 5560 described herein may be executed by any of the processing circuits described herein, such as the control circuit 700 described in with FIGS. 5-6, the circuits 800, 810, 820 described in FIGS. 7-9, the microcontroller 1104 described in with FIGS. 10 and 12, and/or the control circuit 2510 described in FIG. 14.

Various aspects of the subject matter described herein are set out in the following numbered examples:

Example 1. A surgical instrument comprising: a motor configured to drive an end effector between an unarticulated position and an articulated position; a sensor configured to detect an articulation position of the end effector and provide a signal indicative of the articulation position of the end effector; and a control circuit coupled to the sensor and the motor, the control circuit configured to: determine the articulation position of the end effector via the signal provided by the sensor; and provide a drive signal to the motor to articulate the end effector at a velocity corresponding to the signal indicative of the articulation position of the end effector.

Example 2. The surgical instrument of Example 1, wherein the drive signal causes the motor to drive the end effector at a fixed velocity when the articulation position of the end effector is within a designated zone between the unarticulated position and the articulated position.

Example 3. The surgical instrument of Example 2, wherein the designated zone corresponds to a threshold distance from a position between the unarticulated position and the articulated position.

Example 4. The surgical instrument of Example 1 through Example 3, wherein the drive signal varies according to the articulation position of the end effector and the drive signal causes the motor to drive the end effector at a variable velocity according to the articulation position of the end effector.

Example 5. The surgical instrument of Example 1 through Example 4, wherein the drive signal has a variable duty cycle and the duty cycle varies according to the position of the end effector.

Example 6. The surgical instrument of Example 1 through Example 5, wherein the drive signal causes the motor to articulate the end effector at a constant velocity from the unarticulated position to the articulated position.

Example 7. A surgical instrument comprising: an articulation driver configured to drive an end effector that is articulatable between a first position and a second position, the articulation driver configured to drive the end effector from the first position to the second position; a motor coupled to the articulation driver, the motor configured to drive the articulation driver; a sensor configured to detect a position of the articulation driver and provide a signal indicative of the position of the articulation driver; and a control circuit coupled to the motor and the sensor, the control circuit configured to: determine a position of the articulation driver via the signal provided by the sensor; determine an angular position of the end effector according to the signal indicative of the position of the articulation driver; and provide a drive signal to the motor to drive the motor at a velocity corresponding to the angular position of the end effector.

Example 8. The surgical instrument of Example 7, wherein the drive signal causes the motor to drive the end effector at a fixed velocity when the angular position of the end effector is within a designated zone between the first position and the second position.

Example 9. The surgical instrument of Example 8, wherein the designated zone corresponds to a threshold distance from a position between the first position and the second position.

Example 10. The surgical instrument of Example 7 through Example 9, wherein the drive signal varies according to the position of the end effector and the drive signal causes the motor to drive the end effector at a variable velocity according to the position of the end effector.

Example 11. The surgical instrument of Example 7 through Example 10, wherein the drive signal has a variable duty cycle that varies according to the position of the end effector.

Example 12. The surgical instrument of Example 7 through Example 11, wherein the first position is aligned with a longitudinal axis of a shaft.

Example 13. The surgical instrument of Example 7 through Example 12, wherein the first position is a first end of an articulation range of the end effector and the second position is a second end of the articulation range of the end effector.

Example 14. A method of controlling a motor in a surgical instrument, the surgical instrument comprising a motor configured to drive an end effector between an unarticulated position and an articulated position, a sensor configured to detect an articulation position of the end effector and provide a signal indicative of the articulation position of the end effector, and a control circuit coupled to the sensor and the motor, the method comprising: determining, by the control circuit, the articulation position of the end effector via the signal provided by the sensor; and providing, by the control circuit, a drive signal to the motor to articulate the end effector at a velocity corresponding to the signal indicative of the articulation position of the end effector.

Example 15. The method of Example 14, driving, by the control circuit, the motor at a fixed velocity when the articulation position of the end effector is within a designated zone between the unarticulated position and the articulated position.

Example 16. The method of Example 15, wherein the designated zone corresponds to a threshold distance from a position between the first position and the second position.

Example 17. The method of Example 14 through Example 16, driving, by the control circuit, the motor at a variable voltage according to the articulation position of the end effector.

Example 18. The method of Example 14 through Example 17, driving, by the control circuit, the motor at a variable duty cycle according to the articulation position of the end effector.

Example 19. The method of Example 14 through Example 18, driving, by the control circuit, the motor at a constant velocity from the first position to the second position.

Systems and Methods for Controlling Velocity of a Displacement Member of a Surgical Stapling and Cutting Instrument During use of a motorized surgical stapling and cutting instrument it is possible that the force to fire experienced by the cutting member or firing member may be substantially different based on the location of the cutting member or firing during the firing stroke. Generally, the first zone is the most highly loaded and the last zone is the least highly loaded. Therefore, it may be desirable to define the firing stroke into distinct zones with varying cutting member advancement velocity in each zone based on the force to fire load experienced by the firing system and to vary the firing velocity of the cutting member based on the position of the cutting member along the firing stroke. It would be desirable to set the firing velocity at the slowest velocity during in the first zone where the cutting member or firing member is under the highest load and increase the velocity in each subsequent zone. It may be desirable to set the velocity in the first zone by determining the tissue thickness or tissue gap by measuring any combination of current through the motor, time to advance the cutting member to a predefined distance, displacement of the cutting member over a predefined time, or any proxy for load on the motor.

Figure 58:
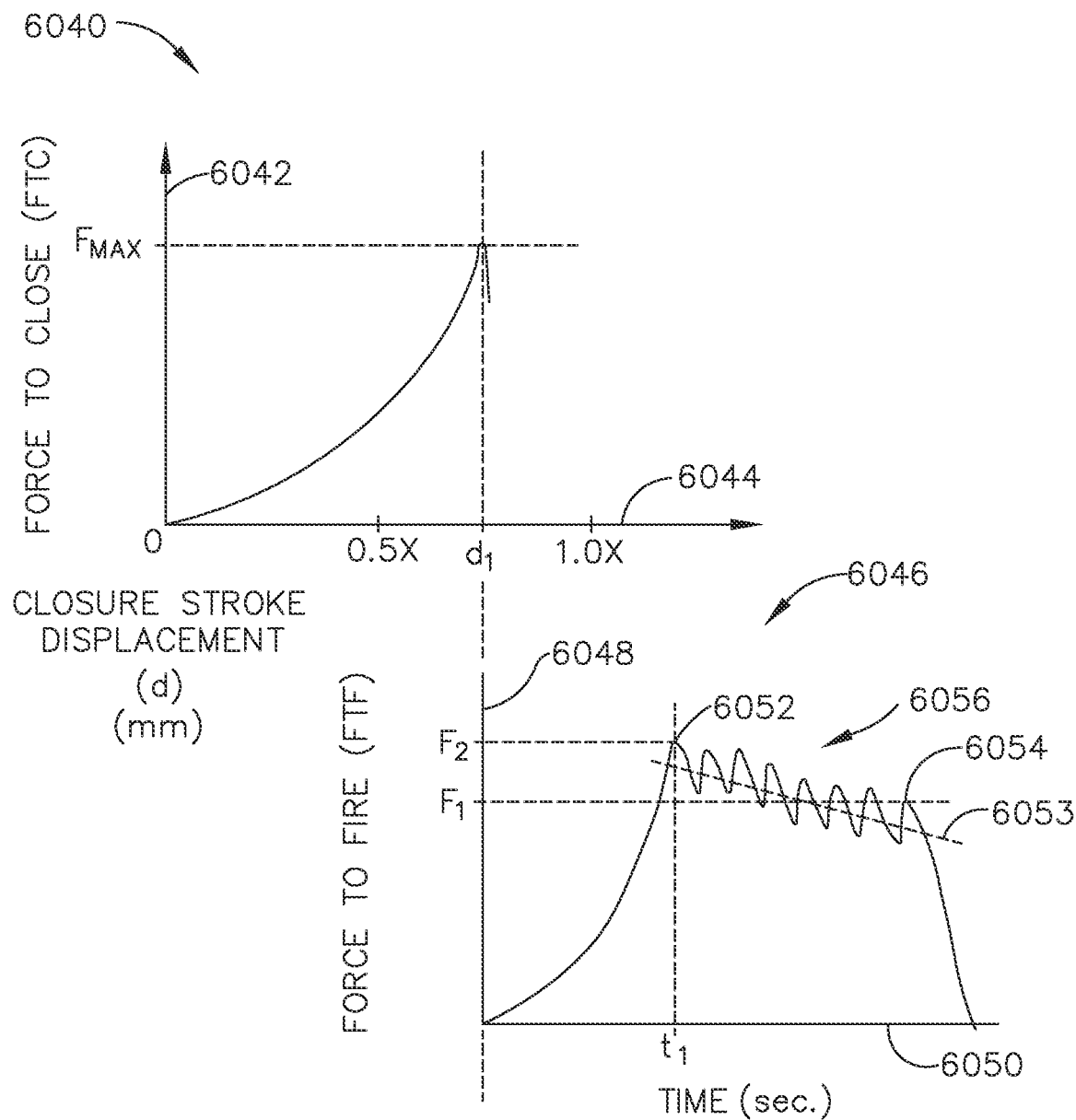
FIG. 58 depicts two diagrams illustrating the force to close (FTC) the anvil of the surgical instrument of FIG. 1 as a function of closure stroke displacement (d) and the force to fire (FTF) the surgical instrument of FIG. 1 as a function of time according to one aspect of this disclosure.

Referring to FIG. 58, a diagram 6040 plots an example of the force applied during a closure stroke to close the end effector 2502 around tissue grasped between the anvil 2516 and the staple cartridge 2518, the closure force plotted as a function of the closure stroke displacement (d). The diagram 6040 comprises two axes. A vertical axis 6042 indicates the force to close (FTC) the end effector 2502 in newtons (N). A horizontal axis 6044 indicates a distance traveled by a closure member such as, for example, the closure tube 260 (FIG. 1) to cause the closure of the end effector 2502. During the closure stroke, the closure tube 260 is translated distally (direction "DD") to move the anvil 2516, for example, relative to the staple cartridge 2518 in response to the actuation of the closure trigger 32 (FIG. 1) in the manner described in the aforementioned reference U.S. Patent Application Publication No. 2014/0263541. In other instances, the closure stroke involves moving a staple cartridge relative to an anvil in response to the actuation of the closure trigger 32. In other instances, the closure stroke involves moving the staple cartridge and the anvil in response to the actuation of the closure trigger 32.

The diagram 6040 indicates that the force to close (FTC) the end effector 2502 increases as the closure tube 260 travels distally. The force to close (FTC) reaches a maximum force ($F_{max}$) at a distance (d) traveled by the closure tube 260 from a starting position. An end effector 300, which is similar in many respects to the end effector 2502, compresses tissue to a maximum threshold corresponding to the maximum force ($F_{max}$). The maximum force ($F_{max}$) depends, at least in part, on the thickness of the tissue grasped by the end effector 2502. In one example, the closure member is configured to travel a distance (d1) of about 0.210" (5.334 mm) to reach a maximum force ($F_{max}$) of about 160 pound-force (711.715 newtons).

FIG. 58 also depicts a diagram 6046 that plots an example of the force applied to fire (FTF) the surgical instrument 2500. The force to fire (FTF) can be applied to advance the I-beam 2514 during a firing stroke of the surgical instrument 2500. The diagram 6046 comprises two axes. A vertical axis 6048 indicates the force, in newtons (N), applied to advance the I-beam 2514 during the firing stroke. The I-beam 2514 is configured to advance the knife 2509 and motivate the drivers 2511 to deploy the staples 2505 during the firing stroke. A horizontal axis 6050 indicates the time in seconds.

Figure 64:
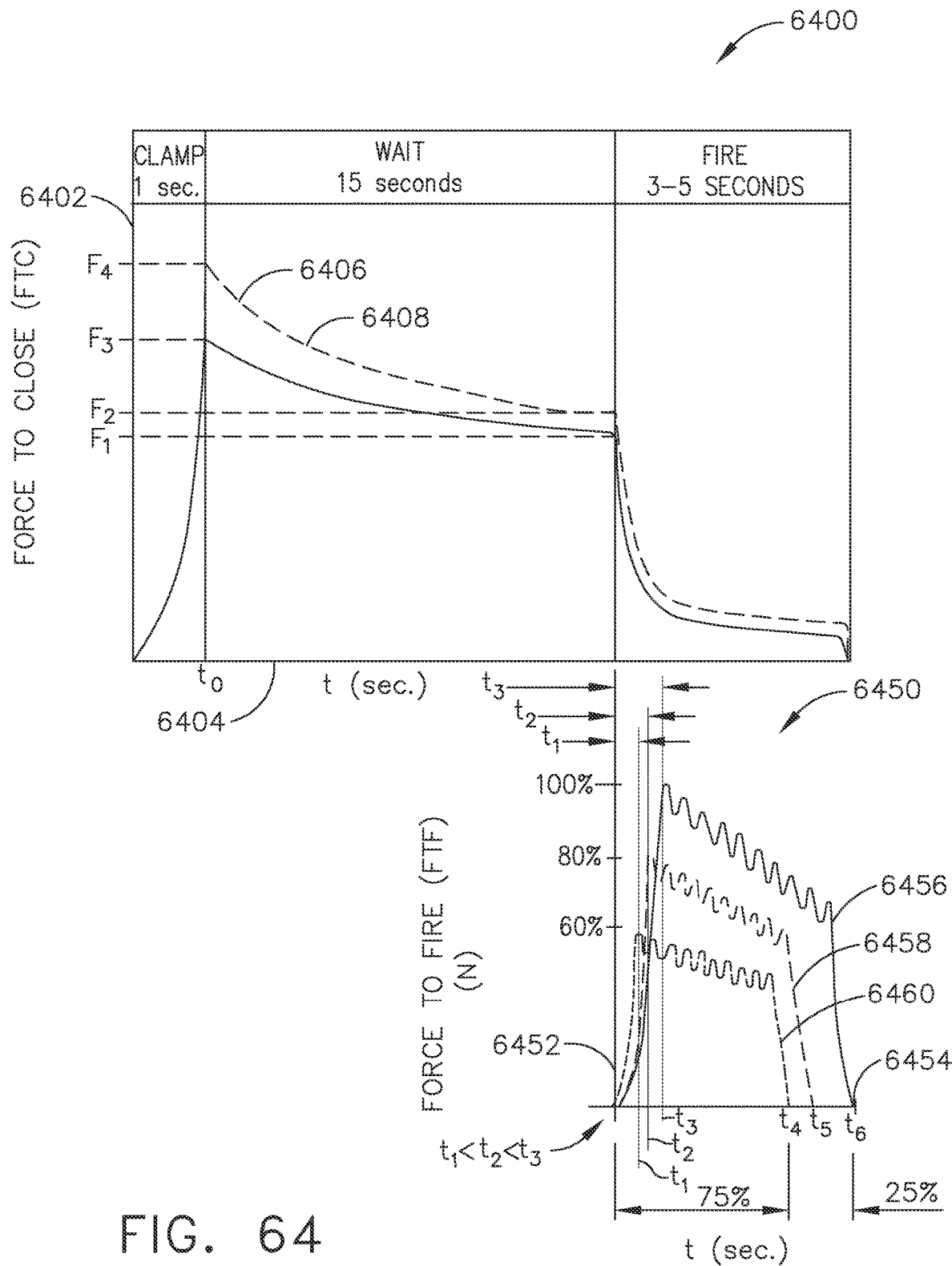
FIG. 64 depicts two diagrams illustrating the force to close the anvil of the surgical instrument of FIG. 1 as a function of time and the force to fire the surgical instrument of FIG. 1 as a function of time according to one aspect of this disclosure.

The I-beam 2514 is advanced from a starting time (t=0). The advancement of the I-beam 2514 is initiated when the force to close (FTC) the end effector 2502 reaches a maximum force ($F_{max}$). Alternatively, as illustrated in FIG. 64, a waiting period can be applied prior to starting the firing stroke. The waiting period allows fluid egress from the compressed tissue which reduces the thickness of the compressed tissue yielding a reduction in the maximum force ($F_{max}$).

The diagram 6046 indicates that the force to fire (FTF) the surgical instrument 2500 increases to a maximum force ($F_2$) at the top of the highest peak 6052. The maximum force ($F_2$) is at an initial section of the firing stroke when the wedge sled 2513. The top of the lowest peak 6054 represents a maximum force ($F_1$), which occurs at final section of the firing stroke. The maximum force ($F_1$) is applied to the I-beam 2514 during engagement of the wedge sled 2513 with the distal staple drivers 2511. In addition, intermediate peaks 6056, which occur at an intermediate section of the firing stroke, between the peak 6052 and the peak 6054, outline a downward slope of 6053 the force needed to fire (FTF) the surgical instrument 2500 during the intermediate section of the firing stroke. The downward slope 6053 begins at a time ($t_1$) corresponding to the maximum force ($F_1$) at the top of the highest peak 6052. The downward slope 6053 generally results from a gradual reduction in the load as the I-beam 2514 advances the wedge sled 2513 through the intermediate portion of the firing stroke beyond the time ($t_1$).

Figure 59:
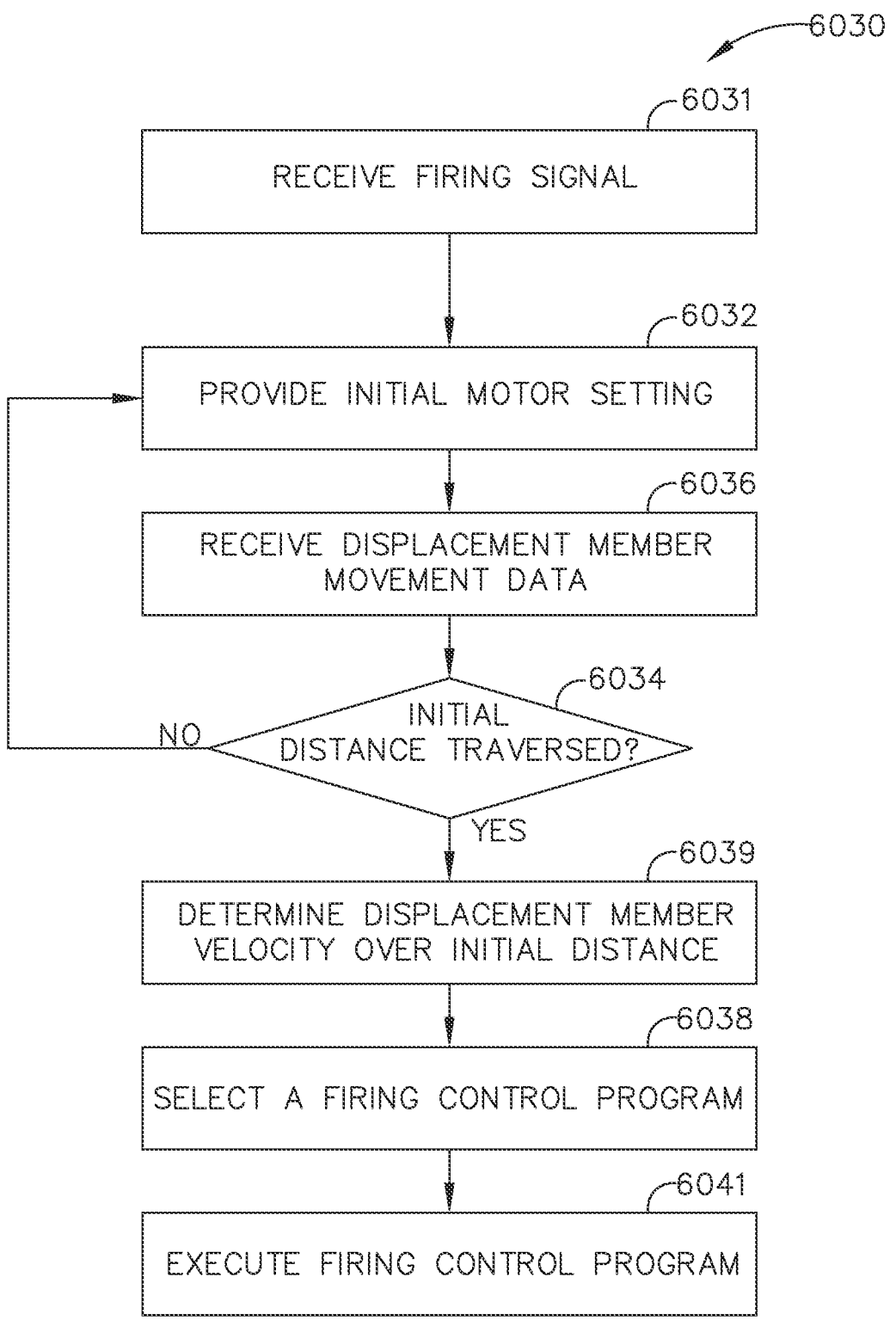
FIG. 59 illustrates a logic flow diagram showing an example of a process of a control program or logic configuration that may be executed by a surgical instrument (e.g., a control circuit of a surgical instrument) to implement an I-beam firing stroke according to one aspect of this disclosure.

FIG. 59 illustrates a logic flow diagram showing one example of a process 6030 of a control program or logic configuration that may be executed by the surgical instrument 2500 (e.g., the control circuit 2510) to implement an I-beam stroke responsive to tissue conditions and/or staple cartridge type. The control circuit 2510 may receive 6031 a firing signal. The firing signal may be received 6031 from the trigger 32 (FIG. 1) or other suitable actuation device. For example, a clinician may place the end effector 2502, clamp tissue between the anvil 2516 and staple cartridge 2518 and then actuate the trigger 32 to begin an I-beam stroke. The trigger 32 may be configured to provide the firing signal to the control circuit 2510 upon actuation.

The control circuit 2510, in response to the firing signal, may provide 6032 an initial motor setting. For example, the initial motor setting may be a motor set point 2522 provided to the motor controller 2508. The motor controller 2508 may translate the initial motor set point 2522 into a PWM signal, voltage signal, or other suitable motor drive signal to drive the motor 2504. In some examples, (e.g., when the control circuit 2510 directly generates the motor drive signal 2524), the initial motor setting may be a motor drive signal 2524 provided directly to the motor 2504. The initial motor setting may correspond to a particular motor velocity, power, or other suitable variable. In some examples where the motor 2504 is a brushed DC motor, the initial motor setting may be a signal having a constant voltage. In some examples where the motor is a brushless DC motor, the initial motor setting may be a signal or set of signals having a constant phase, duty cycle, etc.

The control circuit 2510 may receive 6036 I-beam member movement data. E-member beam movement data may comprise information (e.g., from the position sensor 2534) that describes the position and/or movement of the I-beam

2514. Although receiving 6036 I-beam member movement data may be a portion of the process 6030, in some examples, the control circuit 2510 may receive 6036 I-beam member movement data while the I-beam 2514 is in motion. For example, when the position sensor 2534 is an encoder, the control circuit 2510 may receive pulse signals from the encoder while the I-beam 2514 is moving with each pulse signal representing a quantum of motion. Also, in examples where the motor 2504 is a stepper motor, the control circuit 2510 may derive I-beam member movement data based on the total number of steps that the control circuit 2510 instructs the motor 2504 to execute.

I-beam member movement data may indicate a distance that the I-beam 2514 moved during the initial time period, which may reflect the tissue conditions such as the thickness and/or toughness of the tissue present between the anvil 2516 and the staple cartridge 2518 because different types of tissue will offer different levels of resistance. For example, thicker or tougher tissue may provide more mechanical resistance to the knife and staples. More mechanical resistance may cause the motor 2504 to run more slowly while the initial motor setting is held substantially constant. Similarly, thinner or weaker tissue may provide less mechanical resistance to the knife and staples. This may cause the motor to run faster and traverse more distance while the initial motor setting is held substantially constant.

Figure 60:
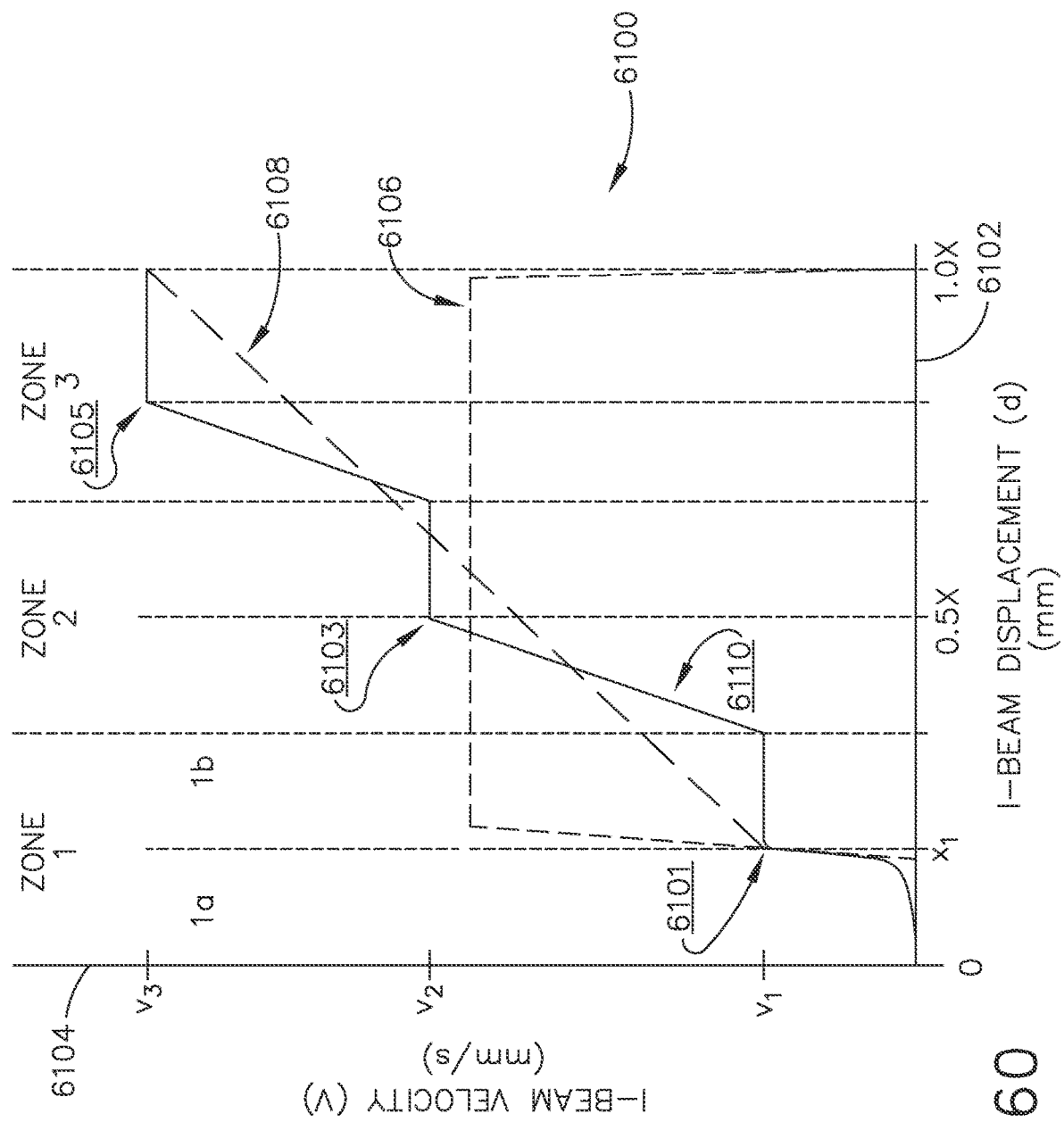
FIG. 60 is a diagram illustrating velocity (v) of the I-beam as a function of firing stroke displacement (d) according to one aspect of this disclosure.

After the initial motor setting is provided, the instrument 2500 may run in an open-loop configuration in a diagnostic first portion (1a) of zone 1, as illustrated in FIG. 60. For example, the motor drive signal 2524 may be held substantially constant. As a result, the actual properties of the motor 2504, such as motor velocity, may drift based on factors including tissue conditions (e.g., tissue thickness, tissue toughness, etc.) For example, when thicker or tougher tissue is present between the anvil 2516 and the staple cartridge 2518, the tissue may provide more mechanical resistance to the knife and/or staples, which may tend to slow the velocity of the I-beam 2514 as the motor setting is held substantially constant.

The control circuit 2510 may be configured to maintain the initial motor setting for an open-loop portion of the I-beam stroke. In the example of FIG. 59, the open-loop portion of the I-beam stroke may continue until the I-beam 2514 has traversed an initial distance. Accordingly, the control circuit 2510 may be configured to maintain the initial motor setting until the I-beam has traversed the initial distance. The initial distance may be, for example, a predetermined portion of the total distance between the firing stroke begin position and the firing stroke end position (e.g., ⅙, ¼, ⅓, etc.). In one example, the initial open-loop distance is a first initial portion (1a) of zone 1 spanning a distance of about 0.200" (5.08 millimeters) from the stroke begin position 2527 (FIG. 13). The control circuit 2510 may determine 6034 from the received I-beam member movement data whether the I-beam 2514 has traversed the initial distance. If not, the control circuit 2510 may continue to provide 6032 the initial motor setting and receive 6036 additional I-beam member movement data.

In some examples, the initial open-loop distance is a diagnostic first portion (1a) of zone 1 spanning a distance selected from range of about 1 millimeter to about 10 millimeters. In some examples, the initial open-loop distance spans a distance selected from range of about 3 millimeters to about 7 millimeters.

The process 6030 may proceed if the control circuit 2510 determines 6034 that the I-beam has traversed the initial distance. In some examples, the control circuit 2510 may maintain a running counter or timer 2531 (FIG. 14) while the initial distance is traversed. When the control circuit 2510 determines that the I-beam has traversed the initial distance, the control circuit 2510 may stop the timer 2531. The control circuit 2510 may determine 6039 an I-beam velocity over the initial distance. The control circuit 2510 may find the I-beam velocity by taking the initial distance divided by the time required to traverse the distance.

Alternatively, in some examples, the open-loop portion may be an initial time period, which may also be referred to as an open-loop time period. The initial time period may be of any suitable length including, for example, 100 milliseconds. A position sensor such as, for example, the position sensor 2534 (FIG. 14) may track the position of the I-beam 2514 during the initial time period. The control circuit 2510 may determine an I-beam velocity over the initial time period. The control circuit 2510 may find the I-beam velocity by taking the distance traversed by the I-beam 2514 during the initial time period divided by the initial time period. The velocity of the I-beam 2514 in the diagnostic first portion (1a) of zone 1 can be indicative of the tissue conditions such as the thickness and/or toughness of the tissue present between the anvil 2516 and the staple cartridge 2518.

Alternatively, in some examples, current (I) drawn by the motor 2504 in the open-loop portion can be used to assess the tissue conditions such as the thickness and/or toughness of the tissue present between the anvil 2516 and the staple cartridge 2518. A sensor such as, for example, a current sensor can be employed to track the current (I) drawn by the motor 2504 in the open-loop portion. One example of a current sensor 2536 is shown in FIG. 14.

Returning now to FIG. 59, the control circuit 2510 may select 6038 a firing control program or configuration, for example, based on the determined I-beam velocity and/or the current (I) drawn by the motor 2504 in the open-loop portion in the diagnostic first portion (1a) of zone 1. The control circuit 2510 may execute 6041 the selected firing control program or logic configuration.

In some examples, the firing control program may determine a target value for the movement of the I-beam 2514 during the remainder of the I-beam stroke. FIG. 60 illustrates a diagram 6100 plotting velocity versus distance traveled along a firing stroke for three example I-beam strokes 6106, 6108, 6110, which can be implemented by the firing control programs selected at 6038. The diagram 6100 includes two axes. A horizontal axis 6102 represents the firing stroke displacement in millimeters. A vertical axis 6104 indicates velocity of the I-beam 2514 in millimeters per second. As illustrated, in FIG. 60, the examples 6106, 6108, 6110 initially have the same I-beam velocity in the diagnostic first portion (1a) of zone 1 of the firing stroke distance.

In the example 6106 of FIG. 60, the firing control program is configured to maintain the velocity of the I-beam 2514 at a predetermined constant, or substantially constant, velocity. The constant velocity may be selected based on the movement of the I-beam during the diagnostic first portion (1a) of zone 1. In some examples, the firing control program may include driving the I-beam 2514 with a constant power. The control circuit 2510 may implement 6041 the firing control program or logic configuration previously selected 6038. For example, the control circuit 2510 may drive the I-beam 2514 with constant velocity by monitoring the position of the I-beam 2514 indicated by the position sensor 2534 and modulating the motor set point 2522 and/or motor drive signal 2524 to maintain a constant velocity. Similarly, the control circuit 2510 may drive the I-beam 2514 with constant power by monitoring the voltage and/or current drawn by the motor 2504 and modulating the motor set point 2522 and/or motor drive signal 2524 to maintain a constant power draw.

As described above in connection with the diagram 6046 of FIG. 58, the force to fire (FTF) gradually decreases as the I-beam 2514 is advanced during the firing stroke. As such, the force to fire (FTF) the I-beam 2514 is generally higher at the beginning of the firing stroke than the middle of the firing stroke, and generally higher at the middle of the firing stroke than the end of the firing stroke. Maintaining a reduced velocity of the I-beam 2514 in portions of the firing stroke where the I-beam 2514 experiences higher loads improves the performance of the motor 2504 and the energy source 2512. First, the total current (I) drawn by the motor 2504 during the firing stroke is reduced, which prolongs the life of the energy source 2512 (FIG. 14). Second, reducing the velocity of the I-beam 2514 in portions of the firing stroke with the higher loads protects the motor 2504 from stalling. The increased resistance may cause the motor 2504 to stall. Stalling is a condition when the motor stops rotating. This condition occurs when the load torque is greater than the motor shaft torque.

To reduce the load or force to fire (FTF) applied to the I-beam 2514, alternative firing control programs are employed by the control circuit 2510. Two of the alternative firing control programs are represented in the examples 6108, 6110 of FIG. 60. FIG. 61B illustrates a logic flow diagram showing one example of a process 6131 of a control program or logic configuration that may be selected 6038 and executed 6041 by the surgical instrument 2500 (e.g., the control circuit 2510) at 6041 to implement an I-beam stroke responsive to tissue conditions and/or staple cartridge type. The firing process 6131 may include driving the I-beam 2514 at a velocity that increases linearly as the I-beam 2514 is advanced along the firing stroke, as illustrated in an example 6108 of FIG. 60.

The control circuit 2510 controls 6132 the motor 2504 to reach a starting velocity (v1) at a predetermined position at a starting point 6101. The control circuit 2510 drives 6134 the I-beam 2514 with a velocity that increases linearly at a predetermined rate as the I-beam 2514 is advanced along the firing stroke by modulating the motor set point 2522 and/or motor drive signal 2524 to yield a linear, or substantially linear, increase in the velocity of the I-beam 2514 as the I-beam 2514 is advanced along the firing stroke. The velocity rate of the I-beam 2514 is maintained 6135 until the end of the firing stroke.

The control circuit 2510 may monitor the position of the I-beam 2514 indicated by the position sensor 2534 and time as indicated by the timer 2531. The data from the position sensor 2534 and the timer 2531 can be employed by the control circuit 2510 to sample the velocity of the I-beam 2514 at discrete positions along the firing stroke. The sampled velocity can be compared against predetermined thresholds to determine how to modulate the motor set point 2522 and/or motor drive signal 2524 to yield the linear, or substantially linear, increase in the velocity of the I-beam 2514 as the I-beam 2514 is advanced along the firing stroke. In some examples, the velocity of the I-beam 2520 is sampled in intervals of 1 millimeter.

In some examples, the absolute positioning system 1100 (FIGS. 10-12) can be employed to sense the position of the I-beam 2514, and the velocity of the I-beam 2520 is sampled in intervals defined by the revolution(s) of the sensor element 1126.

In some examples, the control circuit 2510 is configured to increase the velocity of the I-beam 2514 at a constant, or substantially constant, rate as the I-beam 2514 is advanced through the firing stroke. The rate of increase of the velocity of the I-beam 2514 may be selected based on the movement of the I-beam during the diagnostic first portion (1a) of zone 1. In one example, a look-up table can be employed to determine the rate of increase of the velocity of the I-beam 2514 based on measurements representing the movement of the I-beam during the diagnostic first portion (1a) of zone 1.

As illustrated in FIG. 60, the linear increase in the velocity of the I-beam 2514 begins at a starting point 6101 representing a starting velocity (v1) at a predetermined position in the beginning of a second portion (1b) of zone 1. The starting velocity v1 also can be determined based the movement of the I-beam 2514 during the diagnostic first portion (1a) of zone 1. In one example, a look-up table can be employed to determine the starting velocity v1 based on measurements representing the movement of the I-beam 2514 during the diagnostic first portion (1a) of zone 1. Notably, the starting velocity (v1) of the example 6108 is significantly lower than the constant velocity of the example 6110, which yields a reduced force to fire (FTF) in the example 6108.

The control circuit 2510 also can be configured to determine the starting velocity v1 and/or the rate of increase of the velocity of the I-beam 2514 based on tissue conditions. As described above, the tissue conditions such as the thickness and/or toughness of the tissue present between the anvil 2516 and the staple cartridge 2518 can influence the movement of the I-beam 2514 because different types of tissue will offer different levels of resistance. For example, thicker or tougher tissue may provide more mechanical resistance to the I-beam 2520. More mechanical resistance may cause the motor 2504 to run more slowly while the initial motor setting is held substantially constant. Similarly, thinner or weaker tissue may provide less mechanical resistance to the I-beam 2520. This may cause the motor to run faster and traverse more distance while the initial motor setting is held substantially constant.

In the example 6110 of FIG. 60, a firing control program may include driving or maintaining the I-beam 2514 at a plurality of constant, or substantially constant, velocities at a plurality of discrete or continuous portions or zones within the firing stroke to reduce the load or force to fire (FTF) as the I-beam 2514 is advanced through the firing stroke. The firing stroke distance is divided into three zones: zone 1, zone 2, and zone 3. The load experienced by the I-beam 2514 in zone 1 is greater than zone 2, and the load experienced by the I-beam 2514 in zone 2 is greater than zone 3. To reduce the force to fire (FTF), as illustrated in the example 6110 of FIG. 60, the I-beam 2514 is driven at three constant, or substantially constant, velocities v1, v2, and v3 in zone 1, zone 2, and zone 3, respectively.

In some examples, the number of zones and corresponding velocities can be more or less than three depending on the staple cartridge size and/or tissue conditions. The positioning of I-beam stroke zones in FIG. 60 is just one example. In some examples, different zones may begin at different positions along the end effector longitudinal axis 2515, for example, based on the positioning of tissue between the anvil 2516 and the staple cartridge 2518.

Figure 61A:
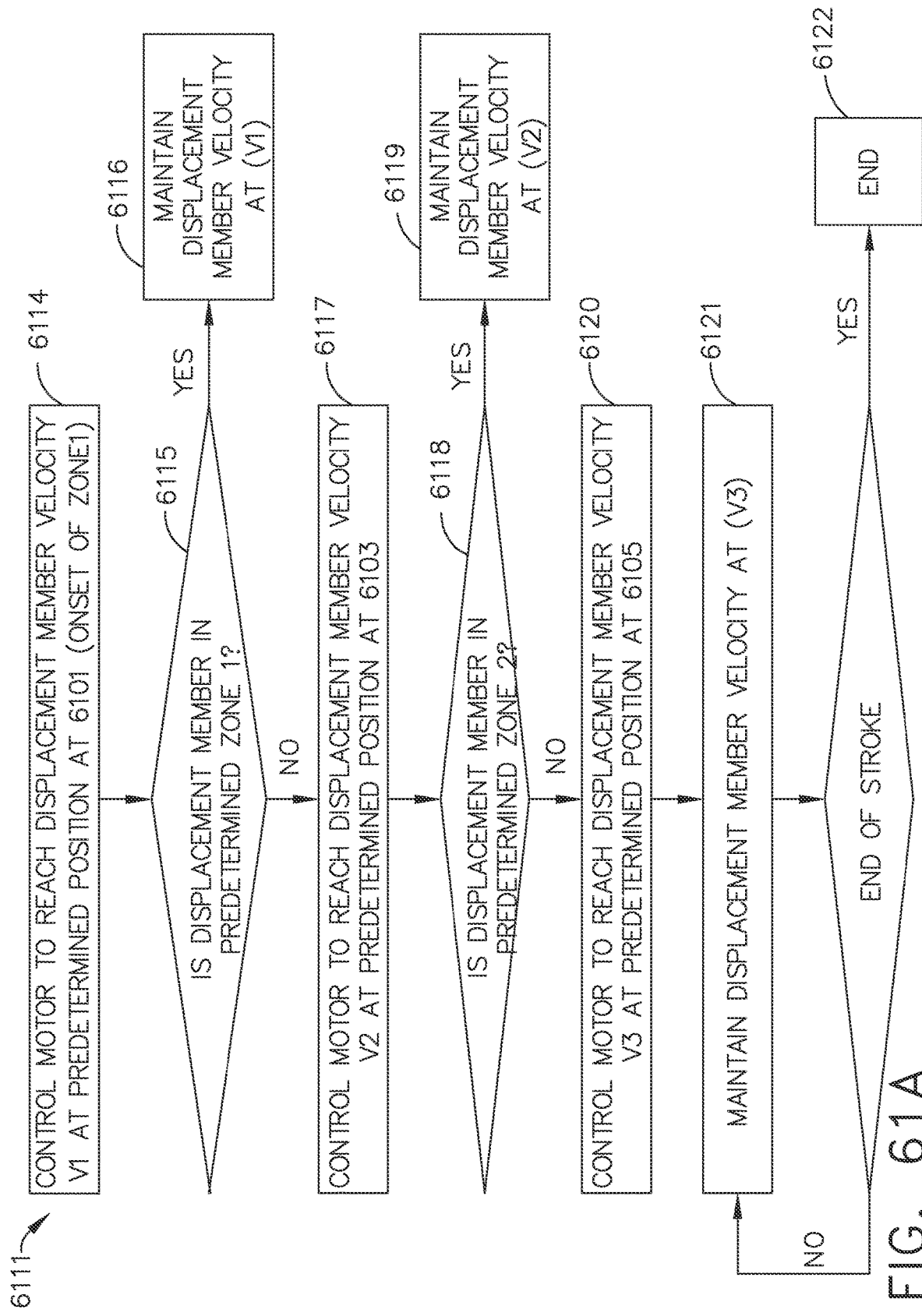
FIG. 61A is a logic flow diagram representing a firing control program or logic configuration according to one aspect of this disclosure.
Figure 61B:
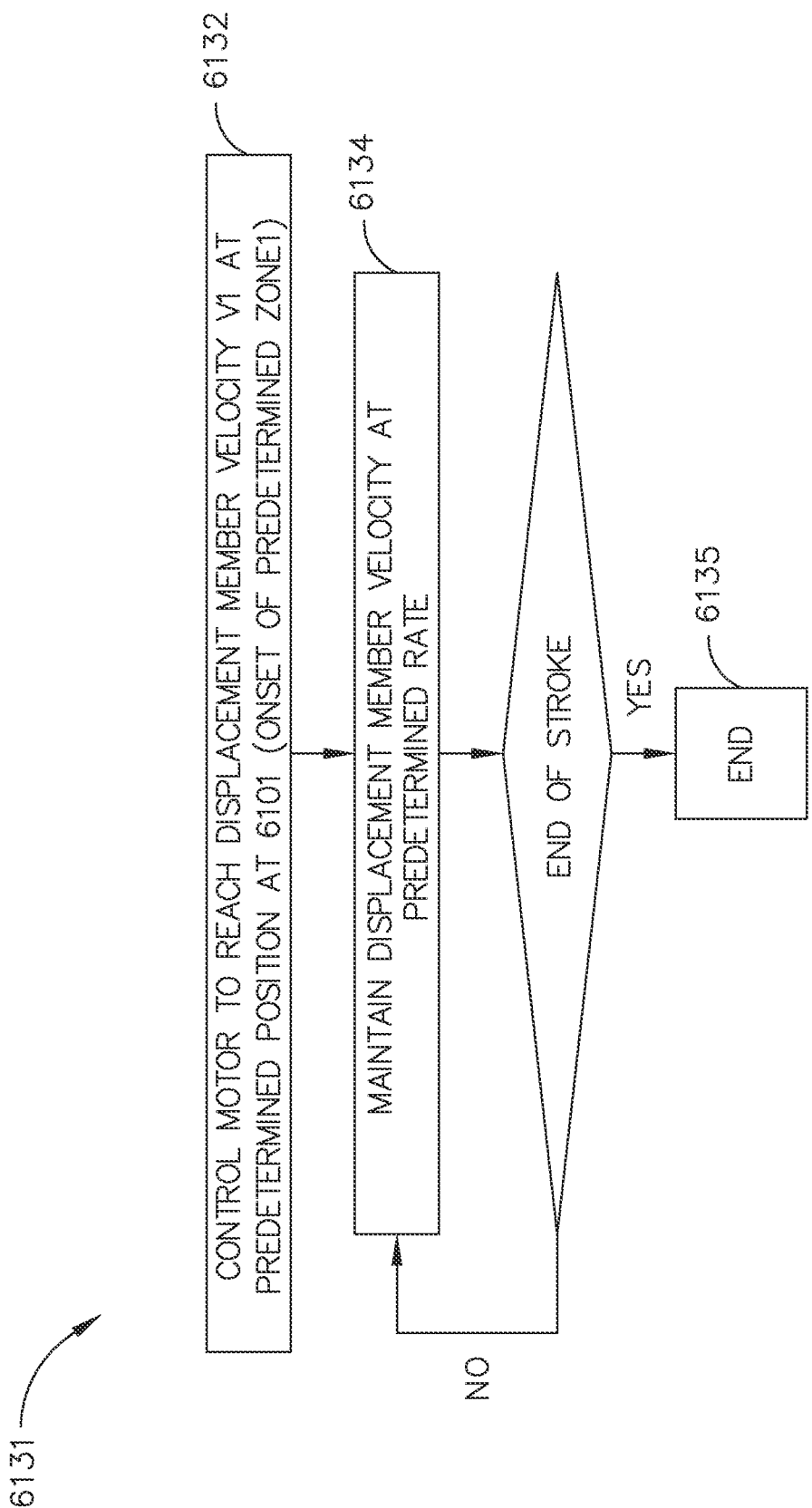
FIG. 61B is a logic flow diagram representing a firing control program or logic configuration according to one aspect of this disclosure.

FIG. 61A illustrates a logic flow diagram showing one example of a process 6111 of a control program or logic configuration that may be selected 6038 and executed 6041 by the surgical instrument 2500 (e.g., the control circuit 2510) at 6041 to implement an I-beam stroke responsive to tissue conditions and/or staple cartridge type. In zone 1, where the I-beam 2514 experiences the highest load, the I-beam 2514 is driven at a slow constant, or substantially constant, velocity (v1). The control circuit 2510 controls 6114 the motor 2504 to reach a velocity (v1) at starting point 6101 (FIG. 60), which represents a predetermined position at the beginning of a second portion (1b) of zone 1. The control circuit 2510 maintains 6116 the velocity of the I-beam 2514 at the velocity (v1) for the remainder of zone 1 beginning at the starting point 6101. At 6115, if the I-beam 2514 is in zone 1, the control circuit 2510 maintains 6116 the velocity of the I-beam 2514 at the velocity (v1). If, however, the I-beam 2514 is no longer in zone 1, the control circuit 2510 controls 6117 the motor 2504 to reach a velocity (v2) at the starting point 6103 (FIG. 60), which represents a predetermined position in zone 2. Notably, the velocity (v1) is significantly lower than the constant velocity of the example 6106, which reduces the force to fire (FTF) in the example 6110 relative to the example 6106.

In zone 2, where the I-beam 2514 experiences an intermediate load, the I-beam 2514 is maintained 6119 at a constant, or substantially constant, velocity (v2) that is higher than the velocity (v1) for the remainder of zone 2. If the control circuit 2510 determines 6118 that the I-beam 2514 is in zone 2, the control circuit 2510 maintains 6119 the velocity of the I-beam 2514 at the velocity (v2). If, however, the I-beam 2514 is no longer in zone 2, the control circuit 2510 controls 6120 the motor 2504 to reach a predetermined velocity (v3) at the starting point 6105 (FIG. 60), which represents a predetermined position in zone 3. The control circuit 2510 maintains 6121 the velocity (v3) until the I-beam 2514 reaches an end of stroke 6122.

As described above, the control circuit 2510 may drive the I-beam 2514 with a constant velocity by monitoring the position of the I-beam 2514 indicated by the position sensor 2534 and modulating the motor set point 2522 and/or motor drive signal 2524 to maintain a constant velocity.

The control circuit 2510 may select the velocity (v1), velocity (v2), and/or velocity (v3) based on the movement of the I-beam 2514 during the diagnostic first portion (1a) of zone 1. In some examples, the control circuit 2510 may select the velocity (v1), velocity (v2), and/or velocity (v3) based on the determined I-beam velocity and/or the current (I) drawn by the motor 2504 in the open-loop portion in the diagnostic first portion (1a) of zone 1. In one example, a look-up table can be employed to determine the velocity (v1), velocity (v2), and/or velocity (v3) based on measurements representing the movement of the I-beam 2514 during the diagnostic first portion (1a) of zone 1.

In one example, the control circuit 2510 may select the constant, or substantially constant, velocity of a zone of the firing stroke based on movement of the I-beam 2514 in one or more previous zones of the firing stroke. For example, the control circuit 2510 may select the velocity of second or intermediate zone based on the movement of the I-beam 2514 in a first zone. Also, the control circuit 2510 may select the velocity of a third zone based on the movement of the I-beam 2514 in a first zone and/or a second zone.

As indicated in the example of FIG. 60, the control circuit 2510 can be configured to maintain a linear, or substantially linear, transition from the velocity (v1) to the higher velocity (v2) in the initial portion of zone 2. The control circuit 2510 may increase the velocity of the I-beam 2514 at a constant rate to yield the linear, or substantially linear, transition from the velocity (v1) to the higher velocity (v2). Alternatively, the control circuit 2510 can be configured to maintain a non-linear transition from the velocity (v1) to the higher velocity (v2) in the initial portion of zone 2.

In addition, the control circuit 2510 can be configured to maintain a linear, or substantially linear, transition from the velocity (v2) to the higher velocity (v3) in the initial portion of zone 3. The control circuit 2510 may increase the velocity of the I-beam 2514 at a constant rate to yield the linear, or substantially linear, transition from the velocity (v2) to the higher velocity (v3). Alternatively, the control circuit 2510 can be configured to maintain a non-linear transition from the velocity (v2) to the higher velocity (v3) in the initial portion of zone 3.

As illustrated in diagram 6230 of FIG. 62, the force to fire (FTF) gradually decreases as the I-beam 2514 is advanced during the firing stroke. As such, the force to fire (FTF) applied to the I-beam 2514 is generally higher at the beginning of the firing stroke than the middle of the firing stroke, and generally higher at the middle of the firing stroke than the end of the firing stroke. Running the motor 2504 at a reduced or low duty cycle in portions of the firing stroke where the I-beam 2514 experiences higher loads improves the performance of the motor 2504 and the energy source 2512. As described above, the total current (I) drawn by the motor 2504 during the firing stroke is reduced, which prolongs the life of the energy source 2512 (FIG. 14). Second, running the motor 2504 at a reduced duty cycle in portions of the firing stroke with the higher loads protects the motor 2504 from stalling.

In some examples, a firing control program may determine a target value for the duty cycle of the motor 2504 based on the position of the I-beam 2514 along the firing stroke. FIG. 62 illustrates a diagram 6200 plotting the duty cycle of the motor 2504 versus distance traveled along a firing stroke for three example firing strokes 6206, 6208, 6210, which can be implemented by the firing control programs selected at 6038. In the diagram 6200, a horizontal axis 6202 represents the firing stroke displacement in millimeters. The vertical axis 6204 indicates the duty cycle of the motor 2504 expressed as a percentage. As illustrated, in FIG. 62, the examples 6206, 6208, 6210 initially have the same duty cycle in a diagnostic first portion (1a) of zone 1 of the firing stroke distance. FIG. 62 illustrates a diagram 6230 which includes examples 6206', 6208', and 6210' corresponding to the examples 6206, 6208, and 6210 of the diagram 6200, respectively. In the diagram 6200, a horizontal axis 6234 represents the time in seconds. The vertical axis 6232 indicates the force to fire (FTF) applied as the I-beam 2514 is advanced through the firing stroke.

In the example 6206 of FIG. 62, a firing control program is configured to run the motor 2504 at a predetermined constant, or substantially constant, duty cycle. The constant duty cycle may be selected based on the movement of the I-beam during the diagnostic first portion (1a) of zone 1. The example 6206' represents the force to fire (FTF) associated running the motor 2504 during the firing stroke at a predetermined constant, or substantially constant, duty cycle.

To reduce the load or force to fire (FTF), as illustrated in the force to fire (FTF) profiles of examples 6208' and 6210', alternative firing control programs are selected at 6038 corresponding to the examples 6208 and 6210 of the diagram 6100. As depicted in the diagram 6230, the examples 6208' and 6210' have lower force to fire (FTF) profiles than the example 6206' and lower maximum force thresholds ($F_1$) and ($F_2$) than the maximum force threshold ($F_3$) of the example 6206'.

The example 6210' represents the force to fire (FTF) profile associated with running the motor 2504 in a closed-loop. During the closed loop portion of the stroke, the control circuit 2510 may modulate the duty cycle of the motor 2504 based on translation data describing a position of the I-beam 2514. During closed loop, the control circuit 2510 is configured to gradually increase the duty cycle of the motor 2504 as the I-beam 2514 is advanced along the firing stroke.

The control circuit 2510 may monitor the position of the I-beam 2514 indicated by the position sensor 2534. The data from the position sensor 2534 can be employed by the control circuit 2510 to set the duty cycle of the motor 2504. In some examples, the duty cycle of the motor 2504 is changed by the control circuit 2510 in intervals of 1 millimeter. In one example, the control circuit 2510 is configured to maintain a substantially linear increase in the duty cycle of the motor 2504 as the I-beam 2514 is advanced through the firing stroke.

In some examples, the absolute positioning system 1100 (FIGS. 10-12) can be employed to sense the position of the I-beam 2514, and the duty cycle of the motor 2504 can be set based on the position of the I-beam 2514 as assessed by the revolution(s) of the sensor element 1126.

In some examples, the control circuit 2510 is configured to increase the duty cycle of the motor 2504 at a substantially constant rate as the I-beam 2514 is advanced through the firing stroke. The rate of increase of the duty cycle of the motor 2504 may be selected based on the movement of the I-beam 2514 during a diagnostic time (t1) in the diagnostic first portion (1a) of zone 1. In one example, a look-up table can be employed to determine the rate of increase of the velocity of the I-beam 2514 based on measurements representing the movement of the I-beam 2514 during a diagnostic time ($t_1$) in the diagnostic first portion (1a) of zone 1.

In one example, a look-up table can be employed to determine the duty cycle of the motor 2504 based on measurements representing the movement of the I-beam 2514 during the diagnostic first portion (1a) of zone 1. The control circuit 2510 also can be configured to determine the duty cycle of the motor 2504 at various positions of the I-beam 2514 along the firing stroke based on tissue conditions. As described above, the tissue conditions such as the thickness and/or toughness of the tissue present between the anvil 2516 and the staple cartridge 2518 can influence the movement of the I-beam 2514 because different types of tissue will offer different levels of resistance.

An alternative example 6208' represents the reduced force to fire (FTF) profile associated with running the motor 2504 at a plurality of constant, or substantially constant, duty cycles at a plurality of discrete or continuous portions or zones within the firing stroke. As described above in connection with the diagram 6100, the firing stroke distance is divided into three zones: zone 1, zone 2, and zone 3. The load experienced by the I-beam 2514 in zone 1 is greater than zone 2, and the load experienced by the I-beam 2514 in zone 2 is greater than zone 3. To reduce the force to fire (FTF), the motor 2504 is run at three different duty cycles set at predetermined positions at points 6201, 6203, and 6205 of zone 1, zone 2, and zone 3, respectively, as illustrated in FIG. 62. In some examples, the number of zones and corresponding duty cycles can be more or less than three depending on the staple cartridge size and/or tissue conditions. The positioning of I-beam stroke zones in FIG. 62 is just one example. In some examples, different zones may begin at different positions along the end effector longitudinal axis 2515, for example, based on the positioning of tissue between the anvil 2516 and the staple cartridge 2518.

In zone 1, where the I-beam 2514 experiences the highest load, the motor 2504 is run at a low duty cycle. As indicated in the example 6208 of FIG. 62, the control circuit 2510 is configured to maintain the duty cycle of the motor 2504 at about 45%, for example, for the remainder of zone 1 beginning at the point 6201, which represents a predetermined position in the beginning of a second portion (1b) of zone 1.

In zone 2, where the I-beam 2514 experiences an intermediate load, the motor 2504 is run at an intermediate duty cycle greater than the duty cycle maintained in zone 1. At the onset of zone 2, the control circuit 2510 is configured to increase the duty cycle of the motor 2504 up to a predetermined duty cycle, which is maintained at a constant, or substantially constant, value by the control circuit 2510 for the remainder of zone 2. As indicated in the example 6208 of FIG. 62, the control circuit 2510 is configured to maintain the duty cycle of the motor 2504 at about 75%, for example, for the remainder of zone 2 beginning at the point 6203, which represents a predetermined position.

In zone 3, where the I-beam 2514 experiences the lowest load, the motor 2504 is run at a duty cycle greater than the duty cycle maintained in zone 2. At the onset of zone 3, the control circuit 2510 is configured to increase the duty cycle of the motor 2504 up to a predetermined duty cycle, which is maintained at a constant, or substantially constant, value by the control circuit 2510 for the remainder of zone 3. As indicated in the example 6208 of FIG. 62, the control circuit 2510 is configured to maintain the duty cycle of the motor 2504 at about 100%, for example, for the remainder of zone 3 beginning at the point 6205, which represents a predetermined position.

The control circuit 2510 may select the duty cycles for zones 1, 2, and 3 based on the movement of the I-beam 2514 during the diagnostic first portion (1a) of zone 1. In some examples, the control circuit 2510 may select the duty cycles for zones 1, 2, and 3 based on the determined I-beam velocity and/or the current (I) drawn by the motor 2504 in the open-loop portion in the diagnostic first portion (1a) of zone 1. In one example, a look-up table can be employed to determine the duty cycles for zones 1, 2, and 3 based on measurements representing the movement of the I-beam 2514 during the diagnostic first portion (1a) of zone 1.

Although the firing control program or logic configuration of the example 6208 depicts three steps with constant, or substantially constant, duty cycles at 45%, 75%, and 100%, other duty cycles are contemplated by the present disclosure. In one example, as illustrated in a diagram 6300 of FIG. 63, a firing control program may include running the motor 2504 at a duty cycle of about 33% in a first zone of the firing stroke, a duty cycle of about 66% in a second zone of the firing stroke, and a duty cycle of about 100% at a third zone of the firing stroke. The different duty cycles can be set to begin at different I-beam positions along the firing stroke, for example.

In one example, the control circuit 2510 may select the constant, or substantially constant, duty cycle of the motor 2504 of a zone of the firing stroke based on movement of the duty cycle of the motor 2504 in one or more previous zones of the firing stroke. For example, the control circuit 2510 may select the duty cycle of a second or intermediate zone based on the duty cycle in a first zone. Also, the control circuit 2510 may select the duty cycle of a third zone based on the duty cycle in a first zone and/or a second zone.

The diagram 6300 illustrates a plot of the duty cycle of the motor 2504 versus distance traveled along a firing stroke for an example firing stroke 6310, which can be implemented by a firing control programs selected at 6038. In the diagram 6300, a horizontal axis 6302 represents the firing stroke displacement in millimeters. The vertical axis 6304 indicates the duty cycle of the motor 2504 expressed as a percentage. As illustrated in the FIG. 63, the example 6310 indicates running the motor 2504 at a duty cycle of about 33% in zone 1 of the firing stroke, a duty cycle of about 66% in zone 2 of the firing stroke, and a duty cycle of about 100% at zone 3 of the firing stroke. Other values for the duty cycles at zone 1, zone 2, and/or zone 3 are contemplated by the present disclosure.

In one example, the motor 2504 can be run, in an initial zone of the firing stroke, at a duty cycle selected from a range of about 25% to about 50%. In one example, the motor 2504 can be run, in intermediate zone of the firing stroke, at a duty cycle selected from a range of about 50% to about 80%. In one example, the motor 2504 can be run, final zone of the firing stroke, at a duty cycle selected from a range of about 75% to about 100%.

Figure 63:
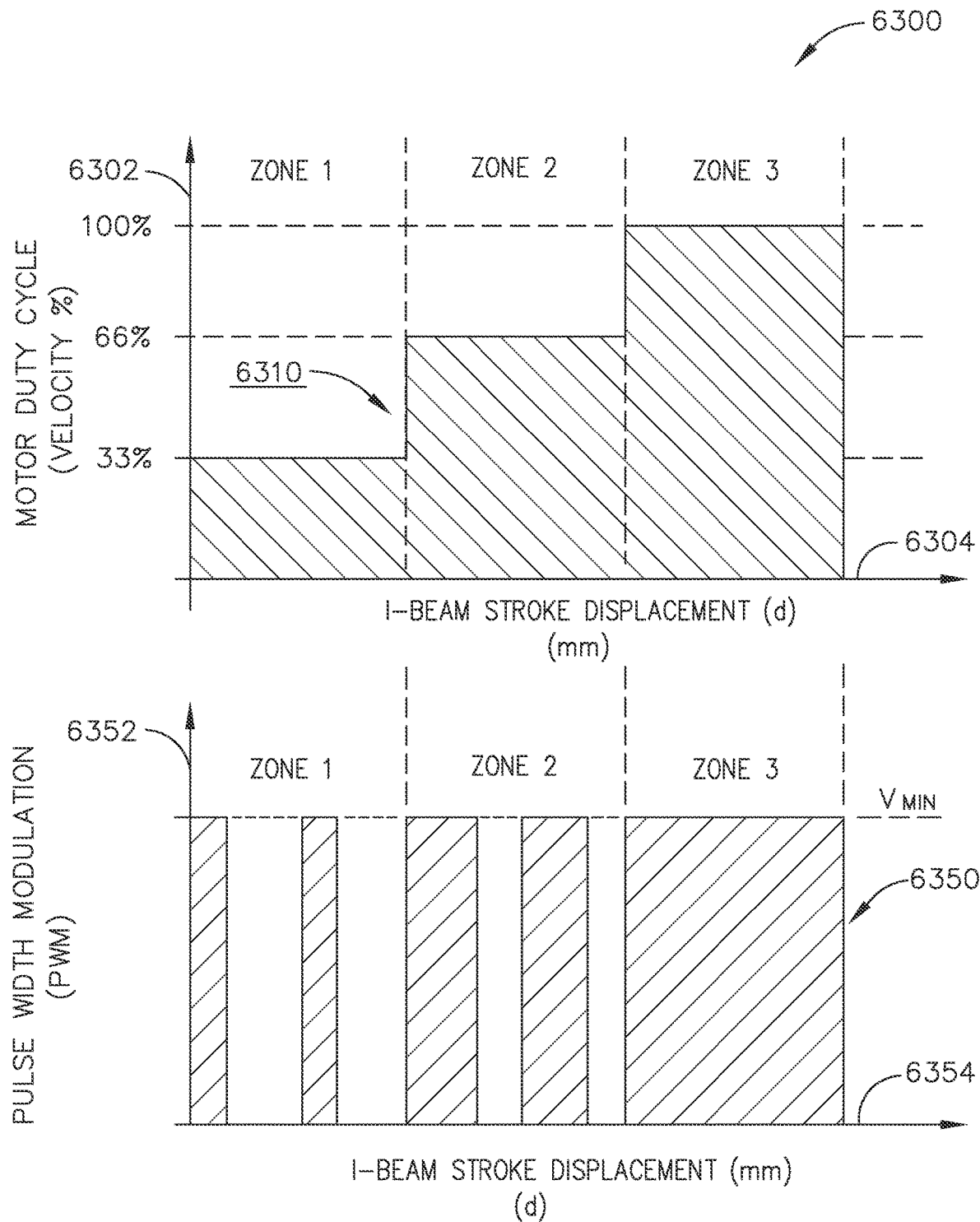
FIG. 63 depicts two diagrams illustrating motor duty cycle (velocity %) of a motor driving the I-beam as a function of I-beam displacement (d), and Pulse-Width Modulation (PWM) as a function of the I-beam displacement (d) according to one aspect of this disclosure.

In some examples, the motor 2504 may be a brushless direct current (DC) electric motor and the motor drive signal 2524 may comprise a pulse-width-modulated (PWM) signal provided to one or more stator windings of the motor 2504. FIG. 63 further illustrates a diagram 6350 depicting an example 6360 indicating pulse-width modulated signals corresponding to the motor duty cycles of zone 1, zone 2, and zone 3 of the example 6310. The diagram 6350 includes two axes. A horizontal axis 6354 represents the firing stroke displacement in millimeters. A vertical axis 6352 indicates pulse-width modulation signals.

A firing control program of the example 6310 may vary the pulse-width of the signal supplied to the motor 2504 depending on the position of the I-beam 2514 along the firing stroke. A first pulse width can be maintained in zone 1. A second pulse width greater than the first pulse width can be maintained in zone 2. A third pulse width greater than the second pulse-width can be maintained in zone 3.

In various examples, the above-described zones 1, 2, and 3 of the firing stroke can be equal, or substantially equal, in distance. In other words, each of the three zones can be about a third of the total distance traveled by the I-beam 2514 during a firing stroke. In other examples, the firing stroke distance can be divided into more or less than three zones that are equal or different in distance.

Referring to FIG. 64, a diagram 6400 plots an example 6408 of the force applied during a closure stroke to close the end effector 2502 relative to tissue grasped between the anvil 2516 and the staple cartridge 2518, the closure force plotted as a function of time. The diagram 6400 comprises two axes. A vertical axis 6402 indicates the force to close (FTC) the end effector 2502 in newtons (N). A horizontal axis 6404 indicates time in seconds. During the closure stroke, the closure tube 260 is translated distally (direction "DD") to move the anvil 2516, for example, relative to the staple cartridge 2518 in response to the actuation of the closure trigger 32 (FIG. 1) in the manner described in the aforementioned reference U.S. Patent Application Publication No. 2014/0263541. In other instances, the closure stroke involves moving a staple cartridge relative to an anvil in response to the actuation of the closure trigger 32. In other instances, the closure stroke involves moving the staple cartridge and the anvil in response to the actuation of the closure trigger 32.

The example 6408 indicates that the force to close (FTC) the end effector 2502 increases during an initial clamping time period ending at a time ($t_0$). The force to close (FTC) reaches a maximum force ($F_3$) at the time ($t_0$). The initial clamping time period can be about one second, for example. A waiting period can be applied prior to initiating a firing stroke. The waiting period allows fluid egress from tissue compressed by the end effector 2502, which reduces the thickness of the compressed tissue yielding a smaller gap between the anvil 2516 and the staple cartridge 2518 and a reduced closure force ($F_1$) at the end of the waiting period. In some examples, a waiting period selected from a range of about 10 seconds to about 20 seconds is typically employed. In the example 6408, a period of time of about 15 seconds is employed. The waiting period is followed by the firing stroke, which typically lasts a period of time selected from a range of about 3 seconds, for example, to about 5 seconds, for example. The force to close (FTC) decreases as the I-beam 2514 is advanced relative to the end effector through the firing stroke.

FIG. 64 also depicts a diagram 6450 that plots three examples 6456, 6458, 6460 of the force applied to advance the I-beam 2514 during the firing stroke of the surgical instrument 2500. The diagram 6450 comprises two axes. A vertical axis 66452 indicates the force, in newtons (N), applied to advance the I-beam 2514 during the firing stroke. The I-beam 2514 is configured to advance the knife 2509 and motivate the drivers 2511 to deploy the staples 2505 during the firing stroke. A horizontal axis 6050 indicates the time in seconds.

The I-beam 2514 is advanced from the stroke begin position 2527 (FIG. 13) at a starting time (t=0) to the stroke end position 2528 (FIG. 13). As the I-beam 2514 is advanced through the firing stroke, the closure assembly surrenders control of the staple cartridge 2518 and the anvil 2516 to the firing assembly, which causes the force to fire (FTF) to increase and the force to close (FTC) to decrease.

Figure 65:
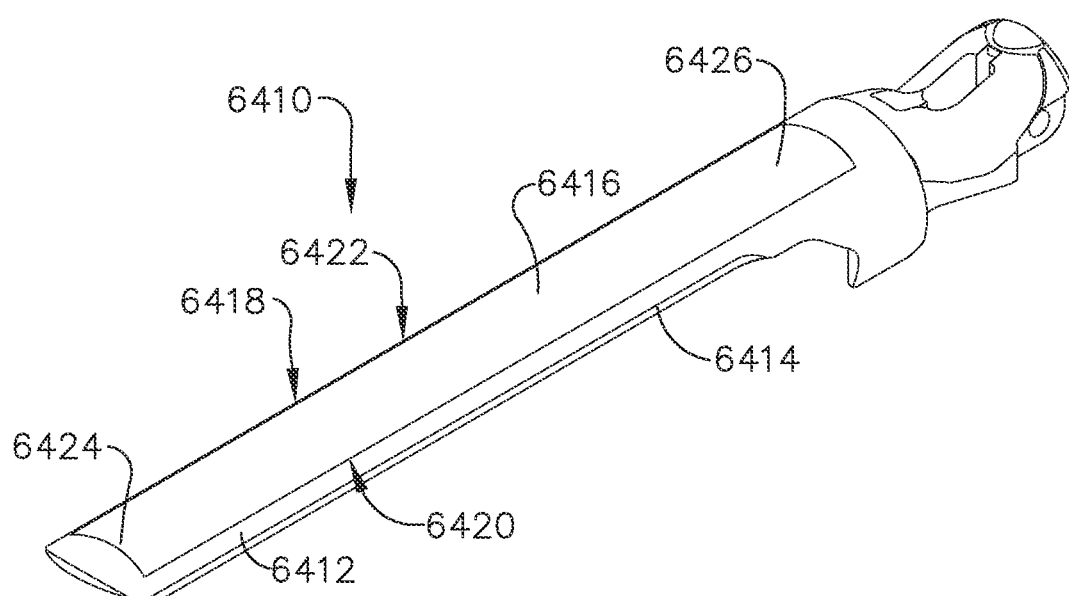
FIG. 65 illustrates an anvil according to one aspect of this disclosure.

In an alternative example 6406, a stiffer anvil 6410 (FIG. 65) is employed. The stiffness of the anvil 6410 of the example 6406 is greater than the stiffness of the anvil of the example 6408. The stiffer anvil 6410 yields greater maximum closure forces ($F_4$) at time (to) and ($F_2$) at the end of the waiting period than the maximum closure forces ($F_3$) and ($F_1$) associated with the anvil of the example 6408. Because of the increased stiffness, the ability of the anvil 6410 of the example 6406 to deflect or bend away from the compressed tissue is less than that of the anvil of the example 6408. Accordingly, the anvil 6410 of the example 6406 experiences a greater load than the anvil of the example 6408 throughout the closure stroke.

The examples 6456 and 6458 of the diagram 6450 are force to fire (FTF) corresponding to the examples 6406 and 6408, respectively, of the diagram 6400. The stiffer anvil 6410 of the examples 6406 and 5458, while encountering a greater force to close (FTC) profile than the anvil of the examples 6408 and 6456, experiences a lesser force to fire (FTF) profile. In the examples 6456 and 6458, the force to fire (FTF) profile is reduced by about 20% because of the increased stiffness of the anvil 6410. Various techniques can be employed in increasing the stiffness of an anvil as described in U.S. patent application Ser. No. 15/385,922, titled SURGICAL INSTRUMENT WITH MULTIPLE FAILURE RESPONSE MODES, and filed Dec. 21, 2019, the entire disclosure of which is hereby incorporated herein by reference.

The stiffer anvil 6410 has an elongate anvil body 6412 that has an upper body portion 6414 that has an anvil cap 6416 attached thereto. In the aspect depicted in FIG. 64, the anvil cap 6416 is roughly rectangular in shape and has an outer cap perimeter 6418. The perimeter 6418 of the anvil cap 6416 is configured to be inserted through the correspondingly-shaped opening formed in an upper body portion and received on axially extending internal ledge portions of the anvil body 6412. The anvil body 6412 and the anvil cap 6416 may be fabricated from suitable metal that is conducive to welding. A first weld 6420 may extend around the entire cap perimeter 6418 of the anvil cap 6416 or it may only be located along the long sides 6422 of the anvil cap 6416 and not the distal end 6424 and/or proximal end 6426 thereof. The first weld 6418 may be continuous or it may be discontinuous or intermittent.

The efficient force to fire (FTF) profile of the example 6458 can be further improved, as indicated in the example 6460, by employing a firing control program, which can be selected at 6038 (FIG. 59), in combination with the stiffer anvil 6410. Any of the firing control programs associated with the previously described examples 6108, 6110, 6208, or 6210 can be employed with the stiffer anvil 6410 to yield a more efficient force to fire profile. In the aspect of the example 6460, the stiffer anvil 6410 is combined with a firing control program that runs the I-beam 2514 at a faster velocity initially followed by a slower velocity when thicker tissue is encountered. The combination of the stiffer anvil 6410 and the firing program can yield a shorter time ($t_1$) to a maximum force to fire (FTF) relative to corresponding times ($t_2$), ($t_3$) of the examples 6456 and 6458. In addition, the combination can yield a shorter time ($t_4$) to the stroke end position 2528 (FIG. 13) of the firing stroke relative to corresponding times ($t_5$) and ($t_6$) of the examples 6456 and 6458. As illustrated in the diagram 6450, the combination yields an additional 20% reduction in the maximum (FTF) compared to the maximum (FTF) of the example 6458. In some examples, the selected firing control program is configured to reduce the velocity of the I-beam 2514 in a first portion of the firing stroke by about one third relative to the velocity employed in connection with the example 6458.

The functions or processes 6030, 6111, 6131 described herein may be executed by any of the processing circuits described herein, such as the control circuit 700 described in with FIGS. 5-6, the circuits 800, 810, 820 described in FIGS. 7-9, the microcontroller 1104 described in with FIGS. 10 and 12, and/or the control circuit 2510 described in FIG. 14.

Various aspects of the subject matter described herein are set out in the following numbered examples:

Example 1. A surgical instrument, comprising: a displacement member; a motor coupled to the displacement member, the motor operable to translate the displacement member; a control circuit coupled to the motor; and a position sensor coupled to the control circuit; wherein the control circuit is configured to: receive a position output of the position sensor indicative of at least one position of the displacement member; and control velocity of the motor to translate the displacement member at a plurality of velocities corresponding to the position output, wherein each of the plurality of velocities is maintained in a predetermined zone.

Example 2. The surgical instrument of Example 1, wherein the control circuit is configured to maintain the translation of the displacement member at a first velocity in a first zone and a second velocity in a second zone, and wherein the second zone is distal to the first zone.

Example 3. The surgical instrument of Example 2, wherein the second velocity is greater than the first velocity.

Example 4. The surgical instrument of Example 3, wherein the control circuit is configured to maintain the translation of the displacement member at a third velocity in a third zone, and wherein the third zone is distal to the second zone.

Example 5. The surgical instrument of Example 4, wherein the third velocity is greater than the second velocity.

Example 6. The surgical instrument of Example 2 through Example 5, further comprising a timer circuit coupled to the control circuit, wherein the timer circuit is configured to measure time elapsed during translation of the displacement member to a predetermined initial position.

Example 7. The surgical instrument of Example 6, wherein the control circuit is configured to determine the first velocity based on the time elapsed during translation of the displacement member to the predetermined initial position.

Example 8. The surgical instrument of Example 1 through Example 7, further comprising an end effector comprising a staple cartridge housing a plurality of staples, and wherein the translation of the displacement member from the proximal position to the distal position causes the staples to be deployed from the staple cartridge.

Example 9. The surgical instrument of Example 1 through Example 8, wherein the control circuit is configured to determine the first velocity based on force or current experienced by the motor.

Example 10. A surgical instrument, comprising: a displacement member; a motor coupled to the displacement member, the motor operable to translate the displacement member; a control circuit coupled to the motor; and a position sensor coupled to the control circuit; wherein the control circuit is configured to: receive a position output of the position sensor indicative of at least one position of the displacement member; and drive the motor to translate the displacement member at a displacement member velocity corresponding to the position of the displacement member.

Example 11. The surgical instrument of Example 10, wherein the control circuit is configured to increase the displacement member velocity at a linear rate from a starting velocity.

Example 12. The surgical instrument of Example 11, further comprising a timer circuit coupled to the control circuit, wherein the timer circuit is configured to measure time elapsed during translation of the displacement member to a predetermined initial position.

Example 13. The surgical instrument of Example 12, wherein the control circuit is configured to determine the starting velocity based on the time elapsed during translation of the displacement member to the predetermined initial position.

Example 14. The surgical instrument of Example 10 through Example 13, further comprising an end effector comprising a staple cartridge housing a plurality of staples, and wherein the translation of the displacement member from the proximal position to the distal position causes the staples to be deployed form the staple cartridge.

Example 15. The surgical instrument of Example 10 through Example 14, wherein the control circuit is configured to determine the first velocity based on force or current experienced by the motor.

Example 16. A surgical instrument, comprising: a displacement member; a motor coupled to the displacement member, the motor operable to translate the displacement member; a control circuit coupled to the motor; and a position sensor coupled to the control circuit; wherein the control circuit is configured to: receive a position output of the position sensor indicative of at least one position of the displacement member along the distance between the proximal position and the distal positon; and drive the motor at a plurality of duty cycles corresponding to the position output, wherein each of the plurality of duty cycles is maintained in a predetermined zone between the proximal position and the distal position.

Example 17. The surgical instrument of Example 16, wherein the control circuit is configured to drive the motor at a first duty cycle in a first zone and a second duty cycle in a second zone, and wherein the second zone is distal to the first zone.

Example 18. The surgical instrument of Example 17, wherein the second duty cycle is greater than the first duty cycle.

Example 19. The surgical instrument of Example 18, wherein the control circuit is configured to drive the motor at a third duty cycle in a third zone, and wherein the third zone is distal to the second zone.

Example 20. The surgical instrument of Example 19, wherein the third duty cycle is greater than the second duty cycle.

Example 21. The surgical instrument of Example 17 through Example 20, further comprising a timer circuit coupled to the control circuit, wherein the timer circuit is configured to measure time elapsed during translation of the displacement member to a predetermined initial position.

Example 22. The surgical instrument of Example 21, wherein the control circuit is configured to determine the first duty cycle based on the time elapsed during translation of the displacement member to the predetermined initial position.

Example 23. The surgical instrument of Example 16 through Example 22, wherein the control circuit is configured to determine the first velocity based on force or current experienced by the motor.

Systems and Methods for Controlling Displacement Member Velocity for a Surgical Instrument During use of a motorized surgical stapling and cutting instrument it is possible that the force to close the closure member and the rate of change of closure force experienced by the end effector may vary and the firing velocity may not be suitable. Therefore, it may be desirable to control the firing velocity of the cutting member or the firing member based on the closure force experienced by the end effector. It also may be desirable to measure the load experienced by the closure member and control the velocity or rate of the cutting member or the firing member based on decreasing load on the closure member.

Figure 66:
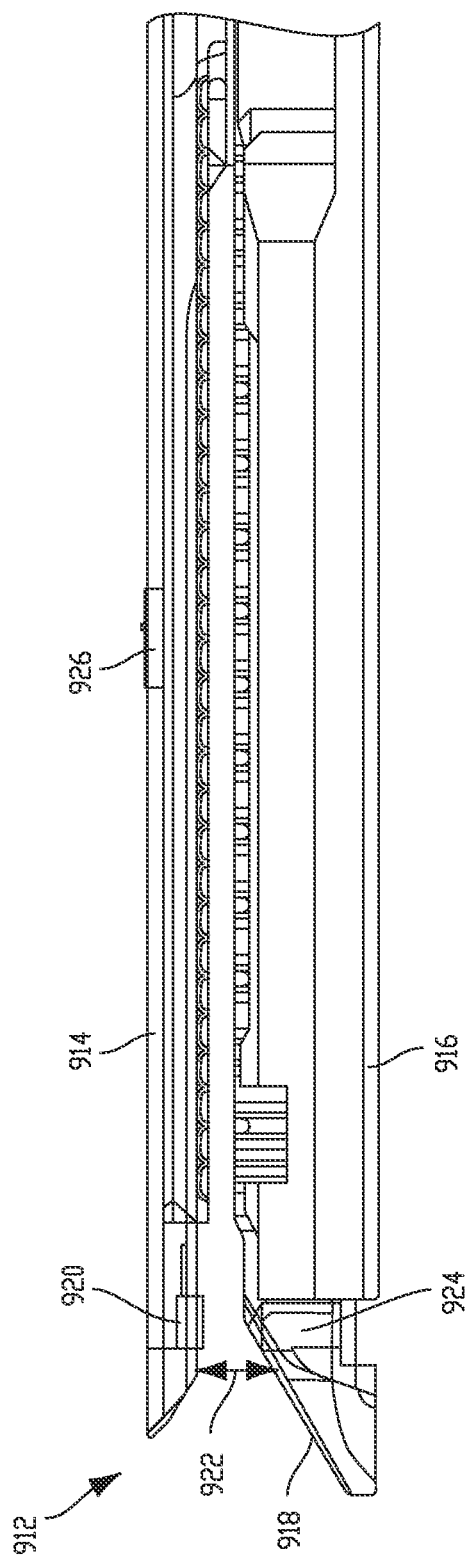
FIG. 66 illustrates a cross-sectional view of an end effector of a surgical instrument according to one aspect of this disclosure.

FIG. 66 illustrates a cross-sectional view of an end effector 912 of a surgical instrument according to one aspect of this disclosure. The end effector 912 is one aspect of the end effector 300 (FIGS. 1 and 4) that may be adapted to operate with surgical instrument 10 (FIG. 1) to measure the various derived parameters such as gap distance versus time, tissue compression versus time, and anvil strain versus time. Accordingly, the end effector 912 may include one or more sensors configured to measure one or more parameters or characteristics associated with the end effector 912 and/or a tissue section captured by the end effector 912. The end effector 912 may comprise a first sensor 920 and a second sensor 926. In various examples, the first sensor 920 and/or the second sensor 926 may comprise, for example, a magnetic sensor such as, for example, a magnetic field sensor, a strain gauge, a pressure sensor, a force sensor, an inductive sensor such as, for example, an eddy current sensor, a resistive sensor, a capacitive sensor, an optical sensor, and/or any other suitable sensor for measuring one or more parameters of the end effector 912. Although the illustrated end effector 912 comprises two sensors, additional or fewer sensors can be employed.

The first sensor 920 and/or the second sensor 926 may comprise, for example, a magnetic field sensor embedded in an anvil 914 and configured to detect a magnetic field generated by a magnet 924 embedded in a jaw member 916 and/or the staple cartridge 918. The anvil 914 is pivotally rotatable between open and closed positions. The strength of the detected magnetic field may correspond to, for example, the thickness and/or fullness of a bite of tissue located between the anvil 914 and the jaw member 916. In certain instances, the first sensor 920 and/or the second sensor 926 may comprise a strain gauge, such as, for example, a micro-strain gauge, configured to measure the magnitude of the strain in the anvil 914 during a clamped condition. The strain gauge provides an electrical signal whose amplitude varies with the magnitude of the strain.

In some aspects, one or more sensors of the end effector 912 such as, for example, the first sensor 920 and/or the second sensor 926 may comprise a pressure sensor configured to detect a pressure generated by the presence of compressed tissue between the anvil 914 and the jaw member 916. In some examples, one or more sensors of the end effector 912 such as, for example, the first sensor 920 and/or the second sensor 926 are configured to detect the impedance of a tissue section located between the anvil 914 and the jaw member 916. The detected impedance may be indicative of the thickness and/or fullness of tissue located between the anvil 914 and the jaw member 916.

The sensors of the end effector 912 such as, for example, the first sensor 920 may be configured to measure the gap 922 between the anvil 914 and the jaw member 916. In certain instances, the gap 922 can be representative of the thickness and/or compressibility of a tissue section clamped between the anvil 914 and the jaw member 916. The gap 922 can be representative of the force applied to the anvil 914 to compress the tissue. In one aspect, the gap 922 between the anvil 914 and the jaw member 916 can be measured by positioning a magnetic field sensor on the anvil 914 and positioning a magnet on the jaw member 916 such that the gap 922 is proportional to the signal detected by the magnetic field sensor and the signal is proportional to the distance between the magnet and the magnetic field sensor. It will be appreciated that the location of the magnetic field sensor and the magnet may be swapped such that the magnetic field sensor is positioned on the jaw member 916 and the magnet is placed on the anvil 914.

The sensors of the end effector 912 such as, for example, the first sensor 920 may be configured to measure one or more forces exerted on the anvil 914 by the closure drive system 30. For example, the first sensor 920 can be at an interaction point between the closure tube 260 (FIG. 3) and the anvil 914 to detect the closure forces applied by the closure tube 260 to the anvil 914. The forces exerted on the anvil 914 can be representative of the tissue compression experienced by the tissue section captured between the anvil 914 and the jaw member 916. In certain aspects, the first sensor 920 and/or other sensors can be positioned at various interaction points along the closure drive system 30 (FIG. 2) to detect the closure forces applied to the anvil 914 by the closure drive system 30. The first sensor 920 and/or the second sensor 926 may be sampled in real time during a clamping operation by a processor as described in FIGS. 5-10, for example, and more particularly, the system 970. The processor receives real-time sample measurements to provide analyze time based information and assess, in real time, closure forces applied to the anvil 914.

Figure 67:
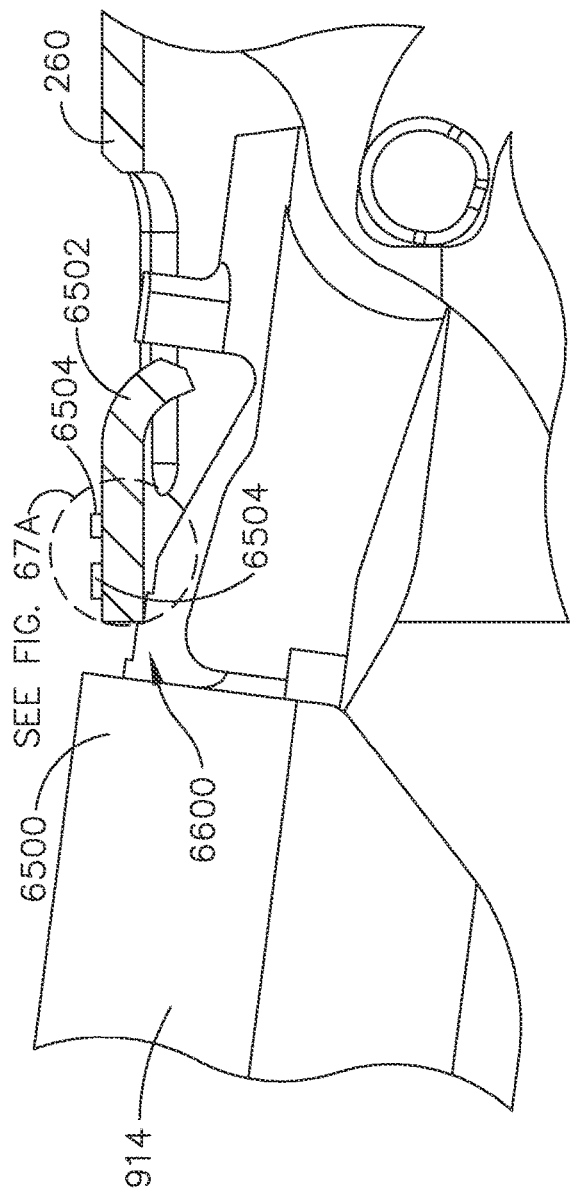
FIG. 67 is a sectional view of an anvil and closure tube sensor arrangement, wherein the anvil is in an open position according to one aspect of this disclosure.
Figure 68:
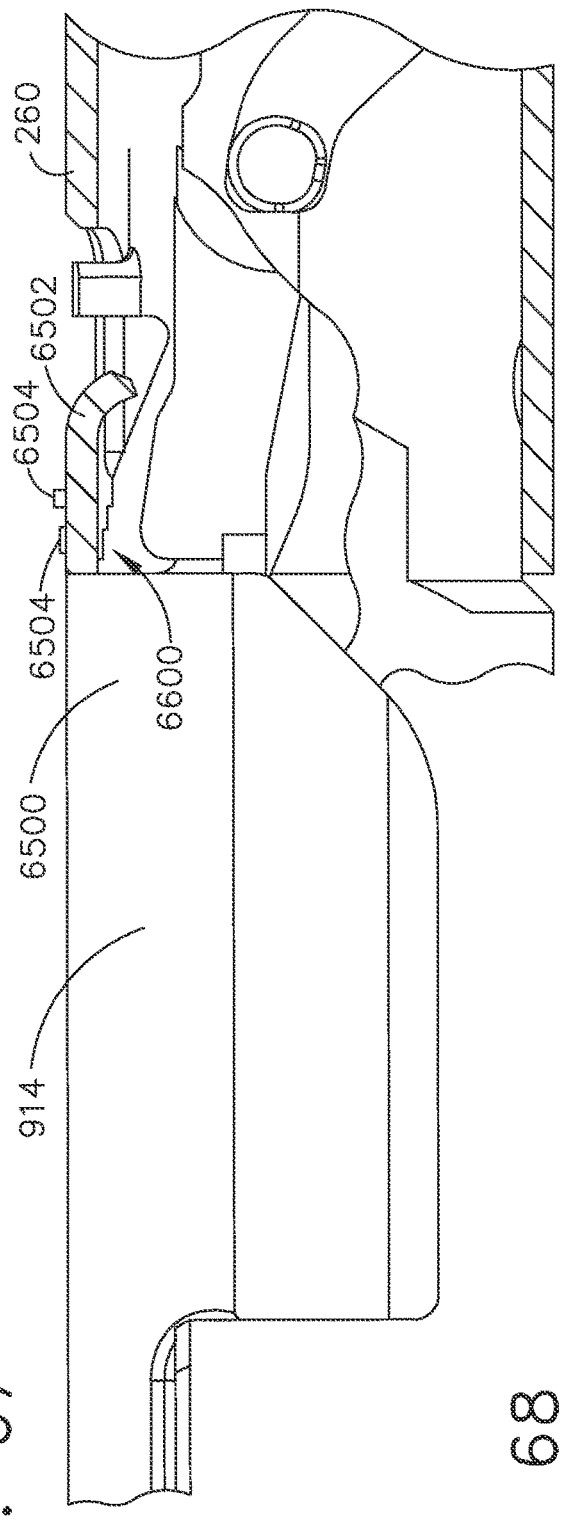
FIG. 68 is a sectional view of an anvil and closure tube sensor arrangement, wherein the anvil is in a closed position according to one aspect of this disclosure.
Figure 67A:
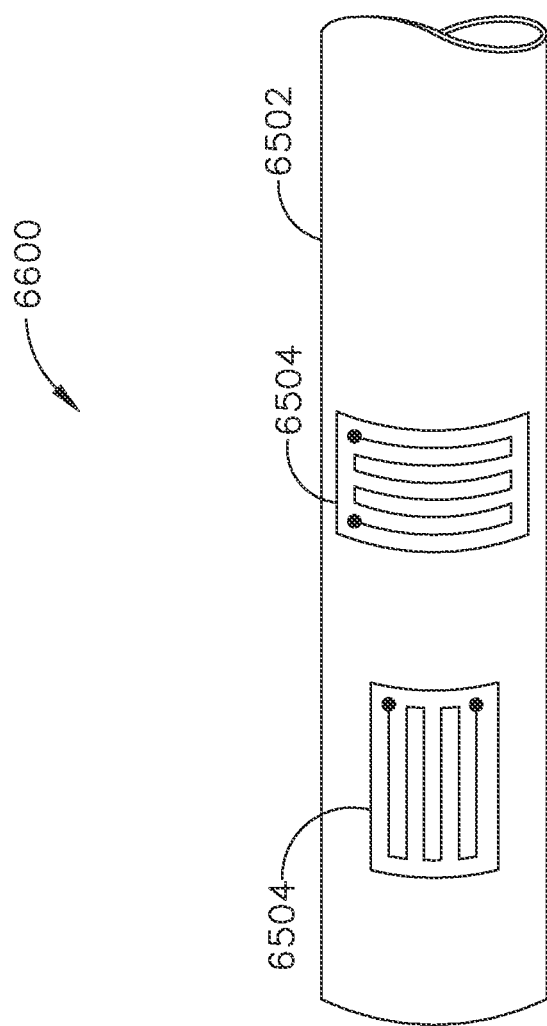
FIG. 67A is a detail view of a distal end of a closure tube including a sensor arrangement according to one aspect of this disclosure.

FIGS. 67-70 are sectional views of an anvil and closure tube sensor arrangement with the anvil 914 in opened and closed positions according to one aspect of this disclosure. As discussed above in respect to FIG. 66, the surgical instrument can include a sensor 6600 or a sensor assembly that is configured to measure a force exerted on the anvil 914 by the closure system. In one aspect, the closure system comprises a closure tube 260. In one such example, the sensor 6600 can be positioned at an interaction point between the proximal end 6500 of the anvil 914 and the distal end 6502 of the closure tube 260. When the closure tube 260 is translated distally to close the anvil 914, the distal end 6502 of the closure tube 260 contacts the proximal end 6500 of the anvil 914, as depicted in FIGS. 68 and 70. The sensor 6600 positioned at this interaction point can therefore measure the absolute or relative degree of force exerted by and between the closure tube 260 and the anvil 914. The sensor 6600 may include strain gauges; hydraulic, pneumatic, piezoelectric, and capacitive load cells; piezoelectric crystal force transducers; and any other type of device capable of sensing pressure or force exerted between the anvil 914 and the closure tube 260. The sensor 6600 can be operably coupled to a processor and/or control circuit as described in FIGS. 5-10 and 14, for example, such that the output from the sensor 6600 is sampled or received by the processor and/or control circuit for utilization thereby. The output of the sensor 6600 can be provided as a digital signal.

The sensor 6600 may be positioned at the distal end 6502 of the closure tube 260 as depicted in FIGS. 67-68. The sensor 6600 may comprise one or more strain gauges 6504. The strain gauges 6504 can be configured to sense an axial or longitudinal strain experienced by the closure tube 260 as it contacts the anvil 914. The strain gauges 6504 may be arranged in a Wheatstone bridge. In another aspect, the sensor 920 may be positioned at the proximal end 6500 of the anvil 914, as depicted in FIGS. 69-70. In this aspect, the sensor 6600 can, for example, comprise a movable member 6512 that is operably coupled to a load cell 6514 that is configured to sense a degree of force from contact with the distal end 6502 of the closure tube 260. The aforementioned examples can additionally be applied interchangeably to either of the anvil proximal end 6500 and the closure tube distal end 6502. In still other aspects, the sensor 6600 can comprise one or more force sensing devices disposed on both the anvil proximal end 6500 and the closure tube distal end 6502.

Figure 71:
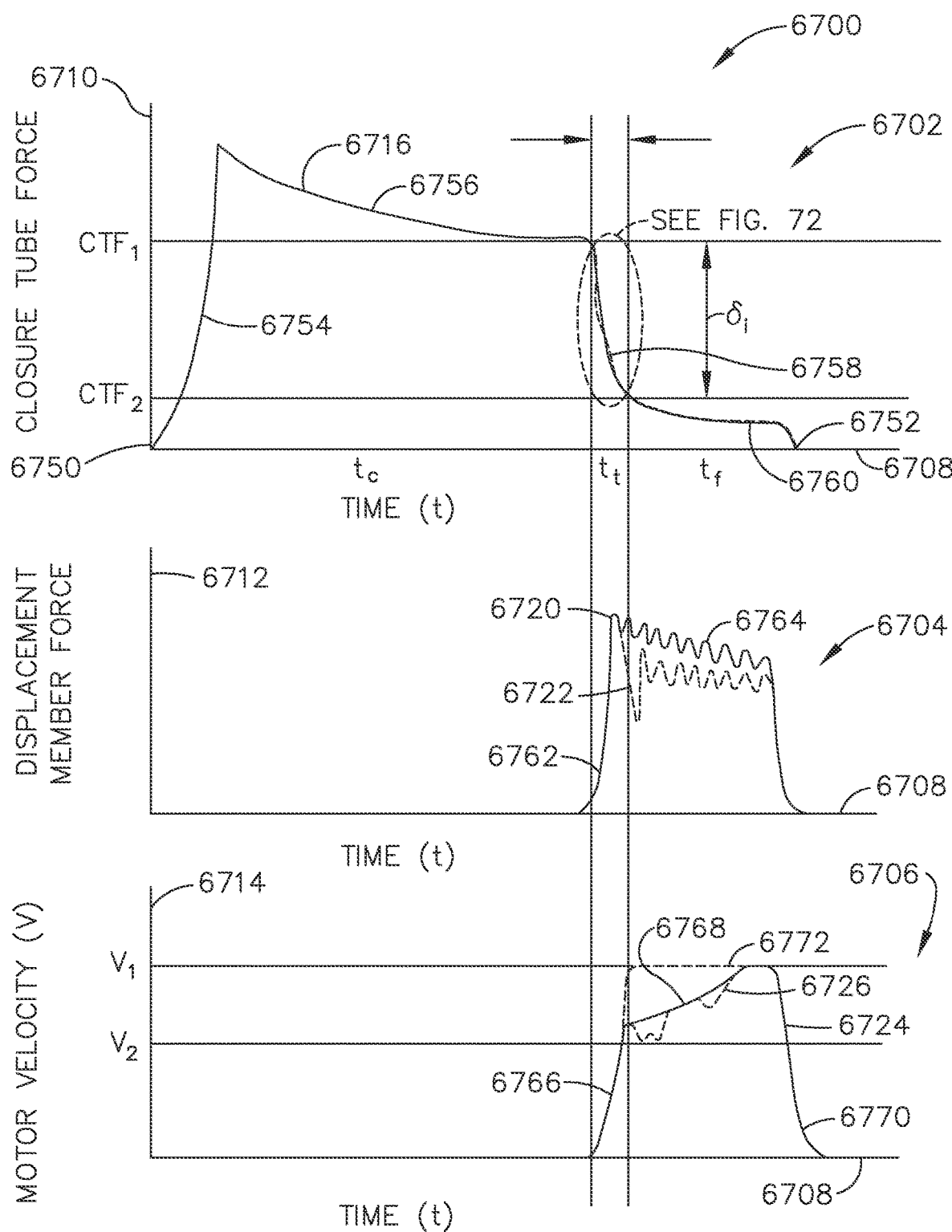
FIG. 71 is a diagram plotting expected versus actual closure tube force, displacement member force, and motor velocity over the course of a clamping and firing operation of the surgical instrument according to one aspect of this disclosure.

FIG. 71 is a diagram 6700 plotting expected versus actual closure tube force, displacement member force, and motor velocity over the course of a clamping and firing operation of the surgical instrument. In the following description of the diagram 6700, reference should also be made to FIGS. 67-70. The diagram 6700 includes a first graph 6702 plotting closure tube force 6710 relative to time 6708, a second graph 6704 plotting displacement member force 6712 relative to time 6708, and a third graph 6706 plotting motor velocity 6714 relative to time 6708. The x-axis plotting time 6708 for each of the first graph 6702, the second graph 6704, an the third graph 6706 are normalized and aligned such that they correspond to a single clamping and firing operation executed by the surgical instrument. Each clamping and firing operation executed by the surgical instrument is delineated into three time periods between the start time 6750 and the end time 6752: the closure time period $t_c$, the transition time period $t_t$, and the firing time period $t_f$.

In the first graph 6702, the expected closure tube force 6716 is plotted across each of the closure time period $t_c$, the transition time period $t_t$, and the firing time period $t_f$. The expected closure tube force 6716 is the expected force that is exerted or experienced by the closure tube 260 when the closure tube 260 is holding the end effector clamped shut. The expected closure tube force 6716 can be measured, for example, by a sensor 6600 configured to detect a force at an interaction point between the closure tube 260 and the anvil 914, as described above. In the second graph 6704, the expected displacement member force 6720 is likewise plotted across these successive time periods. The expected displacement member force 6720 is the expected force that the displacement member 1111 (FIG. 10) is exerted or experienced by the displacement member 1111 as it is translated distally through the end effector to cut and/or staple clamped tissue.

In various aspects, the expected closure tube force 6716, the expected displacement member force 6720, and the expected motor velocity 6724 have been modeled or determined experimentally for a given set of conditions, such as the tissue thickness, the type of operation being performed (cutting, stapling, or a combination thereof), and the type of cartridge. The particular expected closure tube force 6716, expected displacement member force 6720, and expected motor velocity 6724 depicted in FIGS. 71-74 are merely illustrative, however. The expected closure tube force 6716, the expected displacement member force 6720, and the expected motor velocity 6724 can be stored in the memory of the surgical instrument of the surgical instrument and accessed during the operation thereof. The expected closure tube force 6716, the expected displacement member force 6720, and the expected motor velocity 6720 can be stored as algorithms executed by the processor performing run-time calculations, a series of discrete values in a look-up table, a linear or nonlinear best curve fit formula based on the characterization data, or any other such format.

The closure time period $t_c$ begins at the start time 6750 when the operator initiates the use of the surgical instrument by closing the anvil 914, jaw member 916, and/or staple cartridge 918 (FIG. 66) to clamp a tissue at the end effector. The end effector is closed by a closure system that receives an input from the operator and exerts a closure force on the end effector. In one aspect, the closure system comprises a closure tube 260 configured to exert a closure force on the end effector as the closure tube 260 is translated distally. The expected closure tube force 6716 has an initial ramp up period 6754 as the closure tube 260 bears against the corresponding portion of the end effector, causing the end effector to close and clamp or engage the tissue. After the initial ramp up phase 6754, the expected closure tube force 6716 then has a decline phase 6756 as the clamped tissue relaxes. When the clamped tissue relaxes, the closure tube 260 is required to exert less force to keep the tissue clamped by the end effector. The relaxation response from the clamped tissue can be due to, for example, fluid egress from the clamped area and/or a mechanical response from the clamped tissue. The decline phase 6756 of the expected closure tube force 6716 asymptotically approaches a steady state value $CTF_1$ over the closure time period $t_c$ until the displacement member 1111 begins advancing.

Once the displacement member 1111 begins advancing, i.e., is fired, there is a transition time period $t_t$ in the expected closure tube force 6716 as the end effector transitions from being held clamped shut solely by the closure tube 260 to being held clamped shut by a combination of the closure tube 260 and the I-beam 178 (FIG. 4). As described in more detail above, as the displacement member 1111 is advanced distally, portions of the I-beam 178 engage the staple cartridge 304 and/or anvil 306, causing the I-beam 178 to hold the end effector shut during the stapling and/or cutting operation. The I-beam 178 holding the end effector shut as it translates therethrough causes the expected closure tube force 6716 to decline 6758 from $CTF_1$ to $CTF_2$ because less force is required to be exerted by the closure tube 260 to maintain the end effector in the clamped position. Conversely, the expected displacement member force 6720 increases 6762 through the transition time period $t_r$. The increase 6762 in the expected displacement member force 6720 is caused by the increased load experienced by the displacement member 1111 as it exerts a force to maintain the end effector in the clamped position and experiences a load or resistance from the tissue being cut and/or stapled by the I-beam 178. As described in further detail below, the closure tube force and the displacement member force are thus inversely related to each other. The firing of the displacement member 1111 is initiated by a corresponding increase 6766 in the expected motor velocity 6724.

Once the transition time period $t_r$ has ended, the expected closure tube force 6716 gradually declines 6760 during the firing time period $t_f$ when the I-beam 178 advances through the end effector to staple and/or cut the clamped tissue. Conversely, the expected linear displacement force 6720 has a generally sinusoidally shaped decline phase 6764 through the firing time period $t_f$. In one aspect, each peak during the sinusoidal decline phase 6764 corresponds with, for example, the firing of a staple into the clamped tissue by the I-beam 178. With each staple, the force experienced or exerted by the displacement member 1111 decreases for a time period, prior to ramping up again prior to the firing of a subsequent staple. Furthermore, the overall expected displacement member force 6720 gradually declines over the sinusoidal decline phase 6764 because the amount of force required to advance the I-beam 178 through tissue decreases as the tissue is clamped and/or stapled. The stapling and/or cutting operation of the clamped tissue is completed at the end time 6752.

The force experienced by the closure tube 260 and the force experienced by the displacement member 1111 are inversely related to each other during the transition time period $t_r$, $t$ because the more force the displacement member 1111 experiences, the more slowly it advances through the clamped tissue. The more slowly the displacement member 1111 advances, the less the I-beam 178 takes over from the closure tube 260 in holding the end effector shut. The less the I-beam 178 takes over from the closure tube 260, the more force is experienced by the closure tube 260. Therefore, monitoring the actual closure tube force 6718 can effectively be utilized as a proxy to indirectly monitor the function of the displacement member 1111, which is characterized by the force it experiences at it advances, i.e., the actual displacement member force 6722. In one aspect, if the actual closure tube force 6718 is higher than the expected closure tube force 6716, then that means that the actual displacement member force 6722 is lower than the expected displacement member force 6720. When the actual displacement member force 6722 is low, then the load experienced by the displacement member 1111, i.e., the tissue resistance experienced by the I-beam 178, may correspondingly be lower than expected. When the I-beam 178 is encountering low resistance from the tissue, then the motor velocity can be increased in order to advance the I-beam 178 faster. It can be desirable to increase the velocity of the I-beam 178 when low tissue resistances are encountered in order to decrease the amount of time taken by the cutting and/or stapling operation by the surgical instrument. Accordingly, if the actual closure tube force 6718 is lower than the expected closure tube force 6716, then that means that the actual displacement member force 6722 is higher than the expected displacement member force 6720. When the actual displacement member force 6722 is high, then the load experienced by the displacement member 1111, i.e., the tissue resistance experienced by the I-beam 178, may correspondingly be higher than expected. When the I-beam 178 is encountering high resistance from the tissue, then the motor velocity can be decreased in order to advance the I-beam 178 at a slower rate. It can be desirable to decrease the velocity of the I-beam 178 when high tissue resistances are encountered in order to avoid overloading the motor and to avoid staple malformations caused by the staples not being sufficiently driven through the tissue.

Figure 72:
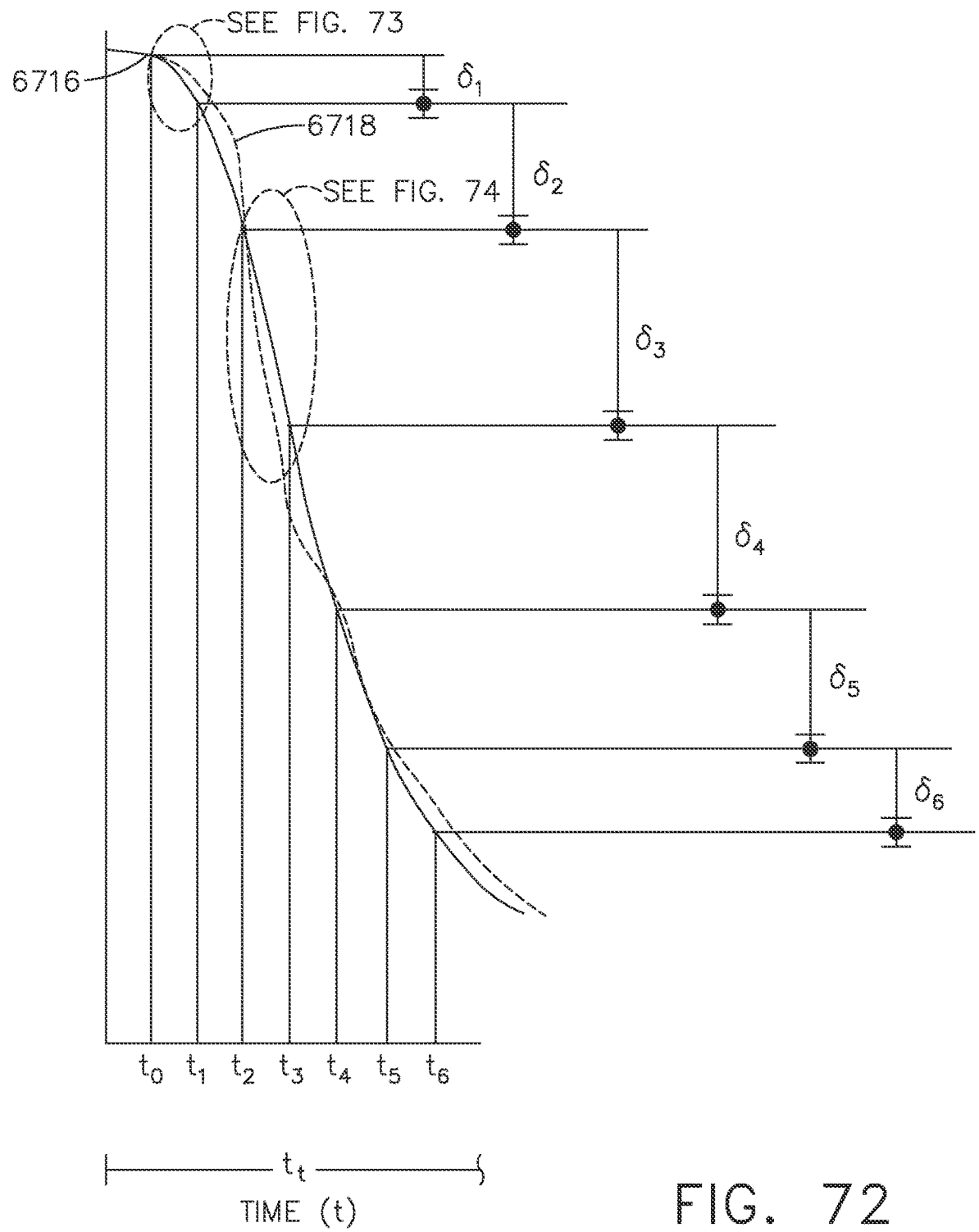
FIG. 72 is a detail view of the transition period of the diagram plotting closure tube force over the course of a clamping and firing operation of the surgical instrument depicted in FIG. 71 according to one aspect of this disclosure.

FIG. 72 is a detail view of the transition period $t_r$ of the first graph 6702 depicted in FIG. 71 according to one aspect of this disclosure. In ideal conditions, the closure tube force behaves in a known manner that is illustrated in one aspect by the expected closure tube force 6716; however, when the surgical instrument is utilized in practice, the actual performance of the surgical instrument will vary due to deviations from expected tissue conditions, environmental factors, and other such variables. As the actual closure tube force 6718 is detectable and the inverse relationship between the closure tube force and the displacement member force is known, the surgical instrument can, in some aspects, be configured to adjust the motor driving the displacement member 1111 to compensate for the variable or unexpected load encountered thereby when deviations in the actual closure tube force 6718 from the expected closure tube force 6716 are detected. As the expected closure tube force 6716 can represent the preferred operational state for the surgical instrument, it can thus be desirable to adjust the actual closure tube force 6718 to match the expected closure tube force 6716 throughout the course of a clamping and firing operation executed by the surgical instrument.

It should be noted that FIGS. 71-74 merely depict examples for the actual closure tube force 6718 and the actual displacement member force 6722 in order to illustrate the principles of various aspects of the surgical instrument. The actual closure tube force 6718 and the actual displacement member force 6722 will vary with each use of the surgical instrument according to varying tissue conditions, varying environmental conditions, the types of operations being performed by the surgical instrument, and so on.

In one aspect, the transition time period $t_r$ is divided into a series of discrete time intervals $t_0, t_1, \ldots t_n$. At each time interval, the control circuit samples the actual closure tube force 6718, calculates or retrieves the expected closure tube force 6716 for the given time interval, and then compares the actual closure tube force 6718 to the expected closure tube force 6716. If the actual closure tube force 6718 is within a threshold of the expected closure tube force 6716, then no action is taken by the surgical instrument. No action is taken by the surgical instrument because, as is discussed above, if the actual closure tube force 6718 is equal or within a tolerance range of the expected closure tube force 6716, then the actual displacement member force 6722 is within an acceptable range of the expected displacement member force 6720. Conversely, if the actual closure tube force 6718 is not within a threshold of the expected closure tube force 6716, then it is known that the actual displacement member force 6722 is not within an acceptable range of the expected displacement member force 6720 and the surgical instrument can adjust the velocity at which the displacement member 1111 is translated in order to compensate. The threshold can include, for example, a percentage range or a set value from the expected closure tube force 6716.

Referring back to FIG. 71, the third graph 6706 depicts various examples of the behavior of the motor velocity driving the I-beam 178 during the firing time period $t_f$ reflecting the relationship between the actual closure tube force 6718 and the actual displacement member force 6722. After the initial incline phase 6766 as the I-beam 178 is fired during the transition time period $t_f$, the motor velocity will correspond to whether the actual closure tube force 6718 is above, within, or below a threshold of the expected closure tube force 6716. If the I-beam 178 is encountering lower than expected resistance, i.e., the displacement member force is less than expected and the closure tube force is greater than expected, then the motor velocity will quickly increase 6772 to a maximum velocity $V_1$ to translate the I-beam 178 at the fastest possible velocity. If the I-beam 178 is encountering expected resistance, i.e., the displacement member and closure tube forces are within acceptable tolerance ranges, then the motor velocity will gradually increase 6768 over the course of the firing stroke of the I-beam 178. If the I-beam is encountering higher than expected resistance, then the motor velocity will dip 6726 one or more times as the higher than expected resistance is encountered by the I-beam 178 in order to avoid overloading the motor. In some aspects, the surgical instrument can be configured to not dip 6726 the motor velocity below a set minimum velocity $V_2$. The motor velocity decreases 6770 to zero as the completion of the firing stroke of the I-beam 178.

Figure 75:
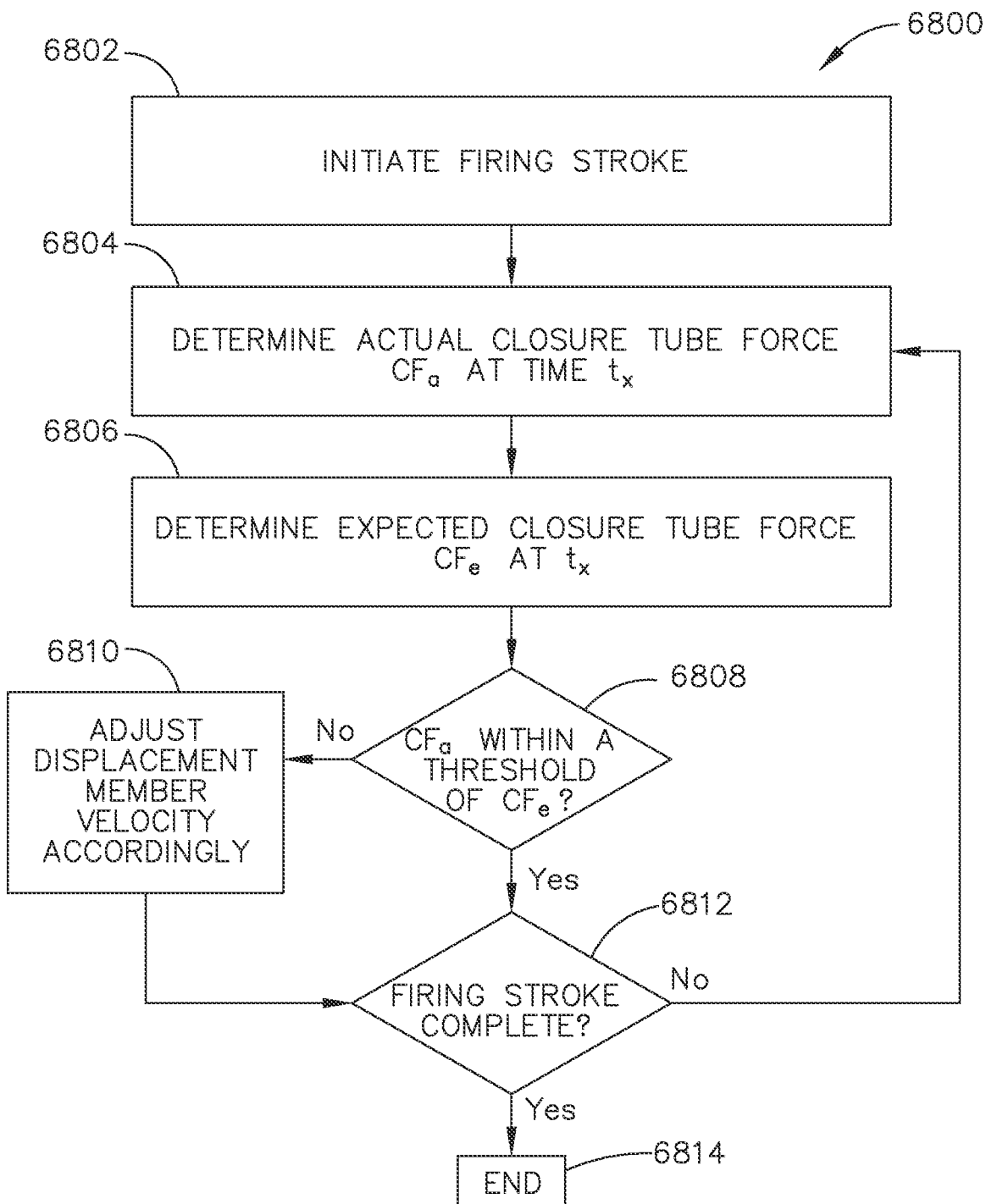
FIG. 75 is a logic flow diagram of a process depicting a control program or a logic configuration for controlling the velocity of the displacement member according to the closure tube force according to one aspect of this disclosure.

FIG. 75 is a logic flow diagram of a process 6800 depicting a control program or a logic configuration for controlling the velocity of the displacement member according to the closure tube force according to one aspect of this disclosure. In the following description of the process 6800, reference also should be made to FIGS. 14 and 67-70. Accordingly, the process 6800 first initiates 6802 a firing stroke of the displacement member 2520, which causes the displacement member 2520 to advance distally into the end effector 2502. Prior to the firing stroke being initiated 6802, tissue has already been clamped by the end effector 2502 due to the action of the closure tube 260.

After the firing stroke has been initiated 6802, in one aspect, the control circuit 2510 then determines 6804 the actual closure force $CF_a$ applied by the closure drive system 30 at a time $t_x$. In some aspects, the actual closure force $CF_a$ can be sensed directly by a sensor configured to detect a force or strain exerted or experienced by the closure tube 260 against the anvil 834 or staple cartridge 2518 at an interaction point. In other aspects, the actual closure tube force $CF_a$ can be determined indirectly by, for example, sensing a force or strain exerted or experienced by a mechanical linkage connecting the closure trigger 32 and the closure tube 260 in maintaining the end effector 2502 in a clamped position.

The process 6800 as executed by the control circuit 2510 next determines 6806 the expected closure tube force $CF_e$ corresponding to the particular time $t_x$. In one aspect, the control circuit 2510 determines 6806 the expected closure tube force $CF_e$ by retrieving the value of the expected closure tube force $CF_e$ corresponding to the time $t_x$ from a look-up table stored, for example, in a memory of the surgical instrument. In another aspect, the control circuit 2510 determines 6806 the expected closure tube force $CF_e$ by calculating the value of the expected closure tube force $CF_e$ according to an algorithm executed by the control circuit 2510.

Figure 73:
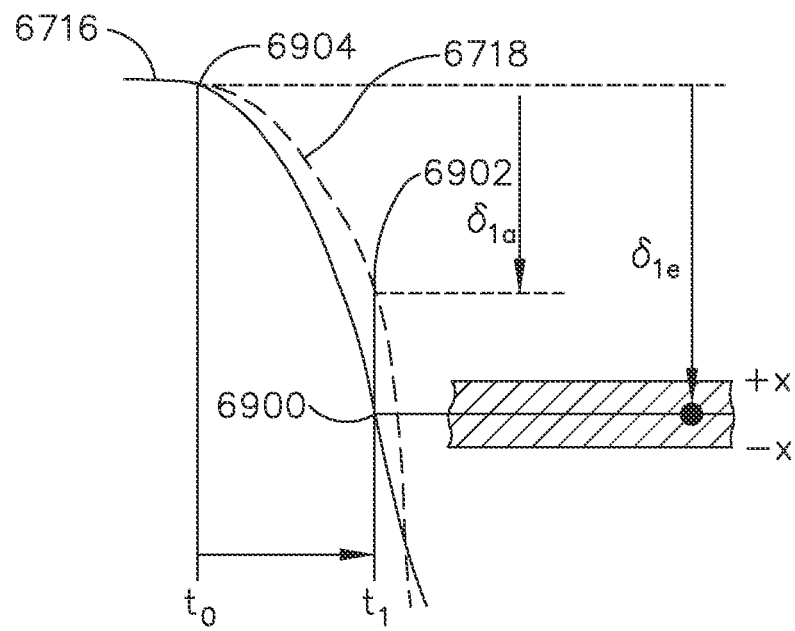
FIG. 73 is a detail is a detail view of a time interval of the transition period of the diagram plotting closure tube force over the course of a clamping and firing operation of the surgical instrument depicted in FIG. 71 according to one aspect of this disclosure.
Figure 74:
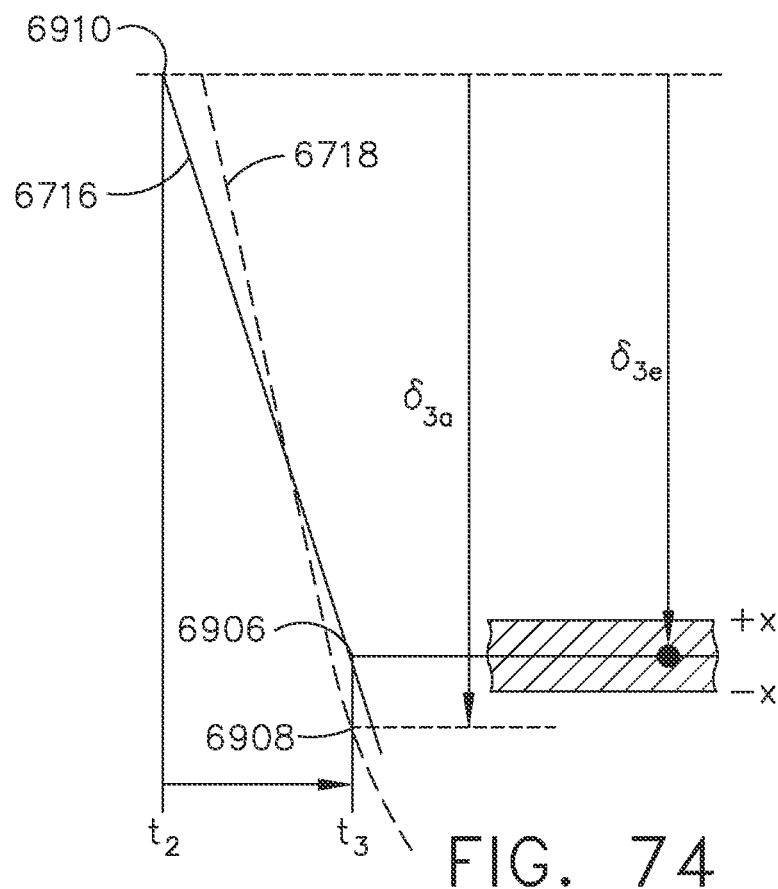
FIG. 74 is a detail is a detail view of a time interval of the transition period of the diagram plotting closure tube force over the course of a clamping and firing operation of the surgical instrument in FIG. 71 according to one aspect of this disclosure.

The process 6800 as executed by the control circuit 2510 next determines 6808 whether the actual closure force $CF_a$ falls within a threshold of the expected closure tube force $CF_e$. In one aspect, the control circuit 2510 determines 6808 whether the actual closure force $CF_a$ falls within a threshold of the expected closure tube force $CF_e$ by directly comparing the two values to determine whether they fall within a threshold of each other. In another aspect, the control circuit takes a derivative of a best fit curve of the expected closure tube force 6716 and the actual closure tube force 6718 over a time interval from a preceding time $t_{x-1}$ to the current time $t_x$ to determine whether the rate of change of the actual closure tube force 6718 is within a threshold of the expected closure tube force 6716. In another aspect as illustrated in FIGS. 73 and 74, the control circuit calculates a first difference $\delta_a$ between the actual closure tube force value the expected closure tube force value of the prior time $t_{x-1}$ and a second difference $\delta_e$ between the expected closure tube force value and the expected closure tube force value of the prior time $t_{x-1}$. The control circuit then compares the differences $\delta_a$, $\delta_e$ at the time $t_x$ to determine whether the first difference $\delta_a$ falls within a threshold $\pm x$ of the second difference $\delta_e$.

For example, FIG. 73 depicts a time interval wherein the actual closure tube force 6718 exceeds the expected closure tube force 6716. As illustrated in FIG. 73, at time $t_1$ the control circuit 2510 determines the actual closure tube force value 6902 and the expected closure tube force value 6900 corresponding to time $t_1$. The control circuit 2510 next calculates a first difference $\delta_{1a}$ between the actual closure tube force value 6902 the expected closure tube force value 6904 of the prior time to and a second difference $\delta_{1e}$ between the expected closure tube force value 6900 and the expected closure tube force value 6904 of the prior time to. The control circuit then compares the differences $\delta_{1a}$, $\delta_{1e}$ at the time $t_1$ to determine whether the first difference $\delta_{1a}$ falls within a threshold $\pm x$ of the second difference $\delta_{1e}$. As the first difference $\delta_{1a}$ is greater than the second difference $\delta_{1e}+x$ (i.e., the actual closure tube force value 6902 is above the tolerance threshold from the expected closure tube force value 6900 at time $t_1$), then the actual displacement member force 6722 is less than the expected displacement member force 6720 and the control circuit 2510 of the surgical instrument can compensate by increasing the velocity at which the I-beam 2514 is translated.

As another example, FIG. 74 depicts a time interval wherein the actual closure tube force 6718 is less than the expected closure tube force 6716. As illustrated in FIG. 74, at time $t_3$ the control circuit 2510 determines the actual closure tube force value 6908 and the expected closure tube force value 6906 corresponding to time $t_3$. The control circuit 2510 next calculates a first difference $\delta_{3a}$ between the actual closure tube force value 6908 the expected closure tube force value 6910 of the prior time $t_2$ and a second difference $\delta_{3e}$ between the expected closure tube force value 6906 and the expected closure tube force value 6910 of the prior time $t_2$. The control circuit then compares the differences $\delta_{3a}$, $\delta_{3e}$ at the time $t_3$ to determine whether the first difference $\delta_{3a}$ falls within a threshold $\pm x$ of the second difference $\delta_{3e}$. As the first difference $\delta_{3a}$ is less than the second difference $\delta_{3e}-x$, then the actual displacement member force 6722 is greater than the expected displacement member force 6720 and the control circuit 2510 of the surgical instrument can compensate by decreasing the velocity at which the displacement member 1111 is translated.

If the actual closure tube force $CF_a$ falls outside the tolerance range of the expected closure tube force $CF_e$, then the process 6800 proceeds along the NO branch and the control circuit 2510 adjusts 6810 the velocity of the displacement member, such as, for example, the I-beam 2514.

In the example in which the displacement member is the I-beam 2514, the velocity at which the I-beam 2514 is translated is adjusted according to whether the actual closure tube force $CF_a$ fell above or below the threshold range of the expected closure tube force $CF_e$. If the actual closure tube force $CF_a$ was above the threshold range of the expected closure tube force $CF_e$, as depicted in FIG. 73, then the control circuit 2510 generates a motor set point signal 2522 that is provided to the motor controller 2508 to drive the motor 2504 at a velocity that is greater than the current velocity at which the motor 2504 is set. Conversely, if the actual closure tube force $CF_a$ was below the threshold range of the expected closure tube force $CF_e$, as depicted in FIG. 74, then the control circuit 2510 generates a motor set point signal 2522 that is provided to the motor controller 2508 to drive the motor 2504 at a velocity that is less than the current velocity at which the motor 2504 is set. In one aspect, the adjustment applied to the motor 2504 can be a fixed value. In another aspect, the adjustment applied to the motor 2504 can be proportional to the degree to which the actual closure tube force $CF_a$ is above or below the threshold range of the expected closure tube force $CF_e$. In yet another aspect, the adjustment applied to the motor 2504 can be calculated by the control circuit 2510 according to a linear or nonlinear function.

If the actual closure tube force $CF_a$ is within the tolerance range of the expected closure tube force $CF_e$, then the process 6800 proceeds along the YES branch and the control circuit 2510 next determines 4084 whether the stroke of the I-beam 2514 is completed. Alternatively, after the velocity of the I-beam 2514 is adjusted 6810, the control circuit 2510 likewise next determines 6812 whether the stroke of the I-beam 2514 is completed. If the firing stroke is complete, then the process 6800 proceeds along the YES branch and the process 6800 is completed 6814. If the firing stroke is not complete, then the process 6800 proceeds along the NO branch and continues a loop of determining 6804 the actual closure tube force $CF_a$, determining 6806 the expected closure tube force $CF_e$, determining 6808 whether they are within a threshold of each other, and adjusting 6810 to the velocity of the I-beam 2514 accordingly for each subsequent time interval $t_{x+1}$, $t_{x+2}$, $t_{x+n}$. Stated differently, the process 6800 continues to monitor the closure tube force and adjust the velocity of the I-beam 2514 accordingly until the cutting and/or stapling operation is completed.

The functions or processes 6800 described herein may be executed by any of the processing circuits described herein, such as the control circuit 700 described in with FIGS. 5-6, the circuits 800, 810, 820 described in FIGS. 7-9, the microcontroller 1104 described in with FIGS. 10 and 12, and/or the control circuit 2510 described in FIG. 14.

Various aspects of the subject matter described herein are set out in the following numbered examples:

Example 1. A surgical instrument comprising: a displacement member movable between a first position and a second position to effect a motion at an end effector; a motor coupled to the displacement member, the motor configured to drive the displacement member between the first position and the second position; and a control circuit coupled to the motor, the control circuit configured to: receive a signal indicative of force from a sensor, the signal indicative of the force applied by a closure tube to the end effector; determine a closure force applied by the closure tube to the end effector; determine whether the closure force is within a threshold of an expected closure force; and set a motor velocity to drive the motor at a velocity that corresponds to the closure force relative to the expected force.

Example 2. The surgical instrument of Example 1, further comprising a sensor coupled to the control circuit, the sensor configured to detect a force exerted at an interaction point between the end effector and the closure tube.

Example 3. The surgical instrument of Example 2, wherein the closure force comprises the force exerted at the interaction point between the end effector and the closure tube.

Example 4. The surgical instrument of Example 1 through Example 3, wherein the control circuit is configured to retrieve the expected closure force from a memory.

Example 5. The surgical instrument of Example 1 through Example 4, wherein the control circuit is configured to compare a value of the closure force to a value of the expected closure force and to determine whether the closure force is within a threshold of the expected closure force based on the results of the comparison.

Example 6. The surgical instrument of Example 1 through Example 5, wherein the control circuit is configured to compare a first difference between the closure force and a prior expected closure force and a second difference between the expected closure force and the prior expected closure force and to determine whether the closure force is within a threshold of the expected closure force based on the results of the comparison.

Example 7. The surgical instrument of Example 1 through Example 6, further comprising: an end effector; and a closure tube coupled to the end effector, the closure tube configured to apply a closure force to the end effector.

Example 8. A surgical instrument comprising: a closure system configured to apply a closure force to an end effector to transition the end effector between an open position and a closed position; a displacement member coupled to the closure system, the displacement member movable between a first position and a second position to effect a motion at the end effector; a motor coupled to the displacement member, the motor configured to drive the displacement member between the first position and the second position; and a control circuit coupled to the motor, the control circuit configured to: determine the closure force exerted by the closure system; retrieve an expected closure force; determine whether the closure force is within a tolerance of the expected closure force; and set the motor to drive the displacement member at a velocity, wherein the velocity corresponds to the closure force relative to the expected closure force.

Example 9. The surgical instrument of Example 8, further comprising a sensor coupled to the control circuit, the sensor configured to detect the closure force.

Example 10. The surgical instrument of Example 9, wherein the sensor is disposed at an interaction point between the closure system and the end effector.

Example 11. The surgical instrument of Example 8 through Example 10, wherein the control circuit is configured to retrieve the expected closure force from a memory.

Example 12. The surgical instrument of Example 8 through Example 11, wherein the control circuit is configured to compare a value of the closure force to a value of the expected closure force and to determine whether the closure force is within a threshold of the expected closure force based on the comparing.

Example 13. The surgical instrument of Example 8 through Example 12, wherein the control circuit is configured to compare a first difference between the closure force and a prior expected closure force and a second difference between the expected closure force and the prior expected force and to determine whether the closure force is within a threshold of the expected closure force based on the results of the comparison.

Example 14. The surgical instrument of claim 8 through Example 13, further comprising: an end effector; and a closure tube coupled to the end effector, the closure tube configured to apply a closure force to the end effector.

Example 15. A method of controlling a motor in a surgical instrument, the surgical instrument comprising a closure system configured to apply a closure force to an end effector to transition the end effector between an open position and a closed position, a displacement member coupled to the closure system, the displacement member movable between a first position and a second position to effect a motion at the end effector, a motor coupled to the displacement member, the motor configured to drive the displacement member between the first position and the second position; and a control circuit coupled to the motor, the method comprising: determining the closure force exerted by the closure system; retrieving an expected closure force; determining whether the closure force is within a tolerance of the expected closure force; and setting a motor velocity for driving the motor, wherein the motor velocity corresponds to the closure force relative to the expected closure force.

Example 16. The method of Example 15, further comprising retrieving, by the control circuit, the expected closure force from the memory.

Example 17. The method of Example 15 through Example 16, further comprising sensing, by a sensor coupled to the control circuit, a force exerted by the closure system at an interaction point with the end effector.

Example 18. The method of Example 17, further comprising determining, by the control circuit, the closure force exerted by the closure system.

Example 19. The method of Example 15 through Example 18, further comprising comparing, by the control circuit, a value of the closure force to a value of the expected closure force and determining, by the control circuit, whether the closure force is within a threshold of the expected closure force based on the results of the comparison.

Example 20. The method of Example 15 through Example 19, further comprising comparing, by the control circuit, a first difference between the closure force and a prior expected closure force and a second difference between the expected closure force and the prior expected force and determining, by the control circuit, whether closure force is within a threshold of the expected closure force based on the results of the comparison.

Control of Motor Velocity of a Surgical Stapling and Cutting Instrument Based on Angle of Articulation During use of a motorized surgical stapling and cutting instrument it is possible that the end effector may articulate or further articulate undesirably. Therefore, it may be desirable to provide a holding load to create a dynamic brake to hold when the end effector is not articulating but the end effector jaws are open to synchronize the motor to the articulation member.

With reference to FIGS. 13 and 14, in one aspect, a surgical instrument 2500 may comprise an end effector 2502 comprising a staple cartridge 2518 and anvil 2516 at a distal end and an I-beam 2514 comprising a cutting edge 2509 to sever tissue. The jaw assembly may be articulatable and may pivot about a longitudinal axis of the instrument shaft. The jaw assembly may pivot about a wrist pivot axis from a first position where the jaw assembly is substantially parallel to the staple cartridge 2518 to a second position where the jaw assembly is not substantially parallel to the staple cartridge 2518. In addition, the jaw assembly may comprise first and second jaw members that are pivotable about a second axis or jaw pivot axis. The jaw pivot axis may be substantially perpendicular to the wrist pivot axis. In some aspects, the jaw pivot axis itself may pivot as the jaw assembly pivots about the wrist pivot axis. The first and second jaw members may be pivotable relative to one another about the jaw pivot axis such that the first and second jaw members may "open" and "close." Additionally, in some aspects, the first and second jaw members are also pivotable about the jaw pivot axis together such that the direction of the first and second jaw members may change.

In one aspect, a surgical instrument 2500 may include an end effector 2502, an articulation joint and an articulation member. The articulation member may be translatable relative to the end effector 2502 a distance from a proximal position to a distal position, wherein the translation of the articulation member causes the articulation joint to articulate. The surgical instrument 2500 may include a motor 2504 operable to translate the articulation member along the distance from the proximal position to the distal position. The motor 2504 may include an engaged condition, a disengaged condition, and a hold condition. The surgical instrument 2500 may further include a control circuit 2510 coupled to the motor 2504 and a position sensor 2534 coupled to the control circuit 2510. The position sensor 2534 may be configured to detect a position of the articulation member along at least a portion of the distance. The control circuit 2510 may be configured to receive position input from the position sensor 2534 indicative of an articulation position of the articulation member. The control circuit 2510 may identify a predetermined threshold corresponding to the articulation position of the articulation member. The control circuit 2510 may determine a control action of the motor 2504, when the motor 2504 is in the disengaged condition, in response to a movement of the articulation member that exceeds the predetermined threshold. The control circuit 2510 may control the movement of the articulation member, wherein controlling the movement of the articulation member comprises engaging the motor 2504 to the hold condition.

One or more of the following features may be included. The control circuit 2510 may be configured to maintain the articulation position in response to the movement of the articulation member that exceeds the predetermined threshold. In maintaining the articulation position, the control circuit may supply pulse width modulation (PWM) of the current (e.g., the motor drive signal 2514) to the motor 2504 in the hold condition to resist the movement of the articulation member. The motor 2504 may include a DC brushed motor. The control circuit 2510 may be configured to inner connect leads to the DC brushed motor when the motor 2504 is in the hold condition. The control circuit 2510 may include a forward condition, a coast condition, and a brake condition. When the control circuit 2510 is in the forward condition, the DC motor is in the engaged condition. When the control circuit 2510 is in the coast condition, the DC motor is in the disengaged condition. When the control circuit 2510 is in the brake condition, the DC motor is in the hold condition. The control circuit 2510 may include a first switch, a second switch, a third switch, and a fourth switch. When the control circuit 2510 is in the forward condition, the second switch and the third switch are in a closed configuration and the first switch and the fourth switch are in an open configuration. When the control circuit is in the brake condition, the first switch and the second switch are in a closed configuration and the third switch and the fourth switch are in an open configuration. When the control circuit 2510 is in the coast condition, the first switch, the second switch, the third switch, and the fourth switch are in an open configuration.

In one aspect, a surgical instrument 2500 may include an end effector 2502 and a rotatable shaft assembly. The rotatable shaft assembly may include a longitudinal axis, a rotational position sensor 2534, and a gear assembly. The rotational position sensor 2534 may be configured to measure the rotation of the rotatable shaft assembly around the longitudinal axis. The surgical instrument 2500 may include a motor 2504 operably connected to the gear assembly of the rotatable shaft assembly. The motor 2504 may be configured to apply a rotary force to rotate the gear assembly. The rotation of the gear assembly rotates the rotatable shaft assembly around the longitudinal axis. The surgical instrument 2500 may further include a control circuit 2510 coupled to the motor 2504. The control circuit 2510 may be configured to monitor a rotational position of the rotatable shaft assembly based on a signal from the rotational position sensor 2534. The control circuit 2510 may also identify a predetermined threshold corresponding to the rotational position of the rotatable shaft assembly. The control circuit 2510 may further determine a control action of the motor 2504 in response to rotational movement of the rotatable shaft assembly that exceeds the predetermined threshold. The control circuit 2510 may control the rotation of the rotatable shaft assembly, wherein controlling the rotation of the rotatable shaft assembly may include resisting the rotation of the rotatable shaft assembly around the longitudinal axis.

One or more of the following features may be included. The control circuit may be configured to maintain a rotational position of the rotatable shaft assembly in response to rotation of the rotatable shaft assembly around the longitudinal axis that exceeds the predetermined threshold. Maintaining the rotational position may include suppling PWM of the current to the motor 2504 to resist the rotation of the rotatable shaft assembly. The motor 2504 may include a DC brushed motor. The control circuit 2510 may be configured to inner connect leads to the DC brushed motor when the motor 2504 to resist the rotation of the rotatable shaft assembly beyond the predetermined threshold.

In one aspect, a surgical instrument 2500 may include a longitudinal shaft assembly. The longitudinal shaft assembly may include a rotatable shaft portion comprising a longitudinal axis and a drive gear and an articulation joint. The drive gear may be configured to rotate about the longitudinal axis. The articulation joint may include an articulation gear. The surgical instrument 2500 may further include a drive assembly. The drive assembly may include a motor 2504, a control circuit 2510 and a drive member. The motor 2504 may include a drive output. The control circuit 2510 may be configured to control the motor 2504. The drive member may be operably connected to the drive output. When the control circuit 2510 is in a rotational condition, the drive member is operably connected to the drive gear of the rotatable shaft portion. When the control circuit 2510 is in an articulation condition, the drive member is operably connected to the articulation gear of the articulation joint. The surgical instrument 2500 may further include an energy source 2512. The control circuit 2510 may comprise an engaged condition, a disengaged condition, and a dynamic brake condition. When the control circuit 2510 is in the engaged condition, the control circuit 2510 supplies the energy source 2512 to the motor 2504 in a series circuit configuration. When the control circuit 2510 is in the disengaged condition, the control circuit 2510 disconnects the energy source 2512 from the motor 2504. When the control circuit 2510 is in the dynamic brake condition, the control circuit 2510 places the energy source 2512 in a parallel circuit condition with the motor 2504.

One or more of the following features may be included. When the control circuit 2510 is in the rotational condition and the dynamic brake condition, the control circuit 2510 may be configured to monitor a rotational position of the rotatable shaft portion based on a signal from a rotational position sensor 2534. The control circuit 2510 may identify a predetermined threshold corresponding to a rotational position of the rotatable shaft portion. The control circuit 2510 may determine a control action of the motor 2504 in response to rotational movement of the rotatable shaft portion that exceeds the predetermined threshold. The control circuit 2510 may control the rotation of the rotatable shaft portion, wherein controlling the rotation of the rotatable shaft portion comprises resisting the rotation of the rotatable shaft portion around the longitudinal axis. When the control circuit 2510 is in the articulation condition and the dynamic brake condition, the control circuit may be configured to monitor an articulation position of the articulation joint based on a signal from an articulation position sensor 2534. The control circuit 2510 may identify a predetermined threshold corresponding to an articulation position of the articulation joint. The control circuit 2510 may determine a control action of the motor 2504 in response to articulation of the articulation joint that exceeds the predetermined threshold. The control circuit 2510 may control the articulation of the articulation joint, wherein controlling the articulation of the articulation joint comprises resisting the articulation of the articulation joint. The motor 2504 may include a DC brushed motor, and the energy source 2512 may include a battery.

In one aspect, a surgical instrument 2500 may include an end effector 2502, an articulation joint and an articulation member. The articulation member may be translatable relative to the end effector 2502 a distance from a proximal position to a distal position, wherein the translation of the articulation member causes the articulation joint to articulate. The surgical instrument 2500 may include a motor 2504 operable to translate the articulation member along the distance from the proximal position to the distal position. The motor 2504 may include an energized condition and a de-energized condition. The surgical instrument 2500 may further include a control circuit 2510 coupled to the motor 2504 and a position sensor 2534 coupled to the control circuit 2510. A user may desire to articulate the end effector 2502 to a predetermined, desired position. To articulate the end effector 2502 to the desired position, the control circuit 2510 may place the motor 2504 in the energized condition. The position sensor 2534 may be configured to detect a current position of the articulation member along at least a portion of the distance. The control circuit 2510 may be configured to receive position input from the position sensor 2534 indicative of a current articulation position of the articulation member. The control circuit 2510 may identify the current articulation position corresponding to the articulation position of the articulation member. The control circuit 2510 may determine a control action of the motor 2504 in response to a current position that does not correspond to a desired position. The control circuit 2510 may control the movement of the articulation member when the current position corresponds to the desired position, wherein controlling the movement of the articulation member comprises placing the motor 2504 in the de-energized condition.

One or more of the following features may be included. The control circuit 2510 may be configured to maintain the articulation position in response to the current position of the articulation member corresponding to the desired articulation position. In maintaining the articulation position, the control circuit may engage an electromagnetic lock. The electromagnetic lock may be created by shorting the motor 2504 when the motor is placed in the de-energized condition. The motor 2504 may include a DC brushed motor. The control circuit 2510 may be configured to inner connect leads to the DC brushed motor when the motor 2504 is in the de-energized to resist the articulation of the end effector 2502 beyond the desired position. Inner connecting the leads to the DC brushed motor creates an internal magnetic resistance within the motor 2504. The internal magnetic resistance prevents any inadvertent back-driving of the motor 2504 by externally applied forces when the end effector 2502 is in operation. Shorting the contacts of the motor 2504 creates a brake to hold the end effector 2502 in its current position, as the mechanical back-drive is combined with the natural resistance of a motor 2504 with shorted coils to passively hold a current articulation position.

In one aspect, a surgical instrument 2500 may include an end effector 2502 and a rotatable shaft assembly. The rotatable shaft assembly may be configured to rotate about a longitudinal axis. The rotatable shaft assembly may comprise a rotational position sensor 2534 and a gear assembly. The rotational position sensor 2534 may be configured to monitor the rotation of the rotatable shaft assembly about the longitudinal axis. The surgical instrument 2500 may include a motor 2504 operably connected to the gear assembly of the rotatable shaft assembly. The motor 2504 may be configured to apply a rotary force to rotate the gear assembly. The rotation of the gear assembly rotates the rotatable shaft assembly around the longitudinal axis. The surgical instrument 2500 may further include a control circuit 2510 coupled to the motor 2504. The control circuit 2510 may be configured to monitor a rotational position of the rotatable shaft assembly based on a signal from the rotational position sensor 2534. The control circuit 2510 may also identify a predetermined desired position corresponding to the rotational position of the rotatable shaft assembly. The control circuit 2510 may be configured to receive position input from the position sensor 2534 indicative of a current rotational position of the rotatable shaft assembly. The control circuit 2510 may identify the current rotational position corresponding to the rotational position of the rotatable shaft assembly. The control circuit 2510 may determine a control action of the motor 2504 in response to a current position that does not correspond to a desired position. The control circuit 2510 may control the movement of the rotatable shaft assembly when the current position corresponds to the desired position, wherein controlling the movement of the rotatable shaft assembly comprises placing the motor 2504 in the de-energized condition.

One or more of the following features may be included. The control circuit 2510 may be configured to maintain the rotational position in response to the current position of the rotatable shaft assembly corresponding to the desired rotational position. In maintaining the rotational position, the control circuit may engage an electromagnetic lock. The electromagnetic lock may be created by shorting the motor 2504 when the motor is placed in the de-energized condition. The motor 2504 may include a DC brushed motor. The control circuit 2510 may be configured to inner connect leads to the DC brushed motor when the motor 2504 is in the de-energized to resist the articulation of the end effector 2502 beyond the desired position. Inner connecting the leads to the DC brushed motor creates an internal magnetic resistance within the motor 2504. The internal magnetic resistance prevents any inadvertent back-driving of the motor 2504 by externally applied forces when the surgical instrument 2500 is in operation. Shorting the contacts of the motor 2504 creates a brake to hold the shaft assembly in its current position, as the mechanical back-drive is combined with the natural resistance of a motor 2504 with shorted coils to passively hold a current rotational position.

In one aspect, a surgical instrument 2500 may include a longitudinal shaft assembly. The longitudinal shaft assembly may include a rotatable shaft portion extending along a longitudinal axis. The longitudinal shaft assembly may further include a drive gear and an articulation joint. The drive gear may be configured to rotate the rotatable shaft portion about the longitudinal axis. The articulation joint may include an articulation gear. The surgical instrument 2500 may further include a drive assembly. The drive assembly may include a motor 2504, a control circuit 2510 and a drive member. The motor 2504 may include a drive output. The control circuit 2510 may be configured to control the motor 2504. The drive member may be operably connected to the drive output. When the control circuit 2510 is in a rotational condition, the drive member is operably connected to the drive gear of the rotatable shaft portion. When the control circuit 2510 is in an articulation condition, the drive member is operably connected to the articulation gear of the articulation joint. The surgical instrument 2500 may further include an energy source 2512. The motor 2504 may comprise an energized condition and a de-energized condition. When the motor 2504 is in the energized condition, the control circuit 2510 supplies the energy source 2512 to the motor 2504 in a series circuit configuration. When the motor 2504 is in the de-energized condition, the control circuit 2510 disconnects the energy source 2512 from the motor 2504.

One or more of the following features may be included. When the control circuit 2510 is in the rotational condition and the motor 2504 is in the energized condition, the control circuit 2510 may be configured to monitor a current rotational position of the rotatable shaft portion based on a signal from a rotational position sensor 2534. The control circuit 2510 may identify a predetermined desired position corresponding to a rotational position of the rotatable shaft portion. The control circuit 2510 may determine a control action of the motor 2504 in response to a current position of the rotatable shaft portion that does not correspond to a desired position. The control circuit 2510 may control the rotation of the rotatable shaft portion when the current position corresponds to the desired position, wherein controlling the rotation of the rotatable shaft portion comprises placing the motor in the de-energized condition. When the control circuit 2510 is in the articulation condition and the motor is in the energized condition, the control circuit may be configured to monitor a current articulation position of the articulation joint based on a signal from an articulation position sensor 2534. The control circuit 2510 may identify a predetermined desired position corresponding to an articulation position of the articulation joint. The control circuit 2510 may determine a control action of the motor 2504 in response to a current position that does not correspond with a desired position. The control circuit 2510 may control the articulation of the articulation joint when the current position corresponds with the desired position, wherein controlling the articulation of the articulation joint comprises placing the motor in a de-energized state. The control circuit 2510 may be configured to maintain the rotational position or articulation position in response to the current position of the rotatable shaft assembly or articulation member corresponding to the desired rotational or articulation position. In maintaining the desired position(s), the control circuit may engage an electromagnetic lock. The electromagnetic lock may be created by shorting the motor 2504 when the motor is placed in the de-energized condition. The motor 2504 may include a DC brushed motor. The control circuit 2510 may be configured to inner connect leads to the DC brushed motor when the motor 2504 is in the de-energized to resist the movement of the rotatable shaft assembly or the end effector 2502 beyond the desired position(s). Inner connecting the leads to the DC brushed motor creates an internal magnetic resistance within the motor 2504. The internal magnetic resistance prevents any inadvertent back-driving of the motor 2504 by externally applied forces when the surgical instrument 2500 is in operation. Shorting the contacts of the motor 2504 creates a brake to hold the shaft assembly and end effector 2502 in their current position, as the mechanical back-drive is combined with the natural resistance of a motor 2504 with shorted coils to passively hold a current rotational/articulation position.

In various aspects, the surgical instrument 2500 can include a single motor 2504 and a clutch or gear assembly. The single motor 2504 can be configured to articulate the end effector 2502, rotate the shaft of the surgical instrument 2500, and translate the firing member of the surgical instrument 2500. A gear or clutch system permits the motor 2504 to transfer its power to the various functions of the surgical instrument 2500. In one aspect, the motor 2504 and the clutch assembly may be configured to engage multiple surgical instrument 2500 functions at the same time. This permits, for example, the surgical instrument 2500 to maintain a dynamic hold or resistance condition with regard to the articulation or rotation of the end effector 2502 and shaft, while allowing the firing of the firing member. In another aspect, the surgical instrument 2500 can include separate motors 2504 for articulation of the end effector 2502, rotation of the shaft, and firing of the end effector 2502.

Reference will now be made in detail to several aspects, including aspects showing example implementations of manual and robotic surgical instruments 2500 with end effectors 2502 comprising sealing and cutting elements. Wherever practicable similar or like reference numbers may be used in the figures and may indicate similar or like functionality. The figures depict example aspects of the disclosed surgical instruments and/or methods of use for purposes of illustration only. Alternative example aspects of the structures and methods illustrated herein may be employed without departing from the scope of this disclosure.

Figure 76:
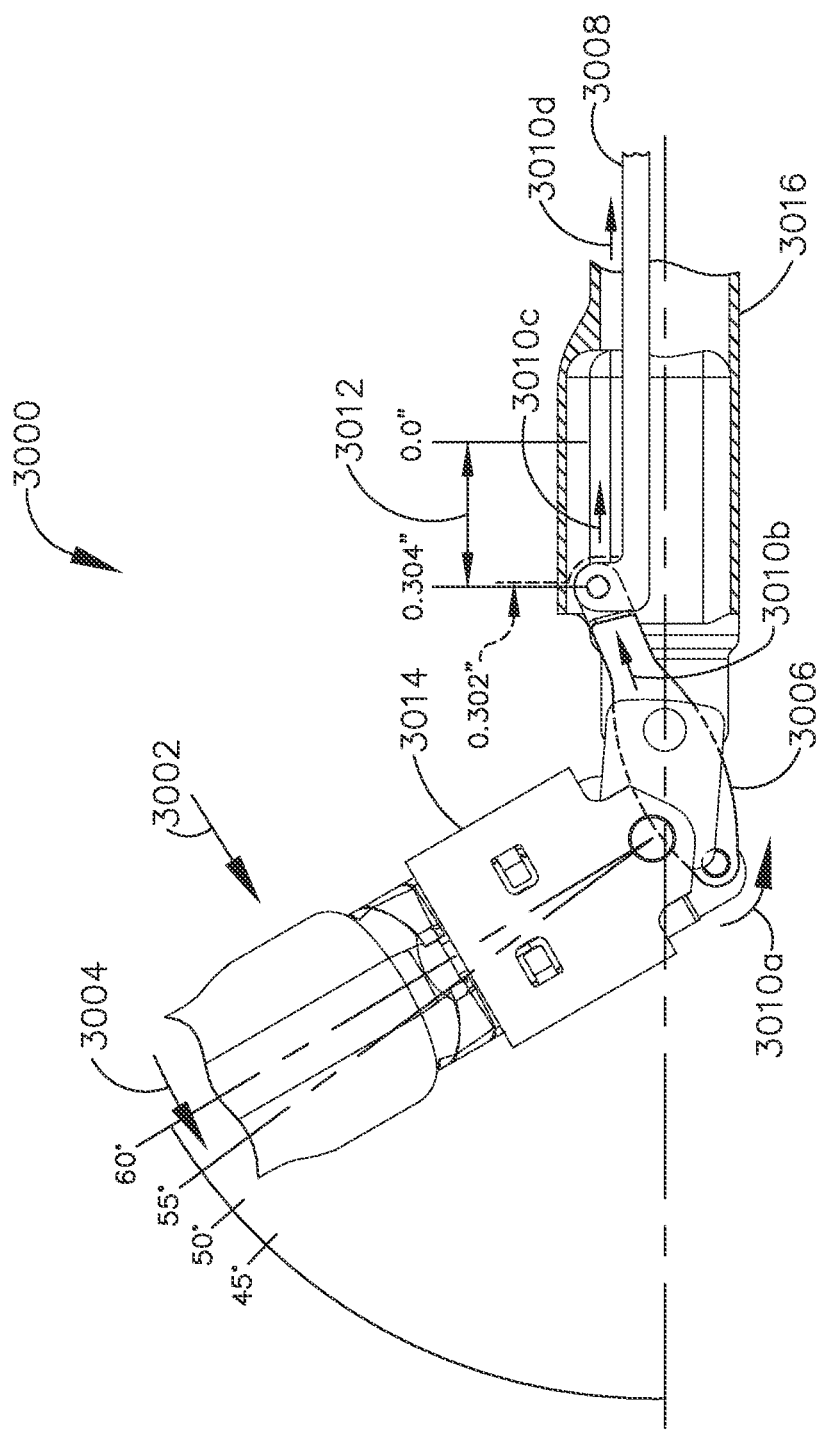
FIG. 76 depicts an example of an articulation mechanism for articulating an end effector of a surgical instrument according to one aspect of this disclosure.

FIG. 76 depicts an example of an articulation mechanism 3000 for articulating an end effector of a surgical instrument according to one aspect of this disclosure. With reference also to FIG. 14, the articulation mechanism 3000 includes an articulation joint 3006 which permits a distal arm 3014 of the surgical instrument 2500 to articulate or pivot with respect to a proximal arm 3016 of the surgical instrument 2500. The articulation joint 3006 may be articulated through the actuation of the articulation rod/member 3008. The articulation rod/member 3008 can have a degree of displacement 3012. In one aspect, the overall degree of displacement can be 0.304". However, in other aspects the degree of displacement 3012 can be greater or less. The articulation rod/member 3008 may be operably coupled to a motor 2504 or actuator which is controlled by a control circuit 2510. In controlling the desired articulation of the distal arm 3014 relative to the proximal arm 3016 of the surgical instrument 2500, the surgical instrument 2500 may include sensors 2534 to detect the articulational movement. In one aspect, a distal arm sensor may detect the angle of articulation of the distal arm 3014 relative to the proximal arm 3016 of the surgical instrument 2500. The distal arm sensor may communicate to the control circuit 2510 through various communications means, for example, wired or wireless means, the location of the distal arm 3014 relative to the proximal arm 3016 of the surgical instrument 2500. In addition, or in the alternative, the surgical instrument 2500 may include an articulation joint sensor 2534 that detects and communicates the articulated position of the distal arm 3014 relative to the proximal arm 3016 to the control circuit 2510. Additionally, or in the alternative, the surgical instrument 2500 may include an articulation rod sensor that measures and detects the displacement of the articulation member 3008 as discussed in reference with FIGS. 16-21. The displacement measured by the articulation sensor 2534 can be related to the articulation displacement of the distal arm 3014 and communicated to the control circuit 2510.

In operation, the articulation mechanism 3000 of the surgical instrument 2500 can be articulated by a technician to permit the end effector 2502 of the surgical instrument 2500 to reach a desired location within a patient. Once the desired articulation is achieved, the motor 2504 can be deactivated and placed into a de-energized condition by the control circuit 2510 to allow the articulation mechanism 3000 to maintain its articulated position. During surgery, outside resistance or force 3002 may act upon the end effector or the distal arm 3014 of the surgical instrument. With the motor in the de-energized condition, the control circuit 2510 can energize an electromagnetic lock to maintain the end effector 2502 in its current articulated position. To create the electromagnetic lock, the control circuit 2510 may be configured to inner connect leads to the motor 2504 when the motor 2504 is in the de-energized condition to resist the articulation of the end effector 2502 beyond the current position. Inner connecting the leads to the motor 2504 creates an internal magnetic resistance within the motor 2504. The internal magnetic resistance prevents any inadvertent back-driving of the motor 2504 by externally applied forces 3010*a-d* when the end effector 2502 is in operation. Shorting the contacts of the motor 2504 creates a brake to hold the end effector 2502 in its current position, as the mechanical back-drive is combined with the natural resistance of a motor 2504 with shorted coils to passively hold a current articulation position. With the motor in the de-energized condition, the control circuit 2510 can continue to monitor the articulation angle 3004 of the end effector 2502 and distal arm 3014 via the various sensors described above. If the change in the articulation angle 3004 no longer corresponds to the desired position, the control circuit 2510 can activate the energized condition of the motor 2504 to articulate the end effector 2502 back into a desired position. By activating the energized condition of the motor 2504, the electromagnetic lock is disabled. When the end effector 2502 is repositioned into a desired position, the control circuit 2510 can, once again, activate the de-energized condition of the motor 2504, thereby energizing the electromagnetic lock to prevent further movement.

Figure 77:
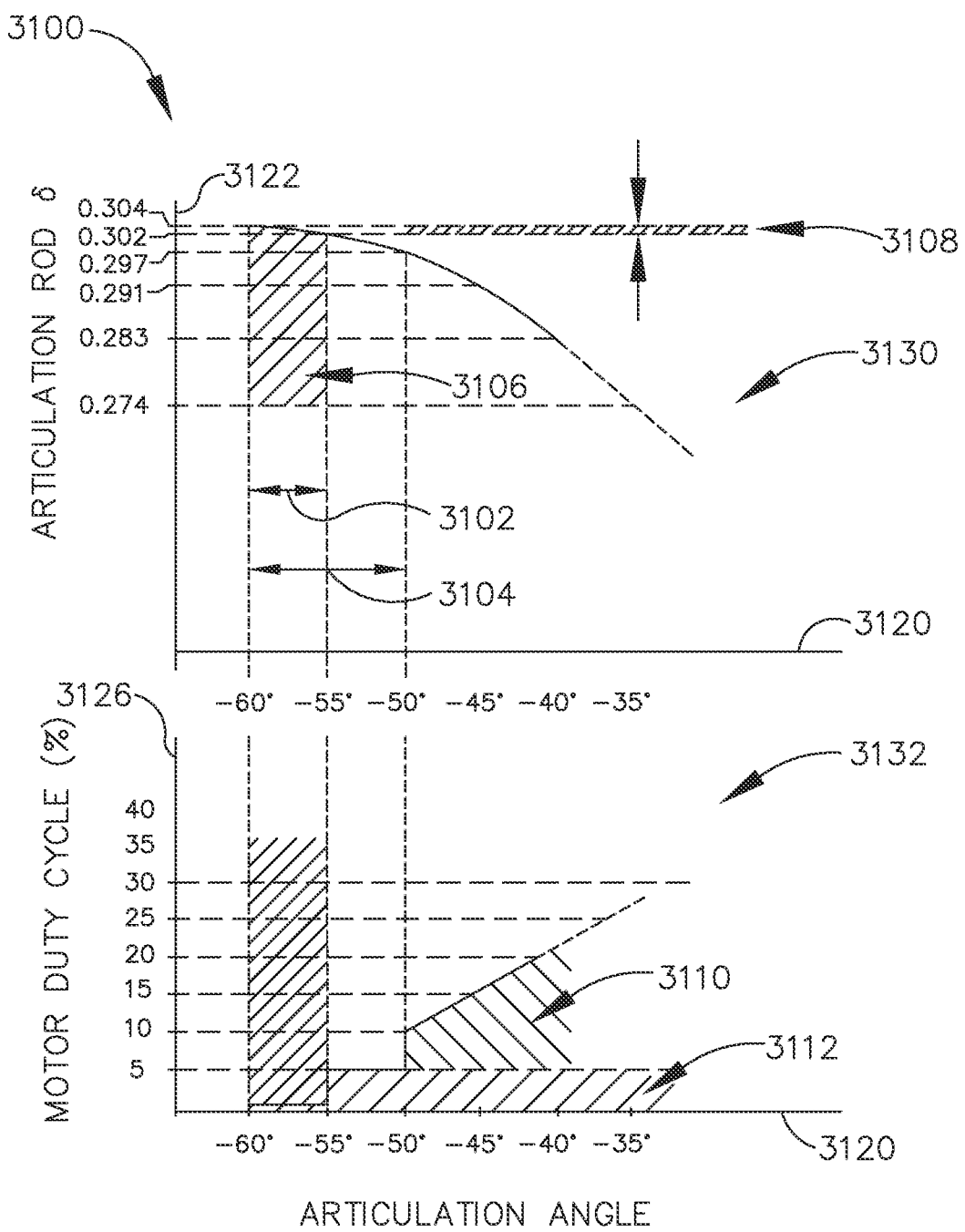
FIG. 77 is a graph of firing rod angle and motor duty cycle as a function of the articulation angle of the end effector according to one aspect of this disclosure.

FIG. 77 illustrates a graph 3100 of firing rod angle and motor duty cycle as a function of the articulation angle of the end effector according to one aspect of this disclosure. The top graph 3130 depicts firing rod displacement ($\delta$) along the vertical axis 3122 as a function of articulation angle in degrees (°) along the horizontal axis 3120. With reference also to FIG. 14, when the articulation rod/member 3008 is within a predetermined range of displacement 3108, the control circuit 2510 triggers a deactivated condition of the motor 2504. The predetermined range of displacement 3108 of the articulation rod 3008 corresponds to an allowable range of articulation angles 3102 for articulation of the distal arm 3014. When the predetermined range 3108 and/or the allowable range 3102 are exceeded, the control circuit 2510 activates a resistive hold mode of the motor 2504 to resist or counteract forces being applied to the distal arm 3014 and holds the distal arm 3014 and articulation rod 3018 within the predetermined/allowable ranges 3108, 3102.

The bottom graph 3132 in FIG. 77 depicts motor duty cycle (%) along the vertical axis 3126 as a function of articulation angle in degrees (°) along the horizontal axis 3120. As the degree of the articulation angle of the distal arm 3104 increasingly departs the predetermined threshold of articulation angles 3102 due to externally applied forces, the motor 2504 applies a force to resist the undesired articulation for an extended duration. In other word, the motor duty cycle increases as the articulation angle increasingly departs from predetermined threshold 3102. By way of example, the bottom graph 3132 in FIG. 77 represents an end effector 2502 with a desired articulation angle of −60°. The allowable range 3102 of articulation angles extends to −55°. When the end effector 2502 is articulated to a degree that falls within the allowable range 3102, the motor duty cycle is minimal. However, as the articulation angle exceeds the boundaries of the allowable range 3102, the control circuit 2510 begins to respond in a more vigorous fashion by activating the resistive hold mode of the motor 2504, thereby increasing the motor duty cycle. In addition to increasing the motor duty cycle, articulating an end effector 2502 to a degree that departs from the allowable range 3102 can increase the driving force, or torque, of the motor 2504. Shaded region 3112 indicates an initial restraint required of the motor 2504 as the articulation angle begins to exceed the boundaries of the allowable range 3102. Shaded region 3110 indicates a progressive restraint required of the motor 2504 as the articulation angle continues to exceed the boundaries of the allowable range 3102. In one aspect, the energy applied to the motor 2504 to resist the externally applied forces does not induce further articulation and/or movement of the end effector 2502, but prevents any additional undesired movement outside of the predetermined range 3102. In other aspects of this disclosure, the energy applied to the motor 2504 to resist the externally applied force can cause the end effector 2502 to articulate or rotate back to the previously set position.

Figure 78:
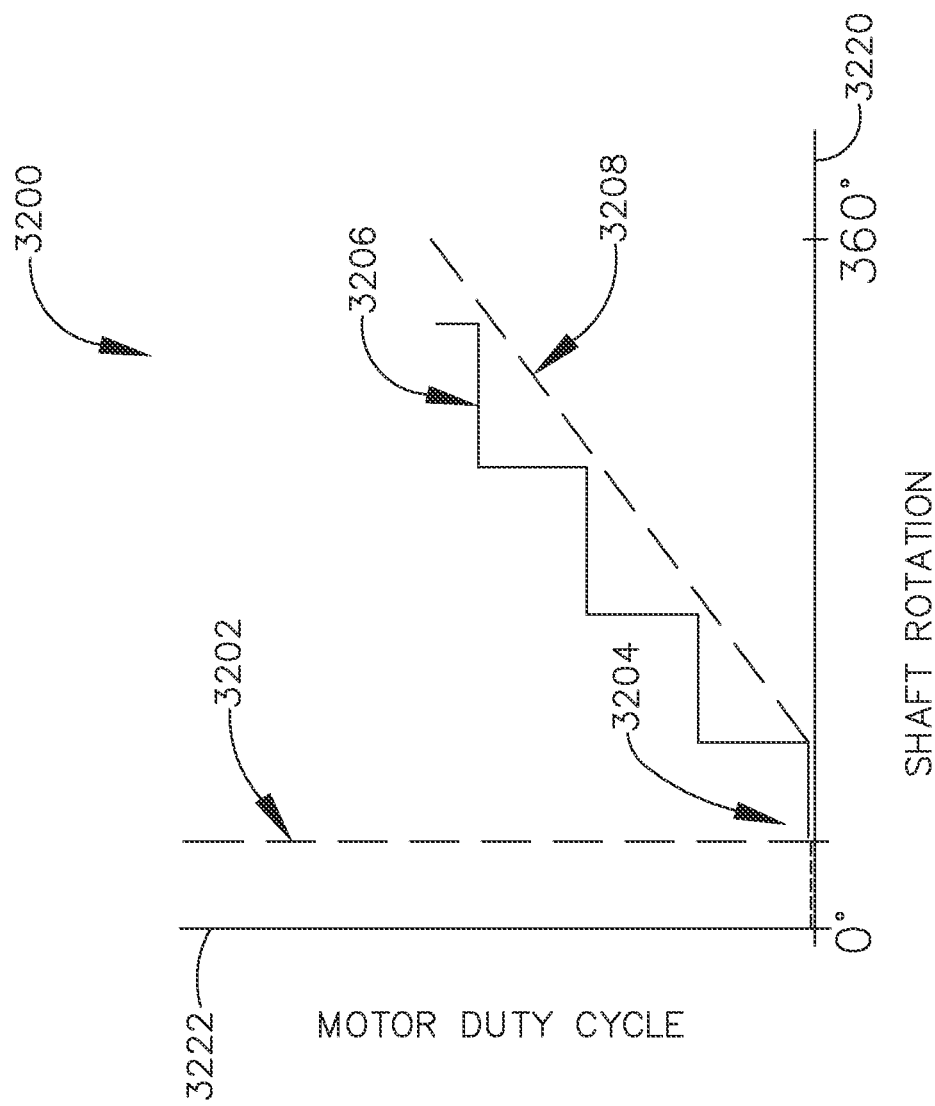
FIG. 78 is a graph of motor duty cycle as a function of the shaft rotation of a surgical instrument according to one aspect of this disclosure.

FIG. 78 illustrates a graph 3200 of motor duty cycle as a function of shaft rotation according to one aspect of this disclosure according to one aspect of this disclosure. The graph 3200 depicts motor duty cycle along the vertical axis 3222 as a function of shaft rotation in degrees (°) along the horizontal axis 3220. With reference also to FIG. 14, the control circuit 2510 permits an initial rotation threshold 3202 before activating the hold features of the motor 2504. In one aspect, the hold features include current modulation proportional to the resistance required to restrict or limit the shaft rotation. As the required motor resistance 3208 increases along with the displacement of the shaft rotation, the current 3204 can be increased. Thus the motor resistance can be increased in a stepwise 3206 fashion. Alternatively, the leads to the motor 2504 can be inner connected whenever the motor 2504 is in the de-energized state. This creates an internal magnetic resistance within the motor 2504 to prevent any inadvertent back-driving of the motor by externally applied forces. The mechanical back-drive is combined with the natural resistance of the motor with shorted coils to passively hold rotation.

In one aspect, the leads to a DC motor of the surgical instrument 2500, when in the de-energized condition, can be inner connected. The inner connection of the DC motor leads can result in an internal magnetic resistance within the motor to prevent inadvertent back driving of the motor 2504 by externally applied forces applied to the end effector 2502. Dynamic and regenerative braking can be achieved with PWM DC motor, brushed, brushless, and/or stepper motors to hold the portions of articulation of the desired location of the end effector 2502. Additionally, or in the alternative, the various dynamic braking mechanisms can be combined with mechanical locks to maintain the desired articulational or rotational position of the end effector. In addition, or in the alternative, the natural resistance of a motor 2504 with shorted coils can be combined with a mechanical brake or lock as a passive method to perform a station keeping function of an articulated or rotated system.

Figure 79:
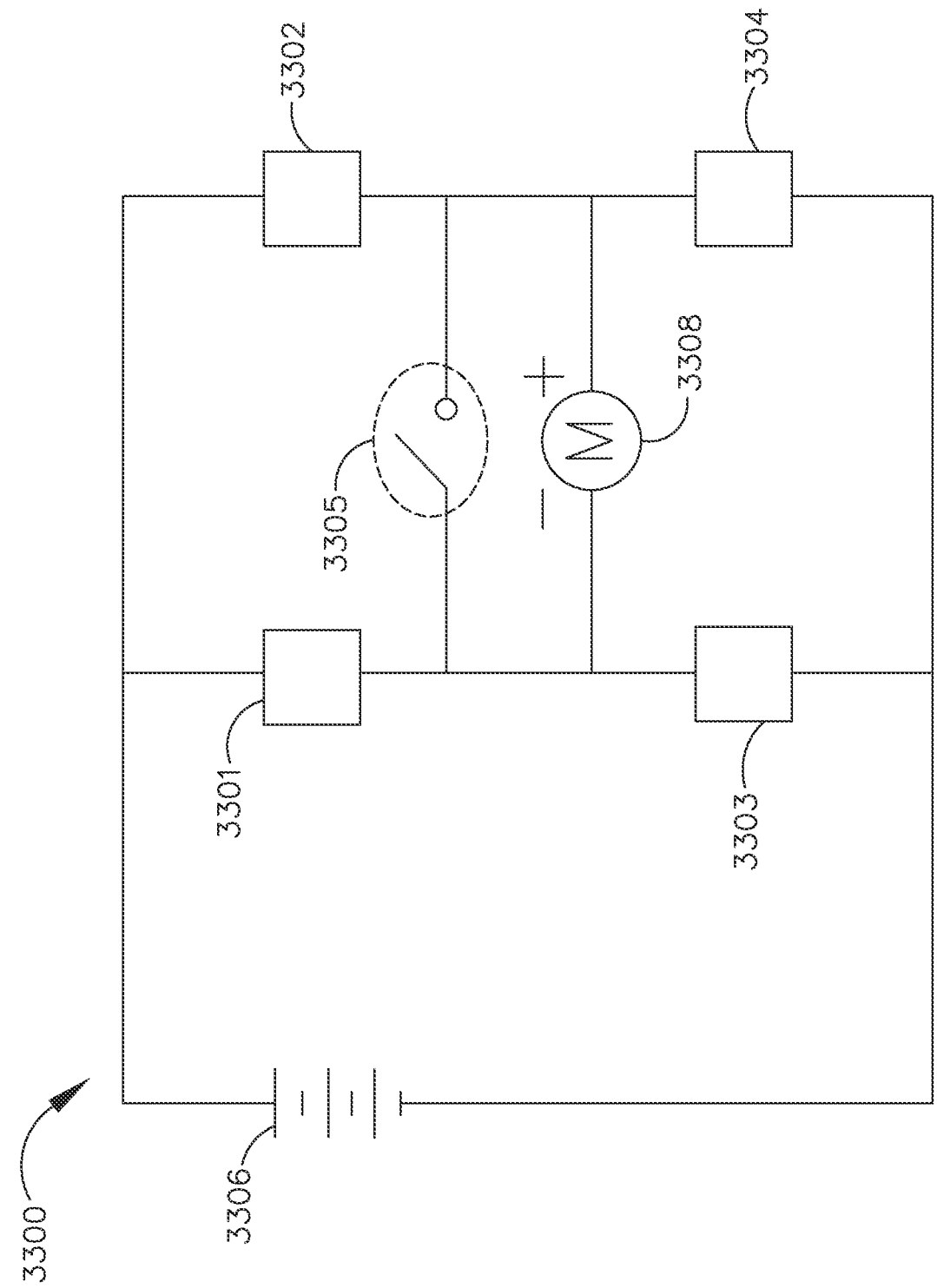
FIG. 79 is a circuit diagram illustrating the circuit configurations of a motor system of a surgical instrument according to one aspect of this disclosure.

FIG. 79 illustrates a control circuit 3300 in accordance with the various aspects discussed above according to one aspect of this disclosure. The circuit 3300 includes a power source 3306, a motor 3308, and a plurality of switches 3301, 3302, 3303, 3304. The circuit can further include alternative switch 3305. The switches 3301-3305 each permit the circuit 3300 to be configured to operate the motor 3308 in a forward mode, a reverse mode, and a resistance or brake mode. When the circuit 3300 is in the forward mode, the switches 3301, 3304, and 3305 may be in the open condition while the switches 3302 and 3303 may be in the closed condition. The forward mode allows the motor 3308 and the power source 3306 to be operated in a series configuration with the motor 3308 operating in the forward direction. When the circuit 3300 is in the reverse mode, the switches 3302, 3303, and 3305 may be in the open condition while the switches 3301 and 3304 may be in the closed condition. The reverse mode allows the motor 3308 and the power source 3306 to be operated in a series configuration with the motor 3308 operating in the reverse direction. Table 1, below, illustrates the various circuit 3300 configurations discussed herein.

TABLE 1

Various Circuit Configurations.

| 1 | 2 | 3 | 4 | |
|---|---|---|---|---|
| 0 | 1 | 1 | 0 | Forward |
| 1 | 0 | 0 | 1 | Reverse |
| 0 | 0 | 1 | 1 | Brake (Static Holding Load) |
| 0 | 0 | 0 | 0 | Alternate Switch 3305 |

1 = Closed; 0 = Open.

In one aspect, the brake mode can use static holding load to provide resistance to outside forces on the articulation or rotation of the distal portion of a surgical instrument. When the circuit 3300 is in the brake mode that provides a static holding load, the switches 3301, 3302, and 3305 may be in the open condition while the switches 3303 and 3304 may be in the closed condition. This brake mode allows the motor 3308 and the power source 3306 to be operated in a static configuration with the circuit configuration creating a static hold. In another aspect, the brake mode can use static holding load to provide resistance to outside forces on the articulation or rotation of the distal portion of a surgical instrument. When the circuit 3300 is in the brake mode that provides a static holding load, the switches 3301, 3302, 3303, 3304 may be in the open condition while the switch 3305 may be in the closed condition. This brake mode allows the motor 3308 to be isolated from the power source 3306. While in this brake mode, the motor 3308 is in a closed loop configuration isolated from the power source with the circuit configuration creating a static hold.

Figure 80:
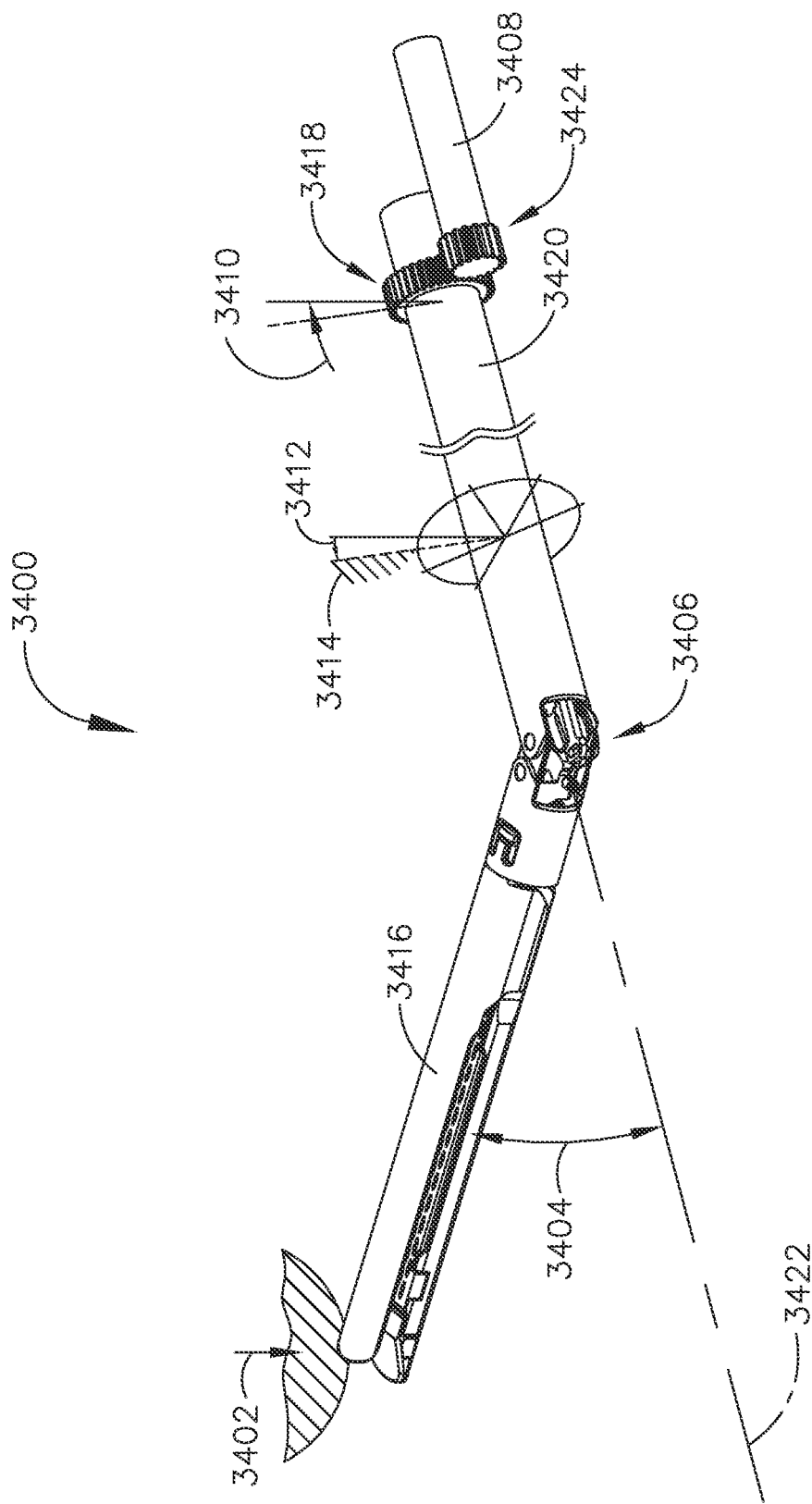
FIG. 80 depicts an example of an articulation mechanism for articulating an end effector of a surgical instrument according to one aspect of this disclosure.

FIG. 80 illustrates a rotatable and articulatable shaft assembly 3400 of a surgical instrument according to one aspect of this disclosure. With reference also to FIG. 79, the shaft assembly 3400 includes a distal end effector portion 3416, a proximal portion 3420, and an articulation mechanism 3406 connecting the distal end effector portion 3416 and the proximal portion 3420. The proximal portion 3420 defines a longitudinal axis 3422. The proximal portion 3420 is configured to rotate about the longitudinal axis 3422. The output of the motor 3308 of the surgical instrument is configured to rotate a rotational drive shaft 3408. The rotational drive shaft includes a drive gear 3424 which operably interfaces with a driven gear 3418 of the proximal portion 3420. As discussed with reference to FIG. 14, the control circuit 2510 can be connected to a rotational sensor 2534 that detects the rotation of the shaft assembly 3400. However, when an outside force 3402 causes the shaft assembly 3400 to rotate beyond a desired position, the control circuit 2510 can activate an energized condition on the motor 3308 (2504) as discussed above with respect to FIGS. 76-79. When the control circuit 2510 activates the energized, the motor 3308 (2504) may apply a force 3410 to oppose the outside rotation force 3402 and/or rotate the shaft assembly 3400 to the desired position. The force 3410 applied by the motor 3308 (2504) may include a passive or active resistance force as discussed above with respect to FIGS. 76-79.

In addition or in the alternative, through the active PWM and current step resistance of the control circuit 2510 and the dynamic and passive resistance of the control circuit configurations, the control circuit 2510 can resist unwanted rotation or articulation of an end effector from outside forces. The control circuit 2510 can permit the end effector and shaft assembly to remain within a desired position during a surgical procedure.

Figure 81:
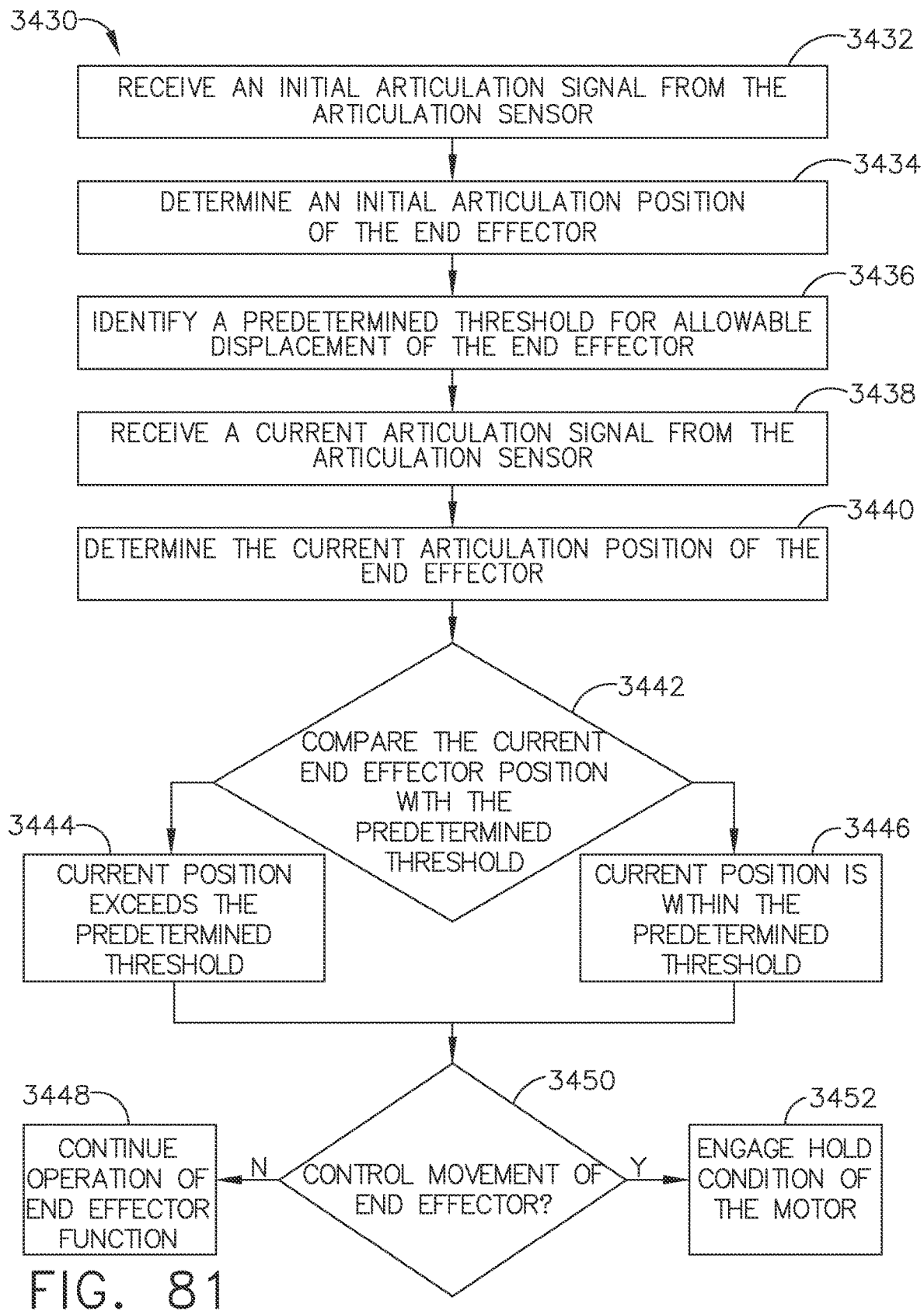
FIG. 81 is a logic flow diagram of a process depicting a control program or logic configuration representing a dynamic articulation control program according to one aspect of this disclosure.

FIG. 81 illustrates a logic flow diagram showing one example of a process 3430 that may be executed by the surgical instrument 2500 (e.g., the control circuit 2510) to resist and control the articulation of the end effector 2502 from outside forces. The control circuit 2510 may receive 3432 an initial articulation signal. The initial articulation signal may be received 3432 from the articulation sensor once the end effector 2502 is in a desired articulation position. For example, a clinician may place the end effector 2502 in a desired position and then clamp tissue between the anvil 2516 and staple cartridge 2518, and then actuate the trigger 32 to begin a firing stroke. The trigger 32 may be configured to provide the firing signal to the control circuit 2510 upon actuation.

Once the end effector 2502 is placed in the desired position, the control circuit 2510, in response to the initial articulation signal, may determine 3434 an initial articulation position of the end effector 2502 from the articulation signal. Upon determining 3434 the initial position, the control circuit 2510 may identify 3436 a predetermined threshold for allowable displacement of the end effector 2502. For example, the surgical instrument 2500 may transition from the articulation mode to the firing mode via the transmission 2506. When in the firing mode, the control circuit 2510 can monitor the articulation position of the end effector 2502.

The control circuit 2510 may receive 3438 a current articulation signal. The current articulation signal may be received 3438 from the articulation sensor once the end effector 2502 is in the firing mode to monitor the position of the end effector 2502 during the firing mode. The current articulation signal may be received 3438 from the articulation sensor. The control circuit 2510, in response to the current articulation signal, may determine 3440 a current articulation position of the end effector 2502 from the current articulation signal. The control circuit 2510 may compare 3442 the current articulation position of the end effector 2502 against the initial articulation position and the predetermined threshold for allowable displacement of the end effector 2502. If the current position exceeds the predetermined threshold 3444, then the control circuit 2510 controls 3450 the movement of the end effector 2502 by engaging 3452 the hold condition of the motor 3308 (2504). For example, when the control circuit compares 3442 the current position of the end effector 2502 against the predetermined threshold and the current position exceeds the predetermined threshold, the control circuit 2510 may switch the transmission 2506 from the firing mode to the control mode. When the control circuit 2510 switches into the control mode, the control circuit 2510 engages 3452 the hold condition of the motor 3308 (2504) to resist unwanted movement of the end effector 2502. The hold condition may include any of the hold conditions as discussed above with respect to FIGS. 76-79. When the control circuit 2502 compares 3442 the current articulation position of the end effector 2502 against the predetermined threshold and the current position is within the predetermined threshold 3446, the control circuit 2510 continues 3448 operation of the end effector function, for example, continues operating in the firing mode.

In another aspect, the surgical instrument 2500 may have a second motor. The original motor 3308 (2504) may be configured to operate the articulation of the end effector 2502. The second motor may be configured to operate the firing drive of the end effector 2502. When the surgical instrument comprises two motors, the controlling 3450 can be completed independently of the firing mode.

In another aspect, the surgical instrument 2500 may have a manual firing drive.

Where the surgical instrument has a manual firing drive, the motor 3308 (2504) may remain engaged with the articulation mechanism during the firing mode. The motor 3308 (2504) may be configured to operate the articulation of the end effector 2502. When the surgical instrument comprises a manual firing drive, the controlling 3450 can be completed independently of the firing mode.

Figure 82:
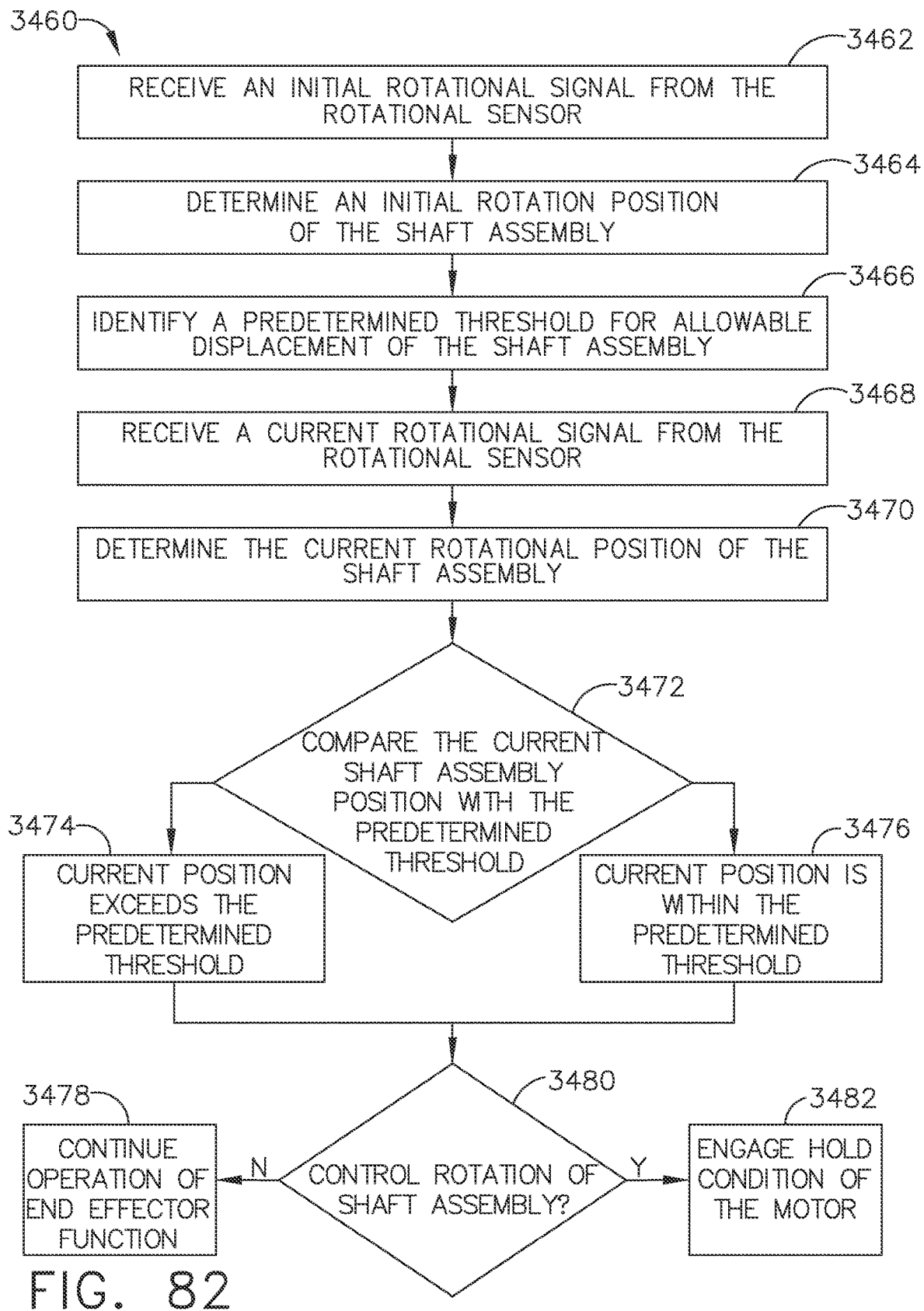
FIG. 82 is a logic flow diagram of a process depicting a control program or logic configuration representing a dynamic rotational control program according to one aspect of this disclosure.

FIG. 82 illustrates a logic flow diagram showing one example of a process 3460 that may be executed by the surgical instrument 2500 (e.g., the control circuit 2510) to resist and control the rotation of the shaft assembly 200 from outside forces. The control circuit 2510 may receive an initial rotational signal 3462. The initial rotational signal may be received 3462 from the rotation sensor once the shaft assembly 200 is in a desired rotational position. For example, a clinician may place the shaft assembly 200 in a desired rotational position and then clamp tissue between the anvil 2516 and staple cartridge 2518, and then actuate the trigger 32 to begin a firing stroke. The trigger 32 may be configured to provide the firing signal to the control circuit 2510 upon actuation.

Once the shaft assembly 200 is placed in the desired rotational position, the control circuit 2510, in response to the initial rotational signal, may determine 3464 an initial rotational position of the shaft assembly 200 from the rotational signal. Upon determining 3464 the initial rotational position, the control circuit 2510 may identify 3466 a predetermined threshold for allowable displacement of the shaft assembly 200. For example, the surgical instrument 2500 may transition from the rotational mode to the firing mode via the transmission 2506. When in the firing mode, the control circuit 2510 can monitor the rotational position of the shaft assembly 200.

The control circuit 2510 may receive 3468 a current rotational signal. The current rotational signal may be received 3468 from the rotation sensor once the shaft assembly 200 is in the firing mode to monitor the position of the shaft assembly 200 during the firing mode. The current rotational signal may be received 3468 from a rotation sensor. The control circuit 2510, in response to the current rotational signal, may determine 3470 a current rotational position of the shaft assembly 200 from the current rotational signal. The control circuit 2510 may compare 3472 the current rotational position of the shaft assembly 200 against the initial rotational position and the predetermined threshold for allowable rotational displacement of the shaft assembly 200. If the current rotational position of the shaft assembly 200 exceeds the predetermined threshold 3474, then the control circuit 2510 will control 3480 the rotation of the shaft assembly 200 by engaging 3482 the hold condition of the motor 3308 (2504). For example, when the control circuit compares 3472 the current position of the shaft assembly 200 against the predetermined threshold and the current position exceeds a boundary of the predetermined threshold, the control circuit 2510 may switch the transmission 2506 from the firing mode to the control mode. When the control circuit 2510 switches into the control mode, the control circuit 2510 then engages 3482 the hold condition of the motor 3308 (2504) to resist unwanted rotation of the shaft assembly 200. The hold condition may include any of the hold conditions as discussed above with respect to FIGS. 76-79 and with respect to articulation of the end effector 2502. When the control circuit 2510 compares 3472 the current rotational position of the shaft assembly 200 against the predetermined threshold and the current rotational position is within the predetermined threshold 3476, the control circuit 2510 continues 3478 operation of the end effector function, for example, continues operating in the firing mode.

Figure 83:
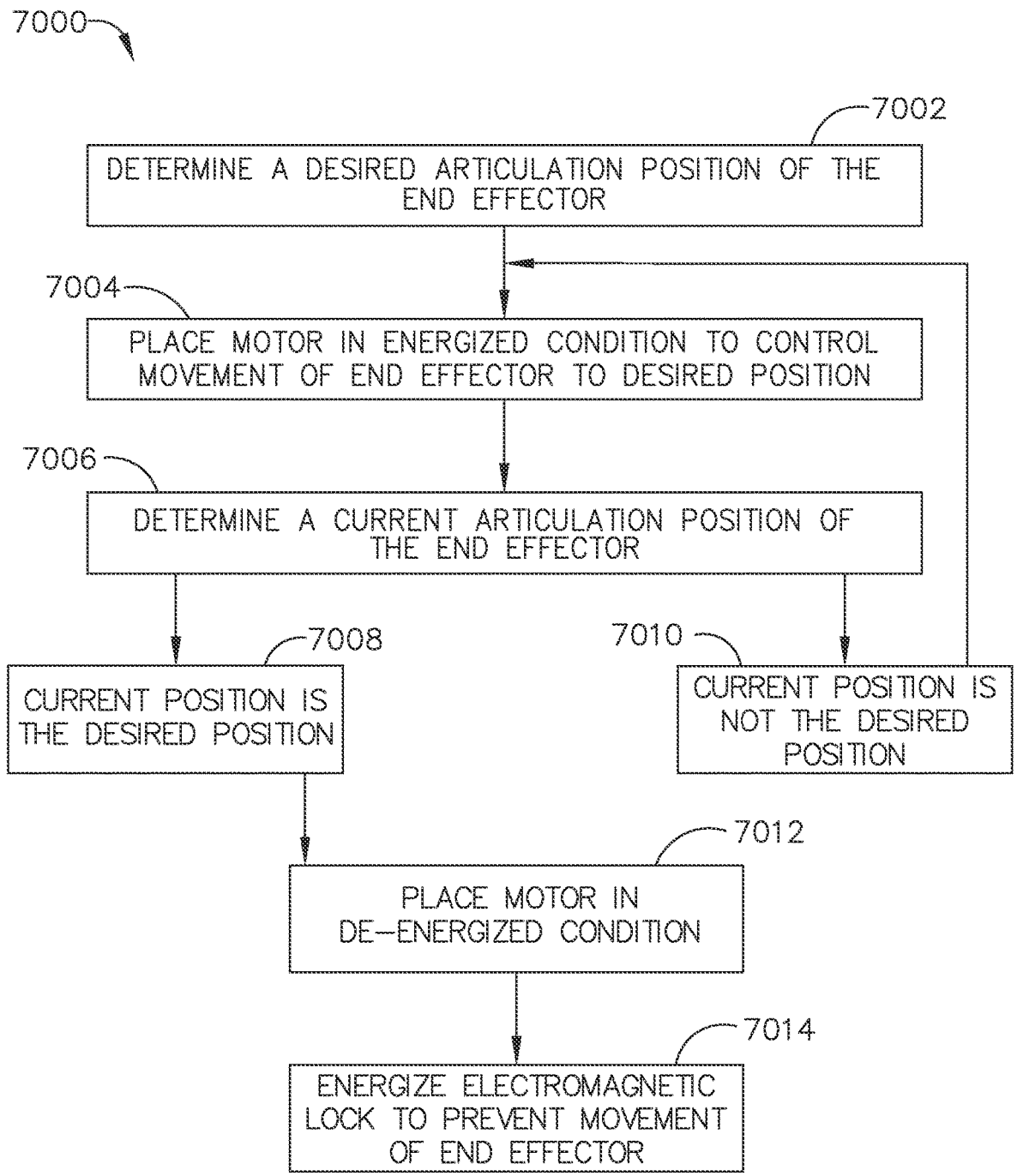
FIG. 83 is a logic flow diagram of a process depicting a control program or logic configuration representing a passive articulation control program according to one aspect of this disclosure.

FIG. 83 illustrates a logic flow diagram showing one example of a process 7000 that may be executed by the surgical instrument 2500 (e.g., the control circuit 2510) to resist and control the articulation of the end effector 2502 from outside forces. The control circuit 2510 may determine a desired articulation position of the end effector 7002. The control circuit 2510 may place the motor in an energized condition to control the movement of the end effector to the desired position 7004. An initial articulation position may be received from the articulation sensor once the end effector 2502 is in a desired articulated position. The control circuit 2510 may be configured to determine a current articulation position of the end effector 7006. If the current position does not correspond to the desired position 7010, the control circuit 2510 may be configured to place the motor in the energized condition to control movement of the end effector to the desired position 7004. Once the current position corresponds to the desired position 7008, the control circuit 2510 may be configured to place the motor in the de-energized condition 7012. When the motor is in the de-energized condition 7012, the control circuit 2510 may be configured to energize an electromagnetic lock to prevent movement of the end effector 7014.

Figure 84:
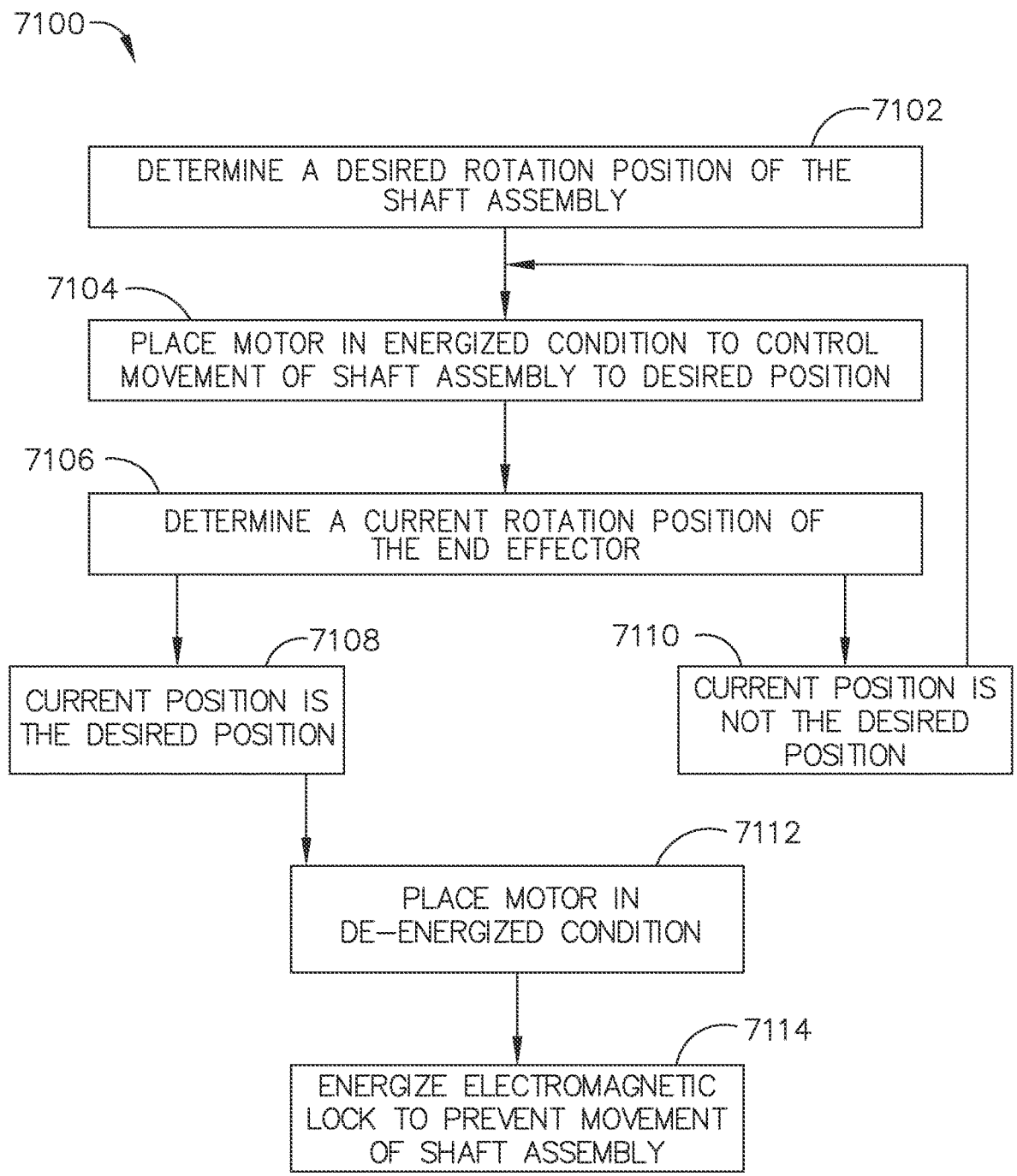
FIG. 84 is a logic flow diagram of a process depicting a control program or logic configuration representing a passive rotational control program according to one aspect of this disclosure.

FIG. 84 illustrates a logic flow diagram showing one example of a process 7100 that may be executed by the surgical instrument 2500 (e.g., the control circuit 2510) to resist and control the rotation of the shaft assembly from outside forces. The control circuit 2510 may determine a desired rotation position of the shaft assembly 7102. The control circuit 2510 may place the motor in an energized condition to control the movement of the shaft assembly to the desired position 7104. An initial rotation position may be received from the rotational position sensor once the shaft assembly is in a desired rotational position. The control circuit 2510 may be configured to determine 7106 a current rotation position of the shaft assembly. If the current position does not correspond to the desired position 7110, the control circuit 2510 may be configured to place the motor in the energized condition to control movement of the shaft assembly to the desired position 7104. Once the current position corresponds to the desired position 7108, the control circuit 2510 may be configured to place the motor in the de-energized condition 7112. When the motor is in the de-energized condition 7112, the control circuit 2510 may be configured to energize an electromagnetic lock to prevent movement of the shaft assembly 7114.

In another aspect, the surgical instrument 2500 may have a second motor. The original motor 3308 (2504) may be configured to operate the rotation of the shaft assembly 200. The second motor may be configured to operate the firing drive of the end effector 2502. When the surgical instrument comprises two motors, the controlling 3480 can be completed independently of the firing mode.

In another aspect, the surgical instrument 2500 may have a manual firing drive. Where the surgical instrument has a manual firing drive, the motor 3308 (2504) may remain engaged with the transmission 2506 during the firing mode. The motor 3308 (2504) may be configured to operate the rotation of the shaft assembly 200. When the surgical instrument comprises a manual firing drive, the controlling 3480 can be completed independently of the firing mode.

In another aspect, control circuit 2510 of the surgical instrument 2500 may be configured to resist and control the articulation of the articulation mechanism and resist and control the rotation of the shaft assembly 200. The resistance and hold functions of the articulation control and the rotational control may operate independently or cooperate to control the overall spatial position of the end effector 2502.

The functions or processes 3430, 3460, 7000, 7100 described herein may be executed by any of the processing circuits described herein, such as the control circuit 700 described in with FIGS. 5-6, the circuits 800, 810, 820 described in FIGS. 7-9, the microcontroller 1104 described in with FIGS. 10 and 12, and/or the control circuit 2510 described in FIG. 14.

Various aspects of the subject matter described herein are set out in the following numbered examples:

Example 1. A surgical instrument, comprising: a motor operable to translate an articulation member along a distance from a proximal position to a distal position, wherein the articulation member is translatable relative to an end effector a distance from a proximal position to a distal position, wherein the translation of the articulation member causes an articulation joint to articulate, and wherein the motor comprises an energized condition and a de-energized condition; a control circuit coupled to the motor; a position sensor coupled to the control circuit, the position sensor configured to detect a position of the articulation member along at least a portion of the distance; and wherein the control circuit is configured to: identify a predetermined desired position corresponding to the articulation position of the articulation member; receive position input from the position sensor indicative of a current articulation position of the articulation member; identify the current articulation position corresponding to the articulation position of the articulation member; determine a control action of the motor in response to a current articulation position of the articulation member that does not correspond to the desired position; and control the movement of the articulation member when the current articulation position corresponds to the desired position, wherein controlling the movement of the articulation member comprises placing the motor in the de-energized condition.

Example 2. The surgical instrument of Example 1, wherein the control circuit is configured to maintain the current position of the articulation member by engaging an electromagnetic lock when the motor is in the de-energized condition.

Example 3. The surgical instrument of Example 2, wherein the electromagnetic lock is created by shorting the motor.

Example 4. The surgical instrument of Example 1 through Example 3, wherein the motor comprises a DC brushed motor.

Example 5. The surgical instrument of Example 4, wherein the control circuit is configured to inner connect leads to the direct current (DC) brushed motor when the motor is in the de-energized condition.

Example 6. The surgical instrument of Example 4 through Example 5, wherein the control circuit comprises a forward condition, a reverse condition, and a brake condition.

Example 7. The surgical instrument of Example 6, wherein the control circuit comprises a first switch, a second switch, a third switch and a fourth switch, wherein when the control circuit is in the forward condition, the second switch and the third switch are in a closed configuration and the first switch and the fourth switch are in an open configuration.

Example 8. The surgical instrument of Example 7, wherein when the control circuit is in the brake condition, the first switch and the second switch are in an open configuration and the third switch and the fourth switch are in a closed configuration.

Example 9. The surgical instrument of Example 7 through Example 8, wherein when the control circuit is in the reverse condition, the first switch and the fourth switch are in a closed configuration and the second switch and the third switch are in an open configuration.

Example 10. A surgical instrument, comprising: a motor configured to couple to a gear assembly of a rotatable shaft assembly, wherein the rotatable shaft assembly is configured to rotate about a longitudinal axis, wherein the rotatable shaft assembly comprises a rotational position sensor configured to measure the rotation of the rotatable shaft assembly around the longitudinal axis, wherein the motor is configured to apply a rotary force to rotate the gear assembly, wherein the rotation of the gear assembly rotates the rotatable shaft assembly about the longitudinal axis, and wherein the motor comprises an energized condition and a de-energized condition; a control circuit coupled to the motor, wherein the control circuit is configured to: monitor a rotational position of the rotatable shaft assembly based on a signal from the rotational position sensor; identify a predetermined desired position corresponding to the rotational position of the rotatable shaft assembly; receive rotational input from the rotational position sensor indicative of a current rotational position of the rotatable shaft assembly; determine a control action of the motor in response to a current rotational position of the rotatable shaft assembly that does not correspond to the desired position; and control the rotation of the rotatable shaft assembly when the current rotational position corresponds to the desired position, wherein controlling the rotation of the rotatable shaft assembly comprises placing the motor in the de-energized condition.

Example 11. The surgical instrument of Example 10, wherein the control circuit is configured to maintain the current position of the rotatable shaft assembly by engaging an electromagnetic lock when the motor is in the de-energized condition.

Example 12. The surgical instrument of Example 11, wherein the electromagnetic lock is created by shorting the motor.

Example 13. The surgical instrument of Example 10 through Example 12, wherein the motor comprises a direct current (DC) brushed motor.

Example 14. The surgical instrument of Example 13, wherein the control circuit is configured to inner connect leads to the DC brushed motor when the motor is in the de-energized condition.

Example 15. A surgical instrument, comprising: a longitudinal shaft assembly, comprising: a rotatable shaft portion comprising a longitudinal axis and a drive gear, wherein the rotatable shaft portion is configured to rotate about the longitudinal axis; and an articulation joint comprising an articulation gear; a drive assembly, comprising: a motor comprising a drive output; a control circuit configured to control the motor; and a drive member operably connected to the drive output, wherein when the control circuit is in a rotational condition, the drive member is operably connected to the drive gear of the rotatable shaft portion, and wherein when the control circuit is in an articulation condition, the drive member is operably connected to the articulation gear of the articulation joint; and a power source; wherein the motor comprises an energized condition and a de-energized condition, wherein when the motor is in the engaged condition, the control circuit supplies the power source to the motor in a series circuit configuration, wherein when the motor is in the de-energized condition, the control circuit disconnects the power source from the motor, and wherein when the motor is in the de-energized condition, an electromagnetic lock is engaged.

Example 16. The surgical instrument of Example 15, wherein when the control circuit is in the rotational condition, the control circuit is configured to: monitor a rotational position of the rotatable shaft portion based on a signal from a rotational position sensor; identify a predetermined desired position corresponding to a rotational position of the rotatable shaft portion; receive rotational input from the rotational position sensor indicative of a current rotational position of the rotatable shaft portion determine a control action of the motor in response to a current rotational position of the rotatable shaft portion that does not correspond to the desired position; control the rotation of the rotatable shaft portion when the current rotational position corresponds to the desired position, wherein controlling the rotation of the rotatable shaft portion comprises placing the motor in the de-energized condition.

Example 17. The surgical instrument of Example 16, wherein the control circuit is configured to maintain the current position of the rotatable shaft portion by engaging an electromagnetic lock when the motor is in the de-energized condition.

Example 18. The surgical instrument of Example 15 through Example 17, wherein when the control circuit is in the articulation condition, the control circuit is configured to: monitor an articulation position of the articulation joint based on a signal from an articulation position sensor; identify a predetermined desired position corresponding to an articulation position of the articulation joint; receive position input from the articulation position sensor indicative of a current articulation position of the articulation joint; determine a control action of the motor in response to a current articulation position of the articulation joint that does not correspond to a desired position; control the articulation of the articulation joint when the current articulation position corresponds to the desired position, wherein controlling the articulation of the articulation joint comprises placing the motor in the de-energized condition.

Example 19. The surgical instrument of Example 18, wherein the control circuit is configured to maintain the current position of the rotatable shaft assembly by engaging an electromagnetic lock when the motor is in the de-energized condition.

Example 20. The surgical instrument of Example 18 through Example 19, wherein the motor comprises a DC brushed motor, and wherein the power supply comprises a battery.

Figure 85:
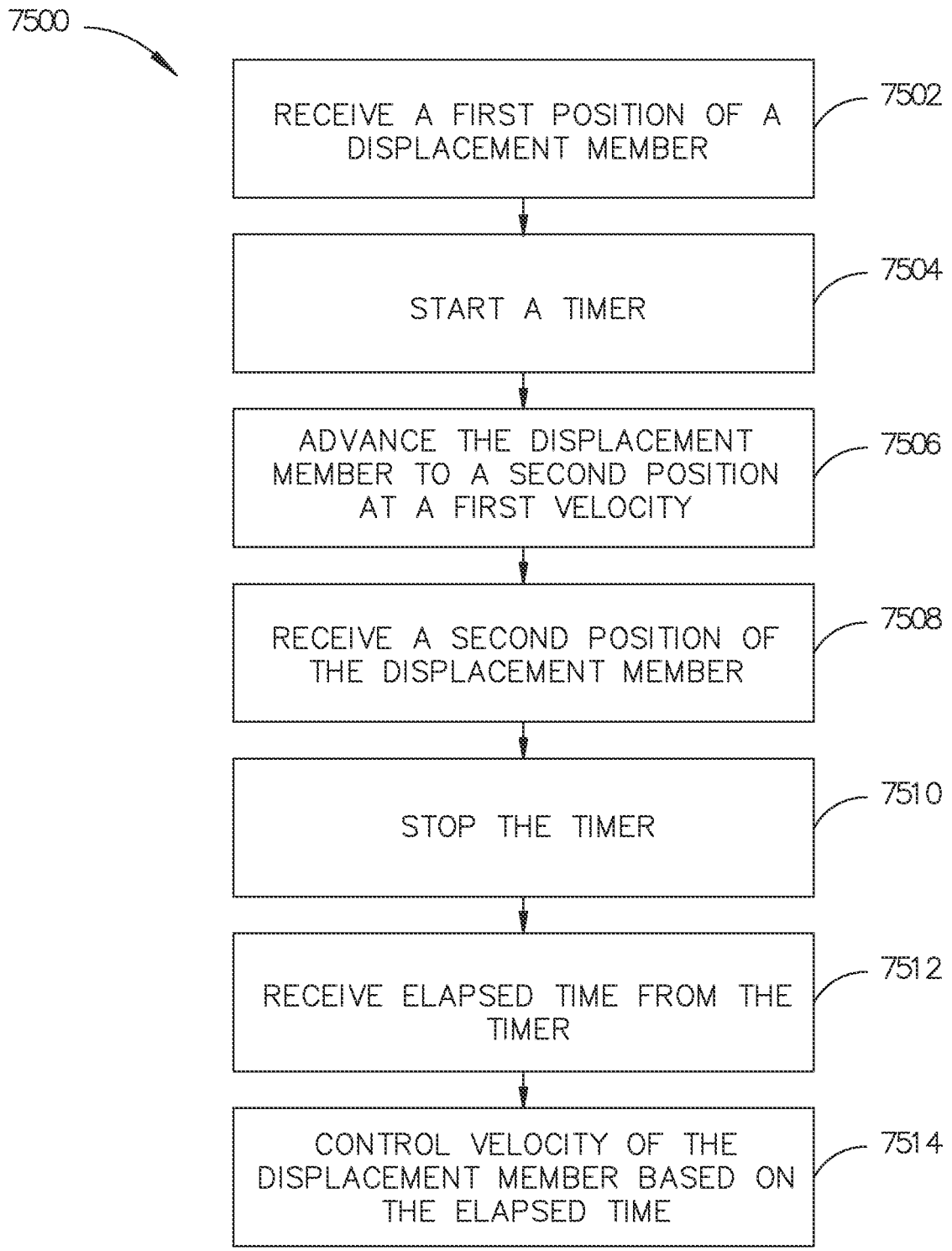
FIG. 85 is a logic flow diagram depicting a process of a control program or a logic configuration for controlling the velocity of a displacement member based on the time taken by the displacement member to move from a first location to a second location according to one aspect of this disclosure.

Techniques for Adaptive Control of Motor Velocity of a Surgical Stapling and Cutting Instrument FIG. 85 illustrates a logic flow diagram showing one example of a process 7500 that may be executed by the surgical instrument 2500 (e.g., the control circuit 2510). Accordingly, with reference also to FIG. 14, the control circuit 2510 receives 7502 a first position of a displacement member, such as, for example, the I-beam 2514, from the position sensor 2534. At the same time, the control circuit 2510 starts 7504 a timer 2531 and advances 7506 the displacement member to a second position at a first velocity. As previously discussed, the control circuit 2510 applies a motor set point 2522 to a motor control 2508 which applies a motor drive signal 2524 to the motor 2504 to advance the displacement member (e.g., I-beam 2514) through a transmission 2506. The position sensor 2534 tracks the position of the of the displacement member and provides the tracking information as feedback to the control circuit 2510. Accordingly, the control circuit 2510 receives 7508 a second position of the displacement member from the position sensor 2534. At that time, the control circuit 2510 stops 7510 the timer and receives 7512 the elapsed time from the timer 2531. The control circuit 2510 then controls 7514 the velocity of the displacement member based on the elapsed time.

In accordance with the process 7500, the control circuit 2510 may determine an anticipated second position of the displacement member based on the first velocity, compare the actual second position of the displacement member with the anticipated second position of the displacement member, and adjust the velocity of the motor to a second velocity based on a difference between the actual second position of the displacement member and the anticipated second position of the displacement. The control circuit 2510 may increase the velocity of the motor 2504 when the actual second position of the displacement member is greater than the anticipated second position of the displacement member. Alternatively, the control circuit 2510 may decrease the velocity of the motor 2504 when the actual second position of the displacement member is less than the anticipated second position of the displacement member.

Various aspects of the subject matter described herein are set out in the following numbered examples:

Example 1. A method of controlling motor velocity in a surgical instrument, the surgical instrument comprising a displacement member configured to translate, a motor coupled to the displacement member to translate the displacement member, a control circuit coupled to the motor, a position sensor coupled to the control circuit, the position sensor configured to measure the position of the displacement member, a timer coupled to the control circuit, the timer configured to measure elapsed time, the method comprising: receiving, by a control circuit, a first position of a displacement member from a position sensor; starting, by the control circuit, a timer; advancing, by the control circuit, the displacement member to a second position by setting a motor velocity to a first velocity; receiving, by the control circuit, the second positon from the position sensor; stopping, by the control circuit, the timer when the displacement member reaches the second position; receiving, by the control circuit, elapsed time from the timer, wherein the elapsed time is the time taken by the displacement to move from the first position to the second positon; and controlling, by the control circuit, velocity of the motor based on the elapsed time.

Example 2. The method of Example 1, comprising: determining, by the control circuit, an anticipated second position of the displacement member based on the first velocity.

Example 3. The method of Example 2, comprising: comparing, by the control circuit, the actual second position of the displacement member with the anticipated second position of the displacement member; and adjusting, by the control circuit, the velocity of the motor to a second velocity based on a difference between the actual second position of the displacement member and the anticipated second position of the displacement.

Example 4. The method of Example 3, comprising: increasing, by the control circuit, the velocity of the motor when the actual second position of the displacement member is greater than the anticipated second position of the displacement member.

Example 5. The method of Example 3, comprising: decreasing, by the control circuit, the velocity of the motor when the actual second position of the displacement member is less than the anticipated second position of the displacement member.

The functions or processes 3430, 3460, 3600, 3700, 3800, 4070, 4200, 4560, 4570, 5100, 5550, 5560, 6030, 6111, 6131, 6800, 7000, 7100, 7500 described herein may be executed by any of the processing circuits described herein, such as the control circuit 700 described in connection with FIGS. 5-6, the circuits 800, 810, 820 described in FIGS. 7-9, the microcontroller 1104 described in connection with FIGS. 10 and 12, and/or the control circuit 2510 described in FIG. 14.

Aspects of the motorized surgical instrument may be practiced without the specific details disclosed herein. Some aspects have been shown as block diagrams rather than detail. Parts of this disclosure may be presented in terms of instructions that operate on data stored in a computer memory. An algorithm refers to a self-consistent sequence of steps leading to a desired result, where a "step" refers to a manipulation of physical quantities which may take the form of electrical or magnetic signals capable of being stored, transferred, combined, compared, and otherwise manipulated. These signals may be referred to as bits, values, elements, symbols, characters, terms, numbers. These and similar terms may be associated with the appropriate physical quantities and are merely convenient labels applied to these quantities.

Generally, aspects described herein which can be implemented, individually and/or collectively, by a wide range of hardware, software, firmware, or any combination thereof can be viewed as being composed of various types of "electrical circuitry." Consequently, "electrical circuitry" includes electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer or processor configured by a computer program which at least partially carries out processes and/or devices described herein, electrical circuitry forming a memory device (e.g., forms of random access memory), and/or electrical circuitry forming a communications device (e.g., a modem, communications switch, or optical-electrical equipment). These aspects may be implemented in analog or digital form, or combinations thereof.

The foregoing description has set forth aspects of devices and/or processes via the use of block diagrams, flowcharts, and/or examples, which may contain one or more functions and/or operation. Each function and/or operation within such block diagrams, flowcharts, or examples can be implemented, individually and/or collectively, by a wide range of hardware, software, firmware, or virtually any combination thereof. In one aspect, several portions of the subject matter described herein may be implemented via Application Specific Integrated Circuits (ASICs), Field Programmable Gate Arrays (FPGAs), digital signal processors (DSPs), Programmable Logic Devices (PLDs), circuits, registers and/or software components, e.g., programs, subroutines, logic and/or combinations of hardware and software components. logic gates, or other integrated formats. Some aspects disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

The mechanisms of the disclosed subject matter are capable of being distributed as a program product in a variety of forms, and that an illustrative aspect of the subject matter described herein applies regardless of the particular type of signal bearing medium used to actually carry out the distribution. Examples of a signal bearing medium include the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.).

The foregoing description of these aspects has been presented for purposes of illustration and description. It is not intended to be exhaustive or limiting to the precise form disclosed. Modifications or variations are possible in light of the above teachings. These aspects were chosen and described in order to illustrate principles and practical application to thereby enable one of ordinary skill in the art to utilize the aspects and with modifications as are suited to the particular use contemplated. It is intended that the claims submitted herewith define the overall scope.

The invention claimed is:

1. A surgical system, comprising:
   an end effector, comprising:
      a first jaw; and
      a second jaw rotatable relative to the first jaw from an open position toward a closed position to capture tissue therebetween;
   a firing beam movable from an unfired position toward a fired position during a firing stroke, wherein the firing beam comprises:
      a first cam configured to engage the first jaw; and
      a second cam configured to engage the second jaw;
   a motor operably coupled to the firing beam, wherein the motor is configured to move the firing beam through the firing stroke;
   a current sensor configured to detect a current draw of the motor during the firing stroke;
   a position sensor configured to detect a position of the firing beam during the firing stroke; and
   a control circuit configured to communicate with the motor, the current sensor, and the position sensor, wherein the control circuit is configured to:
      control the motor to move the firing beam toward the fired position;
      receive a first sensor signal from the current sensor, wherein the first sensor signal is indicative of the current draw;
      receive a second sensor signal from the position sensor, wherein the second sensor signal is indicative of the position of the firing beam;
      conduct a first comparison between the current draw and a current threshold; and
      pause the motor for a first length of time based on the first comparison, wherein the first length of time is determined based on the position of the firing beam.

2. The surgical system of claim 1, further comprising a tissue thickness sensor, wherein the control circuit is configured to receive a third sensor signal from the tissue thickness sensor, wherein the third sensor signal is indicative of a thickness of the tissue, and wherein the first length of time is further determined based on the thickness of the tissue.

3. The surgical system of claim 2, wherein the tissue thickness sensor comprises a magnetic field sensor.

4. The surgical system of claim 1, wherein the control circuit is further configured to:
   control the motor to resume moving the firing beam toward the fired position after the first length of time elapses;
   conduct a second comparison between the current draw and the current threshold; and
   pause the motor for a second length of time based on the second comparison, wherein the second length of time is determined based on the position of the firing beam.

5. The surgical system of claim 4, wherein the second length of time is different than the first length of time.

6. The surgical system of claim 5, wherein the second length of time is less than the first length of time.

7. The surgical system of claim 4, further comprising a tissue thickness sensor, wherein the control circuit is configured to receive a third sensor signal from the tissue thickness sensor, wherein the third sensor signal is indicative of a thickness of the tissue, and wherein the first length of time and the second length of time are further determined based on the thickness of the tissue.

8. A surgical system, comprising:
an end effector, comprising:
a first jaw; and
a second jaw movable relative to the first jaw from an open position toward a closed position to capture tissue therebetween;
a firing beam movable from a proximal position toward a distal position during a firing stroke;
a motor operably coupled to the firing beam, wherein the motor is configured to move the firing beam through the firing stroke;
a current sensor configured to sense a current draw of the motor during the firing stroke;
a position sensor configured to sense a position of the firing beam during the firing stroke; and
a control circuit configured to communicate with the motor, the current sensor, and the position sensor, wherein the control circuit is configured to:
control the motor to move the firing beam toward the distal position;
receive a first sensor signal from the current sensor, wherein the first sensor signal is indicative of the current draw;
receive a second sensor signal from the position sensor, wherein the second sensor signal is indicative of the position of the firing beam;
conduct a first comparison between the current draw and a current threshold;
pause the motor for a first length of time based on the first comparison;
control the motor to resume moving the firing beam toward the distal position based on the first length of time elapsing;
conduct a second comparison between the current draw and the current threshold; and
pause the motor for a second length of time based on the second comparison, wherein the second length of time is different that the first length of time.

9. The surgical system of claim 8, wherein the second length of time is less than the first length of time.

10. The surgical system of claim 8, wherein the first length of time and the second length of time are determined based on the position of the firing beam.

11. The surgical system of claim 8, further comprising a tissue thickness sensor, wherein the control circuit is configured to receive a third sensor signal from the tissue thickness sensor, wherein the third sensor signal is indicative of a thickness of the tissue, and wherein the first length of time is further determined based on the thickness of the tissue.

12. The surgical system of claim 11, wherein the second length of time is further determined based on the thickness of the tissue.

13. The surgical system of claim 11, wherein the tissue thickness sensor comprises a magnetic field sensor.

14. A surgical system, comprising:
an end effector, comprising:
a first jaw; and
a second jaw movable relative to the first jaw from an open position toward a closed position to capture tissue therebetween;
a firing beam movable from an unfired position toward a fired position during a firing stroke;
a motor operably coupled to the firing beam, wherein the motor is configurable between:
an activated state in which the motor drives the firing beam toward the fired position; and
a deactivated state in which the motor ceases to drive the firing beam toward the fired position;
a current sensor configured to detect a current draw of the motor during the firing stroke;
a position sensor configured to detect a position of the firing beam during the firing stroke; and
a control circuit coupled to the motor, the current sensor, and the position sensor, wherein the control circuit is configured to:
transition the motor to the activated state;
receive a first sensor signal from the current sensor, wherein the first sensor signal is indicative of the current draw;
receive a second sensor signal from the position sensor, wherein the second sensor signal is indicative of the position of the firing beam;
conduct a first comparison between the current draw and a current threshold; and
transition the motor to the deactivated state for a first length of time based on the first comparison, wherein the first length of time is determined based on the position of the firing beam.

15. The surgical system of claim 14, further comprising a tissue thickness sensor, wherein the control circuit is configured to receive a third sensor signal from the tissue thickness sensor, wherein the third sensor signal is indicative of a thickness of the tissue, and wherein the first length of time is further determined based on the thickness of the tissue.

16. The surgical system of claim 15, wherein the tissue thickness sensor comprises a magnetic field sensor.

17. The surgical system of claim 14, wherein the control circuit is further configured to:
transition the motor to the activated state based on the first length of time elapsing;
conduct a second comparison between the current draw and the current threshold; and
transition the motor to the deactivated state for a second length of time based on the second comparison, wherein the second length of time is determined based on the position of the firing beam.

18. The surgical system of claim 17, wherein the second length of time is different than the first length of time.

19. The surgical system of claim 18, wherein the second length of time is less than the first length of time.

20. The surgical system of claim 17, further comprising a tissue thickness sensor, wherein the control circuit is configured to receive a third sensor signal from the tissue thickness sensor, wherein the third sensor signal is indicative of a thickness of the tissue, and wherein the first length of time and the second length of time are further determined based on the thickness of the tissue.

* * * * *